(12) United States Patent
Seifermann et al.

(10) Patent No.: US 11,276,825 B2
(45) Date of Patent: Mar. 15, 2022

(54) ORGANIC MOLECULES FOR USE IN ORGANIC DEVICES

(71) Applicant: CYNORA GMBH, Bruchsal (DE)

(72) Inventors: Stefan Seifermann, Bühl (DE); Michael Danz, Eggenstein-Leopoldshafen (DE); Daniel Volz, Karlsruhe (DE)

(73) Assignee: CYNORA GmbH, Bruchsal (DE)

( * ) Notice: Subject to any disclaimer, the term of this patent is extended or adjusted under 35 U.S.C. 154(b) by 505 days.

(21) Appl. No.: 16/322,775

(22) PCT Filed: Aug. 1, 2017

(86) PCT No.: PCT/EP2017/069431
§ 371 (c)(1),
(2) Date: Feb. 1, 2019

(87) PCT Pub. No.: WO2018/024723
PCT Pub. Date: Feb. 8, 2018

(65) Prior Publication Data
US 2021/0184134 A1    Jun. 17, 2021

(30) Foreign Application Priority Data
Dec. 20, 2016 (EP) .................................... 16205427

(51) Int. Cl.
*C07D 403/04* (2006.01)
*C07D 403/14* (2006.01)
(Continued)

(52) U.S. Cl.
CPC ........ *H01L 51/0072* (2013.01); *C07D 403/04* (2013.01); *C07D 403/14* (2013.01);
(Continued)

(58) Field of Classification Search
CPC ... C07D 209/48; C07D 209/82; C07D 403/04
See application file for complete search history.

(56) References Cited

U.S. PATENT DOCUMENTS 10,651,394 B2 * 5/2020 Danz .................. H01L 51/0058
10,651,396 B2   5/2020 Song et al.

FOREIGN PATENT DOCUMENTS

TW    201627284 A    8/2016
WO    2016042070 A1  9/2015
WO    PCT/EP2017/069431  8/2017

* cited by examiner

*Primary Examiner* — Vu A Nguyen
(74) *Attorney, Agent, or Firm* — Ryan, Mason & Lewis, LLP

(57) ABSTRACT

An organic molecules for use in optoelectronic devices is disclosed having a structure of formula A1:

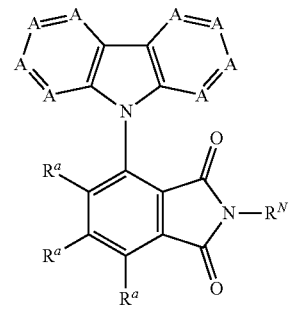

Formula A1 where A, $R^N$, $R^a$ and $R^2$ are as defined herein.

20 Claims, 11 Drawing Sheets

(51) Int. Cl.
*C07D 471/04* (2006.01)
*C07D 209/48* (2006.01)
*C07D 209/82* (2006.01)
*C09K 11/06* (2006.01)
*H01L 51/00* (2006.01)
*H01L 51/50* (2006.01)

(52) U.S. Cl.
CPC ............ *C07D 471/04* (2013.01); *C09K 11/06* (2013.01); *H01L 51/0067* (2013.01); *C09K 2211/1007* (2013.01); *C09K 2211/1018* (2013.01); *H01L 51/5012* (2013.01)

ORGANIC MOLECULES FOR USE IN ORGANIC DEVICES

CROSS-REFERENCE TO RELATED APPLICATIONS

This application claims priority under 35 U.S.C. § 371 to International Application No. PCT/EP2017/069431, filed Aug. 1, 2017, which claims priority to European Patent Application No. 16182868.6 filed Aug. 4, 2016 and European Patent Application No. 16189679.0 filed Sep. 20, 2016, and European Patent Application No. 16205427.4 filed Dec. 20, 2016 the disclosures of which are incorporated by reference herein in their entireties.

FIELD OF INVENTION

The invention relates to purely organic molecules and to the use thereof in organic light-emitting diodes (OLEDs) and in other organic optoelectronic devices.

BACKGROUND

It is a feature of organic optoelectronic devices that either electrical energy is converted to photons (organic light-emitting diodes, OLEDs, or light-emitting electrochemical cells, LEECs) or the reverse process proceeds (organic photovoltaics, OPVs). It is important here that these processes proceed with maximum efficiency. For the field of LEDs, therefore, it is ideally necessary to use materials having maximum photoluminescent quantum yield. Limited efficiencies of OLED materials can be improved through use of efficient materials that exhibit thermally activated delayed fluorescence (TADF), since, by contrast with purely fluorescent materials, it is possible to utilize up to 100% of the excitons rather than 25% of the excitons formed in an OLED. It is also possible here to convert the triplet excitons that arise to singlet excitons, from which state photons can then be emitted. A prerequisite for such thermal repopulation is a small energy gap between the lowest excited singlet level ($S_1$) and triplet level ($T_1$). This can be achieved, for example, through use of copper(I) complexes (in this regard, see, for example, H. Yersin, U. Monkowius, T. Fischer, T. Hofbeck, WO 2010/149748 A1) or else by means of purely organic materials (in this regard, see, for example, Q. Zhang et al., J. Am. Chem. Soc. 2012, 134, 14706, WO 2013161437 A1).

Intensive research in this field shows that there is still a great need for novel materials. For example, there is still a need for deep blue and sky blue TADF OLEDs. Existing blue TADF materials often exhibit long exciton lifetimes and/or low photoluminescence quantum yields, which are bad for efficient and long-lived OLEDs. A measure which can be used for an efficient blue OLED is the quotient of power efficiency in cd/A and the y value of the CIE colour coordinates ($CIE_y$) of the light emitted by the OLED. i.e. an efficiency normalized to the $CIE_y$ value. As well as the properties of the materials that have been mentioned, obtainability is likewise of relevance for commercialization. This includes the availability of synthesis units, and also the complexity for the actual synthesis of the functional material, including the purification thereof.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
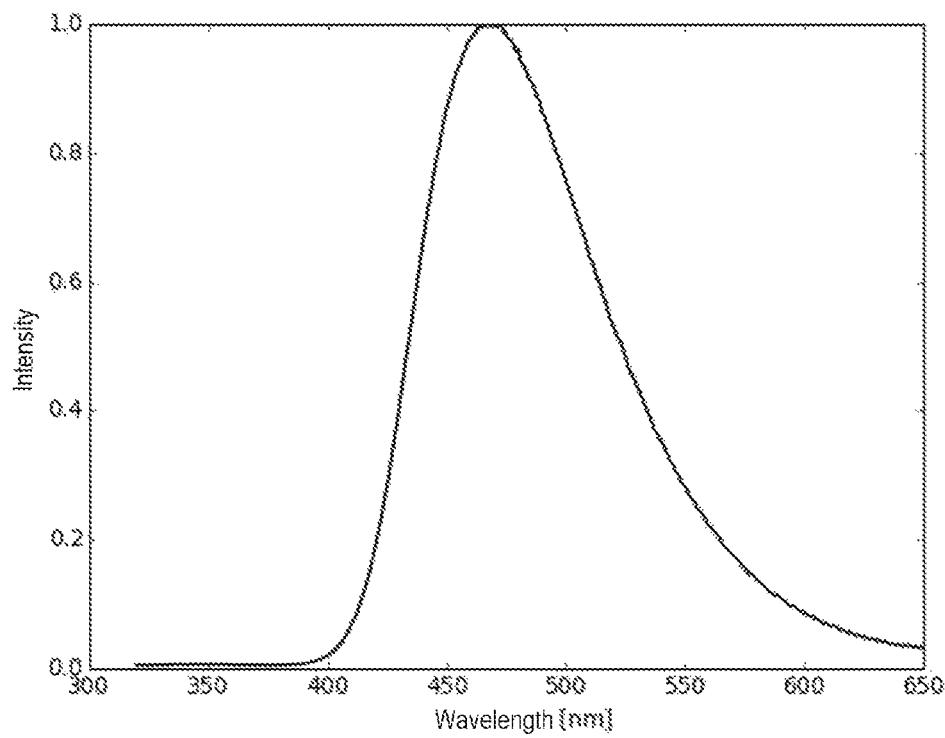
FIG. 1 is an emission spectrum of Example 1 (10% in PMMA).

Exemplary embodiments of the invention will now be discussed in further detail. This invention may, however, be embodied in many different forms and should not be construed as limited to the embodiments set forth herein.

The problem addressed by the present invention was that of providing molecules suitable for use as emitter materials in OLEDs that emit blue light.

It has been found that, surprisingly, through use of suitable donor units in combination with phthalimide acceptor units, it is possible to obtain molecules having emission maxima at wavelengths below 491 nm, which have high quantum yields and short exciton lifetimes. Since the efficiency of the component after optimization of the stack design typically correlates directly with the photoluminescence quantum yield (PLQY) of the emitter material, a technical index analogous to the above-described known efficiency index for blue OLEDs was determined for the molecules according to the invention. This blue material index (BMI) is calculated as the quotient of the PLQY (in %) and the $CIE_y$ colour coordinates of the light emitted by the molecule according to the invention.

The organic molecules according to the invention comprise a structure of the formula A1 or consist of a structure of the formula A1.

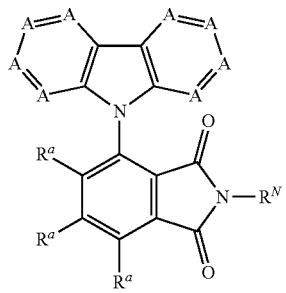

Formula A1 where
A is the same or different at each instance and is $CR^b$ or N;
$R^N$ is selected from the group consisting of methyl, phenyl, xytyl, mesityl, naphthyl, biphenyl, naphthylphenyl, terphenyl and 2,4,6-triphenylphenyl.
$R^a$ at each instance is independently selected from the group consisting of H, deuterium, an alkyl group and an aryl group;
$R^b$ is the same or different at each instance and is H, deuterium, $CF_3$, $C(=O)R^1$, CN, an alkyl group which is unsubstituted or substituted by one or more $R^2$, an aryl group which is unsubstituted or substituted by one or more $R^2$ and is optionally additionally substituted by one or more unsubstituted alkyl groups and/or by one or more unsubstituted or alkyl-substituted aryl groups, a heteroaryl group which is unsubstituted or substituted by one or more $R^2$ and/or by one or more unsubstituted alkyl groups and/or by one or more unsubstituted or alkyl-substituted aryl groups, a group of the sub-formula T1 or a group of the sub-formula T2:

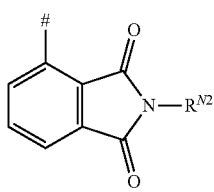

Sub-formula T1

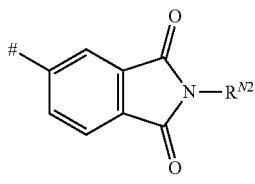

Sub-formula T2 with the following definitions:
$R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group.
$R^1$ at each instance is an aryl group which is unsubstituted or substituted by one or more $R^2$.
$R^2$ is the same or different at each instance and is F, $CF_3$ or CN;
# indicates the point at which the group of the sub-formula T1 or T2 is attached via a single bond to the C in $CR^b$ when A is $CR^b$ where $R^b$ is a group of the sub-formula T1 or is a group of the sub-formula T2;

where at least one and at most four A are N or at least one $R^b$ is selected from the group consisting of $CF_3$, $C(=O)R^1$, CN, an alkyl group substituted by one or more $R^2$, an aryl group substituted by one or more $R^2$ and optionally substituted by one or more unsubstituted alkyl groups and/or by one or more unsubstituted or alkyl-substituted aryl groups, a heteroaryl group which is unsubstituted or substituted by one or more $R^2$ and/or by one or more unsubstituted alkyl groups and/or by one or more unsubstituted or alkyl-substituted aryl groups and a group of the sub-formula T1 or a group of the sub-formula T2:

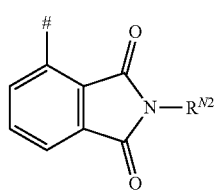

Sub-formula T1

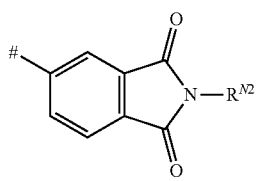

Sub-formula T2 where
$R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group.
# indicates the point at which the group of the sub-formula T1 or T2 is attached via a single bond to the C in $CR^b$ when A is $CR^b$ where $R^b$ is a group of the sub-formula T1 or is a group of the sub-formula T2.

In one embodiment, at least one and at most four A are N or at least one $R^b$ is selected from the group consisting of $CF_3$, $C(=O)R^1$, CN, an alkyl group substituted by one or more $R^2$, a 6-membered aryl group which is unsubstituted or substituted by one or more $R^2$ and optionally substituted by one or more unsubstituted alkyl groups and/or by one or more unsubstituted or alkyl-substituted aryl groups, a 6-membered heteroaryl group which is unsubstituted or substituted by one or more $R^2$ and/or by one or more unsubstituted alkyl groups and/or by one or more unsubstituted or alkyl-substituted aryl groups or a group of the sub-formula T1 or a group of the sub-formula T2:

Sub-formula T1

-continued

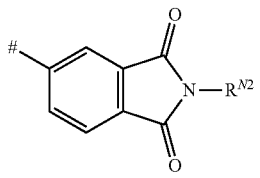

Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group; and where, for the rest, the definitions given above are applicable.

In one embodiment, $R^b$ is as defined above, with the proviso that $R^b$ is not pyridine or pyrimidine.

In one embodiment, the organic molecule comprises or consists of a structure of the formula A2.

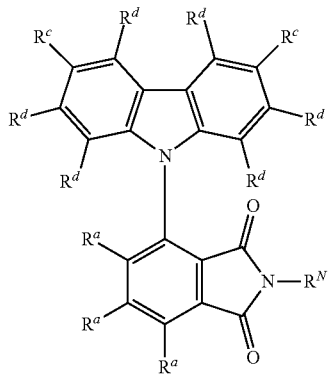

Formula A2 where:
$R^N$ is methyl, phenyl, xylyl, mesityl, naphthyl, biphenyl, naphthylphenyl, terphenyl or 2,4,6-triphenylphenyl;
$R^a$ is the same or different at each instance and is H, deuterium, an alkyl group or an aryl group;
$R^c$ is the same or different at each instance and is $CF_3$, $C(=O)R^1$, CN, an alkyl group substituted by one or more $R^2$, a substituted aryl group optionally substituted by one or more unsubstituted alkyl groups and/or by one or more unsubstituted or alkyl-substituted aryl groups, a heteroaryl group which is unsubstituted or substituted by one or more $R^2$ and/or by one or more unsubstituted alkyl groups and/or by one or more unsubstituted or alkyl-substituted aryl groups, or a group of the sub-formula T1 or a group of the sub-formula T2:

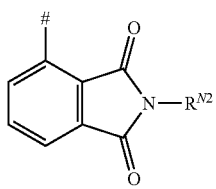

Sub-formula T1

-continued

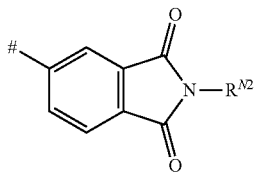

Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group.
# indicates the point at which the group of the sub-formula T1 or T2 is attached via a single bond to the carbazole when $R^c$ is a group of the sub-formula T1 or is a group of the sub-formula T2.
$R^d$ is the same or different at each instance and is H, deuterium. $CF_3$, $C(=O)R^1$, CN, an alkyl group which is unsubstituted or substituted by one or more $R^2$, an aryl group which is unsubstituted or substituted by one or more $R^2$ and/or by one or more unsubstituted alkyl groups and/or by one or more unsubstituted or alkyl-substituted aryl groups or a heteroaryl group which is unsubstituted or substituted by one or more $R^2$ and/or by one or more unsubstituted alkyl groups and/or by one or more unsubstituted or alkyl-substituted aryl groups or a group of the sub-formula T1 or a group of the sub-formula T2:

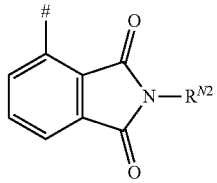

Sub-formula T1

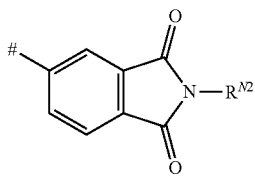

Sub-formula T2 where
$R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group;
# indicates the point at which the group of the sub-formula T1 or T2 is attached via a single bond to the carbazole when $R^d$ is a group of the sub-formula T1 or is a group of the sub-formula T2;
and where, for the rest, the definitions given above are applicable.

In a further embodiment, $R^c$ at each instance is independently selected from the group consisting of $CF_3$, $C(=O)R^1$, CN, an alkyl group substituted by one or more $R^2$, a 6-membered aryl group substituted by one or more $R^2$ and optionally substituted by one or more unsubstituted alkyl groups and/or by one or more unsubstituted or alkyl-substituted aryl groups, a 6-membered heteroaryl group which is unsubstituted or substituted by one or more R² and/or by one or more unsubstituted alkyl groups and/or by one or more unsubstituted or alkyl-substituted aryl groups and a group of the sub-formula T1 or a group of the sub-formula T2:

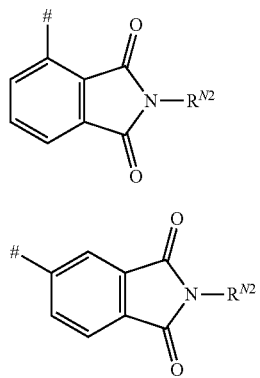

Sub-formula T1

Sub-formula T2 where
$R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group;
# indicates the point at which the group of the sub-formula T1 or T2 is attached via a single bond to the carbazole when $R^c$ is a group of the sub-formula T1 or is a group of the sub-formula T2;
and where, for the rest, the definitions given above are applicable.

In a further embodiment, $R^c$ is as defined above, with the proviso that $R^c$ is not pyridine or pyrimidine.

In a further embodiment, $R^d$ at each instance is H.

In one embodiment, the organic molecule comprises or consists of a structure of the formula A3.

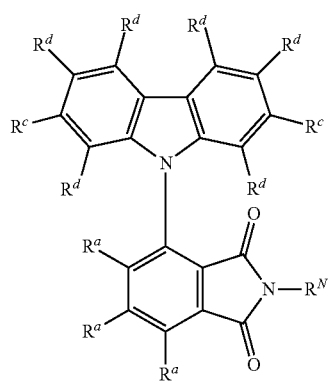

Formula A3 where
$R^N$ is methyl, phenyl, xylyl, mesityl, naphthyl, biphenyl, naphthylphenyl, terphenyl or 2,4,6-triphenylphenyl;
$R^a$ is the same or different at each instance and is H, deuterium, an alkyl group or an aryl group;
$R^c$ at each instance is independently selected from the group consisting of $CF_3$, $C(=O)R^1$, CN, an alkyl group substituted by one or more $R^2$, a substituted aryl group optionally substituted by one or more unsubstituted alkyl groups and/or by one or more unsubstituted or alkyl-substituted aryl groups, a heteroaryl group which is unsubstituted or substituted by one or more $R^2$ and/or by one or more unsubstituted alkyl groups and/or by one or more unsubstituted or alkyl-substituted aryl groups and a group of the sub-formula T1 or a group of the sub-formula T2:

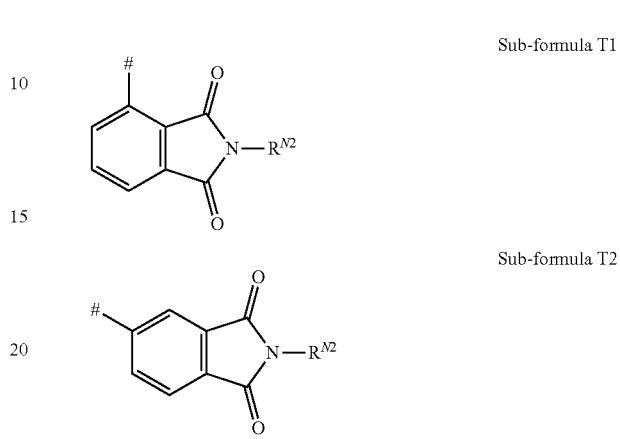

Sub-formula T1

Sub-formula T2 where
$R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group.
# indicates the point at which the group of the sub-formula T1 or T2 is attached via a single bond to the carbazole when $R^c$ is a group of the sub-formula T1 or is a group of the sub-formula T2.

$R^d$ is the same or different at each instance and is independently selected from the group consisting of H, deuterium, $CF_3$, $C(=O)R^1$, CN, an alkyl group which is unsubstituted or substituted by one or more $R^2$, an aryl group which is unsubstituted or substituted by one or more $R^2$ and/or substituted by one or more unsubstituted alkyl groups and/or by one or more unsubstituted or alkyl-substituted aryl groups, a heteroaryl group which is unsubstituted or substituted by $R^2$ and/or by one or more unsubstituted alkyl groups and/or by one or more unsubstituted or alkyl-substituted aryl groups and a group of the sub-formula T1 or a group of the sub-formula T2:

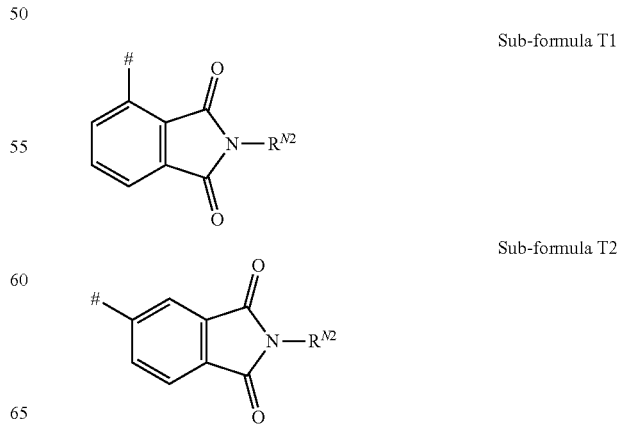

Sub-formula T1

Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$.

$R^{N3}$ is an alkyl group, an aryl group or a heteroaryl group;

# indicates the point at which the group of the sub-formula T1 or T2 is attached via a single bond to the carbazole when $R^d$ is a group of the sub-formula T1 or is a group of the sub-formula T2;

and where, for the rest, the definitions given above are applicable.

In a further embodiment, $R^c$ at each instance is independently selected from the group consisting of $CF_3$, $C(=O)R^1$, CN, an alkyl group substituted by one or more $R^2$, a 6-membered aryl group substituted by one or more $R^2$ and optionally substituted by one or more unsubstituted alkyl groups and/or by one or more unsubstituted or alkyl-substituted aryl groups, a 6-membered heteroaryl group which is unsubstituted or substituted by one or more $R^2$ and/or by one or more unsubstituted alkyl groups and/or by one or more unsubstituted or alkyl-substituted aryl groups and a group of the sub-formula T1 or a group of the sub-formula T2:

Sub-formula T1

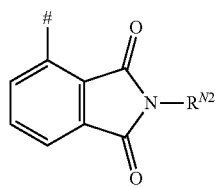

Sub-formula T2

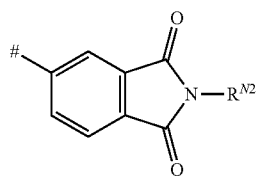

where $R^{N2}$ is an alkyl group, an aryl group which is unsubstituted or substituted by one or more $R^{N3}$ or a heteroaryl group which is unsubstituted or substituted by one or more $R^{N3}$.

$R^{N3}$ is an alkyl group, an aryl group or a heteroaryl group;

# indicates the point at which the group of the sub-formula T1 or T2 is attached via a single bond to the carbazole when $R^c$ is a group of the sub-formula T1 or is a group of the sub-formula T2;

and where, for the rest, the definitions given above are applicable.

In a further embodiment, $R^c$ is as defined above, with the proviso that $R^c$ is not pyridine or pyrimidine.

In a further embodiment. $R^d$ at each instance is H.

In a further embodiment, the organic molecule comprises or consists of a structure of the formula A4

Formula A4

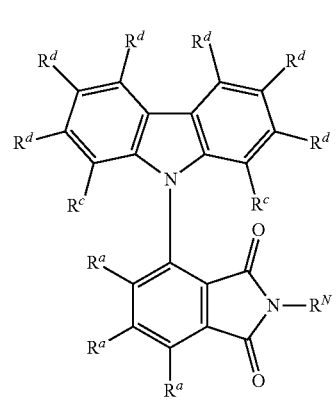

where $R^N$ is methyl, phenyl, xylyl, mesityl, naphthyl, biphenyl, naphthylphenyl, terphenyl or 2,4,6-triphenylphenyl;

$R^a$ is the same or different at each instance and is H, deuterium, an alkyl group or an aryl group;

$R^c$ is the same or different at each instance and is selected from the group consisting of $CF_3$, $C(=O)R^1$, CN, an alkyl group substituted by one or more $R^2$, an aryl group substituted by one or more $R^2$ and optionally substituted by one or more unsubstituted alkyl groups and/or by one or more unsubstituted or alkyl-substituted aryl groups, a heteroaryl group which is unsubstituted or substituted by one or more $R^2$ and/or by one or more unsubstituted alkyl groups and/or by one or more unsubstituted or alkyl-substituted aryl groups and a group of the sub-formula T1 or a group of the sub-formula T2:

Sub-formula T1

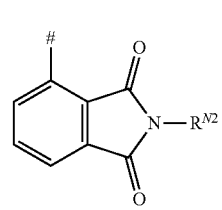

Sub-formula T2

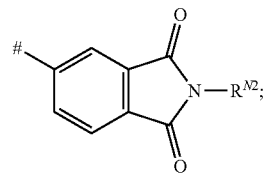

$R^d$ is the same or different at each instance and is independently selected from the group of H, deuterium, $CF_3$, $C(=O)R^1$, CN, an alkyl group which is unsubstituted or substituted by one or more $R^2$, an aryl group which is unsubstituted or substituted by one or more $R^2$ and/or substituted by one or more unsubstituted alkyl groups and/or by one or more unsubstituted or alkyl-substituted aryl groups, a heteroaryl group which is unsubstituted or substituted by $R^2$ and/or by one or more unsubstituted alkyl groups and/or by one or more unsubstituted or alkyl-substituted aryl groups and a group of the sub-formula T1 or a group of the sub-formula T2:

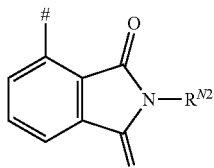

Sub-formula T1

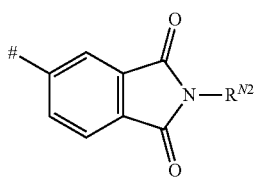

Sub-formula T2 where
$R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group;
# indicates the point at which the group of the sub-formula T1 or T2 is attached via a single bond to the carbazole when $R^c$ and/or $R^d$ is a group of the sub-formula T1 or is a group of the sub-formula T2;
and where, for the rest, the definitions given above are applicable.

In a further embodiment, $R^c$ at each instance is independently selected from the group consisting of $CF_3$, $C(=O)R^1$, CN, an alkyl group substituted by one or more $R^2$, a 6-membered aryl group substituted by one or more $R^2$ and optionally substituted by one or more unsubstituted alkyl groups and/or by one or more unsubstituted or alkyl-substituted aryl groups, a 6-membered heteroaryl group which is unsubstituted or substituted by one or more $R^2$ and/or by one or more unsubstituted alkyl groups and/or by one or more unsubstituted or alkyl-substituted aryl groups and a group of the sub-formula T1 or a group of the sub-formula T2:

and where, for the rest, the definitions given above are applicable.

In a further embodiment, $R^c$ is as defined above, with the proviso that $R^c$ is not pyridine or pyrimidine.

In a further embodiment, $R^d$ at each instance is H.

In a further embodiment, the organic molecule comprises or consists of a structure of the formula A5.

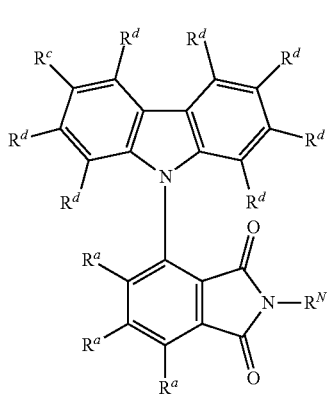

Formula A5 where:
$R^N$ is methyl, phenyl, xylyl, mesityl, naphthyl, biphenyl, naphthylphenyl, terphenyl or 2,4,6-triphenylphenyl;
$R^a$ is the same or different at each instance and is H, deuterium, an alkyl group or an aryl group;
$R^c$ is the same or different at each instance and is $CF_3$, $C(=O)R^1$, CN, an alkyl group substituted by one or more $R^2$, an aryl group substituted by one or more $R^2$ and optionally substituted by one or more unsubstituted alkyl groups and/or by one or more unsubstituted or alkyl-substituted aryl groups, a heteroaryl group which is unsubstituted or substituted one or more by $R^2$ and/or by one or more unsubstituted alkyl groups and/or by one or more unsubstituted or alkyl-substituted aryl groups or a group of the sub-formula T1 or a group of the sub-formula T2:

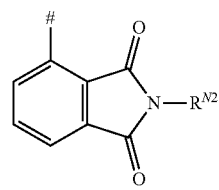

Sub-formula T1

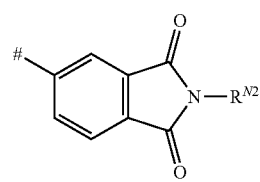

Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group;
# indicates the point at which the group of the sub-formula T1 or T2 is attached via a single bond to the carbazole when $R^c$ is a group of the sub-formula T1 or is a group of the sub-formula T2;

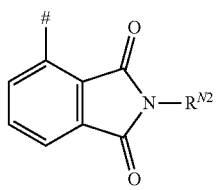

Sub-formula T1

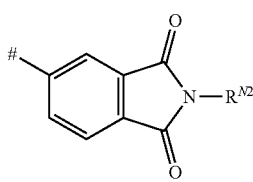

Sub-formula T2 where
$R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group;
# indicates the point at which the group of the sub-formula T1 or T2 is attached via a single bond to the carbazole when $R^c$ is a group of the sub-formula T1 or is a group of the sub-formula T2.

$R^d$ is the same or different at each instance and is H, deuterium. $CF_3$, $C(=O)R^1$, CN, an alkyl group which is unsubstituted or substituted by one or more $R^2$, an aryl group which is unsubstituted or substituted by one or more $R^2$ and/or by one or more unsubstituted alkyl groups and/or by one or more unsubstituted or alkyl-substituted aryl groups, a heteroaryl group which is unsubstituted or substituted by one or more $R^2$ and/or by one or more unsubstituted alkyl groups and/or by one or more unsubstituted or alkyl-substituted aryl groups or a group of the sub-formula T1 or a group of the sub-formula T2:

Sub-formula T1

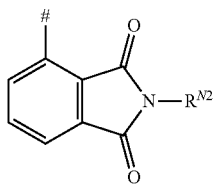

Sub-formula T2

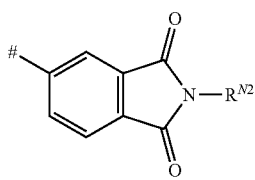

where $R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group.
# indicates the point at which the group of the sub-formula T1 or T2 is attached via a single bond to the carbazole when $R^d$ is a group of the sub-formula T1 or is a group of the sub-formula T2.

In a further embodiment, $R^c$ at each instance is independently selected from the group consisting of $CF_3$, $C(=O)R^1$, CN, an alkyl group substituted by one or more $R^2$, a 6-membered aryl group substituted by one or more $R^2$ and optionally substituted by one or more unsubstituted alkyl groups and/or by one or more unsubstituted or alkyl-substituted aryl groups, a 6-membered heteroaryl group which is unsubstituted or substituted by one or more $R^2$ and/or by one or more unsubstituted alkyl groups and/or by one or more unsubstituted or alkyl-substituted aryl groups and a group of the sub-formula T1 or a group of the sub-formula T2:

Sub-formula T1

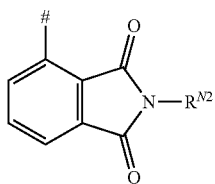

Sub-formula T2

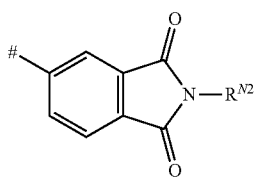

where
$R^{N2}$ is an alkyl group, an aryl group which is unsubstituted or substituted by one or more $R^{N3}$ or a heteroaryl group which is unsubstituted or substituted by one or more $R^{N3}$.
$R^{N3}$ is an alkyl group, an aryl group or a heteroaryl group;
# indicates the point at which the group of the sub-formula T1 or T2 is attached via a single bond to the carbazole when $R^c$ is a group of the sub-formula T1 or is a group of the sub-formula T2;
and where, for the rest, the definitions given above are applicable.

In a further embodiment, $R^c$ is as defined above, with the proviso that $R^c$ is not pyridine or pyrimidine.

In a further embodiment, $R^d$ at each instance is H.

In one embodiment, the organic molecule has a structure of the formula A6.

Formula A6

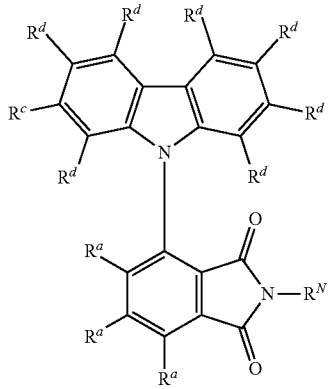

where
$R^N$ is methyl, phenyl, xylyl, mesityl, naphthyl, biphenyl, naphthylphenyl, terphenyl or 2,4,6-triphenylphenyl;
$R^a$ is the same or different at each instance and is H, deuterium, an alkyl group or an aryl group;
$R^c$ at each instance is independently selected from the group consisting of $CF_3$, $C(=O)R^1$, CN, an alkyl group substituted by one or more $R^2$, an aryl group substituted by one or more $R^2$ and optionally substituted by one or more unsubstituted alkyl groups and/or by one or more unsubstituted or alkyl-substituted aryl groups, a heteroaryl group which is unsubstituted or substituted by one or more $R^2$ and/or by one or more unsubstituted alkyl groups and/or by one or more unsubstituted or alkyl-substituted aryl groups or a group of the sub-formula T1 or a group of the sub-formula T2:

Sub-formula T1

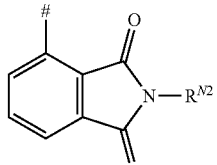

Sub-formula T2

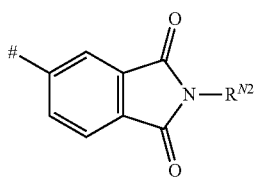

where $R^{N2}$ is an alkyl group, an aryl group which is unsubstituted or substituted by one or more $R^{N3}$ or a heteroaryl group which is unsubstituted or substituted by one or more $R^{N3}$.

$R^{N3}$ is an alkyl group, an aryl group or a heteroaryl group;

# indicates the point at which the group of the sub-formula T1 or T2 is attached via a single bond to the carbazole when $R^c$ is a group of the sub-formula T1 or is a group of the sub-formula T2.

$R^d$ at each instance is independently selected from the group consisting of H, deuterium, $CF_3$, $C(=O)R^1$, CN, an alkyl group which is unsubstituted or substituted by one or more $R^2$, an aryl group which is unsubstituted or substituted by one or more $R^2$ and/or substituted by one or more unsubstituted alkyl groups and/or by one or more unsubstituted or alkyl-substituted aryl groups, a heteroaryl group which is unsubstituted or substituted by $R^2$ and/or by one or more unsubstituted alkyl groups and/or by one or more unsubstituted or alkyl-substituted aryl groups and a group of the sub-formula T1 or a group of the sub-formula T2:

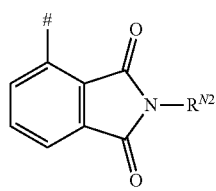

Sub-formula T1

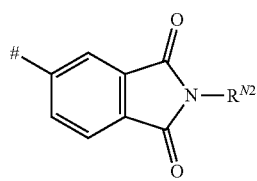

Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$.

$R^{N3}$ is an alkyl group, an aryl group or a heteroaryl group;

# indicates the point at which the group of the sub-formula T1 or T2 is attached via a single bond to the carbazole when $R^d$ is a group of the sub-formula T1 or is a group of the sub-formula T2;

and where, for the rest, the definitions given above are applicable.

In a further embodiment, $R^c$ at each instance is independently selected from the group consisting of $CF_3$, $C(=O)R^1$, CN, an alkyl group substituted by one or more $R^2$, a 6-membered aryl group substituted by one or more $R^2$ and optionally substituted by one or more unsubstituted alkyl groups and/or by one or more unsubstituted or alkyl-substituted aryl groups, a 6-membered heteroaryl group which is unsubstituted or substituted by one or more $R^2$ and/or by one or more unsubstituted alkyl groups and/or by one or more unsubstituted or alkyl-substituted aryl groups and a group of the sub-formula T1 or a group of the sub-formula T2:

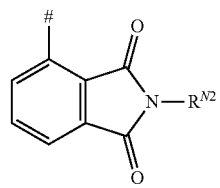

Sub-formula T1

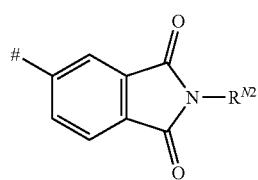

Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$.

$R^{N3}$ is an alkyl group, an aryl group or a heteroaryl group;

# indicates the point at which the group of the sub-formula T1 or T2 is attached via a single bond to the carbazole when $R^c$ is a group of the sub-formula T1 or is a group of the sub-formula T2;

and where, for the rest, the definitions given above are applicable.

In a further embodiment. $R^c$ is as defined above, with the proviso that $R^c$ is not pyridine or pyrimidine.

In a further embodiment, $R^d$ at each instance is H.

In a further embodiment, the organic molecule comprises or consists of a structure of the formula A7.

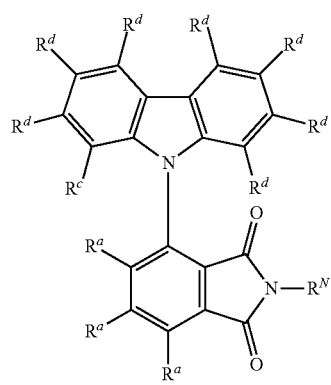

Formula A7 where $R^N$ is methyl, phenyl, xylyl, mesityl, naphthyl, biphenyl, naphthylphenyl, terphenyl or 2,4,6-triphenylphenyl;

$R^a$ is the same or different at each instance and is H, deuterium, an alkyl group or an aryl group;

$R^c$ at each instance is independently selected from the group consisting of $CF_3$, $C(=O)R^1$, CN, an alkyl group substituted by one or more $R^2$, an aryl group substituted by one or more $R^2$ and optionally substituted by one or more unsubstituted alkyl groups and/or by one or more unsubstituted or alkyl-substituted aryl groups, a heteroaryl group which is unsubstituted or substituted by one or more $R^2$ and/or by one or more unsubstituted alkyl groups and/or by one or more unsubstituted or alkyl-substituted aryl groups and a group of the sub-formula T1 or a group of the sub-formula T2:

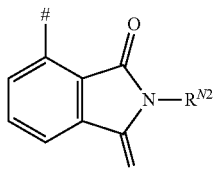

Sub-formula T1

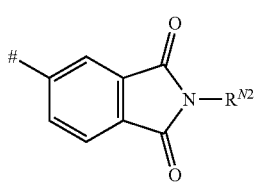

Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$;

$R^{N3}$ is an alkyl group, an aryl group or a heteroaryl group;

\# indicates the point at which the group of the sub-formula T1 or T2 is attached via a single bond to the carbazole when $R^c$ is a group of the sub-formula T1 or is a group of the sub-formula T2.

$R^d$ is the same or different at each instance and is independently selected from the group of H, deuterium, $CF_3$, $C(=O)R^1$, CN, an alkyl group which is unsubstituted or substituted by one or more $R^2$, an aryl group which is unsubstituted or substituted by one or more $R^2$ and/or by one or more unsubstituted alkyl groups and/or by one or more unsubstituted or alkyl-substituted aryl groups, a heteroaryl group which is unsubstituted or substituted by $R^2$ and/or by one or more unsubstituted alkyl groups and/or by one or more unsubstituted or alkyl-substituted aryl groups and a group of the sub-formula T1 or a group of the sub-formula T2:

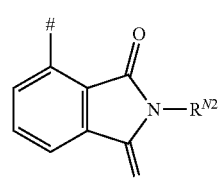

Sub-formula T1

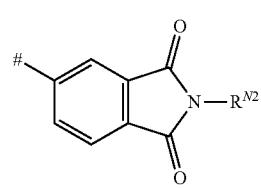

Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$;

$R^{N3}$ is an alkyl group, an aryl group or a heteroaryl group;

\# indicates the point at which the group of the sub-formula T1 or T2 is attached via a single bond to the carbazole when $R^d$ is a group of the sub-formula T1 or is a group of the sub-formula T2;

and where, for the rest, the definitions given above are applicable.

In a further embodiment, $R^c$ at each instance is independently selected from the group consisting of $CF_3$, $C(=O)R^1$, CN, an alkyl group substituted by one or more $R^2$, a 6-membered aryl group substituted by one or more $R^2$ and optionally substituted by one or more unsubstituted alkyl groups and/or by one or more unsubstituted or alkyl-substituted aryl groups, a 6-membered heteroaryl group which is unsubstituted or substituted by one or more $R^2$ and/or by one or more unsubstituted alkyl groups and/or by one or more unsubstituted or alkyl-substituted aryl groups and a group of the sub-formula T1 or a group of the sub-formula T2:

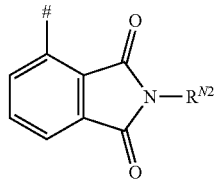

Sub-formula T1

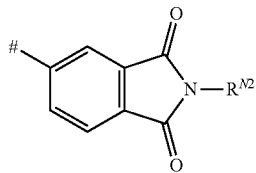

Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$;

$R^{N3}$ is an alkyl group, an aryl group or a heteroaryl group;

\# indicates the point at which the group of the sub-formula T1 or T2 is attached via a single bond to the carbazole when $R^c$ is a group of the sub-formula T1 or is a group of the sub-formula T2;

and where, for the rest, the definitions given above are applicable.

In a further embodiment, $R^c$ is as defined above, with the proviso that $R^c$ is not pyridine or pyrimidine.

In a further embodiment, $R^d$ at each instance is H.

One embodiment relates to an organic molecule of the formula A1, A2, A3, A4, A5, A6 or A7 that has at least one CN group.

An aryl group which may be substituted in each case by the abovementioned radicals and which may be joined to the aromatic system via any desired positions is understood in the context of the invention to mean groups derived from: benzene, naphthalene, anthracene and phenanthrene.

Illustrative phenyl- or alkyl-substituted six-membered aryl groups are especially toluene, ethylbenzene, i-propylbenzene, t-butylbenzene, i-butylbenzene, o-xylene (1.2-dimethylbenzene), m-xylene (1,3-dimethylbenzene), p-xylene (1,4-dimethylbenzene), 1,5-dimethylbenzene, 1,2-diethylbenzene, 1,3-diethylbenzene, 1,4-diethylbenzene, 1,5-diethylbenzene, 1,2-di-i-propylbenzene, 1,3-di-i-propylbenzene, 1,4-di-i-propylbenzene, 1,5-di-i-propylbenzene, 1,2-di-t-butylbenzene, 1,3-di-t-butylbenzene, 1,4-di-t-butylbenzene, 1,5-di-t-butylbenzene, mesitylene (1,3,5-trimethylbenzene), 1,3,5-triethylbenzene, 1,3,5-tri-i-propylbenzene, 1,3,5-tri-t-butylbenzene, phenylbenzene, 1,2-diphenylbenzene, 1,3-diphenylbenzene, 1,4-diphenylbenzene, and 1,3,5-triphenylbenzene.

A heteroaryl group which may be substituted in each case by the abovementioned radicals and which may be joined to the heteroaromatic system via any desired positions is understood in the context of the invention to mean groups derived from: pyridine, pyridazine (1,2-diazine), pyrimidine (1,3-diazine), pyrazine (1,4-diazine), 1,3,5-triazine, acridine, quinoline, isoquinoline, quinoxaline and naphthyridine.

Illustrative phenyl- or alkyl-substituted 6-membered heteroaryl groups are especially 2-picoline (2-methylpyridine), 3-picoline (3-methylpyridine), 4-picoline (4-methylpyridine), 2-ethylpyridine, 3-ethylpyridine, 4-ethylpyridine, 2-i-propylpyridine, 3-i-propylpyridine, 4-i-propylpyridine, 2-t-butylpyridine, 3-t-butylpyridine, 4-t-butylpyridine, 2-i-butylpyridine, 3-i-butylpyridine, 4-i-butylpyridine, 2,3-dimethylpyridine, 2,4-dimethylpyridine, 2,5-dimethylpyridine, 2,6-dimethylpyridine, 2,3-diethylpyridine, 2,4-diethylpyridine, 2,5-diethylpyridine, 2,6-diethylpyridine, 2,3-di-i-propylpyridine, 2,4-di-i-propylpyridine, 2,5-di-i-propylpyridine, 2,6-di-i-propylpyridine, 2,3-di-t-butylpyridine, 2,4-di-t-butylpyridine, 2,5-di-t-butylpyridine, 2,6-di-t-butylpyridine, 2,4,6-trimethylpyridine, 2,4,6-triethylpyridine, 2,4,6-tri-i-propylpyridine, 2,4,6-tri-t-butylpyridine, 2-methylpyrimidine, 4-methylpyrimidine, 5-methylpyrimidine, 2,4-dimethylpyrimidine, 2,5-dimethylpyrimidine, 4,5-dimethylpyrimidine, 4,6-dimethylpyrimidine, 2,4-diethylpyrimidine, 2,5-diethylpyrimidine, 4,5-diethylpyrimidine, 4,6-diethylpyrimidine, 2,4-di-i-propylpyrimidine, 2,5-di-i-propylpyrimidine, 4,5-di-i-propylpyrimidine, 4,6-di-i-propylpyrimidine, 2,4-di-t-butylpyrimidine, 2,5-di-t-butylpyrimidine, 4,5-di-t-butylpyrimidine, 4,6-di-t-butylpyrimidin 2,4,5-trimethylpyrimidine, 2,4,5-triethylpyrimidine, 2,4,5-tri-i-propylpyrimidine, 2,4,5-tri-t-butylpyrimidine, 2,4,5-trimethylpyrimidine, 2,4,6-triethylpyrimidine, 2,4,6-tri-i-propylpyrimidine, 2,4,6-tri-t-butylpyrimidine, 4,5,6-trimethylpyrimidine, 4,5,6-triethylpyrimidine, 4,5,6-tri-i-propylpyrimidine, 4,5,6-tri-t-butylpyrimidine, 4,5,6-trimethylpyrimidine, 2,4-dimethyl-1,3,5-triazine and 2,4-diphenyl-1,3,5-triazine.

In the context of the present invention, an alkyl group in which individual hydrogen atoms may optionally be substituted by the abovementioned groups are understood to mean, for example, the methyl, ethyl, n-propyl, i-propyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl radicals.

The $R^N$ radicals may be attached via any position. In the context of this invention, biphenyl is understood to mean, for example, ortho-biphenyl, para-biphenyl and meta-biphenyl, terphenyl to mean 1,2-diphenylphenyl, 1,3-diphenylphenyl and 1,4-diphenylphenyl, and naphthylphenyl to mean, for example, ortho-naphthylphenyl, meta-naphthylphenyl and para-naphthylphenyl. Illustrative and hence nonlimiting embodiments are:

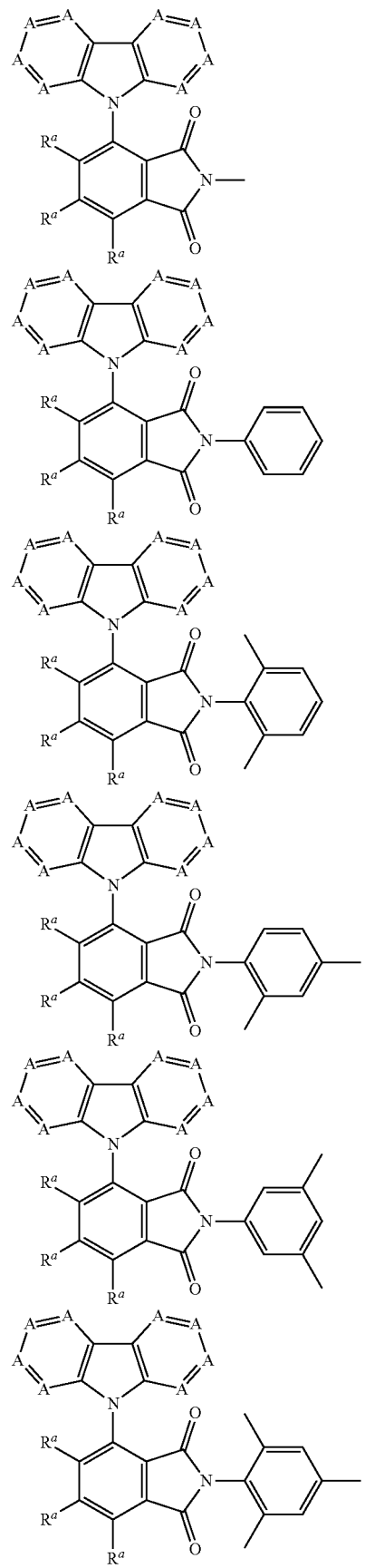

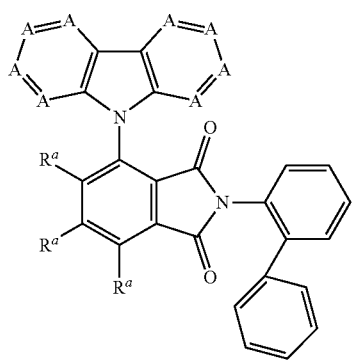
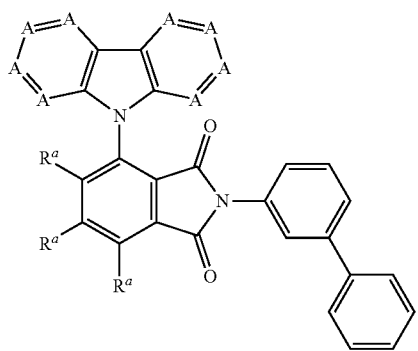
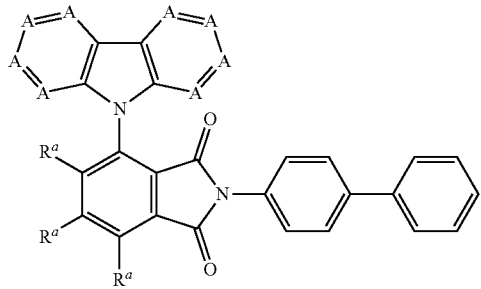
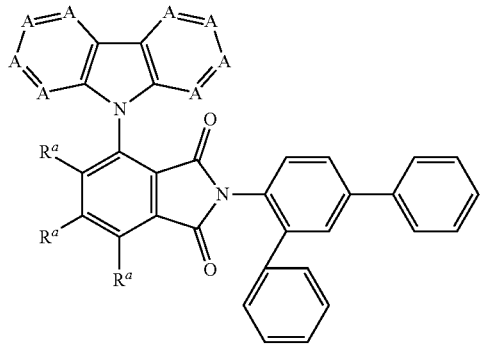
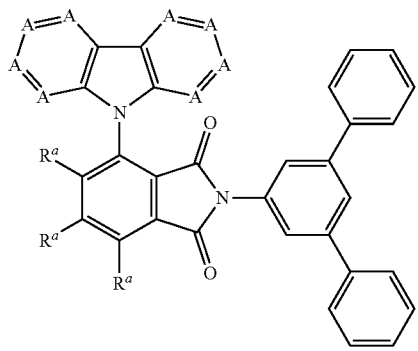
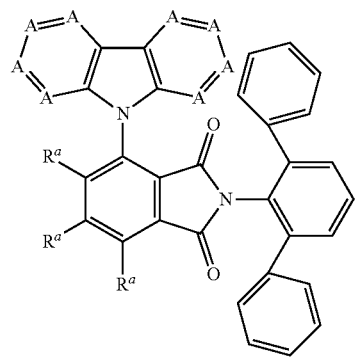
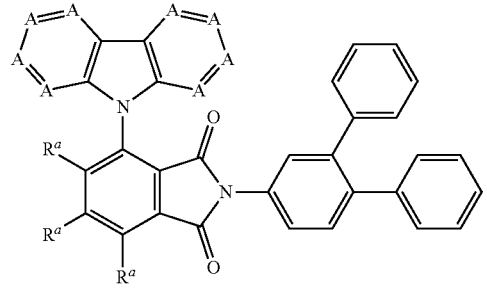
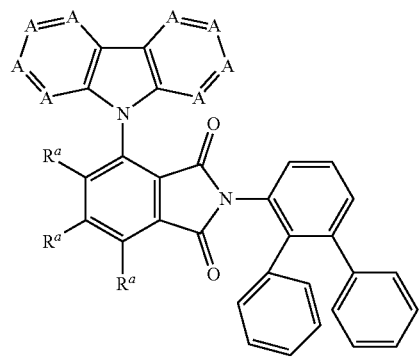
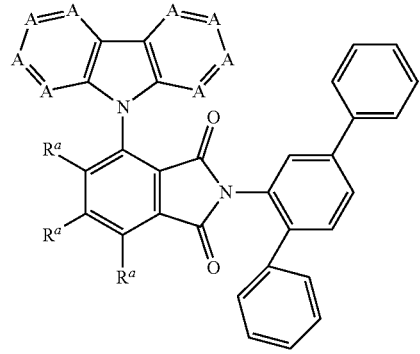
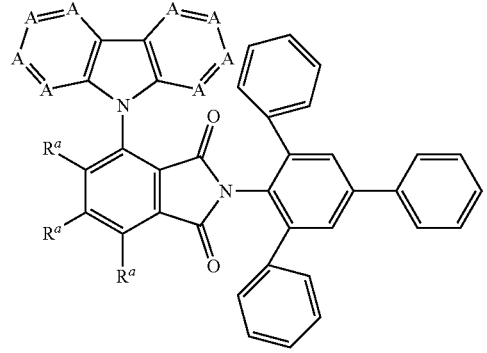

-continued

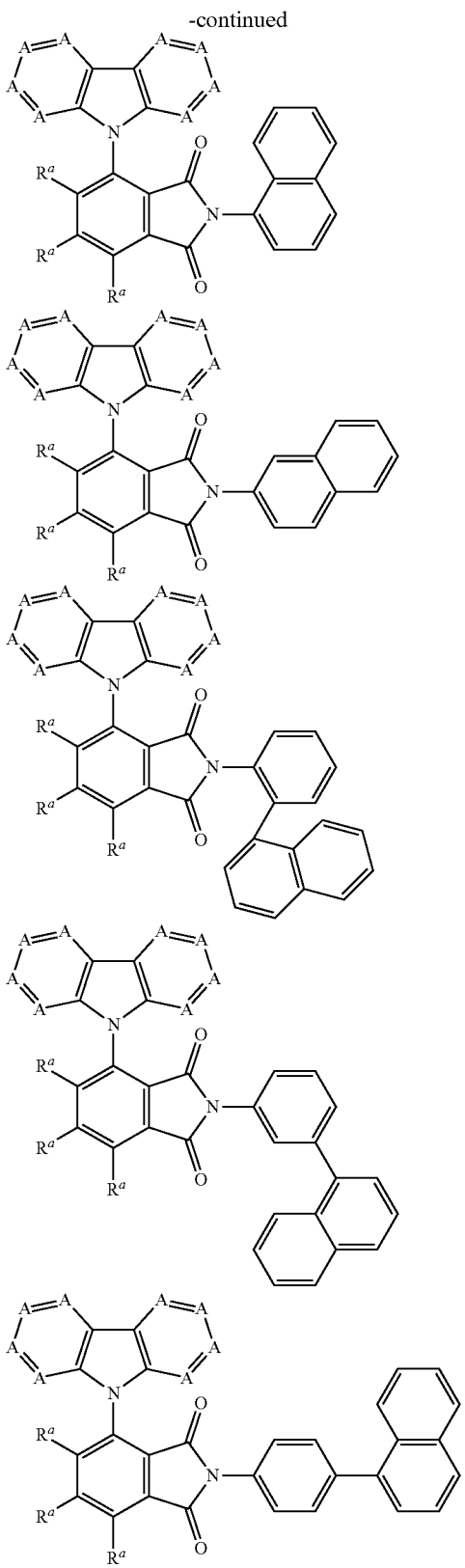

The molecules according to the invention have high photoluminescence quantum yields and short exciton lifetimes, and are therefore advantageous emitter materials for blue OLEDs.

One embodiment of the invention relates to organic molecules having an emission maximum between 420 and 490 nm, more preferably between 430 and 470 nm, even more preferably between 440 and 460 nm.

One embodiment of the invention relates to organic molecules which have an emission lifetime of not more than 150 μs, especially of not more than 100 μs, of not more than 50 μs, or of not more than 10 μs, and/or have a main emission band having a half-height width of less than 120 nm, especially less than 100 nm, less than 80 nm, or less than 60 nm, and/or have a photoluminescence quantum yield (PLQY) of greater than 30%, especially of greater than 35%, of greater than 40%, of greater than 45%, of greater than 50%, or of greater than 60%, and/or have a $\Delta E(S_1-T_1)$ value between the lowermost excited singlet ($S_1$) state and the triplet ($T_1$) state below it of not more than 5000 cm$^{-1}$, especially not more than 3000 cm$^{-1}$, or not more than 1500 cm$^{-1}$ or 1000 cm$^{-1}$.

More particularly, the molecules according to the invention have a blue material index (BMI), the quotient of the PLQY (in %) and its CIE$_y$ colour coordinates of the light emitted by the molecule according to the invention, of greater than 150, especially of greater than 200, of greater than 250 or of greater than 300.

The determination of the $\Delta E(S_1-T_1)$ value can be conducted either by quantum-mechanical calculations by means of computer programs known in the prior art (for example by means of Turbomole programs executing TD-DFT calculations and with reference to CC2 calculations) or—as elucidated further down—by experimental means.

The energy differential $\Delta E(S_1-T_1)$ can be described approximately by quantum-mechanical means, via what is called the exchange integral multiplied by a factor of 2. The value thereof depends directly on the overlap of the molecular orbitals. These molecular orbitals are distributed over different regions in space (partly delocalized over π or π* molecular orbitals). This means that an electronic transition between the different molecular orbitals represents what is called a charge transfer (CT) transition. The smaller the overlap of the molecular orbitals described above, the more marked the electronic charge transfer character. This is then associated with a decrease in the exchange interval and hence a decrease in the energy differential $\Delta E(S_1-T_1)$.

The $\Delta E(S_1-T_1)$ value can be determined experimentally as follows:

For a given organic molecule, the energy gap $\Delta E(S_1-T_1) = \Delta E$ can be determined in a simple manner using the equation (1) given above. Rearrangement gives:

$$\ln\{\mathrm{Int}(S_1 \rightarrow S_0)/\mathrm{Int}(T_1 \rightarrow S_0)\} = \ln\{k(S_1)/k(T_1)\} - (\Delta E/k_B)(1/T) \quad (3)$$

For the measurement of the intensities Int($S_1 \rightarrow S_0$) and Int($T_1 \rightarrow S_0$), it is possible to use any commercial spectrophotometer. A graphic plot of the (logarithmic) intensity ratios ln{Int($S_1 \rightarrow S_0$)/Int($T_1 \rightarrow S_0$)} measured at various temperatures against the reciprocal of the absolute temperature T generally gives a straight line. The measurement is generally conducted within a temperature range from room temperature (300 K) to 77 K or to 4.2 K, the temperature being adjusted by means of a cryostat. The intensities are determined from the (corrected) spectra, where Int($S_1 \rightarrow S_0$) and Int($T_1 \rightarrow S_0$) respectively represent the integrated fluorescence and phosphorescence band intensities, which can be determined by means of the programs integrated into the spectrophotometer. The respective transitions (band intensities) are easy to identify, since the triplet band is at lower energy than the singlet band and gains intensity with falling temperature. The measurements are conducted in oxygen-free dilute solutions (about $10^{-2}$ mol/l) or on thin films composed of the corresponding molecules or on films doped with the corresponding molecules. If a solution is used as the sample, it is advisable to use a solvent or solvent mixture that forms glasses at low temperatures, such as 2-methyl-THF, THF (tetrahydrofuran) or aliphatic hydrocarbons. If a film is used as the sample, it is suitable to use a matrix having a much greater singlet energy and triplet energy than the organic emitter molecules, e.g. PMMA (polymethyl-methacrylate). This film can be applied from solution.

The slope of the straight line is $-\Delta E/k_B$. With $k_B=1.380 \cdot 10^{-23}$ $JK^{-1}=0.695$ $cm^{-1}$ $K^{-1}$, it is possible to directly determine the energy gap.

An equivalent manner of consideration shows that it is also possible to determine the $\Delta E(S_1-T_1)$ value by means of measurement of the temperature dependence of the emission decay time.

A simple, approximate estimation of the $\Delta E(S_1-T_1)$ value can also be undertaken by registering the fluorescence and phosphorescence spectra at low temperature (e.g. 77 K or 4.2 K using a cryostat). The $\Delta E(S_1-T_1)$ value then corresponds approximately to the energy differential between the high-energy rise edges of the fluorescence/phosphorescence band.

The more marked the CT character of an organic molecule, the greater the change in the electronic transition energies as a function of solvent polarity. Thus, even a marked polarity dependence of the emission energies suggests the presence of small $\Delta E(S_1-T_1)$ values.

In a further aspect, the invention relates to the use of the organic molecules as luminescent emitters or as host material in an organic optoelectronic device, especially where the organic optoelectronic device is selected from the group consisting of:
organic light-emitting diodes (OLEDs),
light-emitting electrochemical cells,
OLED sensors, especially in gas and vapour sensors not hermetically shielded from the outside,
organic diodes,
organic solar cells,
organic transistors,
organic field-effect transistors,
organic lasers and
down-conversion elements.

In a further aspect, the invention relates to a composition comprising or consisting of:
(a) at least one organic molecule according to the invention, especially as emitter and/or host, and
(b) at least one (i.e. one, two or more) emitter and/or host material(s) other than the organic molecule according to the invention, and
(c) optionally at least one dye and/or at least one organic solvent.

In one embodiment, the composition according to the invention consists of an organic molecule according to the invention and one or more host materials. The host material(s) especially has/have triplet ($T_1$) and singlet ($S_1$) energy levels at higher energy than the triplet ($T_1$) and singlet ($S_1$) energy levels of the organic molecule according to the invention. In one embodiment, the composition, as well as the organic molecule according to the invention, includes an electron-dominant and a hole-dominant host material. The highest occupied orbital (HOMO) and the lowest unoccupied orbital (LUMO) of the hole-dominant host material are especially at higher energy than those of the electron-dominant host material. The HOMO of the hole-dominant host material is at lower energy than the HOMO of the organic molecule according to the invention, while the LUMO of the electron-dominant host material is at higher energy than the LUMO of the organic molecule according to the invention. In order to avoid exciplex formation between emitter and host material(s), the materials should be chosen such that the energy gaps between the respective orbitals are small. The gap between the LUMO of the electron-dominant host material and the LUMO of the organic molecule according to the invention is especially less than 0.5 eV, preferably less than 0.3 eV, even more preferably less than 0.2 eV. The gap between the HOMO of the hole-dominant host material and the HOMO of the organic molecule according to the invention is especially less than 0.5 eV, preferably less than 0.3 eV, even more preferably less than 0.2 eV.

In a further aspect, the invention relates to an organic optoelectronic device including an organic molecule according to the invention or a composition according to the invention. The organic optoelectronic device especially takes the form of a device selected from the group consisting of organic light-emitting diode (OLED); light-emitting electrochemical cell; OLED sensor, especially gas and vapour sensors that are not hermetically shielded from the outside; organic diode; organic solar cell; organic transistor; organic field effect transistor; organic laser and down-conversion element.

An organic optoelectronic device having
a substrate,
an anode and
a cathode, where the anode or cathode has been applied to the substrate, and
at least one light-emitting layer which is arranged between anode and cathode and includes an organic molecule according to the invention is a further embodiment of the invention.

In one embodiment, the optoelectronic device is an OLED. A typical OLED has, for example, the following layer structure:
1. Substrate (carrier material)
2. Anode
3. Hole injection layer (HIL)
4. Hole transport layer (HTL)
5. Electron blocking layer (EBL)
6. Emitting layer (EML)
7. Hole blocking layer (HBL)
8. Electron transport layer (ETL)
9. Electron injection layer (EIL)
10. Cathode.

Individual layers here are present merely in an optional manner. In addition, two or more of these layers may be combined. And it is possible for individual layers to be present more than once in the component.

In one embodiment, at least one electrode of the organic component is translucent. "Translucent" refers here to a layer which is transparent to visible light. The translucent layer here may be clear and see-through, i.e. transparent, or at least partly light-absorbing and/or partly light-scattering, such that the translucent layer, for example, may also have a diffuse or milky appearance. More particularly, a layer referred to here as translucent is very substantially transparent, such that, in particular, the absorption of light is as low as possible.

In a further embodiment, the organic component, especially an OLED, has an inverted structure. It is a feature of the inverted structure that the cathode is on the substrate and the other layers are applied in a correspondingly inverted manner.
1. Substrate (carrier material)
2. Cathode
3. Electron injection layer (EIL)
4. Electron transport layer (ETL)
5. Hole blocking layer (HBL)
6. Emission layer/emitting layer (EML)
7. Electron blocking layer (EBL)
8. Hole transport layer (HTL)
9. Hole injection layer (HIL)
10. Anode Individual layers here are present merely in an optional manner. In addition, two or more of these layers may be combined. And it is possible for individual layers to be present more than once in the component.

In one embodiment, in the inverted OLED, the anode layer of the typical structure, for example an ITO (indium tin oxide) layer, is connected as the cathode.

In a further embodiment, the organic component, especially an OLED, has a stacked structure. The individual OLEDs here are arranged one on top of another and not one alongside another as usual. A stacked structure can enable the generation of mixed light. For example, this structure can be used in the generation of white light, which is produced by forming the entire visible spectrum, typically by the combination of the emitted light from blue, green and red emitters. In addition, with practically the same efficiency and identical luminance, it is possible to achieve significantly longer lifetimes compared to standard OLEDs. For the stacked structure, it is optionally possible to use what is called a charge generation layer (CGL) between two OLEDs. This consists of an n-doped layer and a p-doped layer, the n-doped layer typically being applied closer to the anode.

In one embodiment—called a tandem OLED—two or more emission layers occur between the anode and cathode. In one embodiment, three emission layers are arranged one on top of another, where one emission layer emits red light, one emission layer emits green light and one emission layer emits blue light, and there are optionally further charge generation, blocker or transport layers applied between the individual emission layers. In a further embodiment, the respective emission layers are applied in a directly adjacent manner. In a further embodiment, there is one charge generation layer in each case between the emission layers. In addition, in an OLED, it is possible to combine directly adjacent emission layers and emission layers separated by charge generation layers.

It is also possible to arrange an encapsulation on top of the electrodes and the organic layers. The encapsulation may take the form, for example, of a glass lid or the form of a thin-film encapsulation.

The carrier material used in the optoelectronic device may, for example, be glass, quartz, plastic, metal, a silicon wafer or any other suitable solid or flexible, optionally transparent material.

The carrier material used may include, for example, one or more materials in the form of a layer, a film, a sheet or a laminate.

Anodes used in the optoelectronic device may, for example, be transparent conductive metal oxides, for example ITO (indium tin oxide), zinc oxide, tin oxide, cadmium oxide, titanium oxide, indium oxide or aluminium zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides.

HIL materials used may, for example, be PEDOT:PSS (poly-3,4-ethylenedioxythiophene:polystyrenesulphonic acid), PEDOT (poly-3,4-ethylenedioxythiophene), m-MTDATA (4,4',4"-tris[phenyl(m-tolyl)amino]triphenylamine), spiro-TAD (2,2',7,7'-tetrakis(N,N-diphenylamino)-9,9-spirobifluorene), DNTPD (4,4'-bis[N-[4-{N,N-bis(3-methylphenyl)amino}phenyl]-N-phenylamino]biphenyl), NPB (N,N'-bis-(1-naphthalenyl)-N,N'-bisphenyl-(1,1'-biphenyl)-4,4'-diamine), NPNPB (N,N'-diphenyl-N,N'-di-[4-(N,N-diphenylamino)phenyl]benzene), MeO-TPD (N,N,N',N'-tetrakis(4-methoxyphenyl)benzene), HAT-CN (1,4,5,8,9,11-hexaazatriphenylenehexacarbonitrile) or spiro-NPD (N,N'-diphenyl-N,N'-bis-(1-naphthyl)-9,9'-spirobifluorene-2,7-diamine). By way of example, the layer thickness is 10-80 nm. In addition, it is possible to use small molecules (e.g. copper phthalocyanine (CuPc, e.g. thickness 10 nm)) or metal oxides, by way of example $MoO_3$, $V_2O_5$.

HTL materials used may be tertiary amines, carbazole derivatives, polystyrenesulphonic acid-doped polyethylenedioxythiophene, camphorsulphonic acid-doped polyaniline, poly-TPD (poly(4-butylphenyldiphenylamine), [alpha]-NPD (poly(4-butylphenyldiphenylamine)), TAPC (4,4'-cyclohexylidenebis[N,N-bis(4-methylphenyl)benzeneamine]), TCTA (tris(4-carbazoyl-9-ylphenyl)amine), 2-TNATA (4,4',4"-tris[2-naphthyl(phenyl)amino]triphenylamine), spiro-TAD, DNTPD, NPB, NPNPB, MeO-TPD, HAT-CN or TrisPcz (9,9'-diphenyl-6-(9-phenyl-9H-carbazol-3-yl)-9H,9'H-3,3'-bicarbazole). By way of example, the layer thickness is 10-100 nm.

The HTL may have a p-doped layer having an inorganic or organic dopant in an organic hole-conducting matrix. Inorganic dopants used may, for example, be transition metal oxides, for instance vanadium oxide, molybdenum oxide or tungsten oxide. Organic dopants used may, for example, be tetrafluorotetracyanoquinodimethane (F4-TCNQ), copper pentafluorobenzoate (Cu(I)pFBz) or transition metal complexes. By way of example, the layer thickness is 10 nm to 100 nm.

Electron blocker layer materials used may, for example, be mCP (1,3-bis(carbazol-9-yl)benzene), TCTA, 2-TNATA, mCBP (3,3-di(9H-carbazol-9-yl)biphenyl), tris-Pcz (9,9-diphenyl-6-(9-phenyl-9H-carbazol-3-yl)-9H,9$^1$H-3,3'-bicarbazole), CzSi (9-(4-tert-butylphenyl)-3,6-bis(triphenylsilyl)-9H-carbazole) or DCB (N,N'-dicarbazolyl-1,4-dimethylbenzene). By way of example, the layer thickness is 10 nm to 50 nm.

The emitter layer EML or emission layer consists of or comprises emitter material or a mixture including at least two emitter materials and optionally one or more host materials. Suitable host materials are, for example, mCP, TCTA, 2-TNATA, mCBP, CBP (4,4'-bis-(N-carbazolyl) biphenyl). Sif87 (dibenzo[b,d]thiophen-2-yltriphenylsilane), Sif88 (dibenzo[b,d]thiophen-2-yl)diphenylsilane) or DPEPO (bis[2-((oxo)diphenylphosphino)phenyl]ether). For emitter material which emits in the green or in the red or a mixture comprising at least two emitter materials, the standard matrix materials are suitable, such as CBP. For emitter material which emits in the blue or a mixture comprising at least two emitter materials, it is possible to use UHG matrix materials (ultra-high-energy gap materials) (see, for example, M. E. Thompson et al., Chem. Mater. 2004, 16, 4743), or other so-called wide-gap matrix materials. Byway of example, the layer thickness is 10 nm to 250 nm.

The hole blocker layer HBL may include, for example, BCP (2,9-dimethyl-4,7-diphenyl-1,10- phenanthroline=bathocuproin), bis(2-methyl-8-hydroxyquinolinato)-(4-phenylphenolato)aluminium(III) (BAlq), Nbphen (2,9-bis(naphthalen-2-yl)-4,7-diphenyl-1,10-phenanthroline), Alq3 (aluminium tris(8-hydroxyquinoline)), TSPO1 (diphenyl-4-triphenylsilylphenylphosphine oxide) or TCB/TCP (1,3,5-tris(N-carbazolyl)benzene/1,3,5-tris(carbazol)-9-yl)benzene). By way of example, the layer thickness is 10 nm to 50 nm.

The electron transport layer ETL may include, for example, materials based on $AIQ_3$, TSPO1, BPyTP2 (2,7-di(2,2'-bipyridin-5-yl)triphenyl), Sif87, Sif88, BmPyPhB (1,3-bis[3,5-di(pyridin-3-yl)phenyl]benzene) or BTB (4,4'-bis-[2-(4,6-diphenyl-1,3,5-triazinyl)]-1,1'-biphenyl). By way of example, the layer thickness is 10 nm to 200 nm.

Materials used in a thin electron injection layer EIL may, for example, be CsF, LiF, 8-hydroxyquinolinolatolithium (Liq), $Li_2O$, $BaF_2$, MgO or NaF.

Materials used in the cathode layer may be metals or alloys, for example Al, Al>AlF, Ag, Pt, Au, Mg, Ag:Mg. Typical layer thicknesses are 100 nm to 200 nm. In particular, one or more metals that are stable under air and/or self-passivating, for example through formation of a thin protective oxide layer, are used.

Suitable materials for encapsulation are, for example, aluminium oxide, vanadium oxide, zinc oxide, zirconium oxide, titanium oxide, hafnium oxide, lanthanum oxide, tantalum oxide.

In one embodiment of the organic optoelectronic device according to the invention, the organic molecule according to the invention is used as emission material in a light-emitting layer EML, where it is used either in the form of a pure layer or in combination with one or more host materials.

One embodiment of the invention relates to organic optoelectronic devices having an external quantum efficiency (EQE) at 1000 $cd/m^2$ of greater than 5%, especially of greater than 8%, especially of greater than 10%, or of greater than 13%, or of greater than 16% and especially of greater than 20%, and/or an emission maximum at a wavelength between 420 nm and 500 nm, especially between 430 nm and 490 nm, or between 440 nm and 480 nm and especially between 450 nm and 470 nm, and/or an LT80 value at 500 $cd/m^2$ of greater than 30 h, especially of greater than 70 h, or of greater than 100 h, or of greater than 150 h and especially of greater than 200 h.

The proportion by mass of the organic molecule according to the invention in the emitter layer EML, in a further embodiment in a light-emitting layer in optical light-emitting devices, especially in OLEDs, is between 1% and 80%. In one embodiment of the organic optoelectronic device according to the invention, the light-emitting layer is applied to a substrate, preferably with application of an anode and a cathode to the substrate and application of the light-emitting layer between the anode and cathode.

The light-emitting layer, in one embodiment, has exclusively an organic molecule according to the invention in 100% concentration, with the anode and the cathode applied to the substrate, and the light-emitting layer applied between the anode and cathode.

In one embodiment of the organic optoelectronic device according to the invention, a hole- and electron-injecting layer has been applied between the anode and cathode, and a hole- and electron-transporting layer between the hole- and electron-injecting layer, and the light-emitting layer between the hole- and electron-transporting layer.

The organic optoelectronic device, in a further embodiment, has: a substrate, an anode, a cathode and at least one hole- and one electron-injecting layer, and at least one hole- and one electron-transporting layer, and at least one light-emitting layer including an organic molecule according to the invention and one or more host materials, the triplet ($T_1$) and singlet ($S_1$) energy levels of which are at higher energy than the triplet ($T_1$) and singlet ($S_1$) energy levels of the organic molecule, with the anode and cathode applied to the substrate, and the hole- and electron-injecting layer applied between the anode and cathode, and the hole- and electron-transporting layer applied between the hole- and electron-injecting layer, and the light-emitting layer applied between the hole- and electron-transporting layer.

In a further aspect, the invention relates to a process for producing an optoelectronic component. This is done using an organic molecule according to the invention.

In one embodiment, the production process encompasses the processing of the organic molecule according to the invention by means of a vacuum evaporation method or from a solution.

The invention also includes a process for producing an optoelectronic device according to the invention, in which at least one layer of the optoelectronic device
- is coated by a sublimation method,
- is coated by an OVPD (organic vapour phase deposition) method,
- is coated by a carrier gas sublimation, and/or
- is produced from solution or by a printing method.

In the production of the optoelectronic device according to the invention, known methods are used. In general, the layers are applied individually to a suitable substrate in successive deposition process steps. In the gas phase deposition, it is possible to employ the commonly used methods, such as thermal evaporation, chemical gas phase deposition (CVD), physical gas phase deposition (PVD). For active-matrix OLED displays, deposition is effected on an AMO-LED backplane as substrate.

Alternatively, it is possible to apply layers from solutions or dispersions in suitable solvents. Illustrative suitable coating methods are spin-coating, dip-coating and jet printing methods. The individual layers can be produced in accordance with the invention either via the same coating method or via different coating methods in each case.

EXAMPLES

General Methods

GM1:

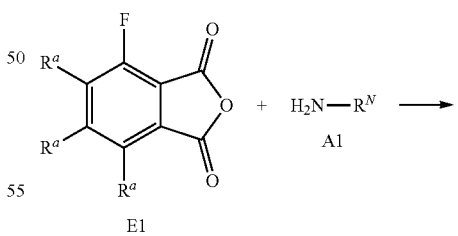

E1

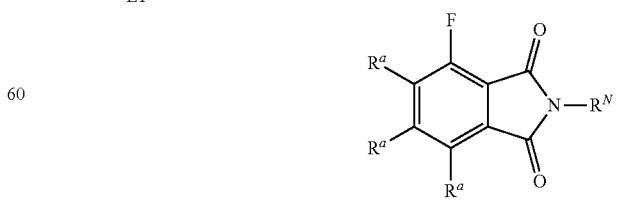

E2

In a round-bottom flask with reflux condenser, E1 (1 equivalent) is suspended in glacial acetic acid. After addition of A1 (1.1 equivalents), the mixture is stirred at 100° C. for 3 hours. After cooling, the reaction solution is concentrated as far as possible on a rotary evaporator. The residue is taken up in $CH_2Cl_2$ and washed twice with saturated $Na_2CO_3$. The combined organic phases are dried over $MgSO_4$. The solvent is removed on a rotary evaporator. After drying under high vacuum. E2 is obtained as product, which can then generally be used without further purification. If required, the product E2 can be purified further by recrystallization.

Illustrative A1 and E2 Combinations

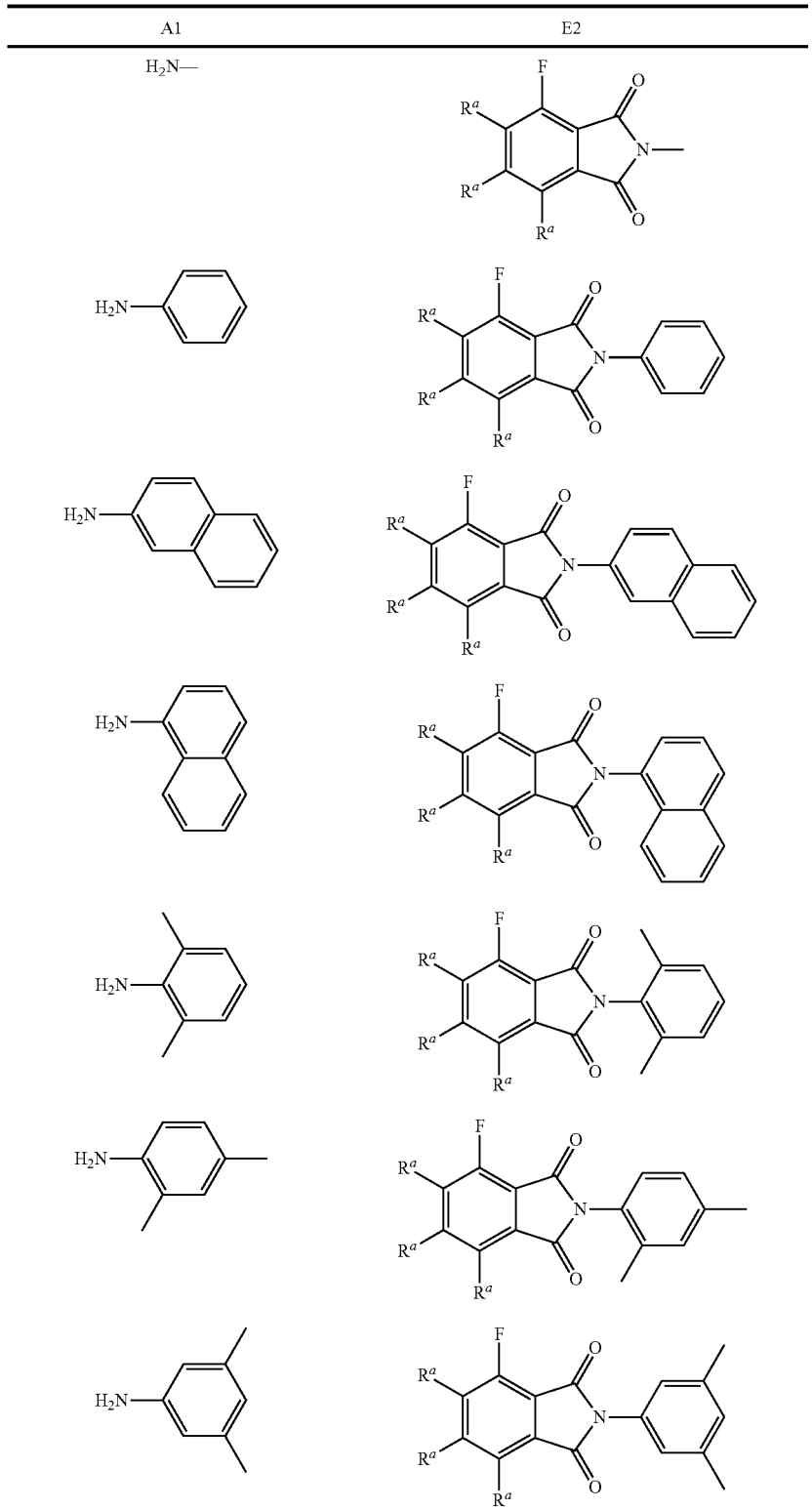

-continued
| A1 | E2 |
|---|---|
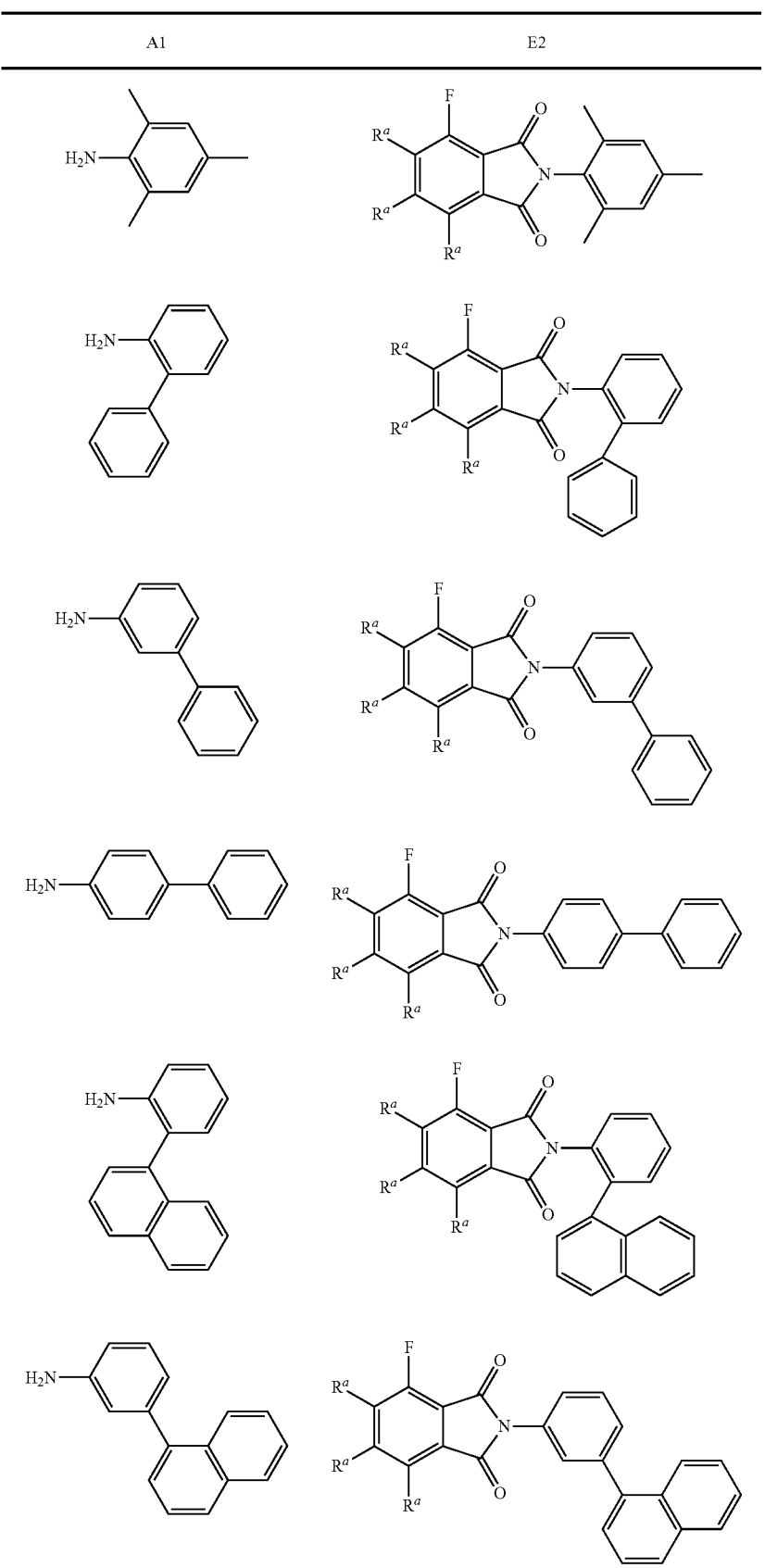

-continued
| A1 | E2 |
|---|---|
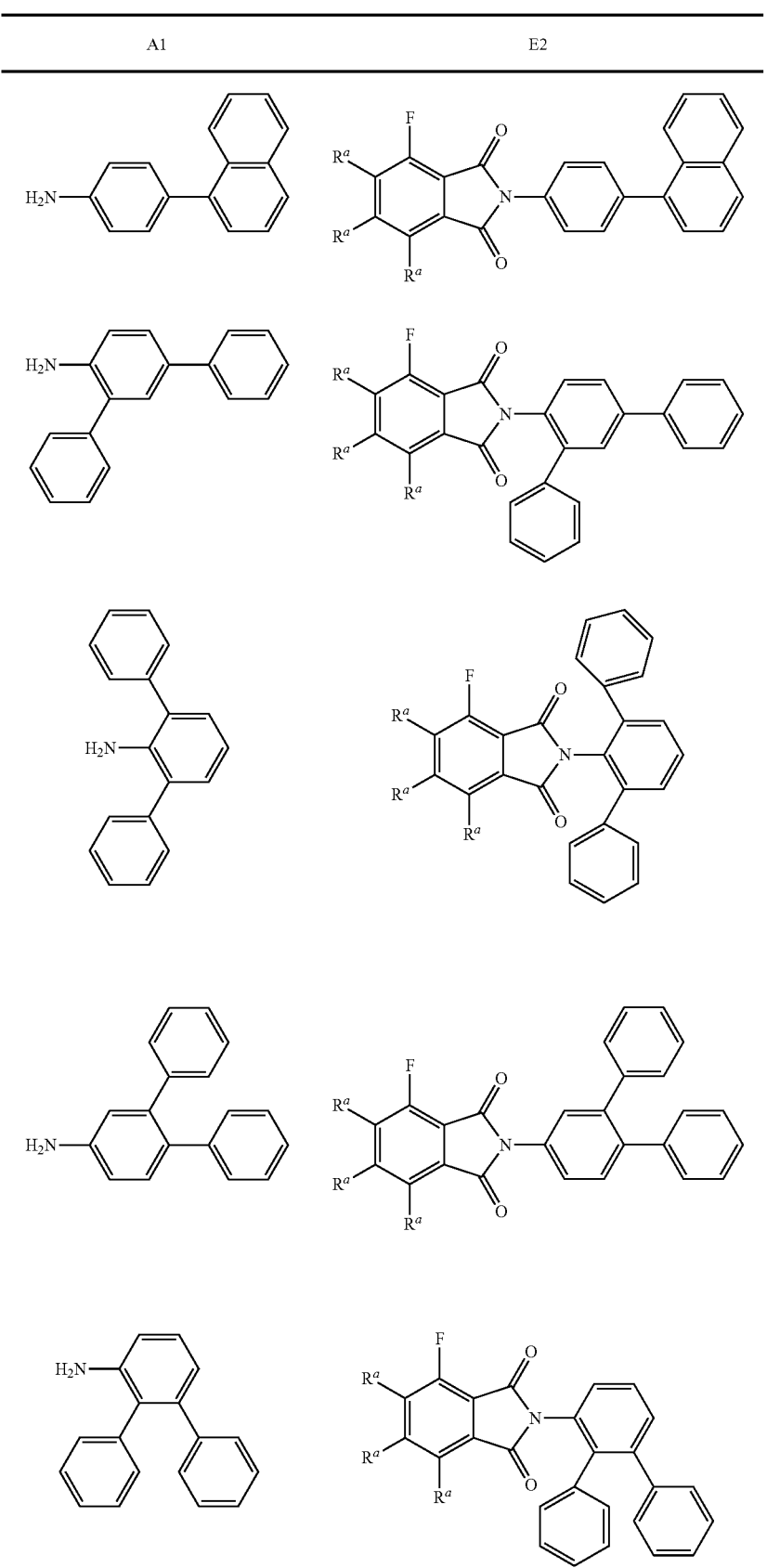

| A1 | E2 |
|---|---|
| 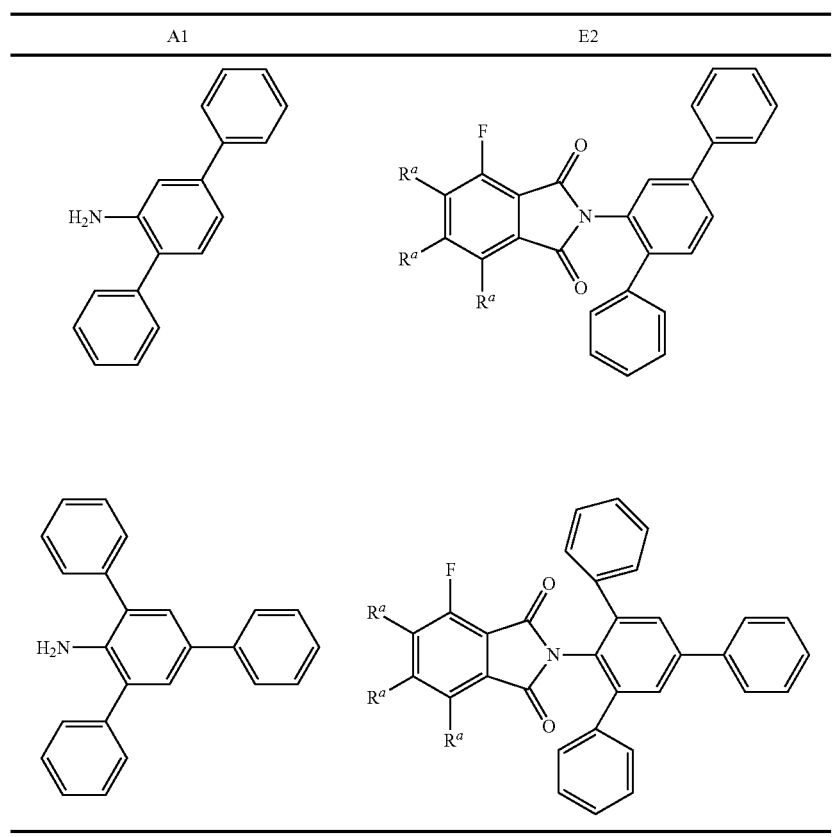 | |

GM2:

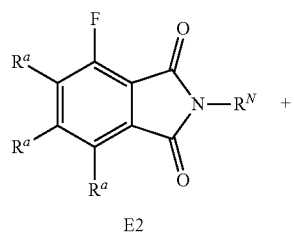

A round-bottom flask is initially charged with phthalimide E2 (1 equivalent), a carbazole derivative E3 (1 equivalent) and $K_3PO_4$ (2 equivalents), and evacuated for 5 min. Under inert gas atmosphere, DMSO (dry) is added and the reaction solution is stirred at 100° C. for 16 h. After cooling, the reaction solution is poured onto water and extracted with $CH_2Cl_2$. After extracting again with $CH_2Cl_2$, the combined organic phases are washed 2× with water and with saturated NaCl solution. This is followed by drying over $MgSO_4$ and removal of the solvent on a rotary evaporator. The respective product can be purified by recrystallization.

GM3:

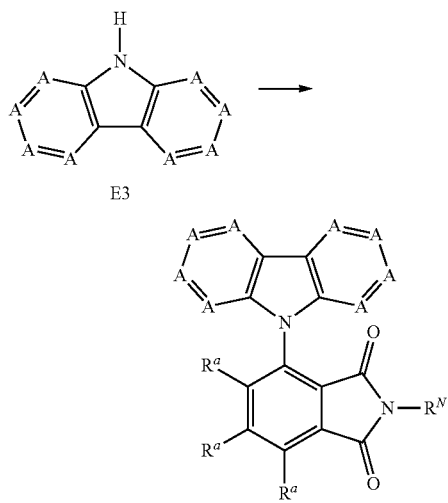

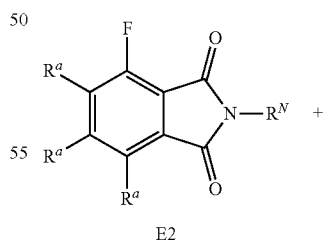

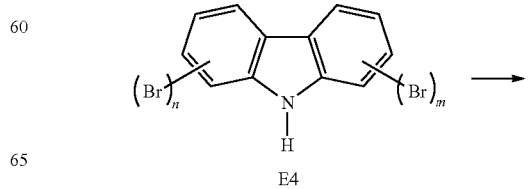

-continued

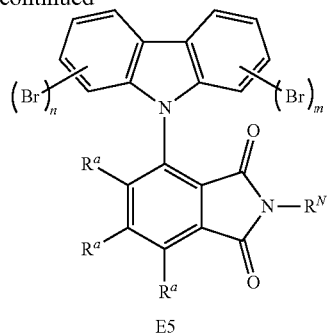

E5 n = 1 to 4,
m = 0 to 4 n=1 to 4, m=0 to 4

A round-bottom flask is initially charged with E2 (1.2 equivalents), a bromine-substituted carbazole E4 (1.0 equivalent) and $K_3PO_4$ (2 equivalents), and evacuated for 5 min. Under inert gas atmosphere, DMSO (dry) is added and the reaction solution is stirred at 100° C. for 16 h. After cooling, the reaction solution is poured onto water and extracted with $CH_2Cl_2$. After extracting again with $CH_2Cl_2$, the combined organic phases are washed 2× with water and with saturated NaCl solution. This is followed by drying over $MgSO_4$ and removal of the solvent on a rotary evaporator. The respective product can be purified by recrystallization. It is possible in accordance with the invention also to use chlorine- or iodine-substituted carbazole rather than bromine-substituted carbazole.

Illustrative E4 and E5 Combinations

| E4 | E5 |
|---|---|
| 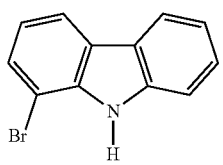 | 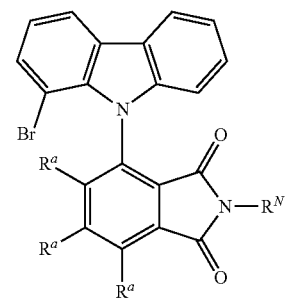 |
| 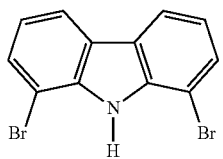 | 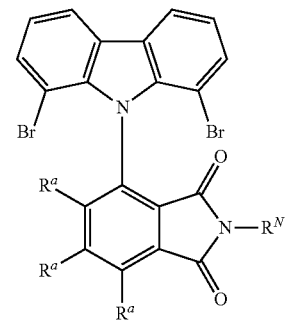 |
| 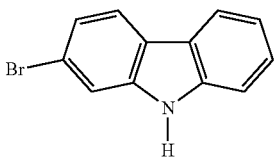 | 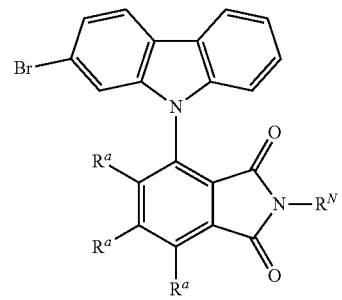 |

-continued
| E4 | E5 |
|---|---|
| 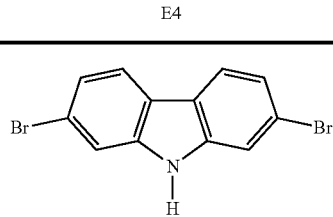 | 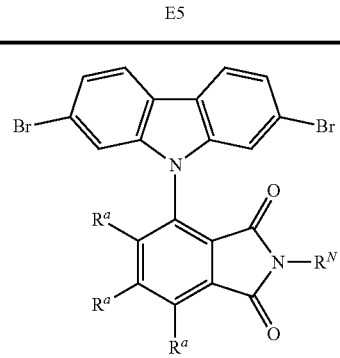 |
| 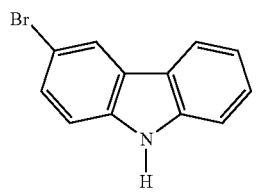 | 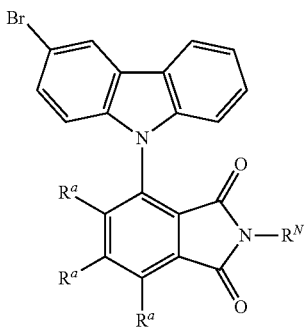 |
| 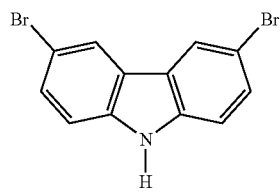 | 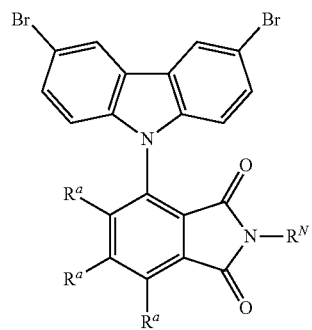 |
| 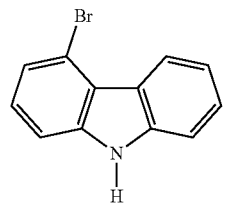 | 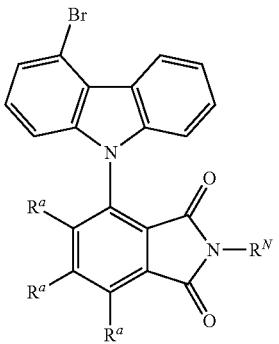 |

| E4 | E5 |
|---|---|
| 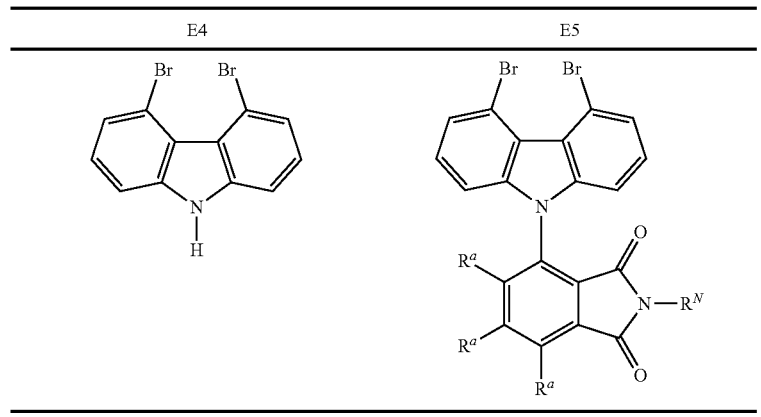 | |

GM4:
Stage 1

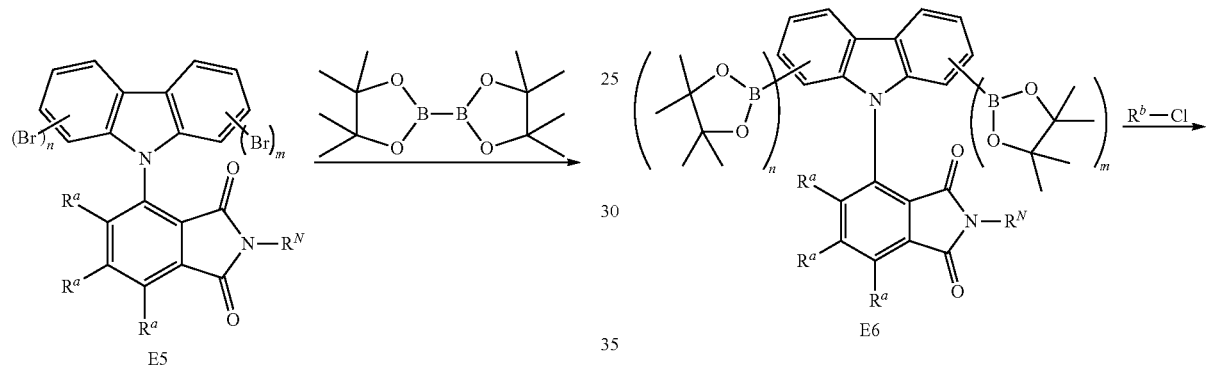

E5 (1.00 equivalent), bis(pinacolato)diboron (1.5×(n+m) equivalents), tris(dibenzylideneacetone)dipalladium (0.01 equivalent), 2-(dicyclohexylphosphino)-2',4',6'-triisopropylbiphenyl (0.04 equivalent) and tribasic potassium phosphate (3n+3m equivalents) are stirred under nitrogen in dioxane at 110° C. for 12 to 24 h. The crude product obtained can be purified by recrystallization.

Stage 2:

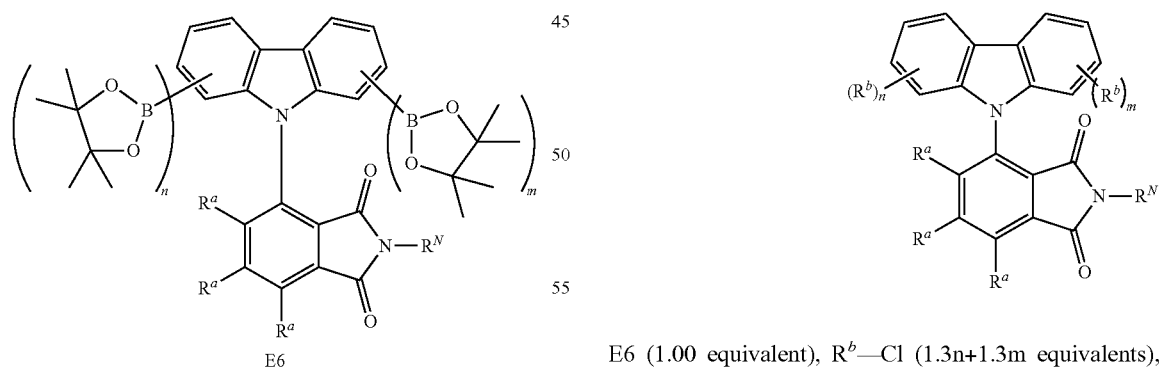

E6 (1.00 equivalent), $R^b$—Cl (1.3n+1.3m equivalents), tris(dibenzylideneacetone)dipalladium (0.01 equivalent), 2-(dicyclohexylphosphino)-2',4',6'-triisopropylbiphenyl (0.04 equivalent) and tribasic potassium phosphate (2.5n+2.5m equivalents) are stirred under nitrogen in a toluene/water (10:1) mixture at 100° C. for 12-24 h. The crude product obtained is purified by flash chromatography or by recrystallization.

It is also possible in accordance with the invention to use $R^b$—Br or $R^b$—I rather than $R^b$—Cl.

GM5:

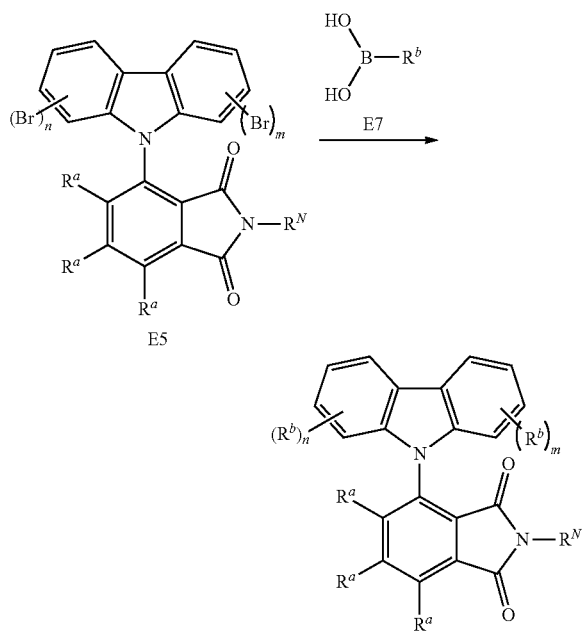

E5 (1.00 equivalent), the appropriate boronic acid of the $R^b$ radical E7 (1.3n+1.3m equivalents), tris(dibenzylideneacetone)dipalladium (0.01 equivalent), 2-(dicyclohexylphosphino)-2',4',6'-triisopropylbiphenyl (0.04 equivalent) and tribasic potassium phosphate (3n+3m equivalents) are stirred under nitrogen in dioxane at 110° C. for 12-24 h. The crude product obtained is purified by flash chromatography or by recrystallization.

It is also possible in accordance with the invention to use a corresponding boronic ester rather than a boronic acid.

The molecules according to the invention can each be obtained according to GM2 or a combination of GM3 and GM4 or GM3 and GM5. The products from the synthesis routes differ in each case merely by the yields or purity obtained prior to the purification. After appropriate purification, the products are of equivalent quality.

Calculations by Density Functional Theory

For the optimization of the molecular structures, the BP86 functional (Becke, A. D. Phys. Rev. A1988, 38, 3098-3100; Perdew, J. P. Phys. Rev. B1986, 33, 8822-8827) was used, using the resolution-of-identity (RI) approximation (Sierka, M.; Hogekamp, A.; Ahlrichs, R. J. Chem. Phys. 2003, 118, 9136-9148; Becke, A. D., J. Chem. Phys. 98 (1993) 5648-5652; Lee, C; Yang, W; Parr, R. G. Phys. Rev. B 37 (1988) 785-789). Excitation energies were calculated in the BP86-optimized structure by the time-dependent DFT method (TD-DFT) using the B3LYP functional (Becke, A. D., J. Chem. Phys. 98 (1993) 5648-5652; Lee, C; Yang, W; Parr, R. G. Phys. Rev. B 37 (1988) 785-789; Vosko, S. H.; Wilk, L.; Nusair, M. Can. J. Phys. 58 (1980) 1200-1211; Stephens, P. J.; Devlin, F. J.; Chabalowski, C. F.; Frisch, M. J. J. Phys. Chem. 98 (1994) 11623-11627). In all calculations, def2-SV(P) basis sets (Weigend, F.; Ahlrichs, R. Phys. Chem. Chem. Phys. 2005, 7, 3297-3305; Rappoport, D.; Furche, F. J. Chem. Phys. 2010, 133, 134105/1-134105/11) and an m4 grid were used for numerical integration. All DFT calculations were conducted with the Turbomole software package (version 6.5) (TURBOMOLE V6.4 2012, a development by the University of Karlsruhe and Forschungszentrum Karlsruhe GmbH, 1989-2007, TURBOMOLE GmbH, since 2007; http://www.turbomole.com).

Photophysical Measurements

Pretreatment of Optical Glasses

All glassware (cuvettes and substrates made from quartz glass, diameter: 1 cm) was cleaned after each use: Three rinses each time with dichloromethane, acetone, ethanol, demineralized water, placing in 5% Hellmanex solution for 24 h, thorough rinsing-out with demineralized water. For drying, the optical glassware was blown dry with nitrogen.

Sample Preparation: Solutions 1-2 mg of the sample were dissolved in 100 ml of the particular solvent; concentration $10^{-5}$ mol/l. The cuvette was sealed air-tight and degassed for 10 min.

Sample Preparation, Film: Spin-Coating (Instrument: Spin 150, SPS Euro.)

Sample concentration corresponded to 10 mg/ml, made up in toluene or chlorobenzene. Programme: 1) 3 s at 400 rpm; 2) 20 sec at 1000 rpm at 1000 rpm/s, 3) 10 s at 4000 rpm at 1000 rpm/s. After coating, the films were dried at 70° C. under air on an LHG precision hotplate for 1 min.

Absorption Spectroscopy

Solutions: UV-vis spectra were recorded on a Thermo Scientific instrument, model: Evolution 201. (See Sample preparation: solutions)

Film: UV-vis spectra were recorded on a Thermo Scientific instrument, model: Evolution 201. (See Sample preparation, film: spin-coating)

Photoluminescence Spectroscopy and TCSPC

Steady-state emission spectroscopy was conducted with a Horiba Scientific fluorescence spectrometer, model: Fluoro-Max-4, equipped with a 150 W xenon arc lamp, excitation and emission monochromators and a Hamamatsu R928 photomultiplier tube, and also a TSCPC option. Emission and excitation spectra were corrected by means of standard correction curves.

The emission decay times were likewise measured with this system using the TCSPC method with the FM-2013 accessories and a TCSPC hub from Horiba Yvon Jobin. Excitation sources: NanoLED 370 (wavelength: 371 nm, pulse duration: 1.1 ns). NanoLED 290 (wavelength: 294 nm, pulse duration: <1 ns), SpectraLED 310 (wavelength: 314 nm), SpectraLED 355 (wavelength: 355 nm).

The evaluation (exponential fitting) was effected with the Datamation software package and the DAS 6 evaluation software. The fit was reported by the chi-squared method $$c^2 = \sum_{k=1}^{i} \frac{(e_i - o_i)^2}{e_i}$$

with $e_i$: parameter predicted by the fit and $o_i$: parameter measured.

Determination of Quantum Efficiency

The photoluminescence quantum yield (PLQY) was measured by means of an Absolute PL Quantum Yield Measurement C9920-03G system from Hamamatsu Photonics. This consists of a 150 W xenon gas discharge lamp, automatically adjustable Czerny-Turner monochromators (250 nm to 950 nm) and an Ulbricht sphere with highly reflective Spectralon coating (a Teflon derivative), connected via a glass fibre cable to a PM A-12 multichannel detector with a BT (back-thinned) CCD chip having 1024×122 pixels (size 24×24 µm). The quantum efficiency and the CIE coordinates were evaluated with the aid of the U6039-05 software, version 3.6.0, for G9920-OXG (PMA-12). The emission maximum is reported in nm, the quantum yield φ in %, and the CIE colour coordinates as x,y values.

The PLQY was determined for polymer films, solutions and powder samples by the following protocol:
1) Performance of quality assurance: The reference material used is anthracene in ethanol with known concentration.
2) Determining the excitation wavelength: First of all, the absorption maximum of the organic molecule was determined and it was excited therewith.
3) Performance of sample analysis: The absolute quantum yield of degassed solutions and films was determined under a nitrogen atmosphere. The calculation was effected within the system according to the following equation:

$$\Phi_{PL} = \frac{n_{photon},\text{ emitted}}{n_{photon},\text{ absorbed}} = \frac{\int \frac{\lambda}{hc}\left[Int^{sample}_{emitted}(\lambda) - Int^{sample}_{absorbed}(\lambda)\right]d\lambda}{\int \frac{\lambda}{hc}\left[Int^{reference}_{emitted}(\lambda) - Int^{reference}_{absorbed}(\lambda)\right]d\lambda}$$

with the photon count $n_{photon}$ and the intensity Int.
Production and Characterization of Organic Electroluminescent Devices from the Gas Phase With the organic molecules according to the invention, it is possible to create OLED devices by means of vacuum sublimation methodology. If a layer contains two or more components, the ratio of these is reported in percent by mass.

These as yet unoptimized OLEDs can be characterized in a standard manner; for this purpose, the electroluminescent spectra, the external quantum efficiency (measured in %) as a function of brightness, calculated from the light detected by the photodiode, and the current are recorded. The lifetime of the OLEDs can be determined from the plot of the electroluminescence spectra against time. The LT50 value reported corresponds here to the time at which the luminance has dropped to 50% of the starting value. Analogously, the LT70 value corresponds to the time at which the luminance has dropped to 70% of the starting value.

Example 1

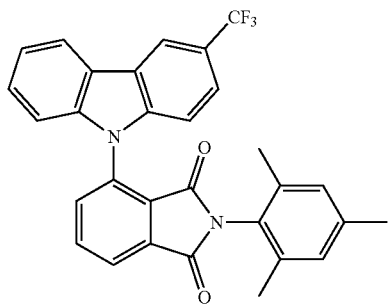 [SMILES: Cc1cc(C)c(N2C(=O)c3cccc(-n4c5ccccc5c5cc(C(F)(F)F)ccc54)c3C2=O)c(C)c1]

Example 1 was prepared according to GM2 from 3-trifluoromethyl-9H-carbazole and N-mesityl-3-fluorophthalimide in a yield of 49%.
$^1$H NMR (500 MHz, chloroform-d) δ 8.40 (m, 1H), 8.17 (dt, J=7.7, 1.0 Hz, 1H), 8.15 (dd, J=7.4, 1.0 Hz, 1H), 8.05 (t, J=7.7 Hz, 1H), 7.97 (dd. J=8.0, 1.0 Hz, 1H), 7.63 (dd, J=8.8, 1.8 Hz, 1H), 7.46 (dd, J=8.3, 7.2, 1.2 Hz, 1H), 7.37 (ddd, J=8.0, 7.3, 1.0 Hz, 1H), 7.28-7.24 (m, 3H), 6.95-6.92 (m, 2H), 2.27 (s, 3H), 2.11 (s, 3H), 2.09 (s, 3H).
$^{19}$F NMR (471 MHz, CDCl3) δ −60.38.

FIG. 1 shows the emission spectrum of Example 1 (10% in PMMA). The emission maximum is at 469 nm. The photoluminescence quantum yield (PLQY) is 39% and the full width at half maximum (FWHM) is 90 nm (0.49 eV). A CIE$_y$ of 0.24 and a BMI of 163 are found. The emission lifetime is 7.5 μs.

Example 2

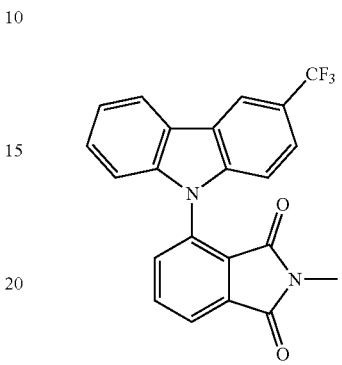

Example 2 was prepared according to GM2 from 3-trifluoromethyl-9H-carbazole and N-methyl-3-fluorophthalimide in a yield of 67%.

Figure 2:
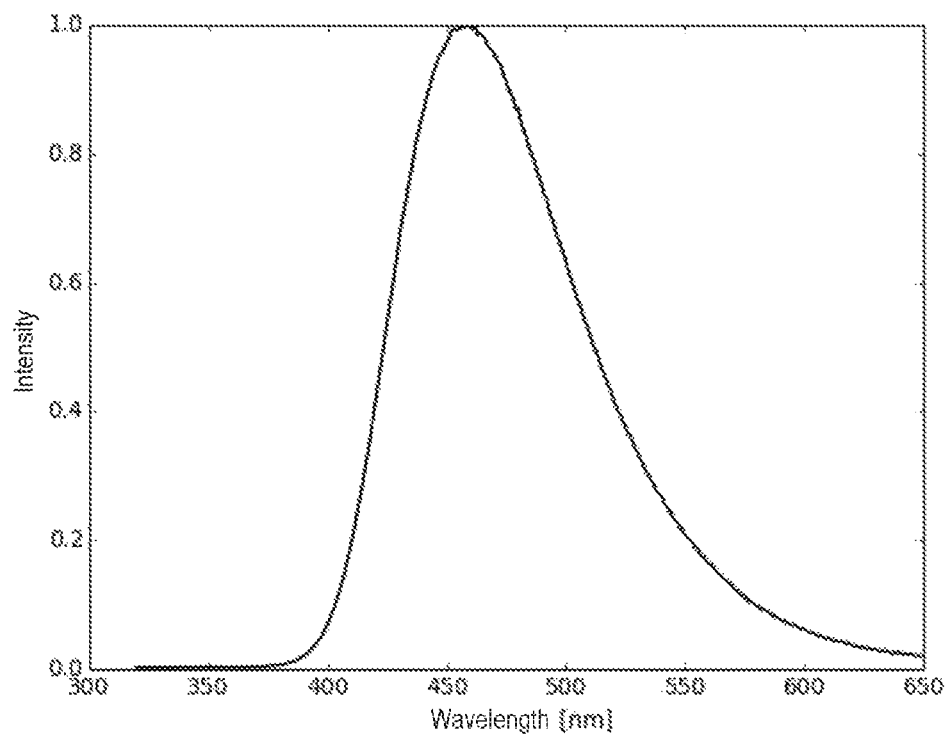
FIG. 2 is an emission spectrum of Example 2 (10% in PMMA).

FIG. 2 shows the emission spectrum of Example 2 (10% in PMMA). The emission maximum is at 458 nm. The photoluminescence quantum yield (PLQY) is 34% and the full width at half maximum (FWHM) is 88 nm (0.50 eV). A CIE$_y$ of 0.19 and a BMI of 179 are found. The emission lifetime is 10.5 μs.

Example 3

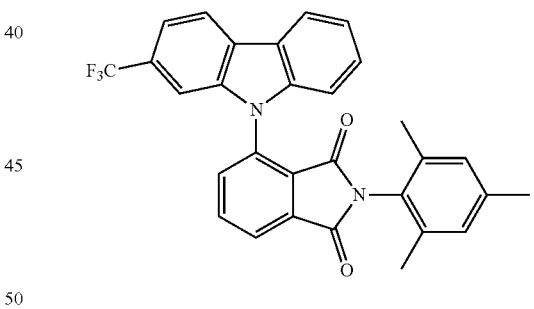

Example 3 was prepared according to GM2 from 2-trifluoromethyl-9H-carbazole and N-mesityl-3-fluorophthalimide in a yield of 57%.
$^1$H NMR (500 MHz, chloroform-d) δ 8.22 (d, J=8.1 Hz, 1H), 8.18 (dt, J=7.8, 0.9 Hz, 1H), 8.15 (dd, J=7.4, 1.0 Hz, 1H), 8.06 (t. J=7.8 Hz, 1H), 7.97 (dd, J=8.0, 0.9 Hz, 1H), 7.56 (dd, J=8.2, 1.4 Hz, 1H), 7.48 (ddd, J=8.3, 7.2, 1.2 Hz, 1H), 7.44 (s, 1H), 7.37 (td, J=7.6, 0.9 Hz, 1H), 7.31 (d, J=8.3 Hz, 1H), 6.95 (s, 1H), 6.93 (s, 1H), 2.27 (s, 3H), 2.12 (s, 3H), 2.09 (s, 3H).

Figure 3:
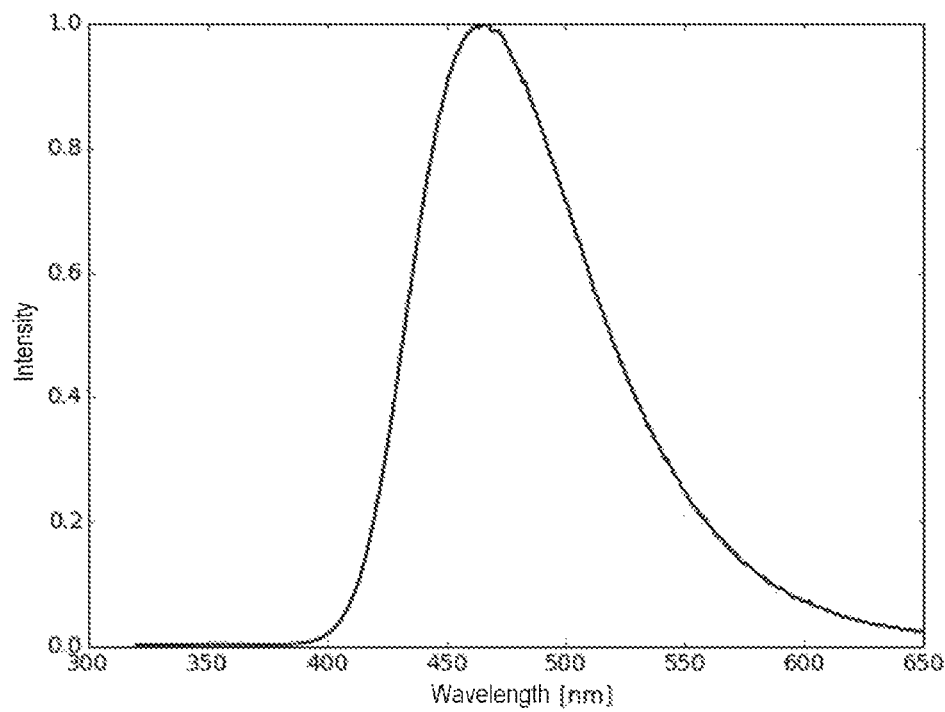
FIG. 3 is an emission spectrum of Example 3 (10% in PMMA).

FIG. 3 shows the emission spectrum of Example 3 (10% in PMMA). The emission maximum is at 467 nm. The photoluminescence quantum yield (PLQY) is 46% and the full width at half maximum (FWHM) is 86 nm (0.47 eV). A CIE$_y$ of 0.22 and a BMI of 209 are found. The emission lifetime is 8.5 μs.

Example 4

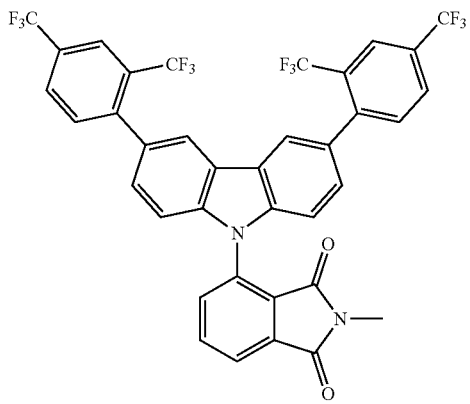 [SMILES: CN1C(=O)c2cccc(-n3c4ccc(-c5ccc(C(F)(F)F)cc5C(F)(F)F)cc4c4cc(-c5ccc(C(F)(F)F)cc5C(F)(F)F)ccc43)c2C1=O]

Example 4 was prepared according to GM5 from 3-(3,6-dibromocarbazolyl)-N-methylphthalimide and 2,4-trifluoromethylphenyl-1-boronic acid in a yield of 44%.

$^1$H NMR (500 MHz, chloroform-d) δ 8.09 (m, 2H), 8.06 (dd, J=7.2, 1.2 Hz, 1H), 8.05-8.03 (m, 2H), 7.99 (t, J=7.6 Hz, 1H), 7.95 (dd, J=8.0, 1.2 Hz, 1H), 7.88-7.83 (m, 2H), 7.63 (d, J=7.9 Hz, 2H), 7.39 (dd, J=8.4, 1.6 Hz, 2H), 7.23 (d. J=8.4 Hz, 2H), 3.16 (s, 3H).

$^{19}$F NMR (471 MHz, CDCl3) δ −57.00, −62.66.

Figure 4:
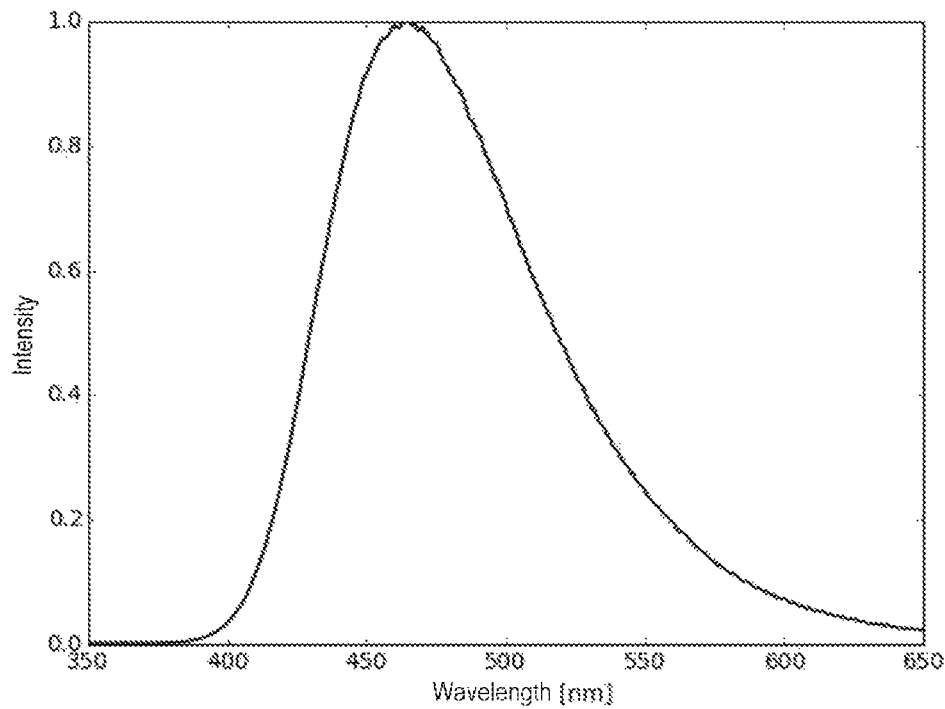
FIG. 4 is an emission spectrum of Example 4 (10% in PMMA).

FIG. 4 shows the emission spectrum of Example 4 (10% in PMMA). The emission maximum is at 465 nm. The photoluminescence quantum yield (PLQY) is 50% and the full width at half maximum (FWHM) is 89 nm (0.49 eV). A $CIE_y$ of 0.21 and a BMI of 238 are found.

Example 5

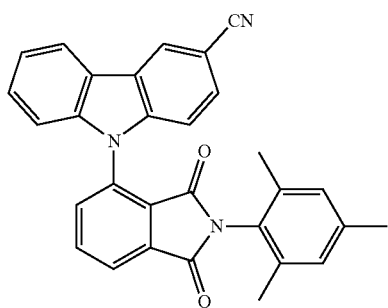 [SMILES: Cc1cc(C)c(N2C(=O)c3cccc(-n4c5ccccc5c5cc(C#N)ccc54)c3C2=O)c(C)c1]

Example 5 was prepared according to GM2 from 3-cyano-9H-carbazole and N-mesityl-3-fluorophthalimide in a yield of 62%.

$^1$H NMR (500 MHz, chloroform-d) δ 8.47-8.43 (m, 1H), 8.18-8.14 (m, 2H), 8.07 (t, J=7.7 Hz, 1H), 7.96 (dd, J=8.0, 1.0 Hz, 1H), 7.64 (dd, J=8.5, 1.6 Hz, 1H), 7.49 (ddd, J=8.4, 7.3, 1.2 Hz, 1H), 7.42-7.37 (m, 1H), 7.28-7.22 (m, 2H), 6.93 (m, 2H), 2.27 (s, 3H), 2.10 (s, 3H), 2.07 (s, 3H).

Figure 5:
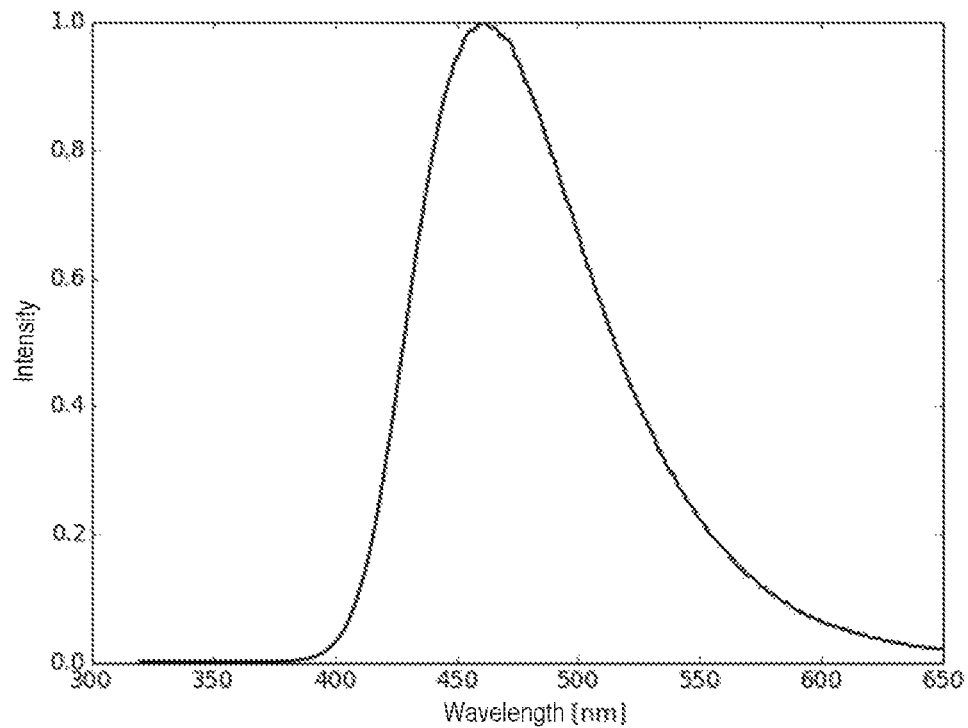
FIG. 5 is an emission spectrum of Example 5 (10% in PMMA).

FIG. 5 shows the emission spectrum of Example 5 (10% in PMMA). The emission maximum is at 462 nm. The photoluminescence quantum yield (PLQY) is 36% and the full width at half maximum (FWHM) is 87 nm (0.49 eV). A $CIE_y$ of 0.20 and a BMI of 180 are found. The emission lifetime is 6.6 μs.

Example 6

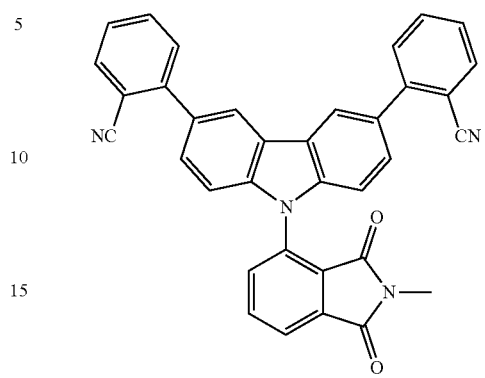

Example 6 was prepared according to GM5 from 3-(3,6-dibromocarbazolyl)-N-methylphthalimide and 2-cyanophenylboronic acid in a yield of 61%.

$^1$H NMR (500 MHz, chloroform-d) δ 8.38 (d, J=1.7 Hz, 2H), 8.06 (dd, J=7.3, 1.1 Hz, 1H), 7.99 (t, J=7.7 Hz, 1H), 7.93 (dd, J=7.9, 1.1 Hz, 1H), 7.83-7.78 (m, 2H), 7.71-7.63 (m, 6H), 7.45 (ddd, J=7.8, 6.4, 2.3 Hz, 2H), 7.28 (d, J=8.5 Hz, 2H), 3.15 (d, J=1.1 Hz, 3H).

Figure 6:
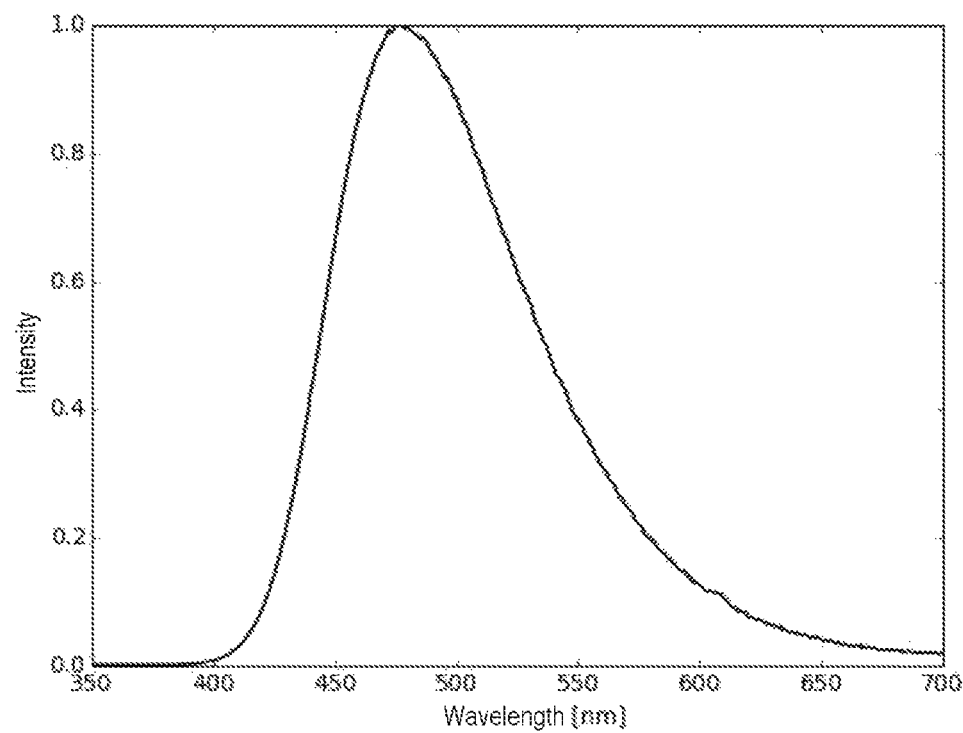
FIG. 6 is an emission spectrum of Example 6 (10% in PMMA).

FIG. 6 shows the emission spectrum of Example 6 (10% in PMMA). The emission maximum is at 477 nm. The photoluminescence quantum yield (PLQY) is 56% and the full width at half maximum (FWHM) is 93 nm (0.48 eV). A $CIE_y$ of 0.30 and a BMI of 187 are found. The emission lifetime is 59 μs.

Example 7

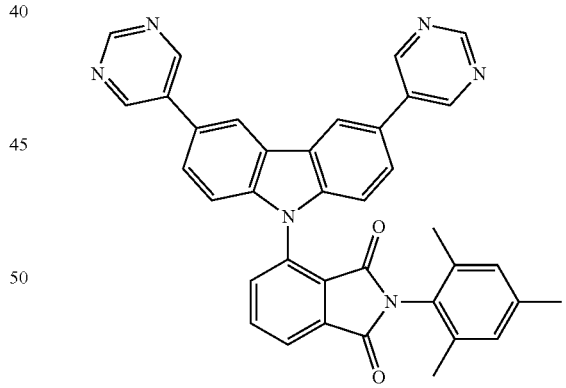

Example 7 was prepared according to GM5 from 3-(3,6-dibromocarbazolyl)-N-mesitylphthalimide and pyrimidine-5-boronic acid in a yield of 22%.

$^1$H NMR (500 MHz, chloroform-d) δ 9.22 (s, 2H), 9.07 (s, 4H), 8.40 (d, J=1.7 Hz, 2H), 8.21-8.17 (m, 1H), 8.11 (t, J=7.7 Hz, 1H), 8.06-8.01 (m, 1H), 7.65 (dd, J=8.5, 1.8 Hz, 2H), 7.39 (d, J=8.5 Hz, 2H), 6.93 (s, 2H), 2.26 (s, 3H), 2.11 (s, 6H).

Figure 7:
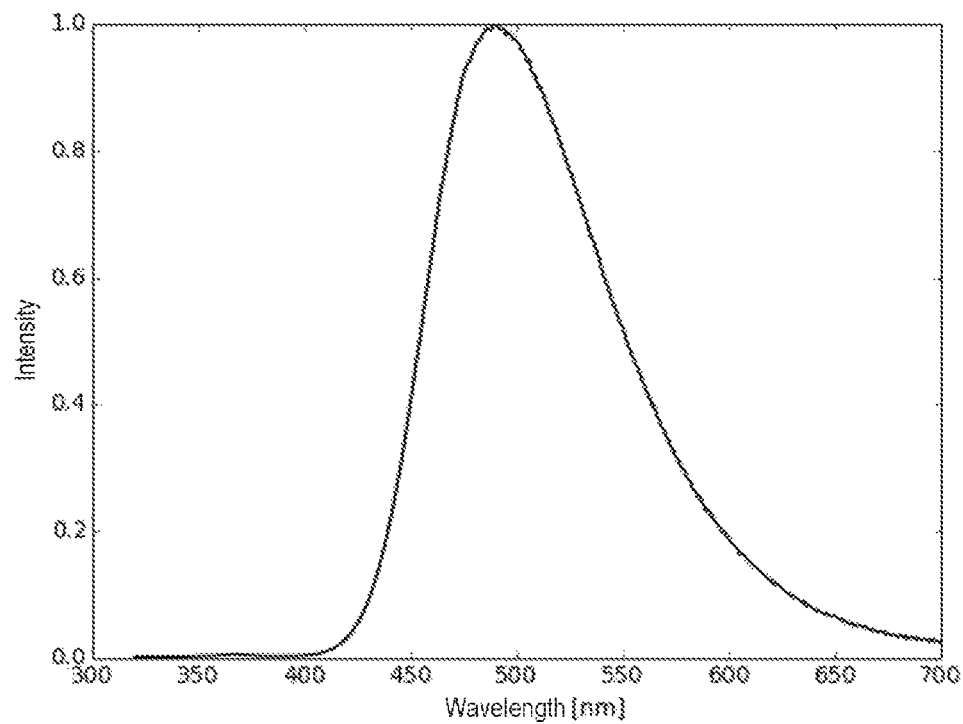
FIG. 7 is an emission spectrum of Example 7 (10% in PMMA).

FIG. 7 shows the emission spectrum of Example 7 (10% in PMMA). The emission maximum is at 490 nm. The photoluminescence quantum yield (PLQY) is 58% and the full width at half maximum (FWHM) is 97 nm (0.48 eV). A CIE$_y$ of 0.38 and a BMI of 153 are found. The emission lifetime is 9.8 µs.

Example 8

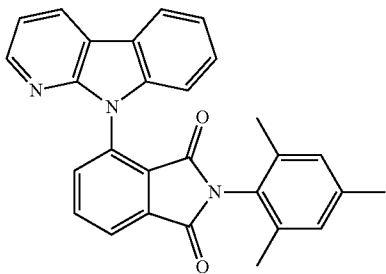 [SMILES: Cc1cc(C)c(N2C(=O)c3cccc(-n4c5ccccc5c5cccnc54)c3C2=O)c(C)c1]

Example 8 was prepared according to GM2 from N-mesityl-3-fluorophthalimide and 9H-pyrido[2,3-b]indole in a yield of 26%.

$^1$H NMR (500 MHz, chloroform-d) δ 8.41-8.35 (m, 2H), 8.14-8.11 (m, 1H), 8.09 (dd, J=6.4, 2.0 Hz, 1H), 8.06-8.00 (m, 2H), 7.47 (td, J=7.6, 7.1, 1.2 Hz, 1H), 7.38-7.33 (m, 2H), 7.25 (dd, J=7.7, 4.9 Hz, 1H), 6.93 (s, 1H), 6.91 (s, 1H), 2.26 (s, 3H), 2.14 (s, 3H), 2.08 (s, 3H).

Figure 8:
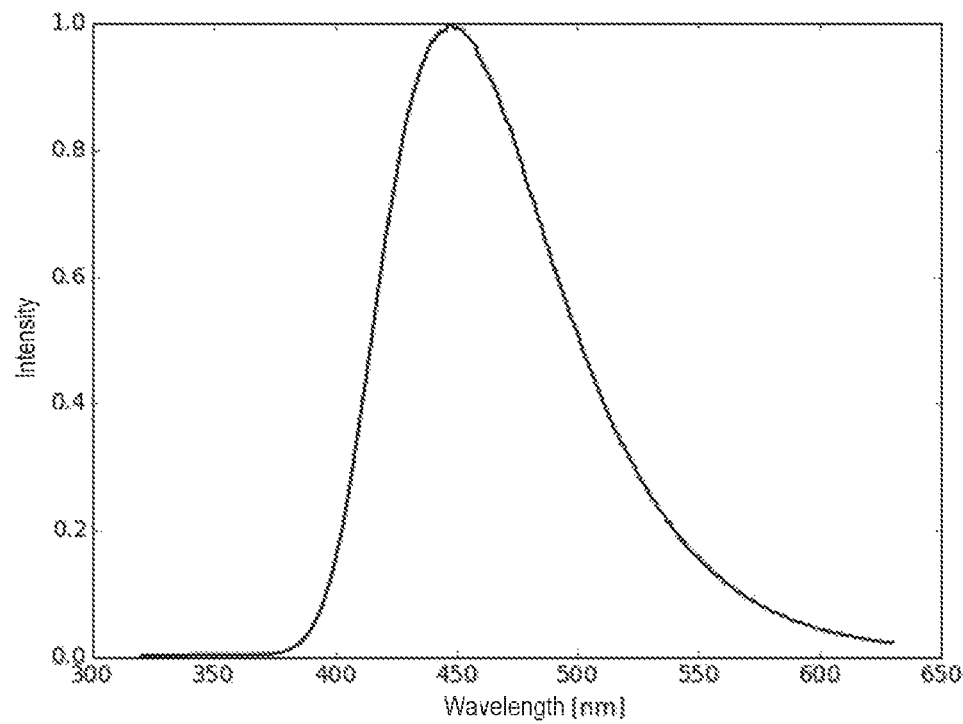
FIG. 8 is an emission spectrum of Example 8 (10% in PMMA).

FIG. 8 shows the emission spectrum of Example 8 (10% in PMMA). The emission maximum is at 448 nm. The photoluminescence quantum yield (PLQY) is 32% and the full width at half maximum (FWHM) is 86 nm (0.51 eV). A CIE$_y$ of 0.15 and a BMI of 213 are found.

Example 9

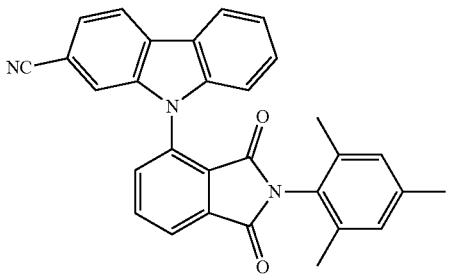 [SMILES: Cc1cc(C)c(N2C(=O)c3cccc(-n4c5ccccc5c5ccc(C#N)cc54)c3C2=O)c(C)c1]

Example 9 was synthesized by the following method:

In a Schlenk flask, under a nitrogen atmosphere, 3-(2-bromocarbazolyl)-N-mesitylphthalimide (1 equivalent) and CuCN (1.5 equivalents) in dry DMF (2 ml per mmol of aryl bromide) were heated to 150° C. for 24 h. After cooling to room temperature, the brown precipitate formed was filtered off and washed with DMF. By adding twice the volume of water to the filtrate, the crude product was precipitated as a yellow-green solid. The precipitate was filtered off, washed with water and taken up in ethyl acetate. The resulting solution was dried over MgSO$_4$ and freed of the solvent under reduced pressure. The residue was purified by MPLC (eluent: CH$_2$Cl$_2$/cyclohexane 50:50-100:0). Yield: 12%.

$^1$H NMR (500 MHz, chloroform-d) δ 8.20 (dd, J=8.0, 0.7 Hz, 1H), 8.19-8.15 (m, 2H), 8.08 (t, J=7.7 Hz, 1H), 7.97 (dd, J=8.0, 1.0 Hz, 1H), 7.56 (dd, J=8.1, 1.3 Hz, 1H), 7.53-7.47 (m, 2H), 7.38 (ddd, J=8.0, 7.2, 0.9 Hz, 1H), 7.30-7.27 (m, 1H), 6.95 (s, 1H), 6.93 (s, 1H), 2.28 (s, 3H), 2.14 (s, 3H), 2.08 (s, 3H).

Figure 9:
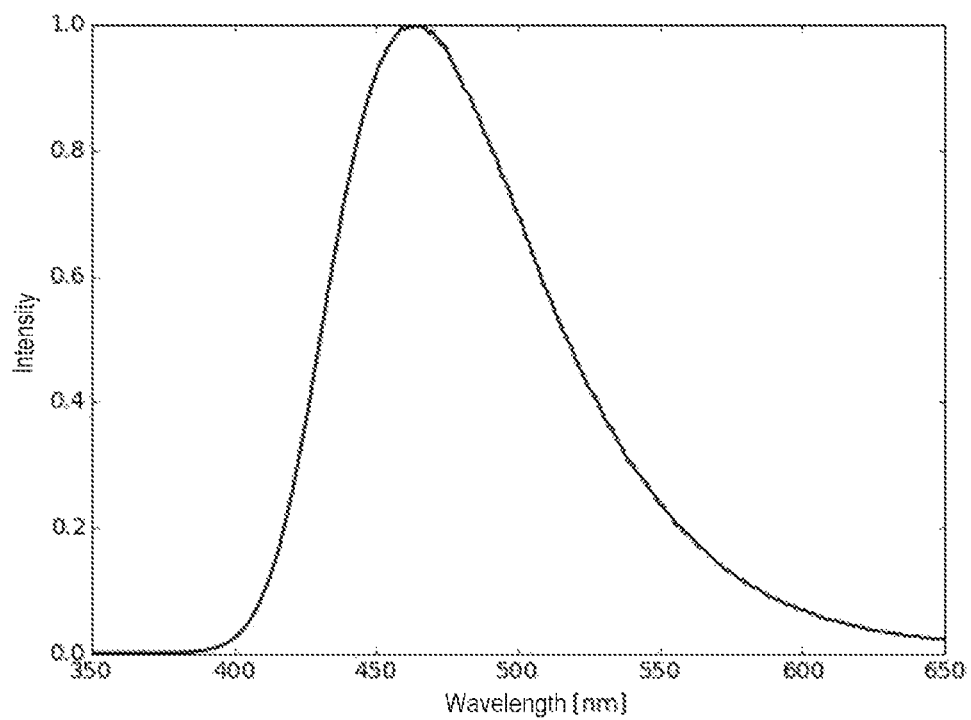
FIG. 9 is an emission spectrum of Example 9 (10% in PMMA).

FIG. 9 shows the emission spectrum of Example 9 (10% in PMMA). The emission maximum is at 463 nm. The photoluminescence quantum yield (PLQY) is 36% and the full width at half maximum (FWHM) is 87 nm (0.48 eV). A CIE$_y$ of 0.21 and a BMI of 171 are found.

Example 10

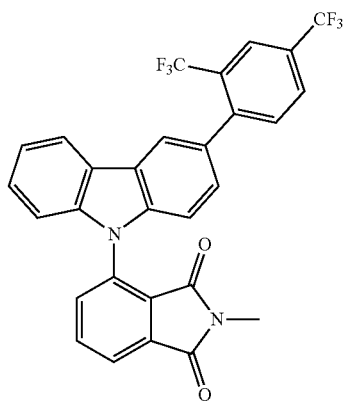 [SMILES: CN1C(=O)c2cccc(-n3c4ccccc4c4cc(-c5ccc(C(F)(F)F)cc5C(F)(F)F)ccc43)c2C1=O]

Example 10 was prepared according to GM5 from 3-(3-bromocarbazolyl)-N-methylphthalimide and 2,4-bis(trifluoromethyl)phenylboronic acid in a yield of 46%.

$^1$H NMR (500 MHz, chloroform-d) δ 8.14 (dt, J=7.7, 0.9 Hz, 1H), 8.10 (d, J=1.6 Hz, 1H), 8.06-8.04 (m, 1H), 8.03 (dd, J=7.3, 1.1 Hz, 1H), 7.98-7.93 (m, 1H), 7.90 (dd, J=8.0, 1.1 Hz, 1H), 7.88-7.84 (m, 1H), 7.63 (d, J=8.0 Hz, 1H), 7.43 (ddd, J=8.4, 7.2, 1.2 Hz, 1H), 7.37-7.31 (m, 2H), 7.20 (d, J=8.4 Hz, 1H), 7.18-7.16 (m, 1H), 3.14 (s, 3H).

$^{19}$F NMR (471 MHz, CDCl3) δ −57.02, −62.64.

Figure 10:
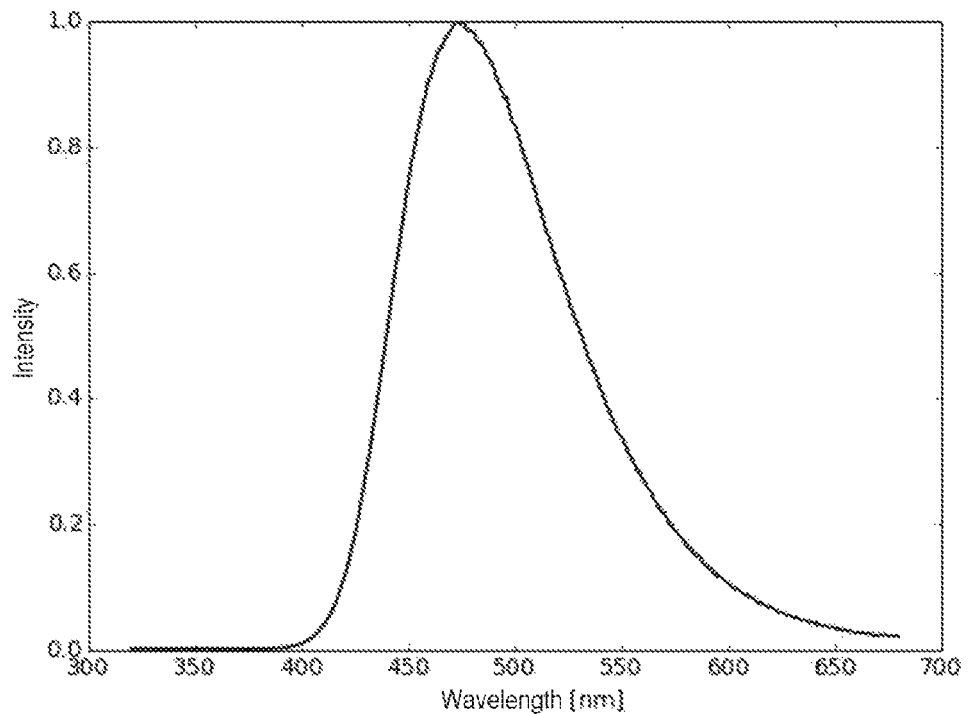
FIG. 10 is an emission spectrum of Example 10 (10% in PMMA).

FIG. 10 shows the emission spectrum of Example 10 (10% in PMMA). The emission maximum is at 474 nm. The photoluminescence quantum yield (PLQY) is 61% and the full width at half maximum (FWHM) is 92 nm (0.49 eV). A CIE$_y$ of 0.28 and a BMI of 218 are found. The emission lifetime is 7.0 µs.

Example 11

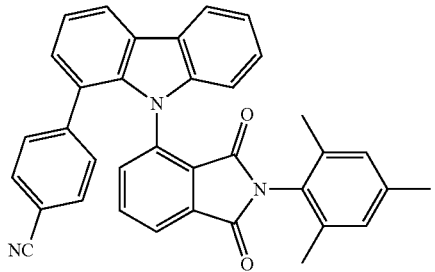 [SMILES: Cc1cc(C)c(N2C(=O)c3cccc(-n4c5ccccc5c5cccc(-c6ccc(C#N)cc6)c54)c3C2=O)c(C)c1]

Example 11 was prepared according to GM5 from 3-(1-bromocarbazolyl)-N-mesitylphthalimide and 4-cyanophenylboronic acid in a yield of 22%.

$^1$H NMR (500 MHz, chloroform-d) δ 8.22 (dd, J=7.8, 1.2 Hz, 1H), 8.19-8.16 (m, 1H), 7.80 (dd, J=7.4, 0.9 Hz, 1H), 7.56 (t, J=7.7 Hz, 1H), 7.44-7.37 (m, 3H), 7.37-7.24 (m, 7H), 7.05 (dt, J=8.2, 0.9 Hz, 1H), 6.96 (s, 1H), 6.90 (s, 1H), 2.27 (s, 3H), 2.15 (s, 3H), 1.99 (s, 3H).

Figure 11:
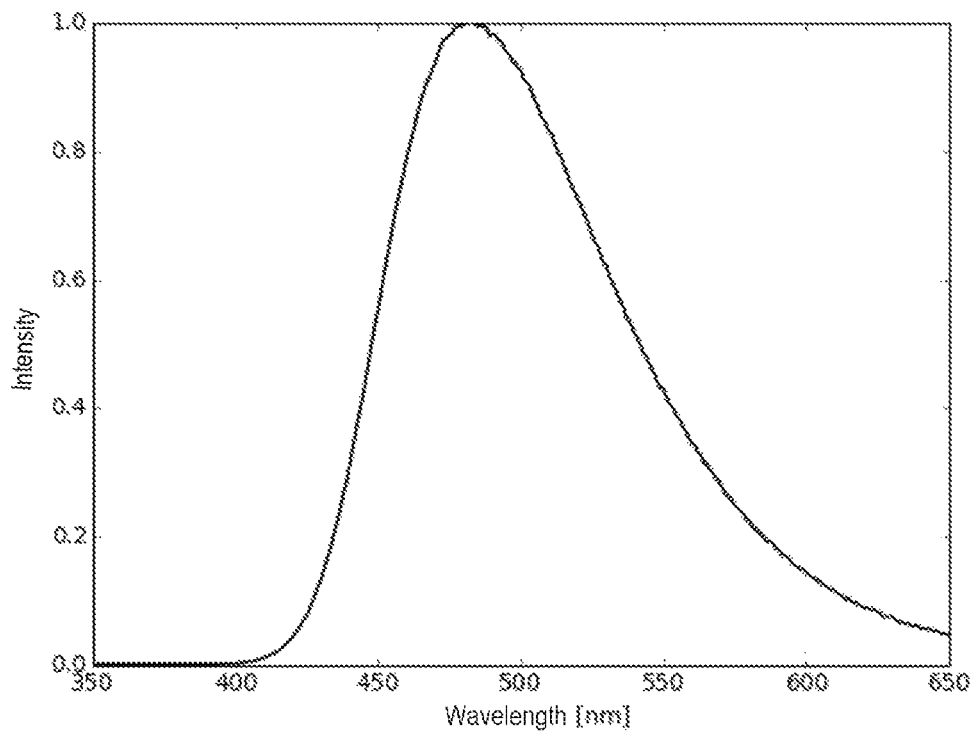
FIG. 11 is an emission spectrum of Example 11 (10% in PMMA).

FIG. 11 shows the emission spectrum of Example 11 (10% in PMMA). The emission maximum is at 482 nm. The photoluminescence quantum yield (PLQY) is 61% and the full width at half maximum (FWHM) is 94 nm (0.48 eV). A CIE$_y$ of 0.33 and a BMI of 185 are found.

Example 12

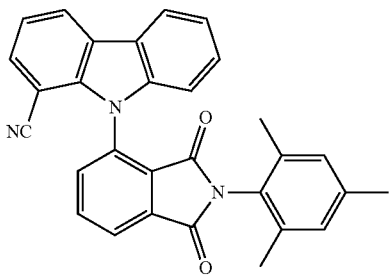 [SMILES: Cc1cc(C)c(N2C(=O)c3cccc(-n4c5ccccc5c5cccc(C#N)c54)c3C2=O)c(C)c1]

Example 12 was prepared by the following method:

In a two-neck flask with reflux condenser, under a nitrogen atmosphere, 3-(1-bromocarbazolyl)-N-mesitylphthalimide (1 equivalent) and CuCN (1.5 equivalents) in dry DMF were heated to 250° C. over 15 h. After cooling to RT, the crude product was precipitated out of the reaction solution by adding the same volume of water. The precipitate was filtered off and treated with CH$_2$Cl$_2$. The resulting solution was washed with water, dried over MgSO$_4$ and freed of the solvent under reduced pressure. The residue was washed with hot ethanol. The wash solution was discarded and the residue was recrystallized from toluene. Yield: 69%.

$^1$H NMR (500 MHz, chloroform-d): δ=8.35 (dd, J=7.9, 1.2 Hz, 1H), 8.19 (dd, J=7.4, 1.0 Hz, 1H), 8.16 (dt, J=7.8, 0.9 Hz, 1H), 8.05 (t, J=7.7 Hz, 1H), 7.98 (dd, J=7.9, 0.9 Hz, 1H), 7.66 (dd, J=7.6, 1.2 Hz, 1H), 7.48 (ddd, J=8.3, 7.2, 1.2 Hz, 1H), 7.39 (td, J=7.6, 0.9 Hz, 1H), 7.33 (t, J=7.7 Hz, 1H), 7.24 (dt, J=8.3, 0.8 Hz, 1H), 6.94 (bs, 1H), 6.87 (bs, 1H), 2.25 (s, 3H), 2.20 (s, 3H), 2.00 (s, 3H) ppm.

Figure 12:
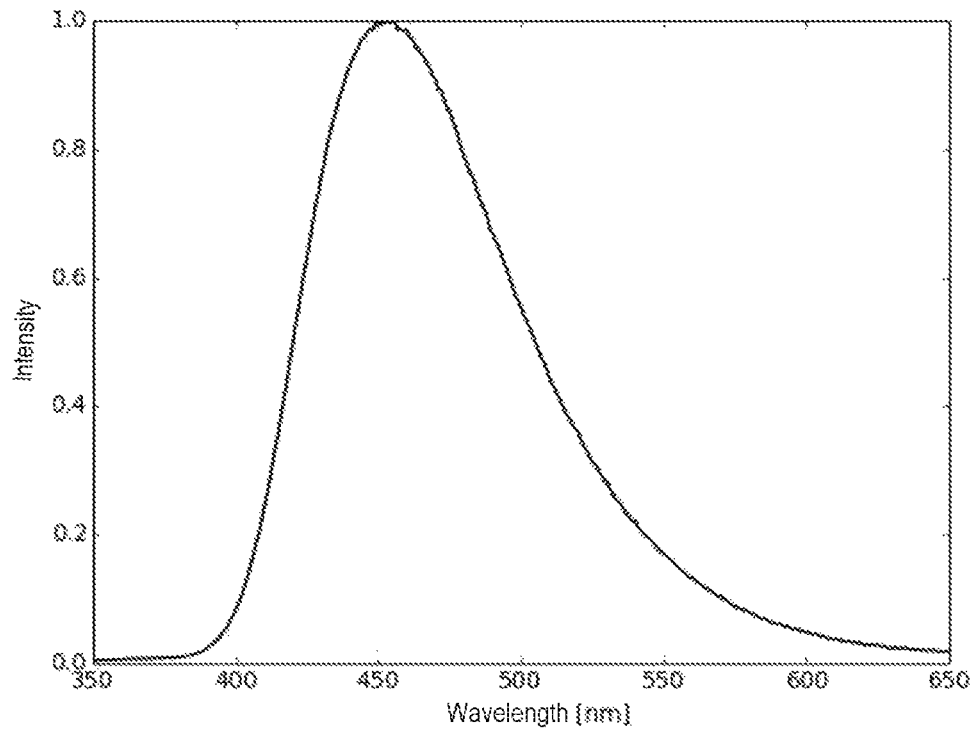
FIG. 12 is an emission spectrum of Example 12 (10% in PMMA).

FIG. 12 shows the emission spectrum of Example 12 (10% in PMMA). The emission maximum is at 453 nm. The photoluminescence quantum yield (PLQY) is 44% and the full width at half maximum (FWHM) is 84 nm (0.49 eV). A CIE$_y$ of 0.16 and a BMI of 275 are found.

Example 13

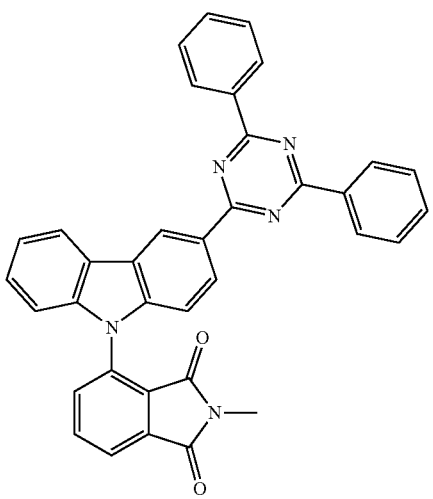 [SMILES: CN1C(=O)c2cccc(-n3c4ccccc4c4cc(-c5nc(-c6ccccc6)nc(-c6ccccc6)n5)ccc43)c2C1=O]

Example 13 was prepared according to GM4 proceeding from 3-(3-bromocarbazolyl)-N-methylphthalimide in a yield of 57%.

$^1$H NMR (500 MHz, chloroform-d) δ 9.62-9.61 (m, 1H), 8.89 (dd, J=8.7, 1.7 Hz, 1H), 8.86-8.81 (m, 4H), 8.41-8.38 (m, 1H), 8.07 (dd, J=7.3, 1.0 Hz, 1H), 7.99 (t, J=7.6 Hz, 1H), 7.93 (dd, J=7.9, 1.0 Hz, 1H), 7.66-7.58 (m, 6H), 7.48-7.44 (m, 1H), 7.42 (td, J=7.4, 1.2 Hz, 1H), 7.29-7.26 (m, 1H), 7.21-7.19 (m, 1H), 3.13 (s, 3H).

Figure 13:
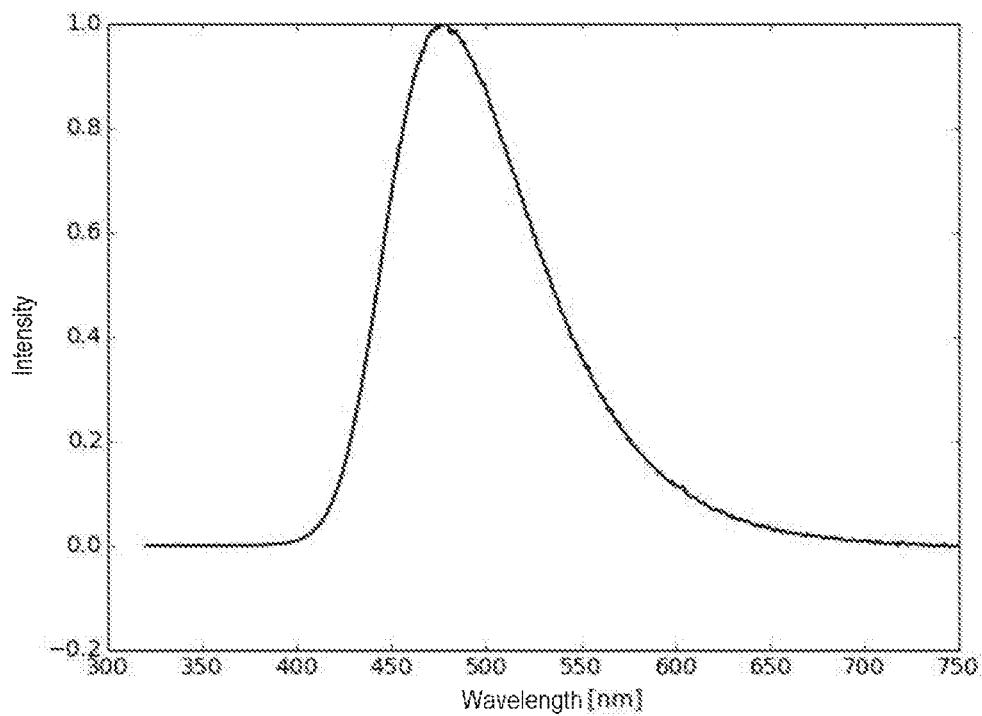
FIG. 13 is an emission spectrum of Example 13 (10% in PMMA).

FIG. 13 shows the emission spectrum of Example 13 (10% in PMMA). The emission maximum is at 478 nm. The photoluminescence quantum yield (PLQY) is 58% and the full width at half maximum (FWHM) is 92 nm (0.48 eV). A CIE$_y$ of 0.30 and a BMI of 193 are found.

Example 14

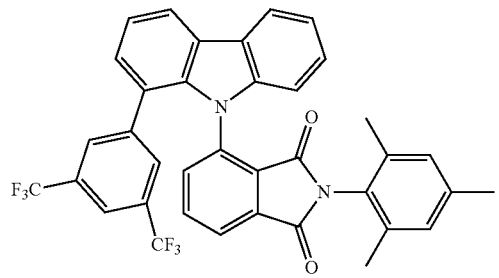 [SMILES: Cc1cc(C)c(N2C(=O)c3cccc(-n4c5ccccc5c5cccc(-c6cc(C(F)(F)F)cc(C(F)(F)F)c6)c54)c3C2=O)c(C)c1]

Example 14 was prepared according to GM5 from 3-(1-bromocarbazolyl)-N-mesitylphthalimide and 3,5-bis(trifluoromethyl)benzeneboronic acid in a yield of 49%.

$^1$H NMR (500 MHz, chloroform-d) δ 8.26 (dd. J=7.8, 1.2 Hz, 1H), 8.20-8.16 (m, 1H), 7.76 (dd, J=7.4, 0.9 Hz, 1H), 7.79-7.47 (br. s., 2H), 7.61 (s, 1H), 7.45 (t, J=7.6 Hz, 1H), 7.41 (t, J=7.41 Hz, 1H), 7.39-7.32 (m, 3H), 7.25 (dd, J=8.0, 0.9 Hz, 1H), 7.01-6.97 (m, 1H), 6.95-6.92 (m, 1H), 6.91-6.89 (m, 1H), 2.27 (s, 3H), 2.10 (s, 3H), 2.03 (s, 3H).

$^{19}$F NMR (471 MHz, CDCl3) δ −62.5.

Figure 14:
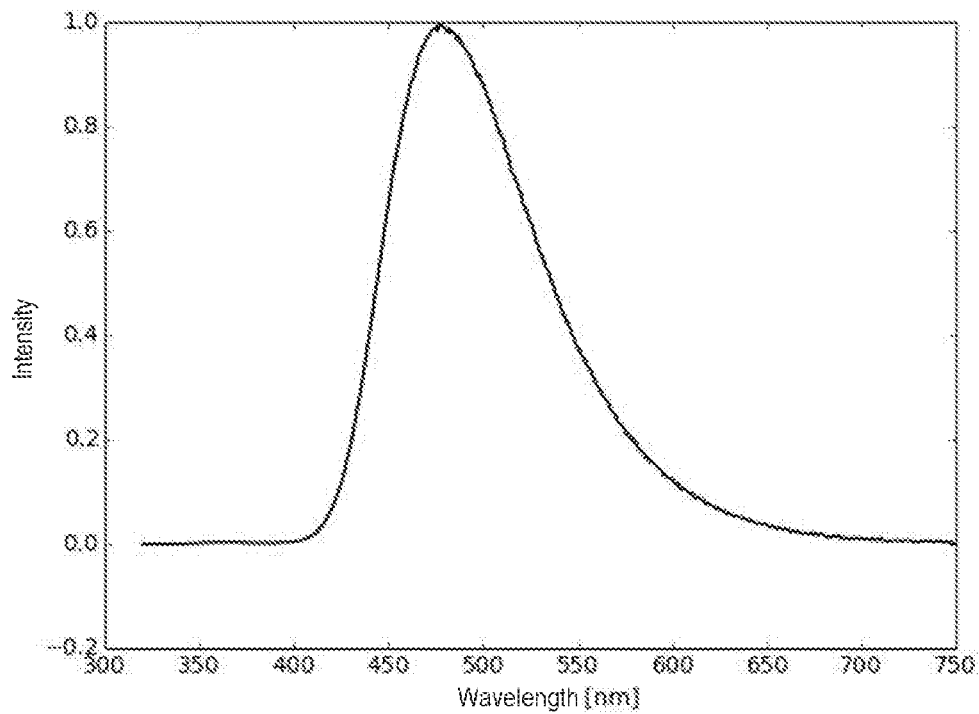
FIG. 14 is an emission spectrum of Example 14 (10% in PMMA).

FIG. 14 shows the emission spectrum of Example 14 (10% in PMMA). The emission maximum is at 477 nm. The photoluminescence quantum yield (PLQY) is 65% and the full width at half maximum (FWHM) is 93 nm (0.48 eV). A CIE$_y$ of 0.31 and a BMI of 210 are found.

Example 15

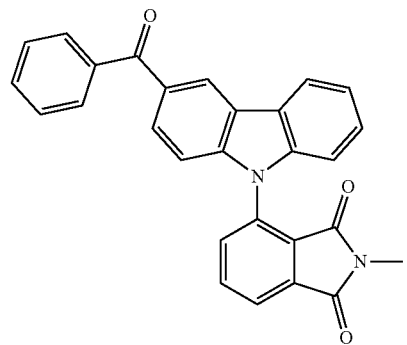 [SMILES: CN1C(=O)c2cccc(-n3c4ccccc4c4cc(C(=O)c5ccccc5)ccc43)c2C1=O]

$^1$H NMR (500 MHz, chloroform-d) δ 8.65 (dd, J=1.7, 0.6 Hz, 1H), 8.17 (dt, J=7.8, 1.0 Hz, 1H), 8.06 (dd, J=7.4, 1.0

Hz, 1H), 7.98 (t. J=7.8 Hz, 1H), 7.96 (dd, J=8.6, 1.6 Hz, 1H), 7.89-7.85 (m, 3H), 7.64-7.59 (m, 1H), 7.55-7.50 (m, 2H), 7.44 (ddd, J=8.3, 7.2, 1.2 Hz, 1H), 7.36 (ddd. J=8.1, 7.2, 1.0 Hz, 1H), 7.19-7.15 (m, 2H), 3.12 (s, 3H).

Figure 15:
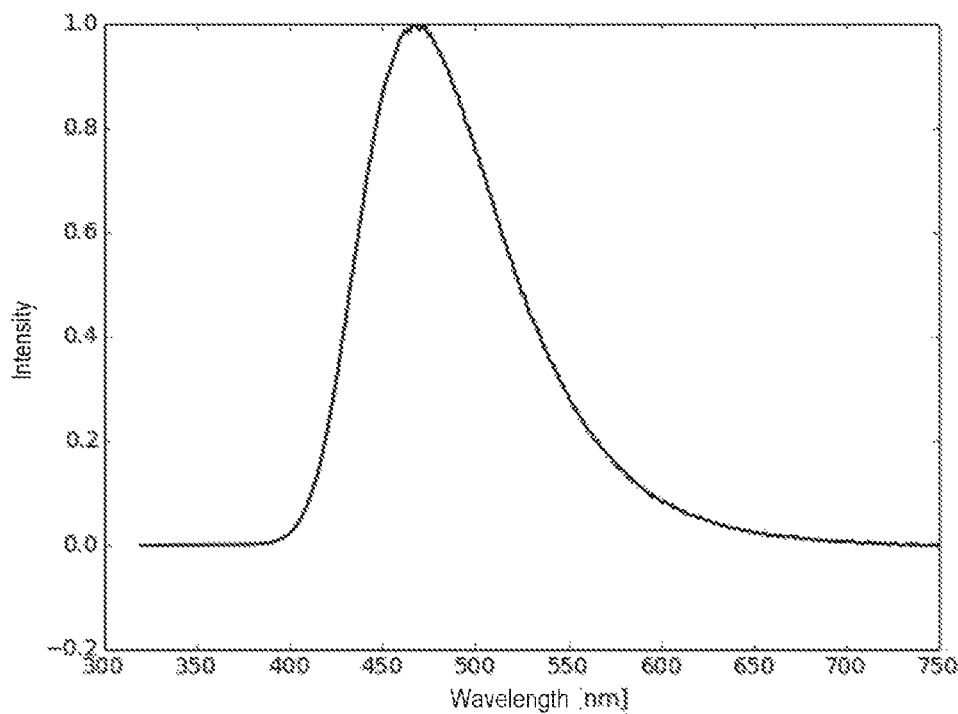
FIG. 15 is an emission spectrum of Example 15 (10% in PMMA).

FIG. 15 shows the emission spectrum of Example 15 (10% in PMMA). The emission maximum is at 467 nm. The photoluminescence quantum yield (PLQY) is 48% and the full width at half maximum (FWHM) is 92 nm (0.50 eV). A $CIE_y$ of 0.24 and a BMI of 200 are found.

Example 16

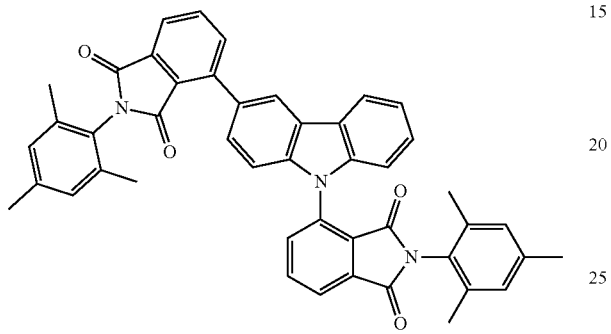

Example 16 was prepared according to GM4 by the conversion of 3-(3-bromocarbazolyl)-N-mesitylphthalimide to the corresponding boronic acid pinacol ester and subsequent reaction with N-mesityl-3-chlorophthalimide in a yield of 87%.

$^1$H NMR (500 MHz, chloroform-d) δ 8.14 (d, J=7.7 Hz, 1H), 8.10 (dd, J=6.9, 1.4 Hz, 1H), 8.03-7.99 (m, 1H), 7.99-7.94 (m, 2H), 7.89-7.82 (m, 2H), 7.68 (dd. J=8.5, 1.8 Hz, 1H), 7.40 (ddd, J=8.3, 7.2, 1.2 Hz, 1H), 7.35-7.23 (m, 4H), 6.97 (s, 2H), 6.93 (m, 2H), 2.30 (s, 3H), 2.27 (s, 3H), 2.14 (s, 3H), 2.13 (s, 3H), 2.12 (s, 3H), 2.11 (s, 3H).

Figure 16:
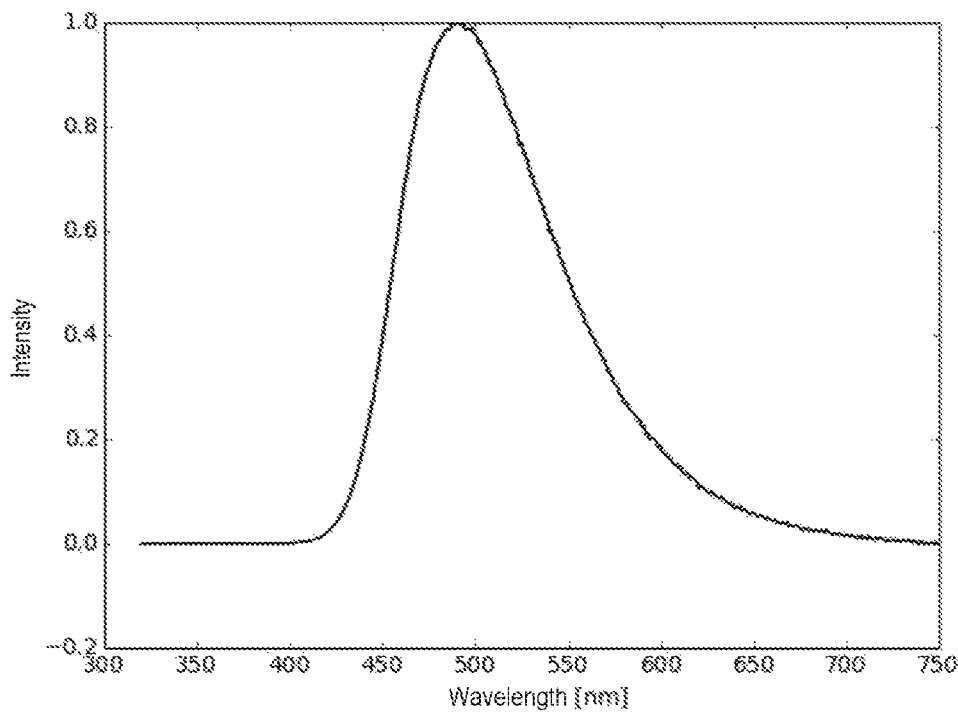
FIG. 16 is an emission spectrum of Example 16 (10% in PMMA).

FIG. 16 shows the emission spectrum of Example 16 (10% in PMMA). The emission maximum is at 489 nm. The photoluminescence quantum yield (PLQY) is 59% and the full width at half maximum (FWHM) is 97 nm (0.48 eV). A $CIE_y$ of 0.39 and a BMI of 151 are found.

Example 17

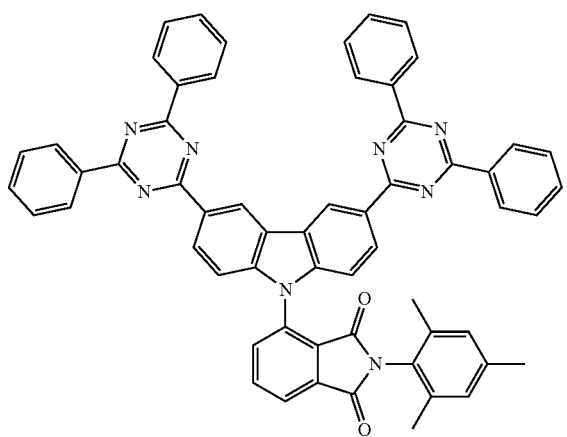 [SMILES: Cc1cc(C)c(N2C(=O)c3cccc(-n4c5ccc(-c6nc(-c7ccccc7)nc(-c7ccccc7)n6)cc5c5cc(-c6nc(-c7ccccc7)nc(-c7ccccc7)n6)ccc54)c3C2=O)c(C)c1]

Example 17 was prepared according to GM4 by the conversion of 3-(3,6-dibromocarbazolyl)-N-mesitylphthalimide to the corresponding bis(boronic acid pinacol ester) and subsequent reaction with chlorodiphenyltriazine in a yield of 79%.

$^1$H NMR (500 MHz, chloroform-d): δ=9.77 (dd, J=1.7, 0.6 Hz, 2H), 8.93 (dd, J=8.7, 1.7 Hz, 2H), 8.88-8.86 (m, 8H), 8.23 (dd, J=7.2, 1.2 Hz, 1H), 8.15-8.09 (m, 2H), 7.68-7.62 (m, 12H), 7.40 (dd, J=8.6, 0.6 Hz, 2H), 6.94 (s, 2H), 2.26 (s, 3H), 2.16 (s, 6H) ppm.

Figure 17:
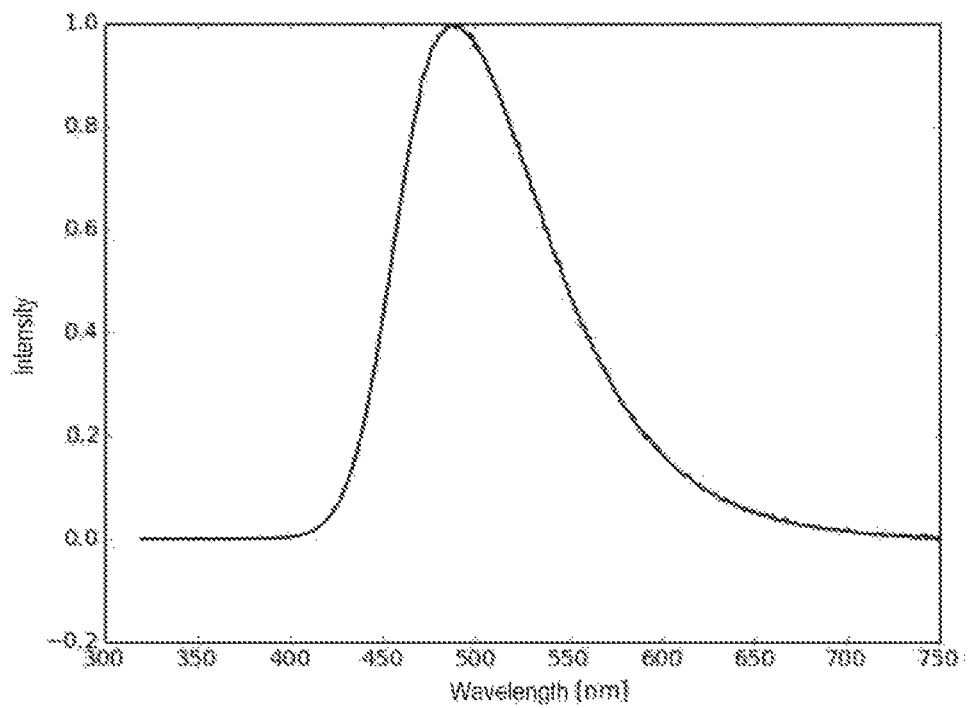
FIG. 17 is an emission spectrum of Example 17 (10% in PMMA).

FIG. 17 shows the emission spectrum of Example 17 (10% in PMMA). The emission maximum is at 488 nm. The photoluminescence quantum yield (PLQY) is 55% and the full width at half maximum (FWHM) is 94 nm (0.47 eV). A $CIE_y$ of 0.37 and a BMI of 149 are found.

Example 18

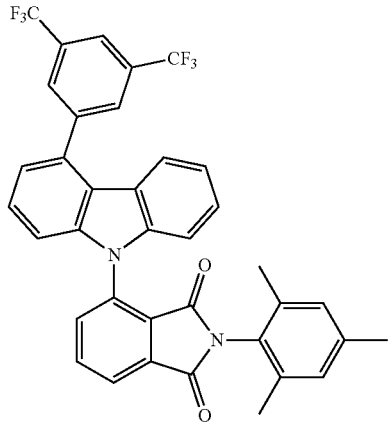 [SMILES: Cc1cc(C)c(N2C(=O)c3cccc(-n4c5ccccc5c5c(-c6cc(C(F)(F)F)cc(C(F)(F)F)c6)cccc54)c3C2=O)c(C)c1]

Example 18 was prepared according to GM5 from 3-(4-bromocarbazolyl)-N-mesitylphthalimide and 3,5-bis(trifluoromethyl)benzeneboronic acid in a yield of 63%.

$^1$H NMR (500 MHz, chloroform-d): δ=8.16 (d, J=1.0 Hz, 1H), 8.15 (d, J=1.0 Hz, 2H), 8.07 (t, J=7.7 Hz, 1H), 8.01 (s, 1H), 7.99 (dd, J=7.9, 1.0 Hz, 1H), 7.46 (dd, J=8.3, 7.3 Hz, 1H), 7.37 (ddd, J=8.3, 7.1, 1.2 Hz, 1H), 7.33 (dt, J=8.1, 0.9 Hz, 1H), 7.28 (dd, J=8.3, 0.9 Hz, 1H), 7.24 (d, J=8.1 Hz, 1H), 7.17 (dd, J=7.4, 0.9 Hz, 1H), 7.08 (ddd, J=8.1, 7.1, 1.0 Hz, 1H), 6.93 (s, 2H), 2.27 (s, 3H), 2.12 (s, 3H), 2.09 (s, 3H) ppm.

Figure 18:
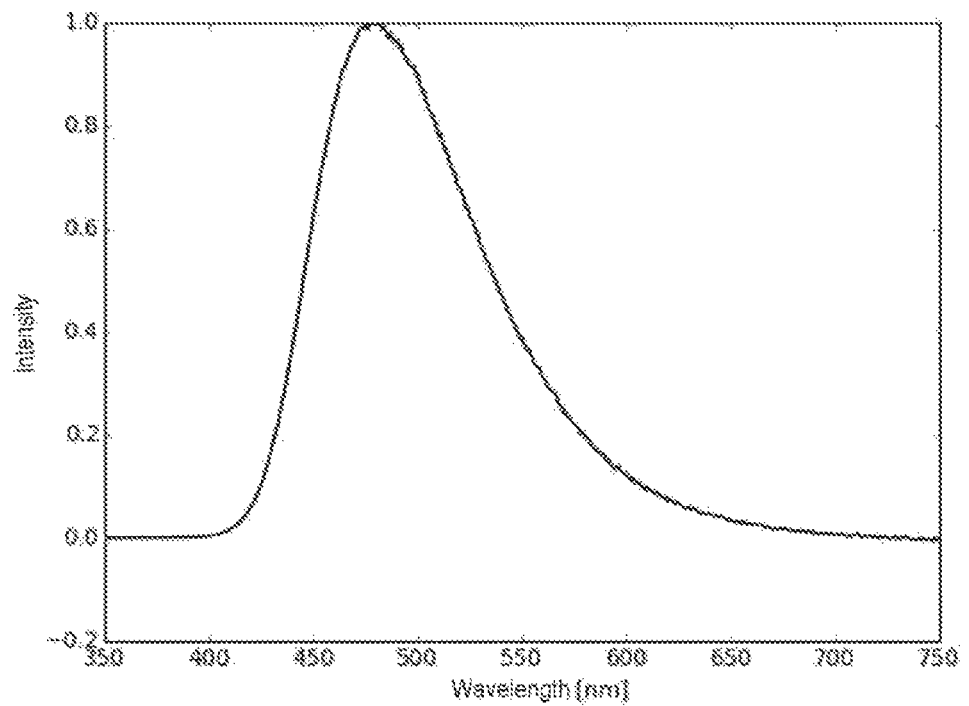
FIG. 18 is an emission spectrum of Example 18 (10% in PMMA).

FIG. 18 shows the emission spectrum of Example 18 (10% in PMMA). The emission maximum is at 480 nm. The photoluminescence quantum yield (PLQY) is 58% and the full width at half maximum (FWHM) is 92 nm (0.48 eV). A $CIE_y$ of 0.31 and a BMI of 187 are found.

Example 19

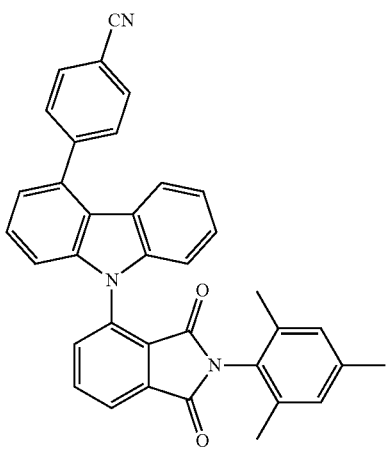 [SMILES: Cc1cc(C)c(N2C(=O)c3cccc(-n4c5ccccc5c5c(-c6ccc(C#N)cc6)cccc54)c3C2=O)c(C)c1]

Example 19 was prepared according to GM5 from 3-(4-bromocarbazolyl)-N-mesitylphthalimide and 4-cyanophenylboronic acid in a yield of 42%.

$^1$H NMR (500 MHz, chloroform-d): δ=8.14 (dd, J=7.4, 1.0 Hz, 1H), 8.05 (t, J=7.7 Hz, 1H), 7.98 (dd, J=8.0, 1.0 Hz, 1H), 7.85-7.76 (m, 2H), 7.78-7.76 (m, 2H), 7.44 (dd, J=8.3, 7.3 Hz, 1H), 7.40 (dt, J=8.0, 0.9 Hz, 1H), 7.35-7.33 (m, 1H), 7.24 (d, 1H), 7.22 (dt, J=8.3, 0.9 Hz, 1H), 7.12 (dd, J=7.3, 0.9 Hz, 1H), 7.07 (ddd. J=8.1, 7.0, 1.0 Hz, 1H), 6.93 (s, 2H), 2.27 (s, 3H), 2.12 (s, 3H), 2.09 (s, 3H) ppm.

Figure 19:
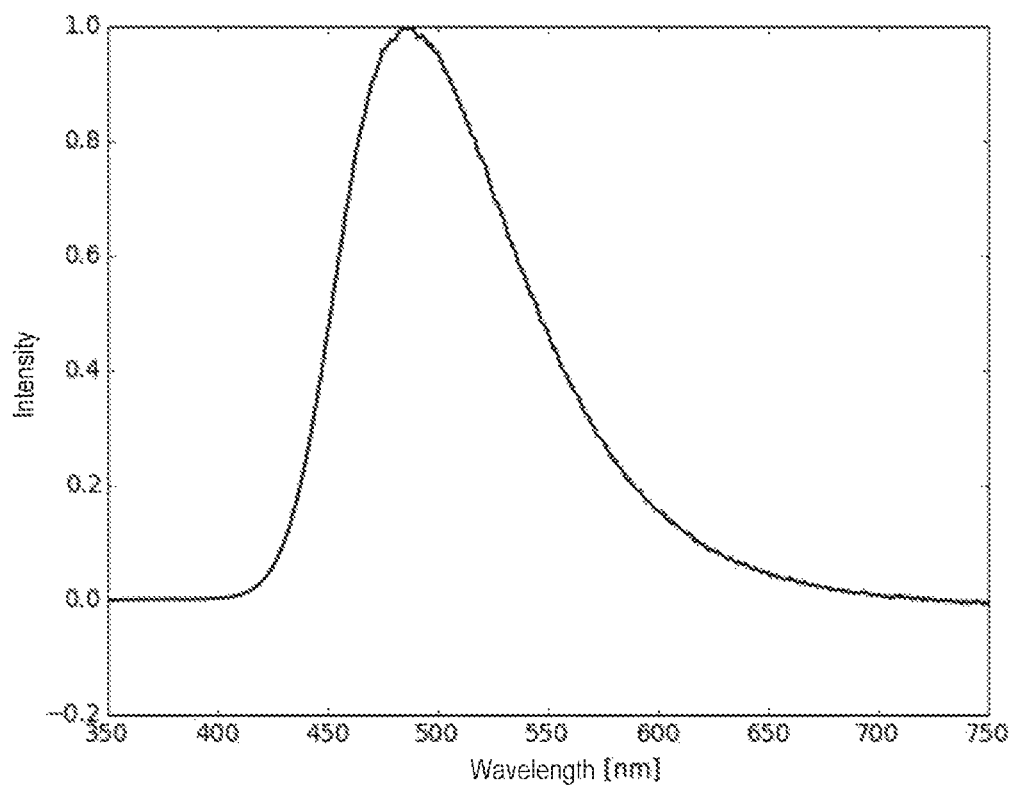
FIG. 19 is an emission spectrum of Example 19 (10% in PMMA).
Figure 20:
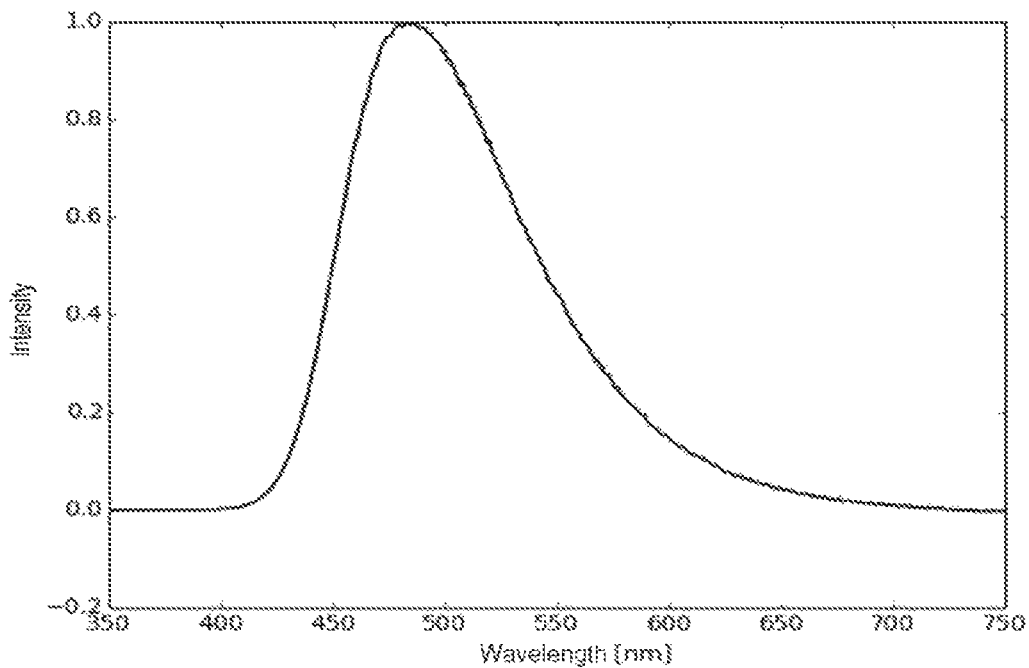
FIG. 20 is an emission spectrum of Example 20 (10% in PMMA).

FIG. 19 shows the emission spectrum of Example 19 (10% in PMMA). The emission maximum is at 486 nm. The photoluminescence quantum yield (PLQY) is 56% and the full width at half maximum (FWHM) is 94 nm (0.47 eV). A CIE$_y$ of 0.36 and a BMI of 156 are found.

Example 20

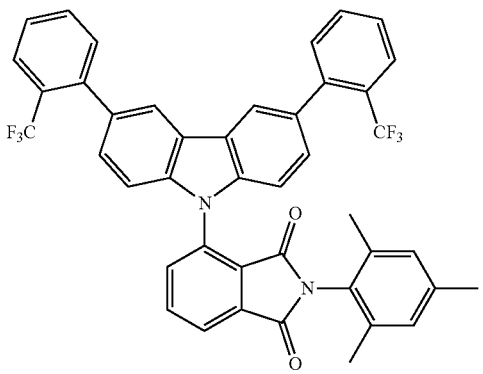 [SMILES: Cc1cc(C)c(N2C(=O)c3cccc(-n4c5ccc(-c6ccccc6C(F)(F)F)cc5c5cc(-c6ccccc6C(F)(F)F)ccc54)c3C2=O)c(C)c1]

Example 20 was prepared according to GM5 from 3-(3,6-dibromocarbazolyl)-N-mesitylphthalimide and 2-trifluoromethylphenylboronic acid in a yield of 40%.

$^1$H NMR (500 MHz, chloroform-d): δ=8.12 (dd, J=7.1, 1.3 Hz, 1H), 8.09-8.03 (m, 4H), 7.77 (d. J=7.7 Hz, 2H), 7.58 (t, J=7.6 Hz, 2H), 7.48 (d. J=7.9 Hz, 2H), 7.44 (d, J=7.8 Hz, 2H), 7.38 (d, J=7.4 Hz, 2H), 7.28 (d, J=8.5 Hz, 2H), 6.96 (s, 2H), 2.29 (s, 3H), 2.14 (s, 6H) ppm.

The emission spectrum of Example 20 (10% in PMMA) was measured. The emission maximum is at 484 nm. The photoluminescence quantum yield (PLQY) is 68% and the full width at half maximum (FWHM) is 94 nm (0.48 eV). A CIE$_y$ of 0.35 and a BMI of 194 are found.

Example 21

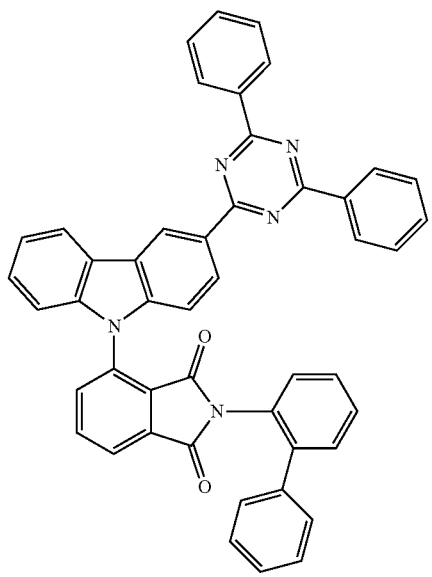 [SMILES: O=C1c2cccc(-n3c4ccccc4c4cc(-c5nc(-c6ccccc6)nc(-c6ccccc6)n5)ccc43)c2C(=O)N1c1ccccc1-c1ccccc1]

Example 21 was prepared according to GM4 proceeding from 3-(3-bromocarbazolyl)-N-(o-biphenyl)phthalimide in a yield of 66%.

$^1$H NMR (500 MHz, chloroform-d): δ (ppm)=9.54 (dd, J=12.2, 1.6 Hz), 8.87-8.85 (m), 8.83-8.81 (m), 8.73 (dd, J=8.7, 1.7 Hz), 8.33-8.31 (m), 8.05 (td. J=7.5, 1.0 Hz), 7.98 (td, J=7.7, 3.1 Hz, 1H), 7.92 (dd, J=7.9, 1.1 Hz), 7.91 (dd, J=7.9, 1.1 Hz), 7.65-7.27 (m), 6.60-6.57 (m). The product consists of two rotamers, the NMR signals of which obscure one another.

Figure 21:
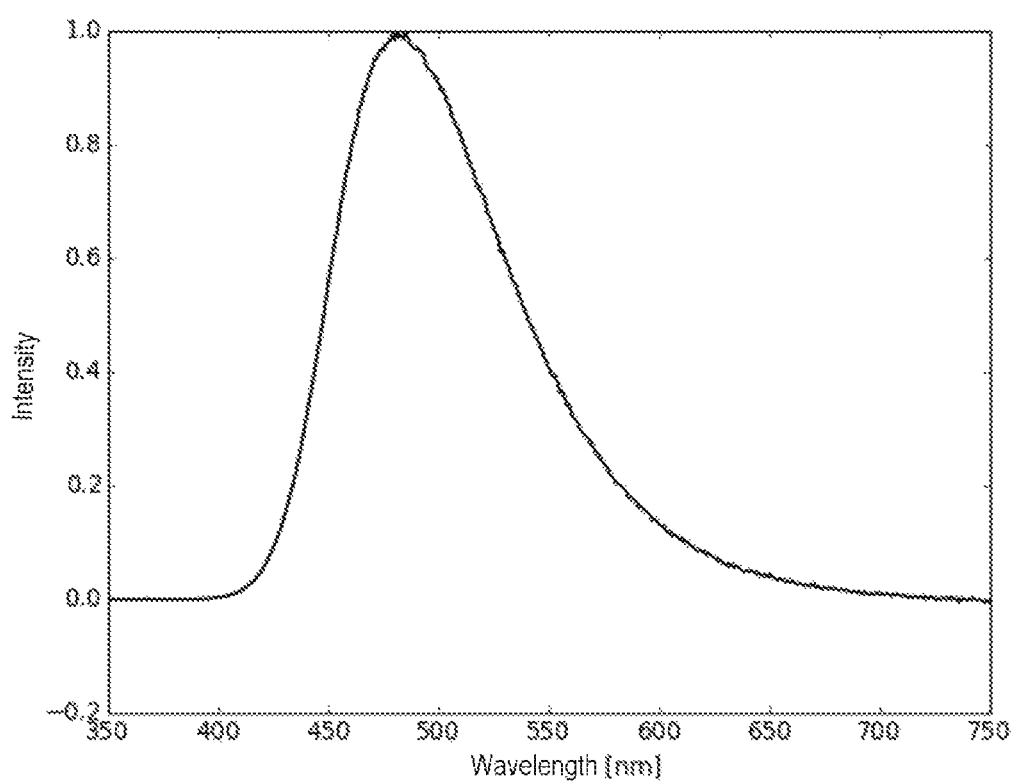
FIG. 21 is an emission spectrum of Example 21 (10% in PMMA).

FIG. 21 shows the emission spectrum of Example 21 (10% in PMMA). The emission maximum is at 481 nm. The photoluminescence quantum yield (PLQY) is 68% and the full width at half maximum (FWHM) is 92 nm (0.47 eV). A CIE$_y$ of 0.33 and a BMI of 206 are found. The emission lifetime is 5.7 μs.

Example 22

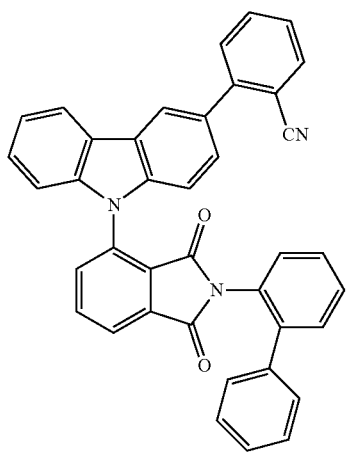 [SMILES: N#Cc1ccccc1-c1ccc2c(c1)c1ccccc1n2-c1cccc2c1C(=O)N(c1ccccc1-c1ccccc1)C2=O]

Example 22 was prepared according to GM4 proceeding from 3-(3-bromocarbazolyl)-N-(o-biphenyl)phthalimide in a yield of 42%.

The emission spectrum of Example 22 (10% in PMMA) was recorded. The emission maximum is at 489 nm. The photoluminescence quantum yield (PLQY) is 62% and the full width at half maximum (FWHM) is 97 nm (0.48 eV). A $CIE_y$ of 0.37 and a BMI of 168 are found. The emission lifetime is 5.9 µs.

Example 23

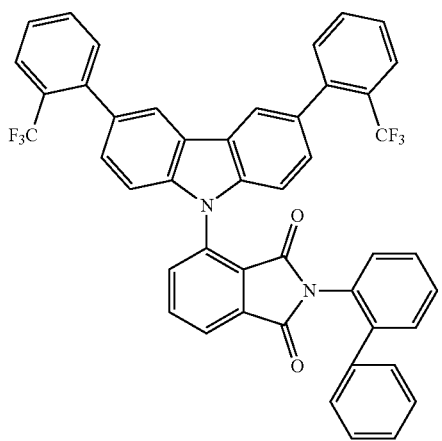 [SMILES: O=C1c2cccc(-n3c4ccc(-c5ccccc5C(F)(F)F)cc4c4cc(-c5ccccc5C(F)(F)F)ccc43)c2C(=O)N1c1ccccc1-c1ccccc1]

Example 23 was prepared according to GM5 from 3-(3,6-dibromocarbazolyl)-N-(o-biphenyl)phthalimide and 2-trifluoromethylphenylboronic acid in a yield of 80%.

The emission spectrum of Example 23 (10% in PMMA) was measured. The emission maximum is at 483 nm. The photoluminescence quantum yield (PLQY) is 68% and the full width at half maximum (FWHM) is 93 nm (0.47 eV). A $CIE_y$ of 0.34 and a BMI of 200 are found.

Example 24

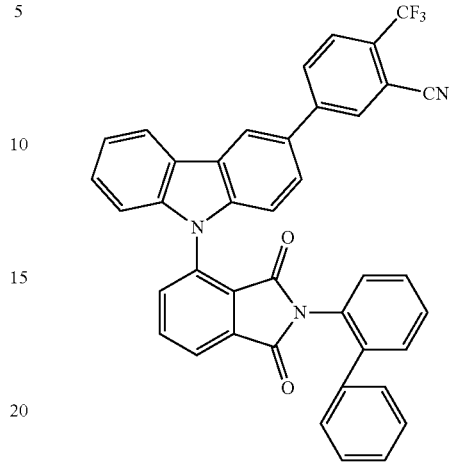

Example 24 was prepared according to GM4 by the conversion of 3-(3-bromocarbazolyl)-N-(o-biphenyl)phthalimide to the corresponding bis(boronic acid pinacol ester) and subsequent reaction with 3-bromo-6-trifluoromethyl-benzonitrile in a yield of 64%.

The emission spectrum of Example 24 (10% in PMMA) was measured. The emission maximum is at 491 nm. The photoluminescence quantum yield (PLQY) is 65% and the full width at half maximum (FWHM) is 96 nm (0.48 eV). A $CIE_y$ of 0.37 and a BMI of 176 are found.

Example 25

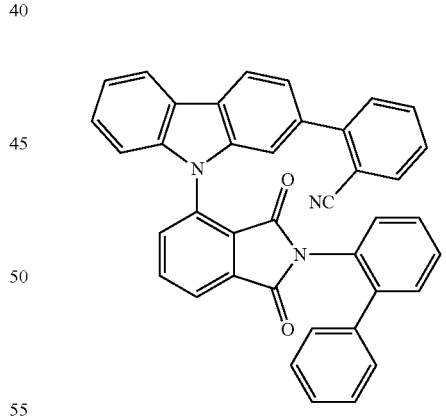

Example 25 was prepared according to GM4 by the conversion of 3-(2-bromocarbazolyl)-N-(o-biphenyl)phthalimide to the corresponding bis(boronic acid pinacol ester) and subsequent reaction with 2-bromobenzonitrile in a yield of 97%.

The emission spectrum of Example 25 (10% in PMMA) was recorded. The emission maximum is at 476 nm. The photoluminescence quantum yield (PLQY) is 61% and the full width at half maximum (FWHM) is 91 nm (0.48 eV). A $CIE_y$ of 0.29 and a BMI of 210 are found.

Example 26

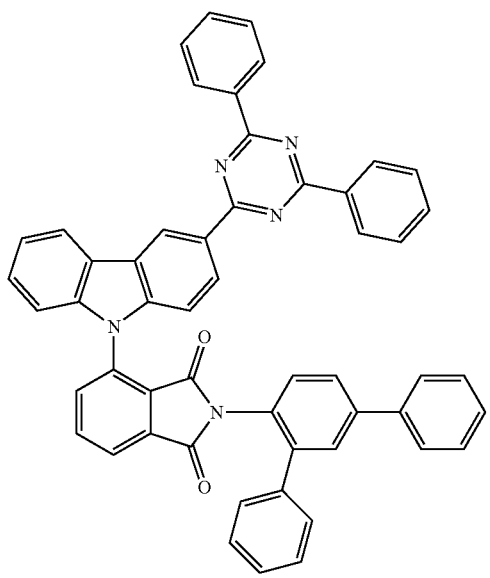 [SMILES: O=C1c2cccc(-n3c4ccccc4c4cc(-c5nc(-c6ccccc6)nc(-c6ccccc6)n5)ccc43)c2C(=O)N1c1ccc(-c2ccccc2)cc1-c1ccccc1]

Example 26 was prepared according to GM4 by the conversion of 3-(2-bromocarbazolyl)-N-(o-(meta-terphenyl))phthalimide to the corresponding bis(boronic acid pinacol ester) and subsequent reaction with chlorodiphenyltriazine in a yield of 44%.

The emission spectrum of Example 26 (10% in PMMA) was recorded. The emission maximum is at 486 nm. The photoluminescence quantum yield (PLQY) is 65% and the full width at half maximum (FWHM) is 93 nm (0.47 eV). A $CIE_y$ of 0.36 and a BMI of 181 are found. The emission lifetime is 5.6 µs.

Example 27

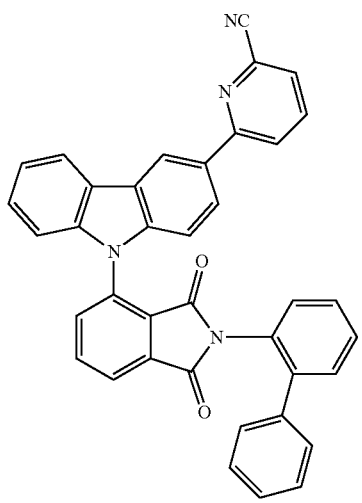 [SMILES: N#Cc1cccc(-c2ccc3c(c2)c2ccccc2n3-c2cccc3c2C(=O)N(c2ccccc2-c2ccccc2)C3=O)n1]

Example 27 was prepared according to GM4 by the conversion of 3-(2-bromocarbazolyl)-N-(o-biphenyl)phthalimide to the corresponding bis(boronic acid pinacol ester) and subsequent reaction with 2-bromo-6-cyanopyridine in a yield of 13%.

The emission spectrum of Example 27 (10% in PMMA) was recorded. The emission maximum is at 489 nm. The photoluminescence quantum yield (PLQY) is 61% and the full width at half maximum (FWHM) is 97 nm (0.48 eV). A $CIE_y$ of 0.38 and a BMI of 160 are found.

Example 28

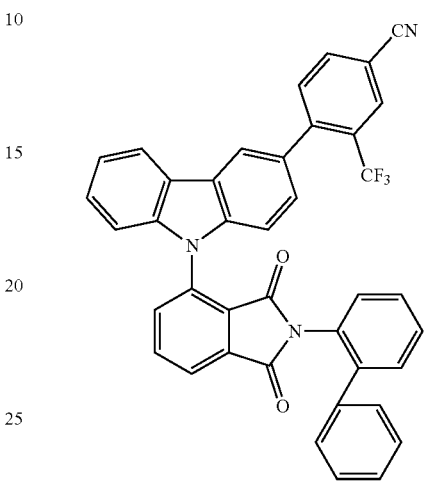

Example 28 was prepared according to GM4 by the conversion of 3-(3-bromocarbazolyl)-N-(o-biphenyl)phthalimide to the corresponding bis(boronic acid pinacol ester) and subsequent reaction with 4-bromo-3-trifluoromethyl-benzonitrile in a yield of 94%.

The emission spectrum of Example 28 (10% in PMMA) was measured. The emission maximum is at 479 nm. The photoluminescence quantum yield (PLQY) is 63% and the full width at half maximum (FWHM) is 92 nm (0.46 eV). A $CIE_y$ of 0.31 and a BMI of 203 are found.

Example 29

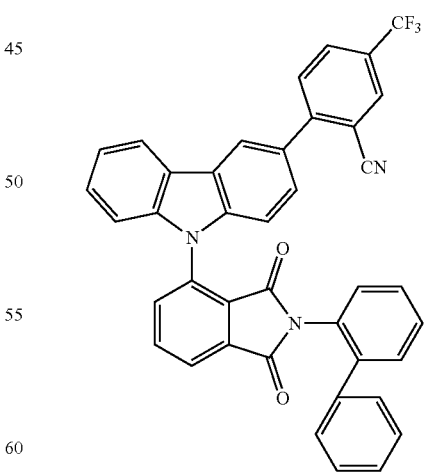

Example 29 was prepared according to GM4 by the conversion of 3-(3-bromocarbazolyl)-N-(o-biphenyl)phthalimide to the corresponding bis(boronic acid pinacol ester) and subsequent reaction with 2-bromo-5-trifluoromethyl-benzonitrile in a yield of 36%.

The emission spectrum of Example 29 (10% in PMMA) was measured. The emission maximum is at 475 nm. The photoluminescence quantum yield (PLQY) is 67% and the full width at half maximum (FWHM) is 91 nm (0.48 eV). A $CIE_y$ of 0.29 and a BMI of 231 are found.

Example 30

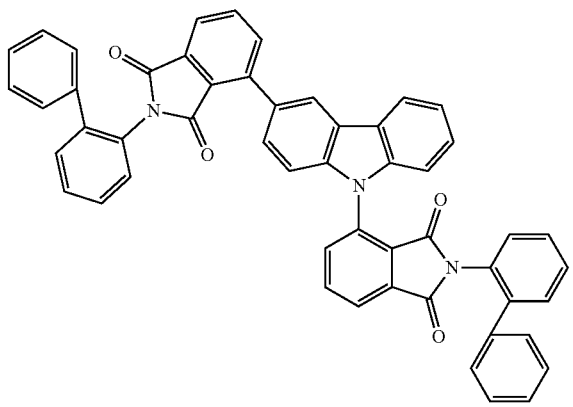 [SMILES: O=C1c2cccc(-c3ccc4c(c3)c3ccccc3n4-c3cccc4c3C(=O)N(c3ccccc3-c3ccccc3)C4=O)c2C(=O)N1c1ccccc1-c1ccccc1]

Example 30 was prepared according to GM4 by the conversion of 3-(3-bromocarbazolyl)-N-(o-biphenyl)phthalimide to the corresponding boronic acid pinacol ester and subsequent reaction with N-(o-biphenyl)phthalimido-3-chlorophthalimide in a yield of 45%.

The emission spectrum of Example 30 (10% in PMMA) was measured. The emission maximum is at 490 nm. The photoluminescence quantum yield (PLQY) is 61% and the full width at half maximum (FWHM) is 96 nm (0.48 eV). A $CIE_y$ of 0.38 and a BMI of 161 are found.

Example 31

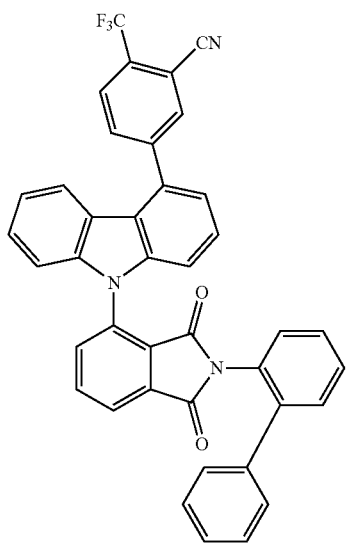 [SMILES: N#Cc1cc(-c2cccc3c2c2ccccc2n3-c2cccc3c2C(=O)N(c2ccccc2-c2ccccc2)C3=O)ccc1C(F)(F)F]

Example 31 was prepared according to GM4 by the conversion of 3-(4-bromocarbazolyl)-N-(o-biphenyl)phthalimide to the corresponding bis(boronic acid pinacol ester) and subsequent reaction with 3-bromo-6-trifluoromethylbenzonitrile in a yield of 40%.

The emission spectrum of Example 31 (10% in PMMA) was measured. The emission maximum is at 474 nm. The photoluminescence quantum yield (PLQY) is 61% and the full width at half maximum (FWHM) is 93 nm (0.48 eV). A $CIE_y$ of 0.33 and a BMI of 203 are found.

Example 32

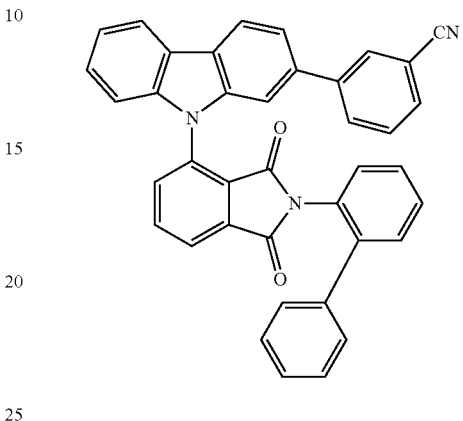

Example 32 was prepared according to GM5 from 3-(2-bromocarbazolyl)-N-(o-biphenyl)phthalimide and 3-cyanophenylboronic acid in a yield of 31%.

The emission spectrum of Example 32 (10% in PMMA) was measured. The emission maximum is at 474 nm. The photoluminescence quantum yield (PLQY) is 54% and the full width at half maximum (FWHM) is 93 nm (0.48 eV). A $CIE_y$ of 0.32 and a BMI of 169 are found.

Examples D1 and D2

Example 3 and Example 5 were tested in OLEDs having the following structure:

| Layer | Thickness | D1 | D2 |
|---|---|---|---|
| 10 | 100 nm | Al | Al |
| 9 | 2 nm | Liq | Liq |
| 8 | 30 nm | TPBi | TPBi |
| 7 | 10 nm | DPEPO | DPEPO |
| 6 | 20 nm | 3:DPEPO 20:80 | 5:DPEPO 30:70 |
| 5 | 10 nm | CzSi | CzSi |
| 4 | 20 nm | TCTA | TCTA |
| 3 | 50 nm | NPB | NPB |
| 2 | 20 nm | m-MTDATA | m-MTDATA |
| 1 | 120 nm | ITO | ITO |

Performance Data

| OLED component | Maximum power efficiency (lm/W) | Maximum current yield (cd/A) | Maximum EQE (%) | $\lambda_{max}$ (nm) |
|---|---|---|---|---|
| D1 | 12.8 ± 0.6 | 26.0 ± 0.5 | 12.7 ± 0.3 | 476 |
| D2 | 12.6 ± 0.6 | 25.1 ± 0.5 | 12.3 ± 0.2 | 474 |

Example D3

Example 21 was tested in an OLED component ("component D3") with the following structure (proportion of the molecule according to the invention in the emission layer is reported in percent by mass):

| Layer | Thickness | Material |
|---|---|---|
| 9 | 100 nm | Al |
| 8 | 2 nm | Liq |
| 7 | 40 nm | NBPhen |
| 6 | 20 nm | Example 21 (10%):H1 |
| 5 | 10 nm | TCTA |
| 4 | 110 nm | NPB |
| 3 | 5 nm | HAT-CN |
| 2 | 50 nm | PEDOT |
| 1 | 130 nm | ITO |
| Substrate | | glass |

Performance Data

| | |
|---|---|
| $EQE_{max}$ (maximum external quantum efficiency) | 11.7 ± 0.3% |
| EQE at 500 cd/m² | 9.3 ± 0.2% |
| LT 80 at 500 cd/m² | 131 h |

The emission maximum is at 478 nm.

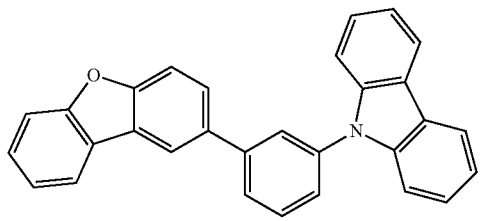

H1

Example D4

Example 21 was tested in an OLED component ("component D4") with the following structure (proportion of the molecule according to the invention in the emission layer is reported in percent by mass):

| Layer | Thickness | Material |
|---|---|---|
| 7 | 100 nm | Al |
| 6 | 2 nm | Liq |
| 5 | 40 nm | NBPhen |
| 4 | 20 nm | Example 21 (30%):mCBP |
| 3 | 10 nm | TCTA |
| 2 | 80 nm | NPB |
| 1 | 130 nm | ITO |
| Substrate | | glass |

Performance Data

| | |
|---|---|
| $EQE_{max}$ (maximum external quantum efficiency) | 8.91 ± 0.03% |
| EQE at 1000 cd/m² | 8.74 ± 0.02% |
| LT 80 at 1000 cd/m² | 72 h |

The emission maximum is at 486 nm; CIEx was determined as 0.24 and CIEy as 0.39 at 4.5 V.

Further Examples

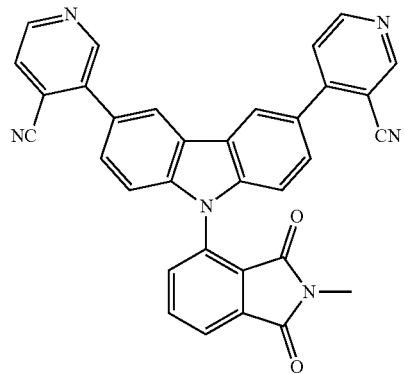

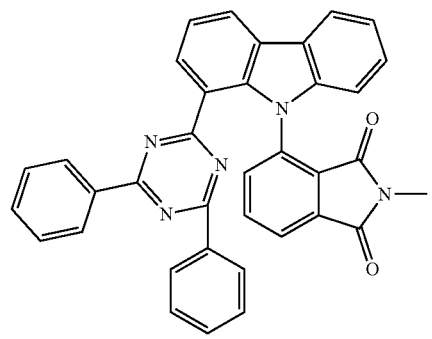

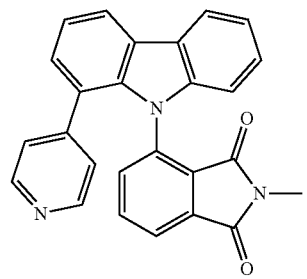

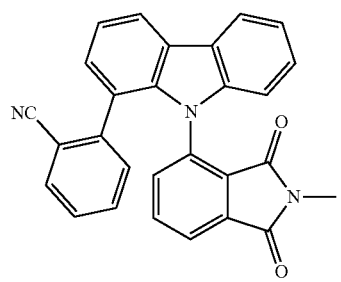

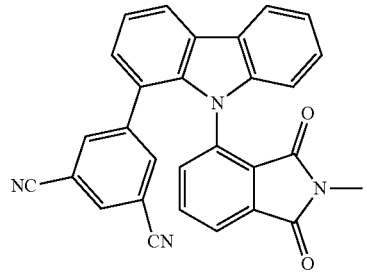

-continued
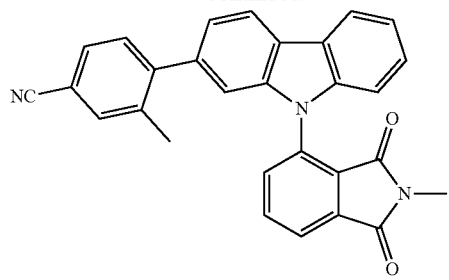
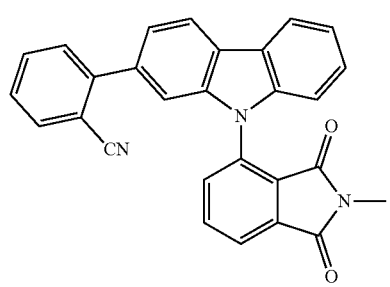
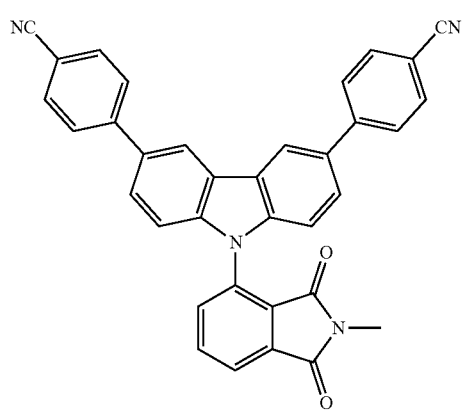
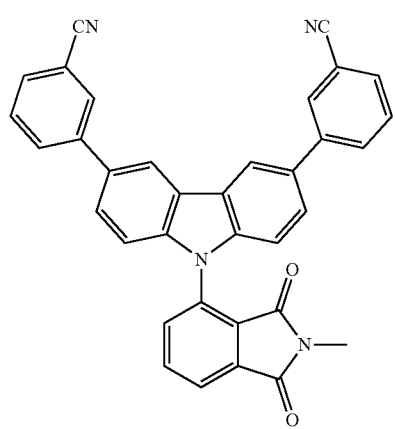
-continued
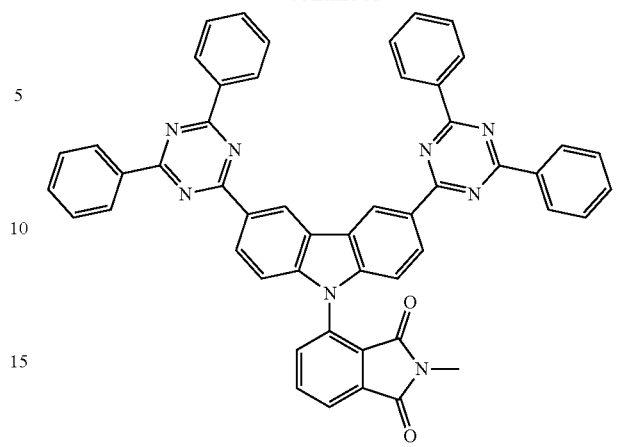
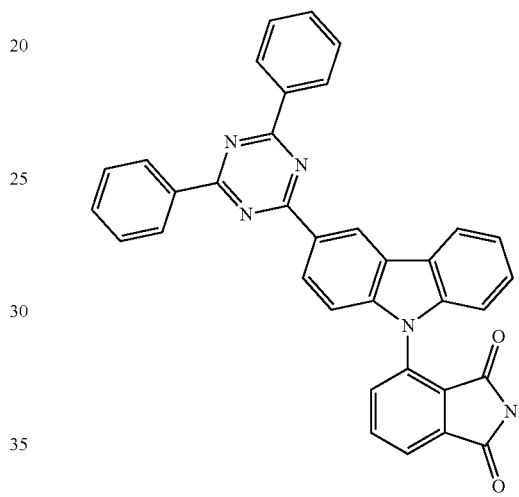
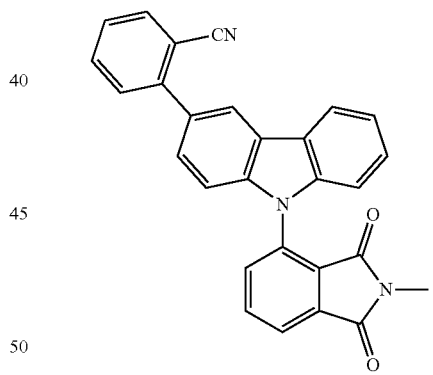
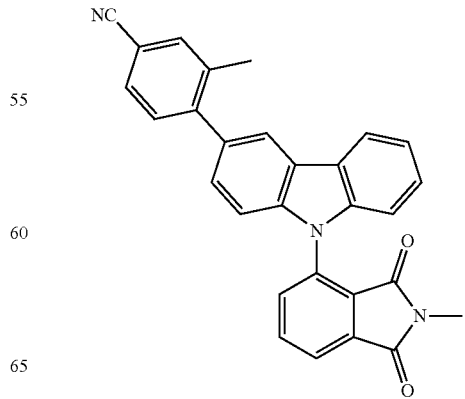

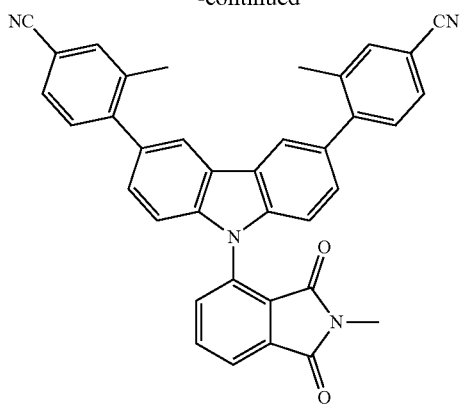
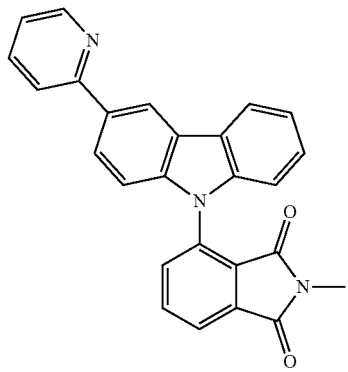
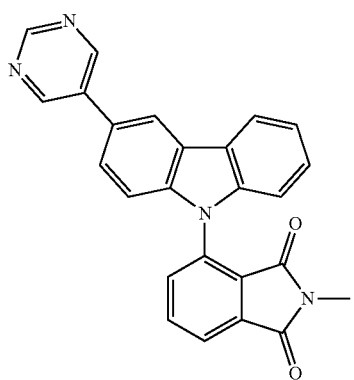
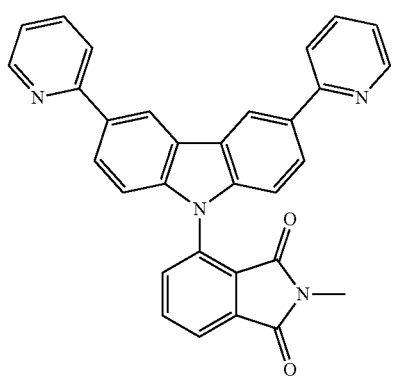
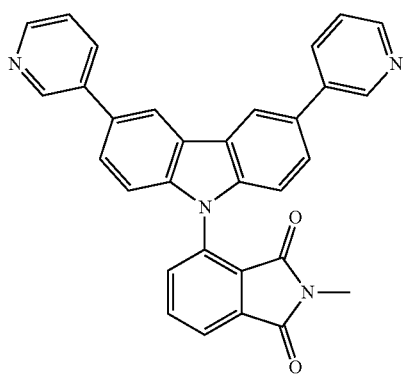
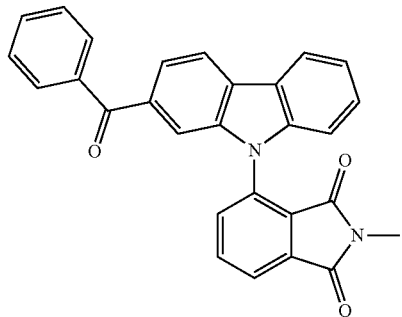
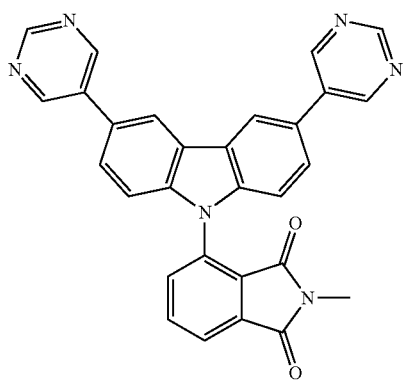
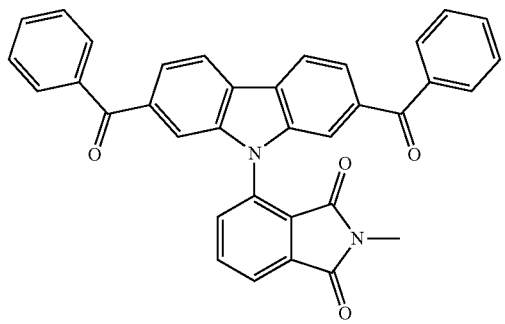

71
-continued
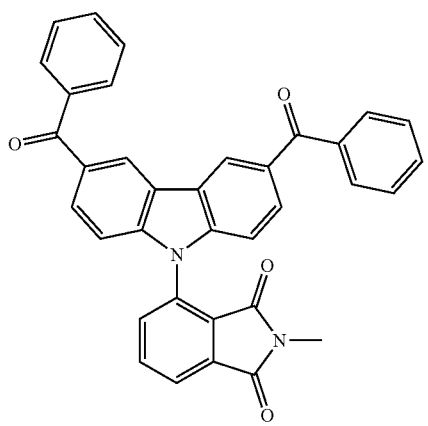
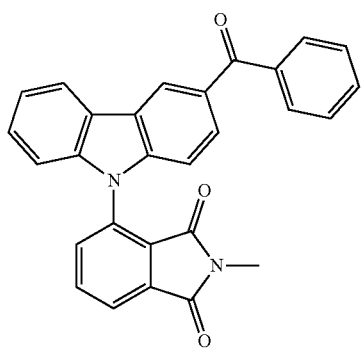
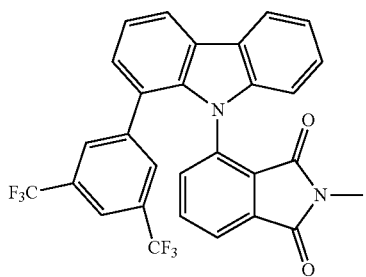
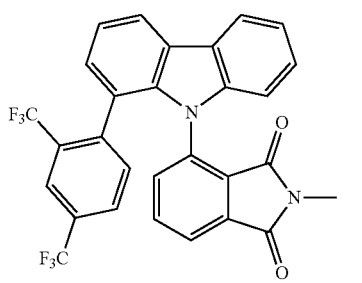
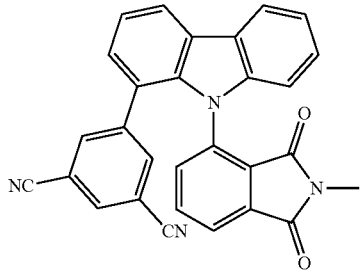
72
-continued
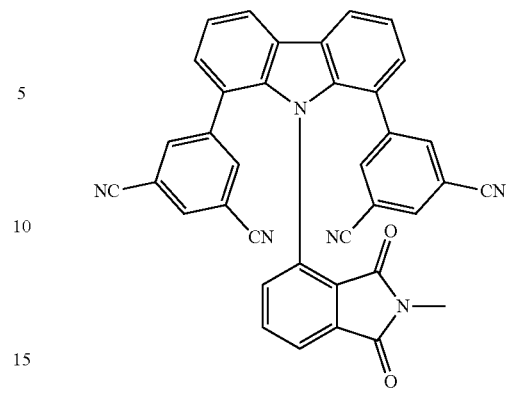
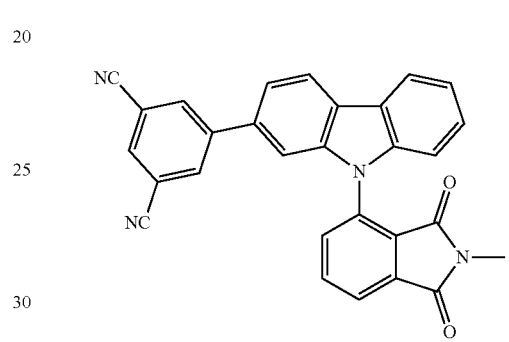
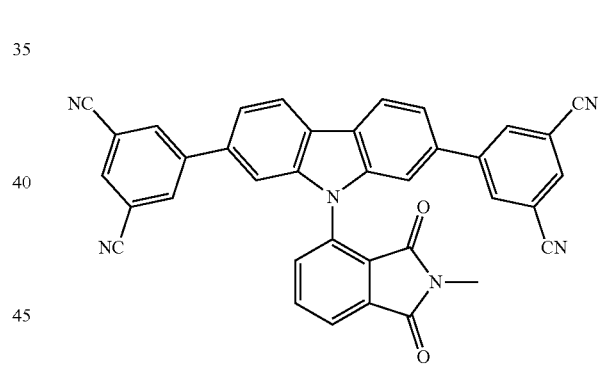
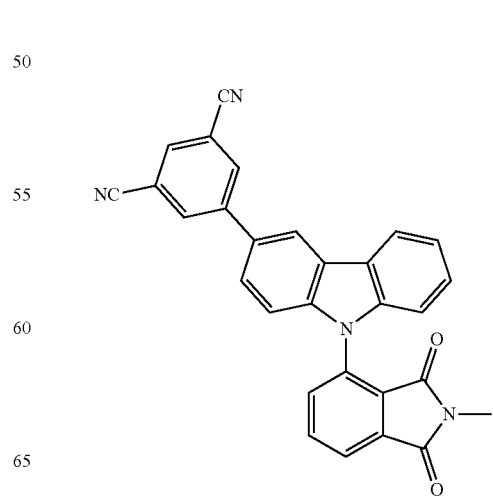

73
-continued
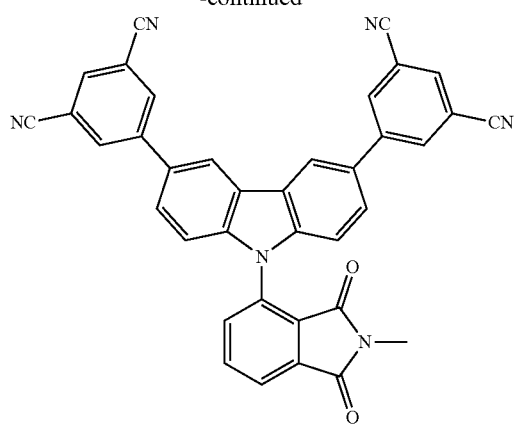
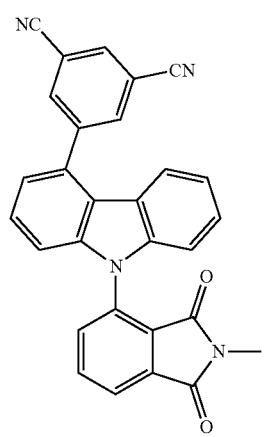
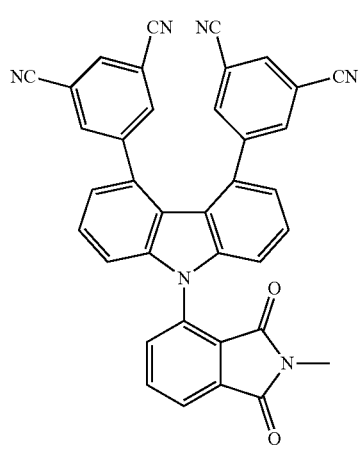
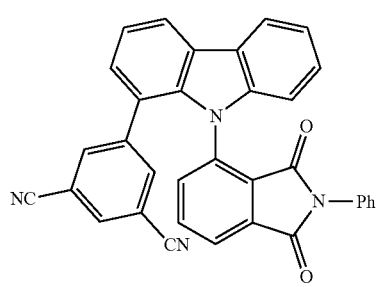
74
-continued
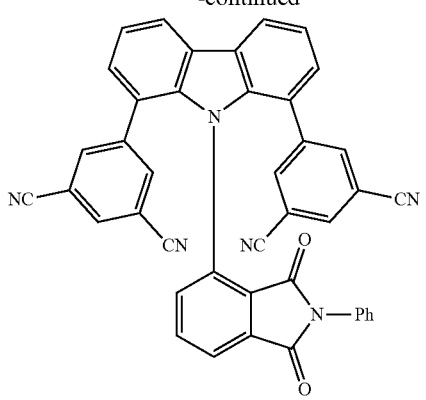
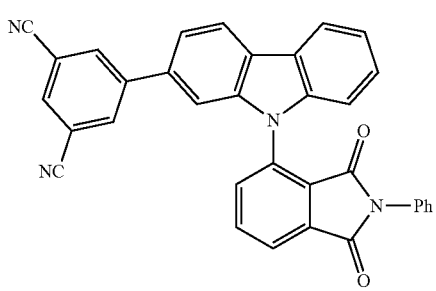
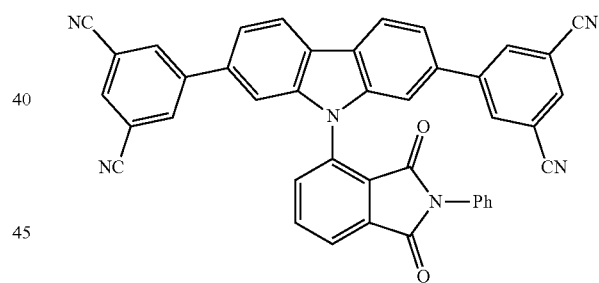
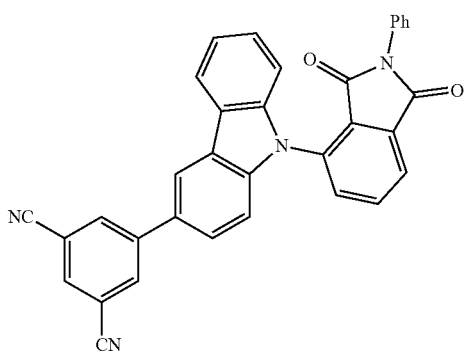

75
-continued
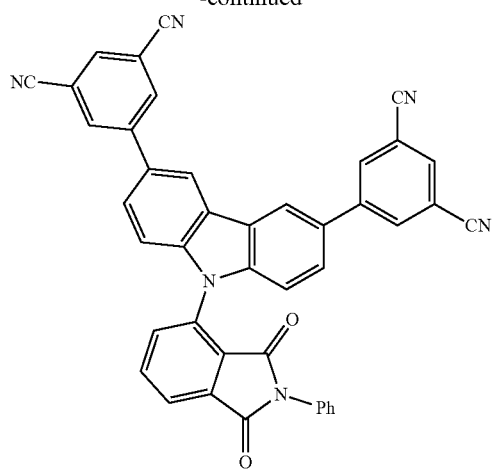
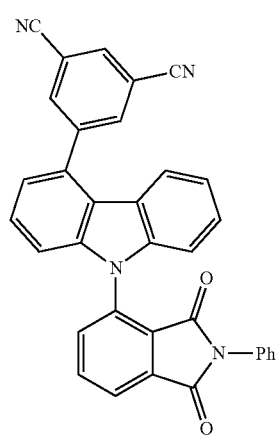
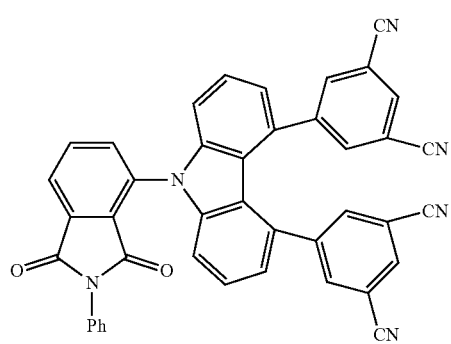
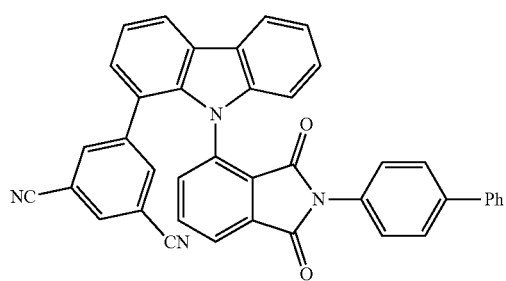
76
-continued
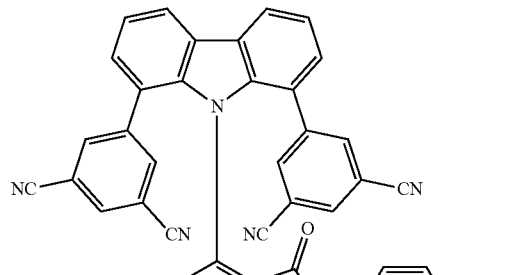
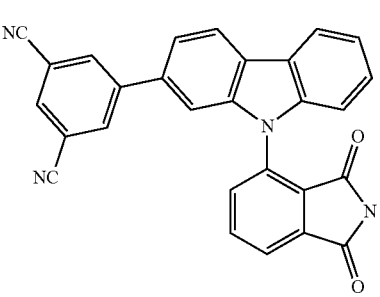
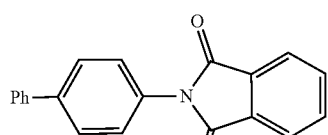
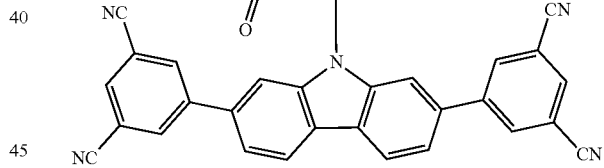
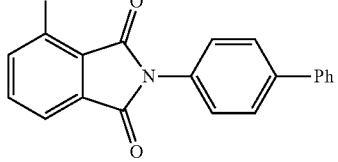

77
-continued
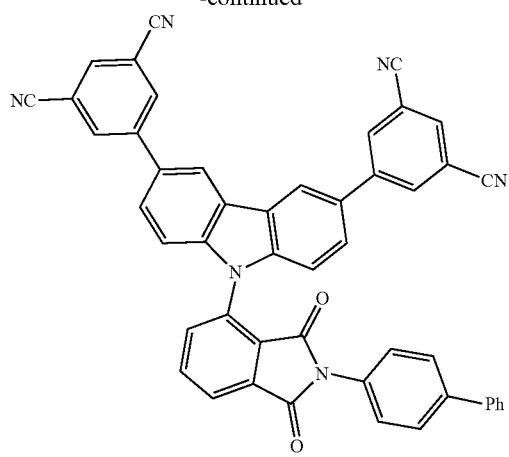
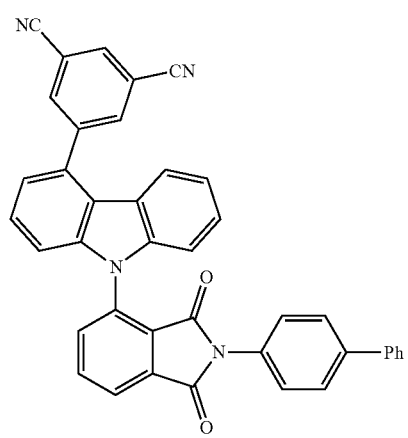
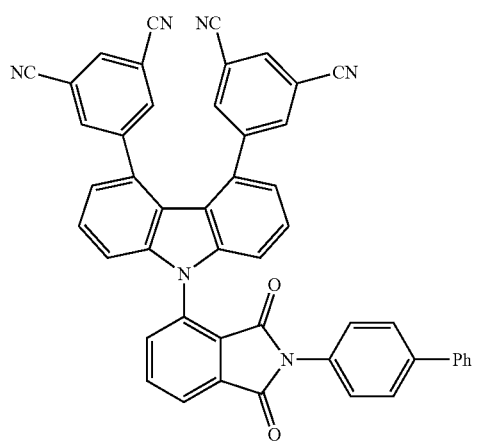
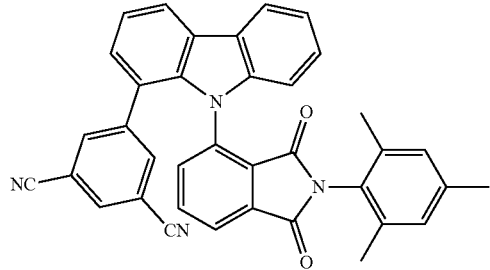
78
-continued
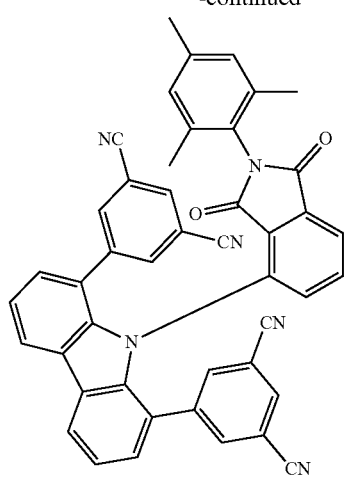
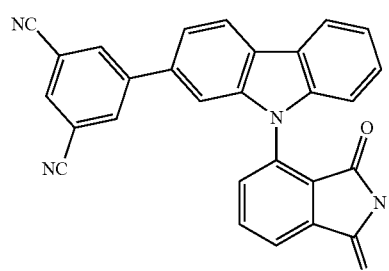
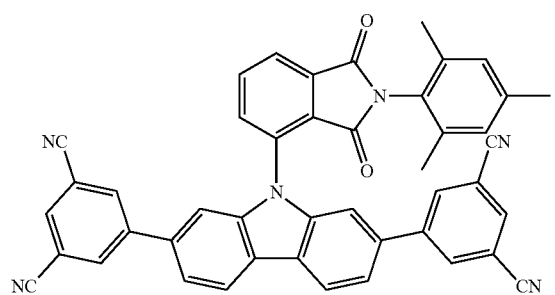
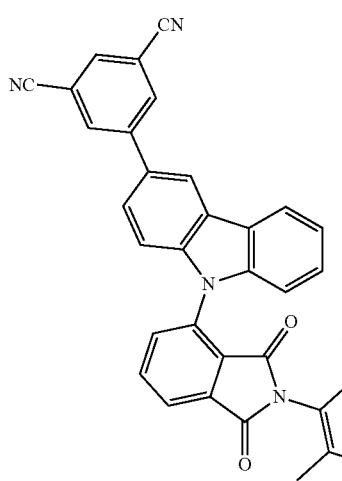

79
-continued
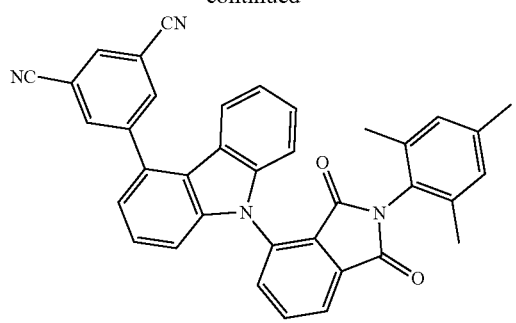
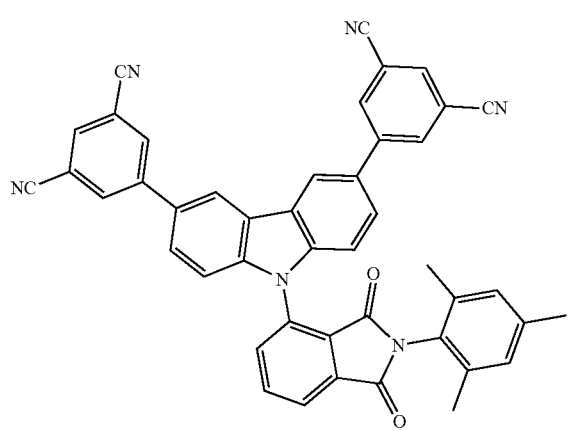 [SMILES: Cc1cc(C)c(N2C(=O)c3cccc(-n4c5ccc(-c6cc(C#N)cc(C#N)c6)cc5c5cc(-c6cc(C#N)cc(C#N)c6)ccc54)c3C2=O)c(C)c1]
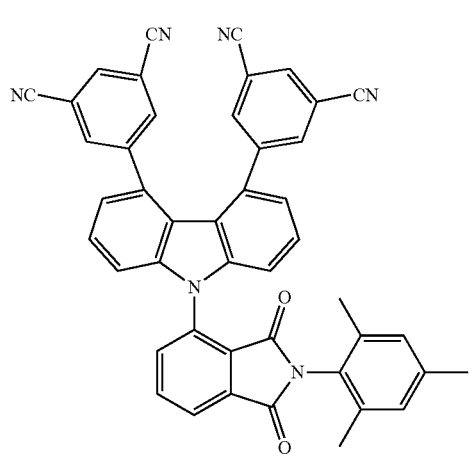
80
-continued
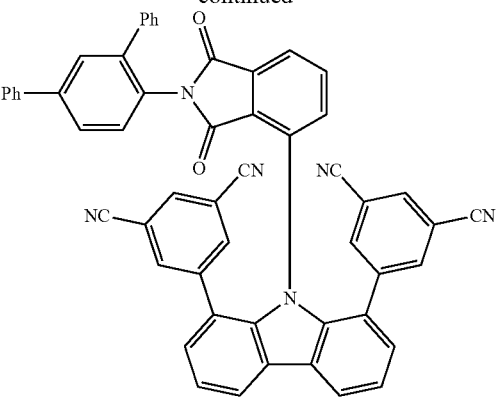
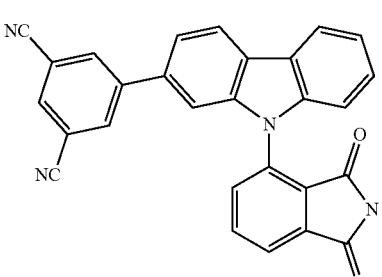
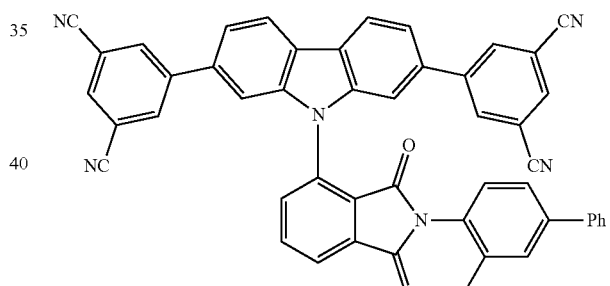
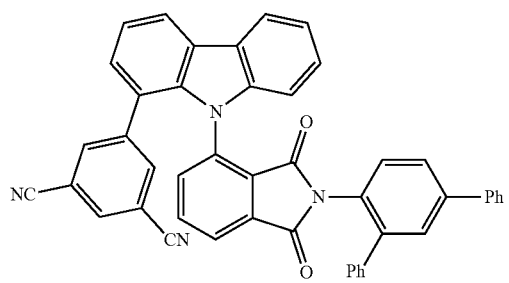
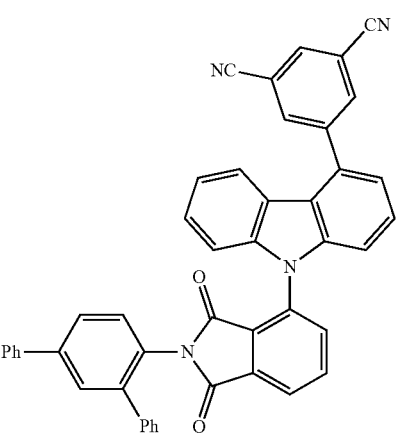

81
-continued
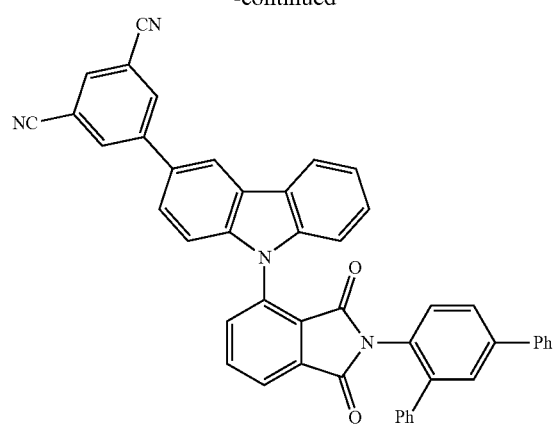
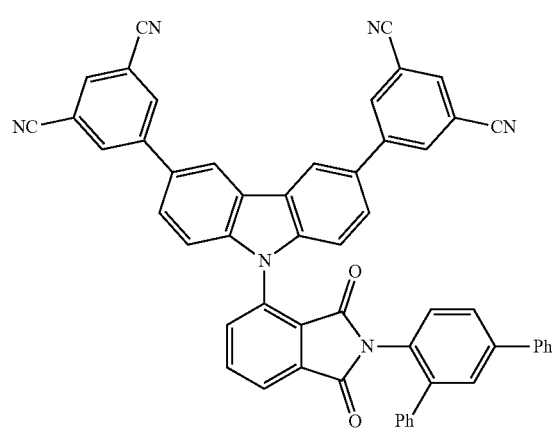
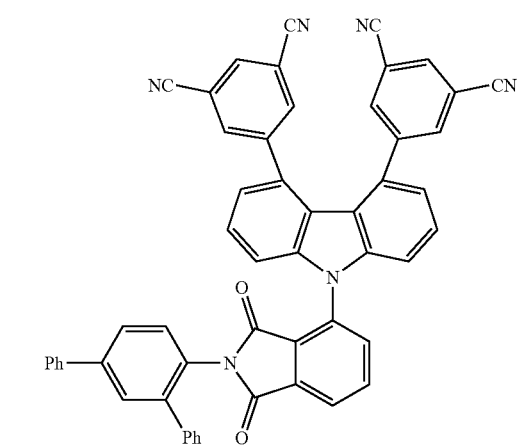
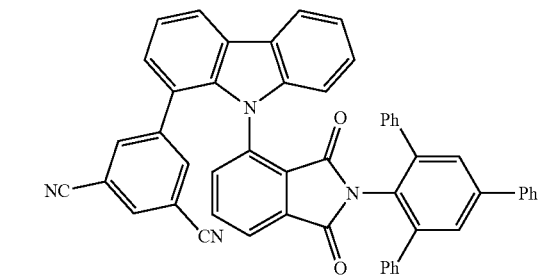
82
-continued
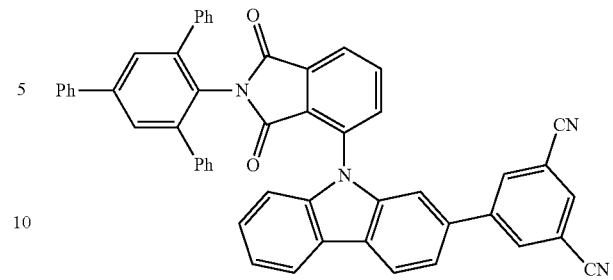
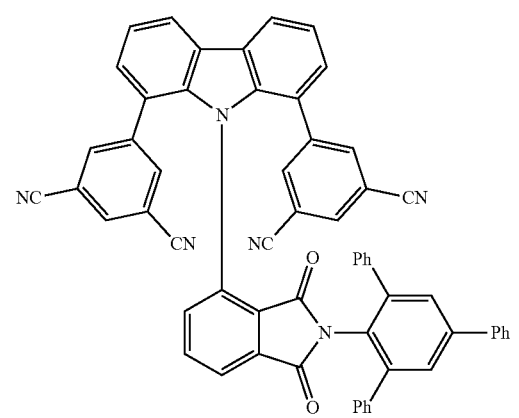
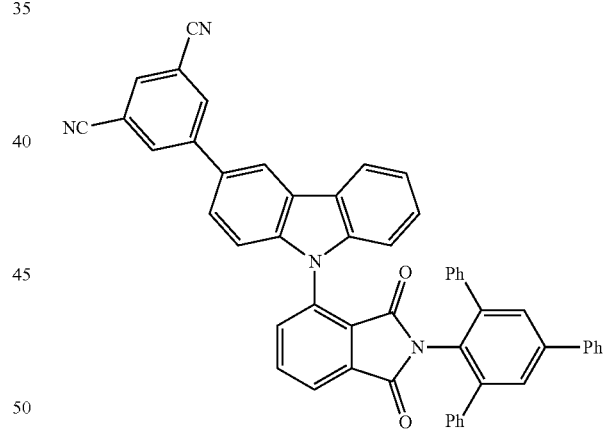
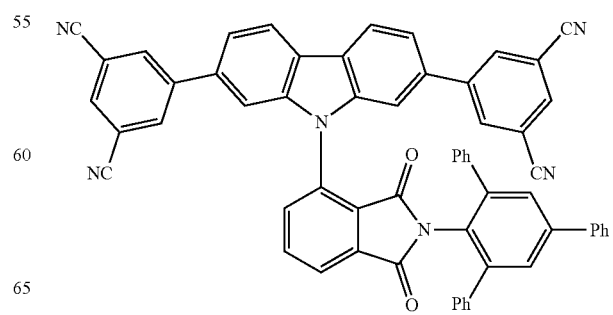

-continued
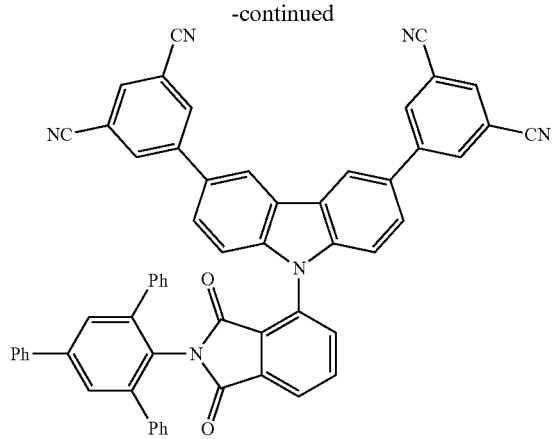
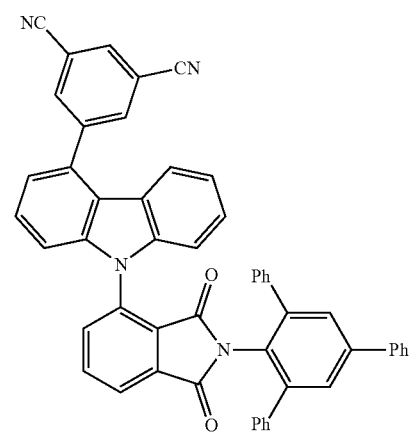
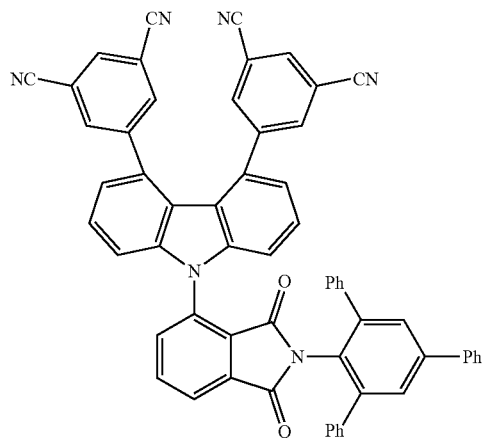
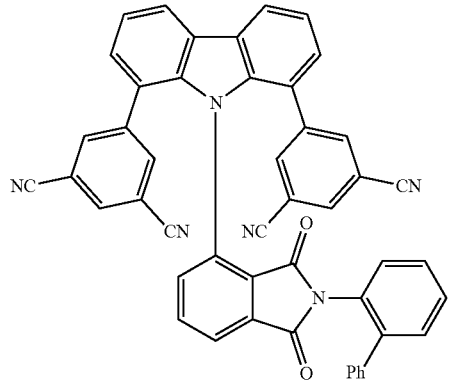
-continued
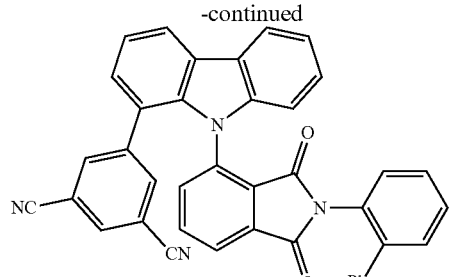
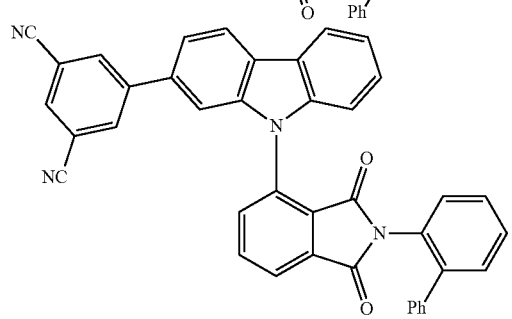
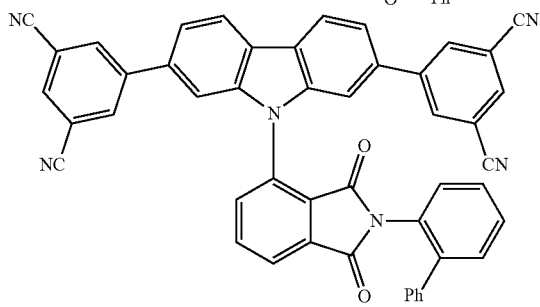
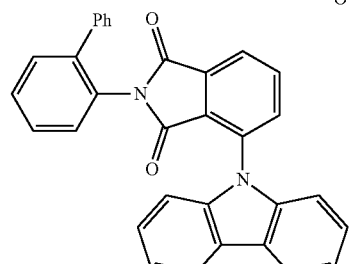
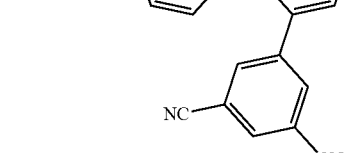
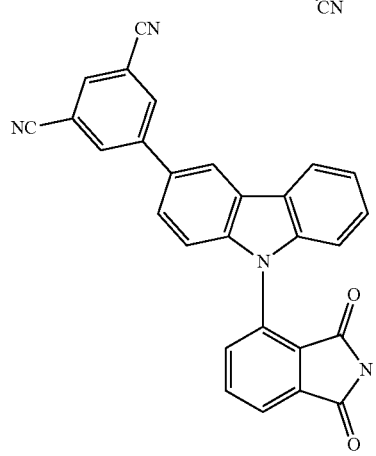

85
-continued
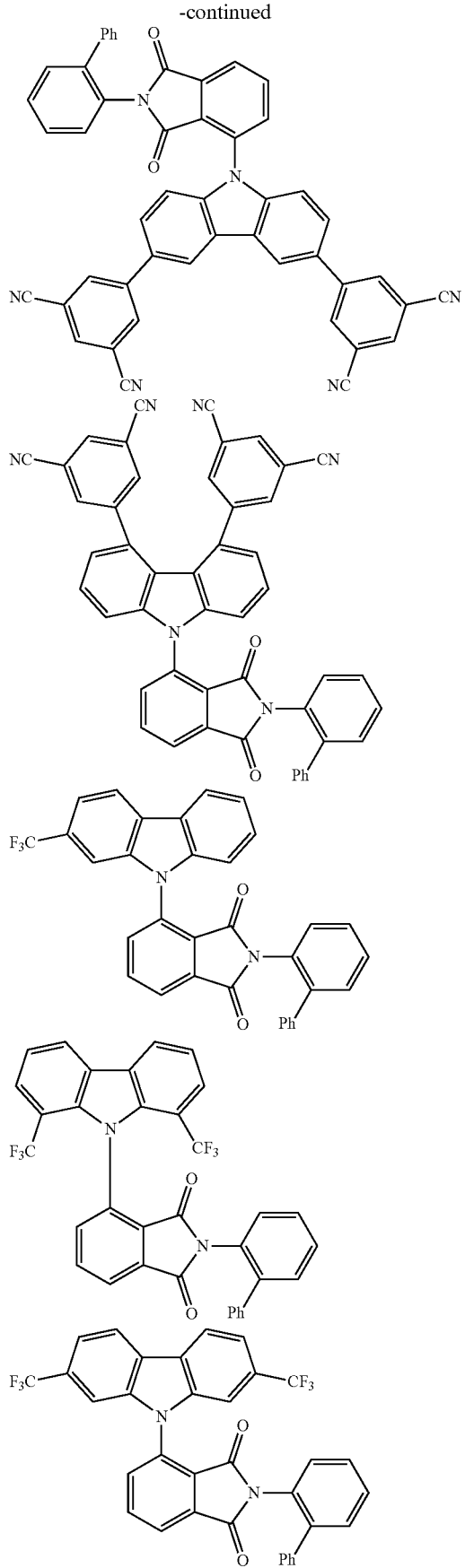
86
-continued
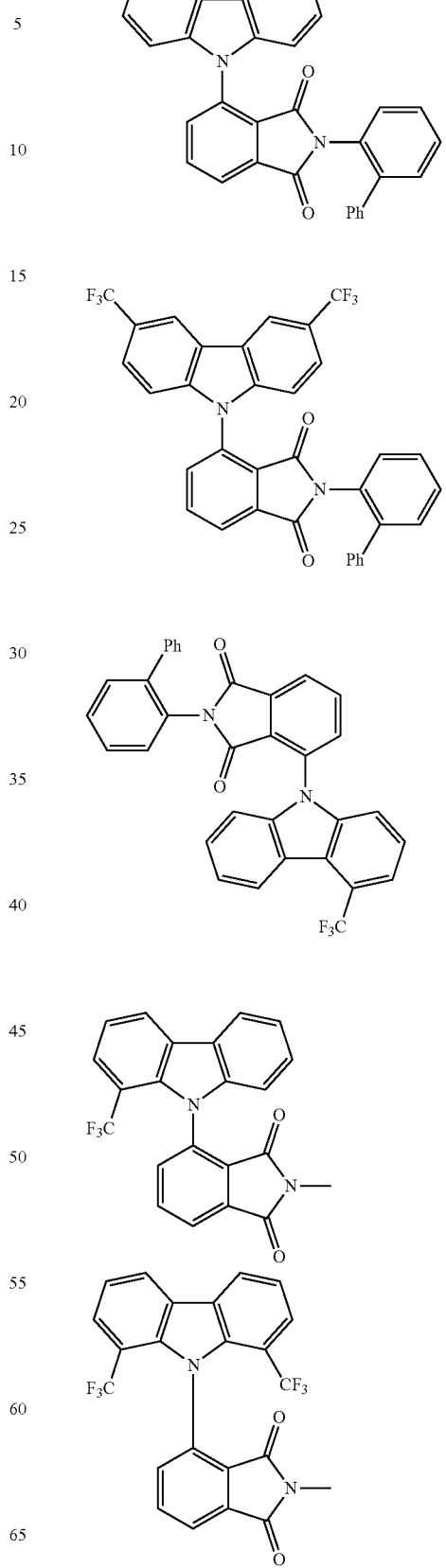

87
-continued
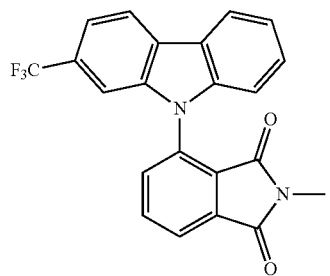
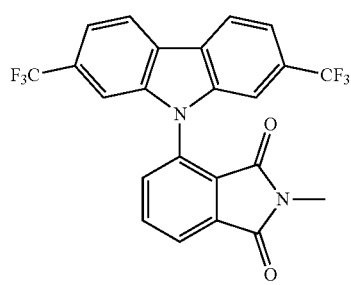
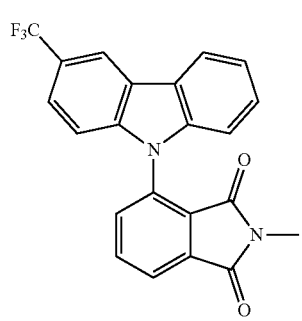
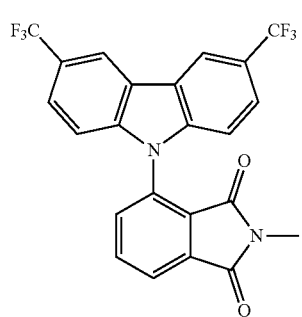
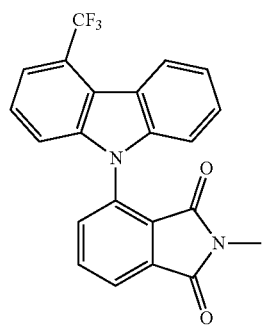
88
-continued
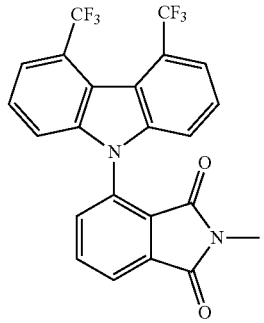
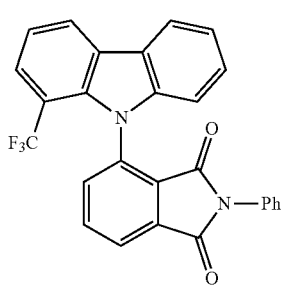
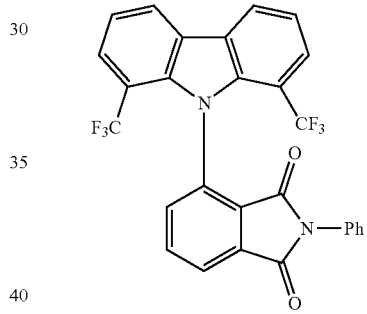
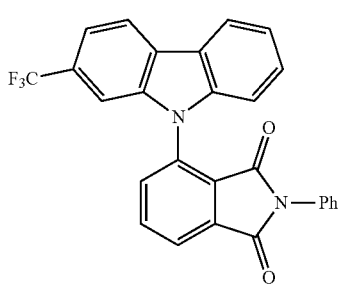
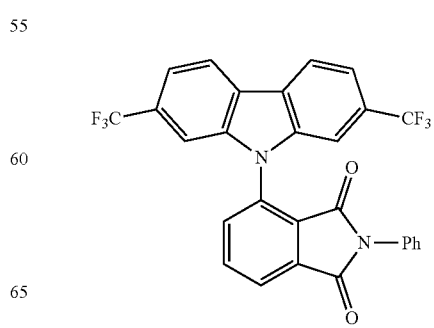

-continued
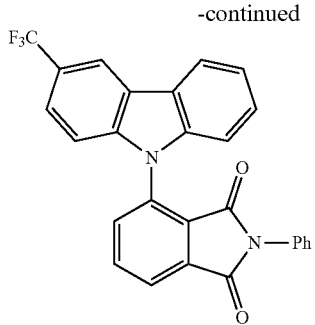
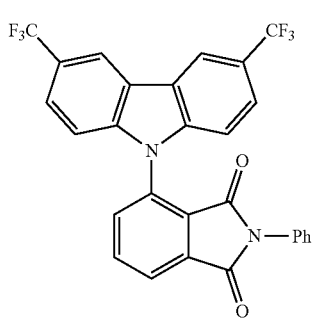
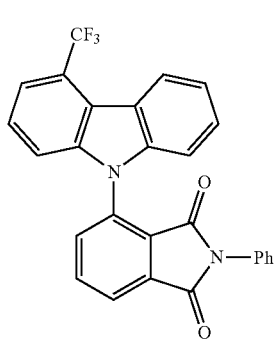
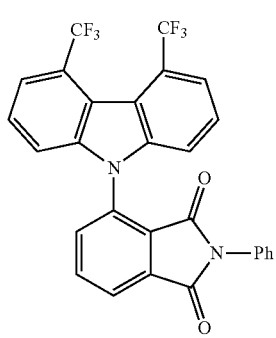
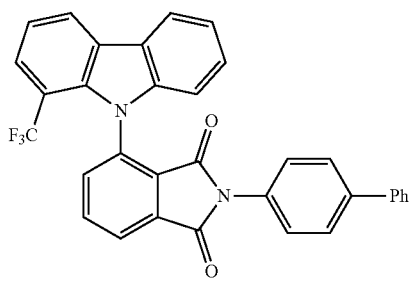
-continued
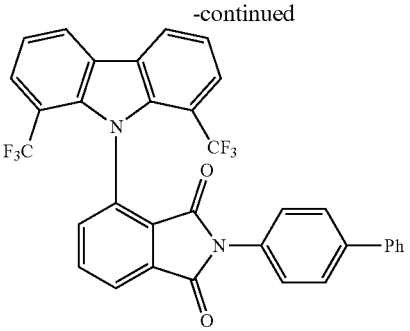
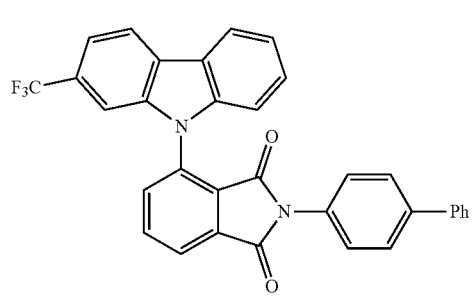
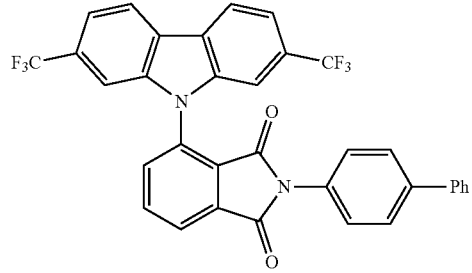
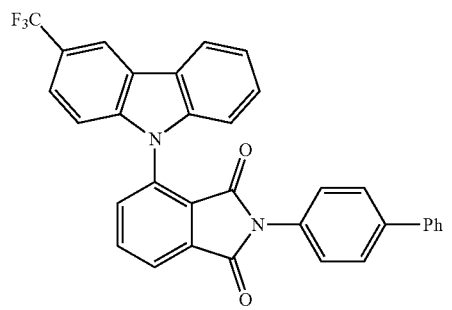
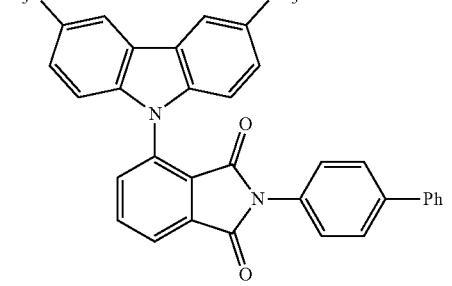

-continued
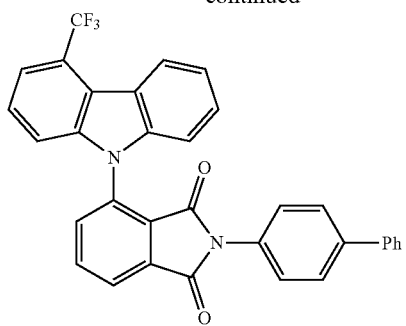
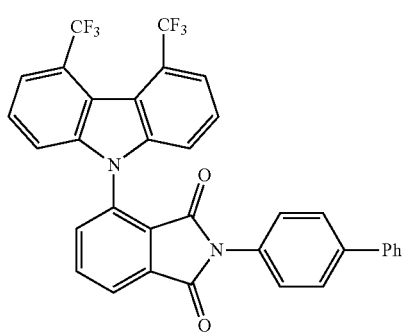
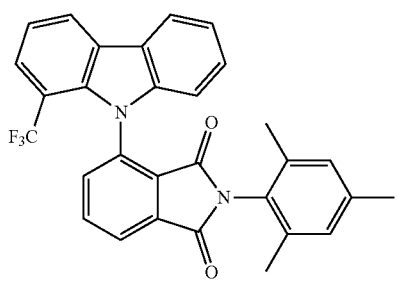
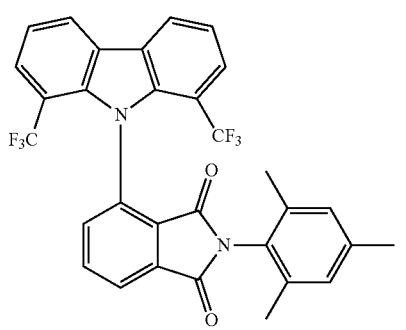
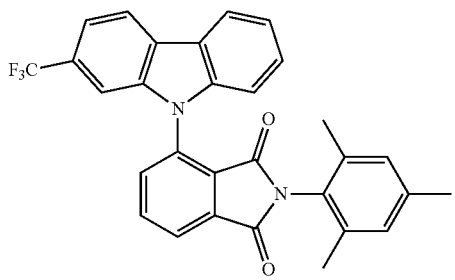
-continued
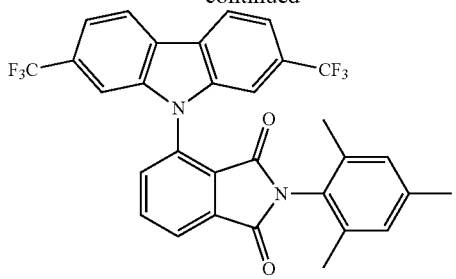
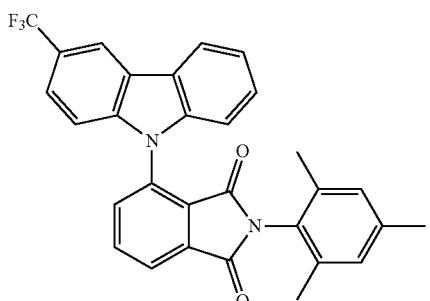
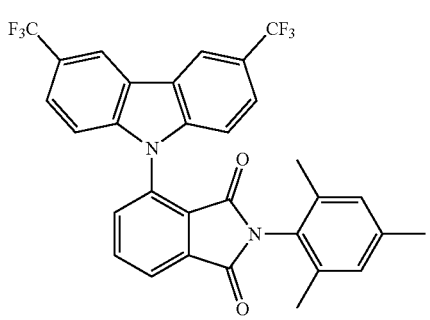
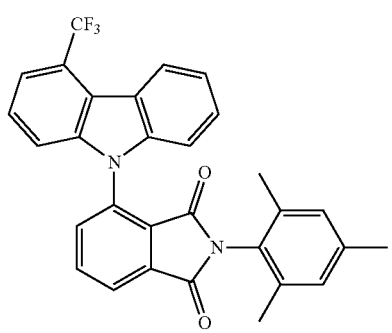
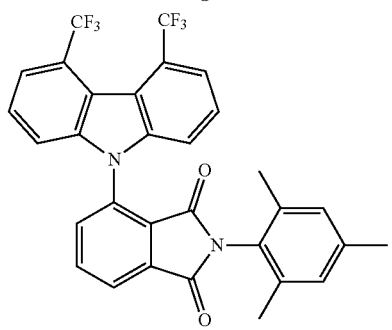

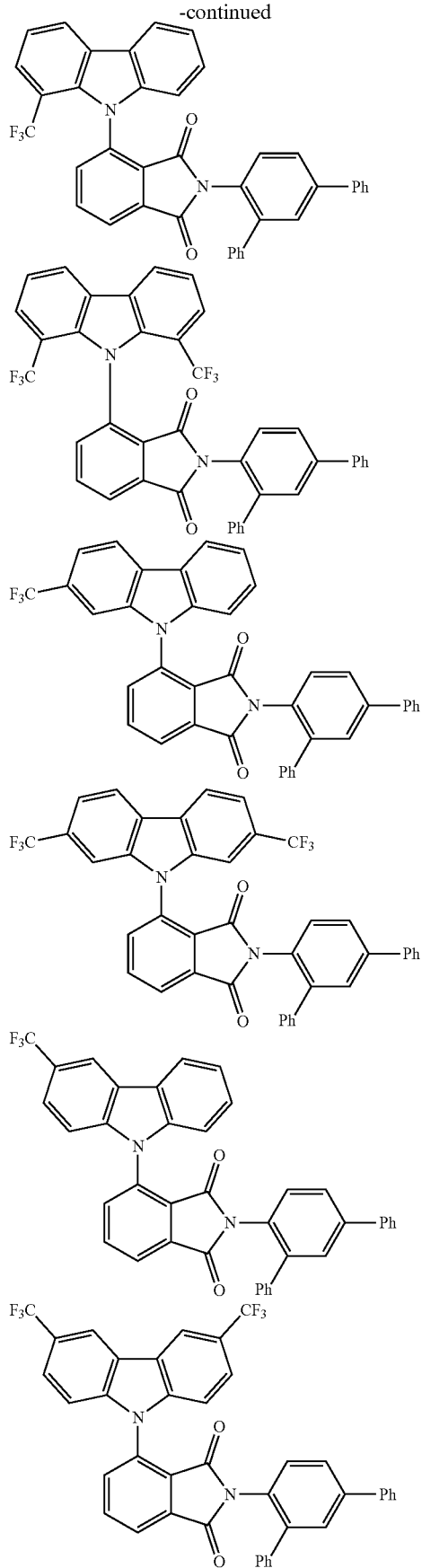
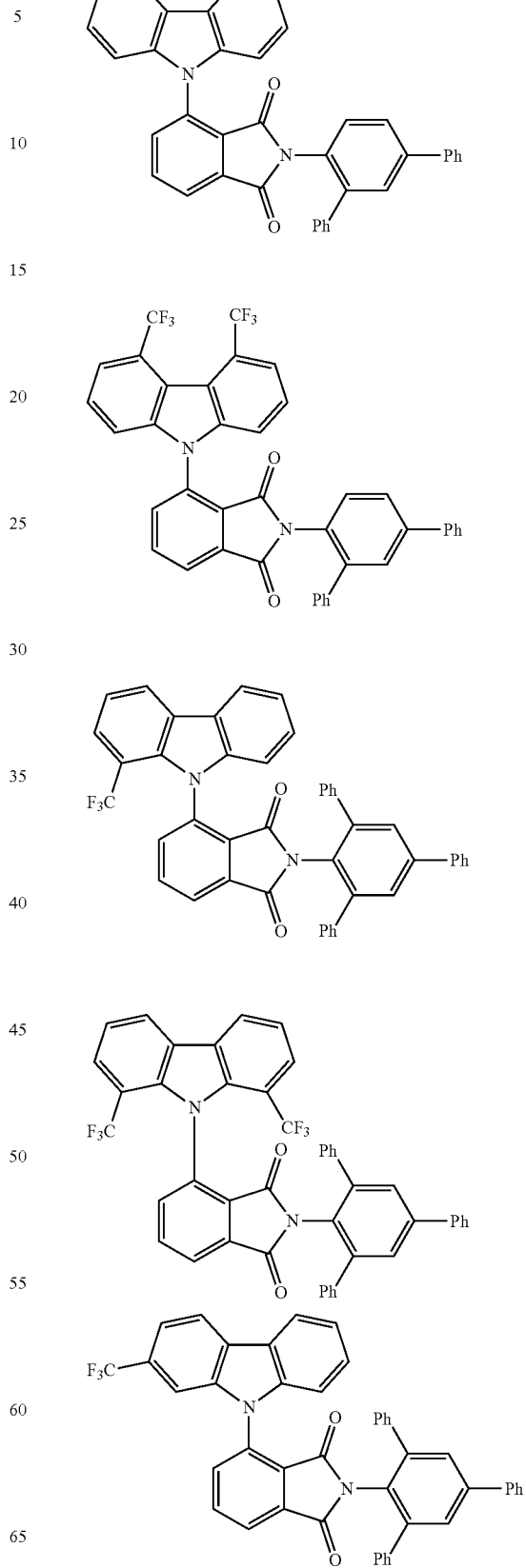

-continued
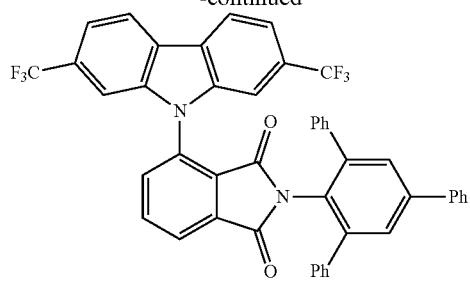
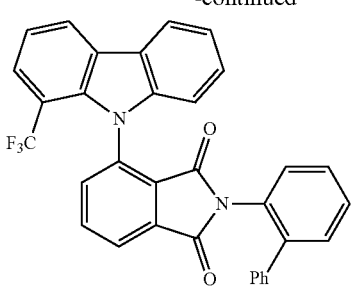
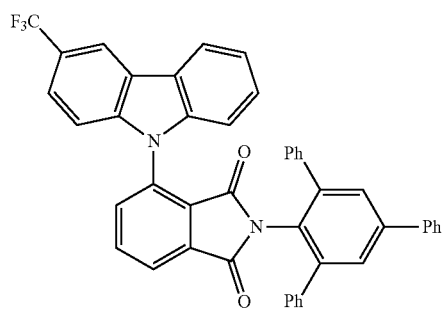
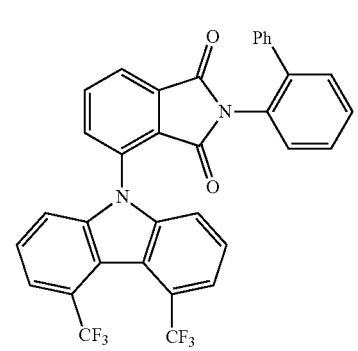
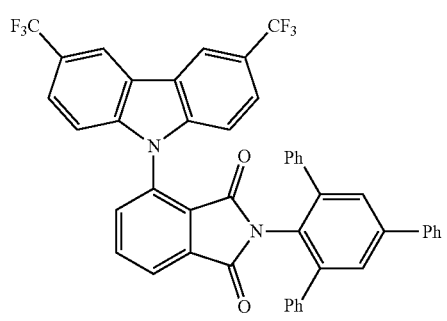
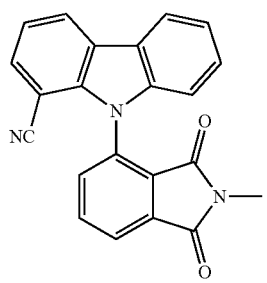
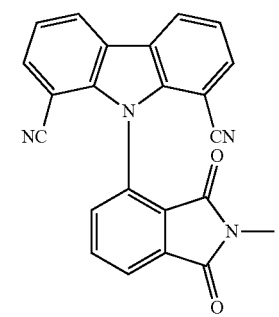
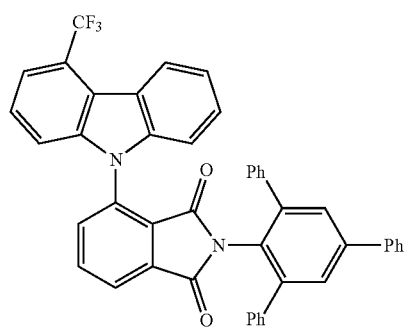
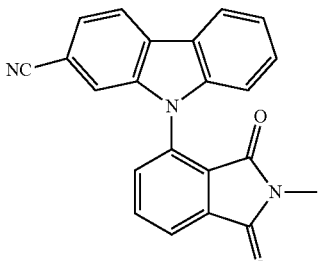
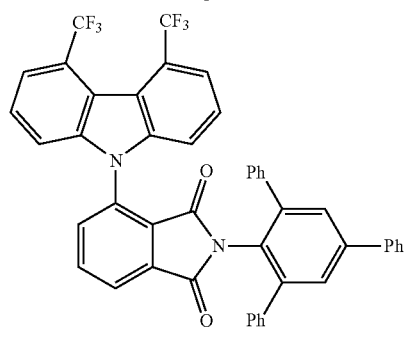
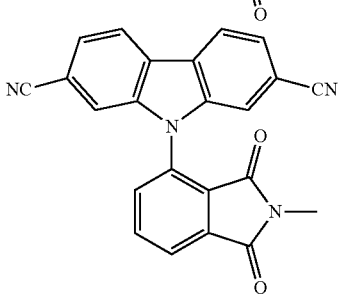

-continued
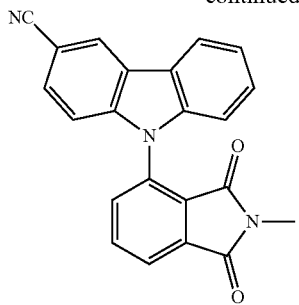
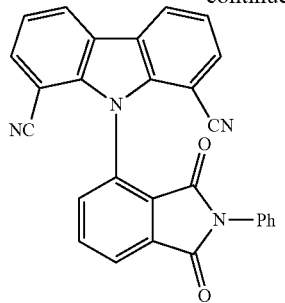
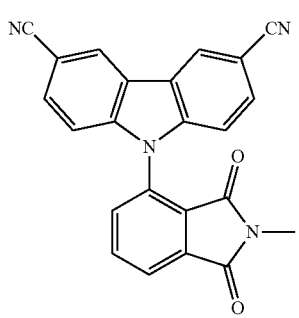
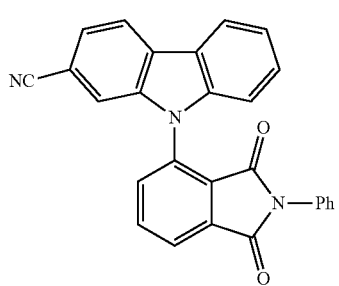
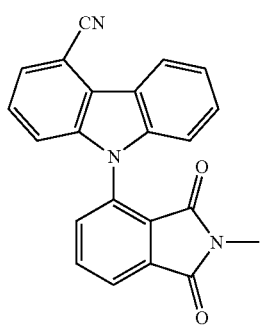
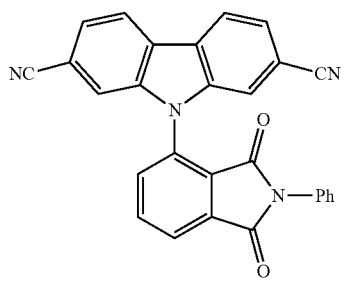
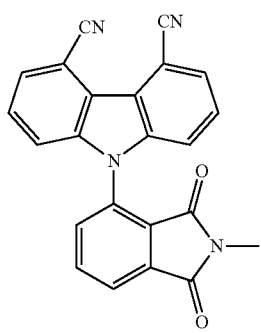
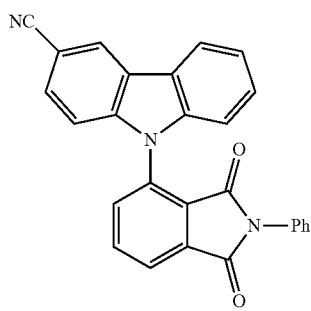
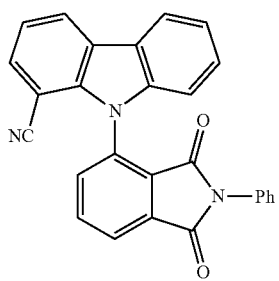
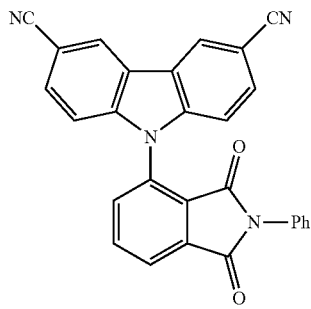

99
-continued
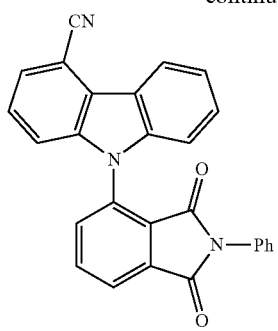
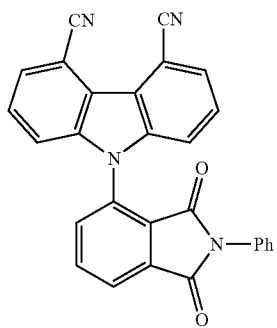
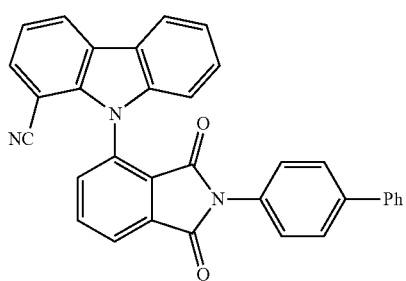
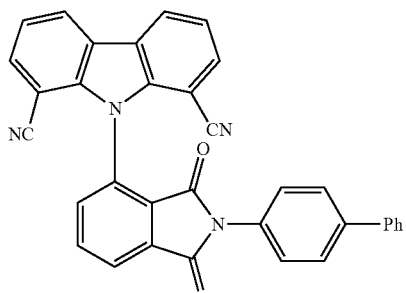
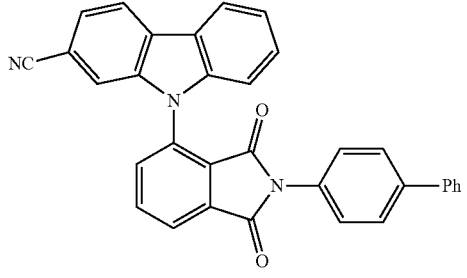
100
-continued
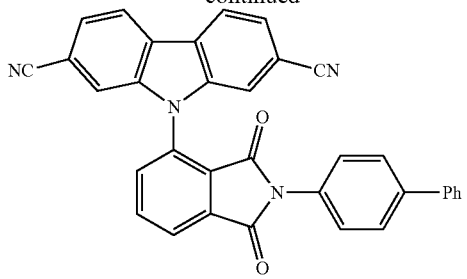
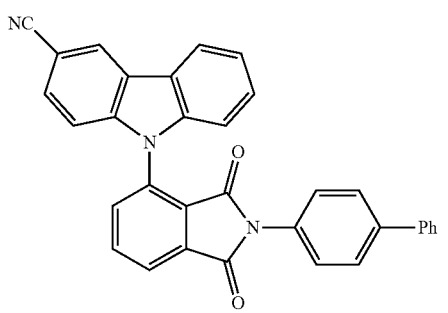
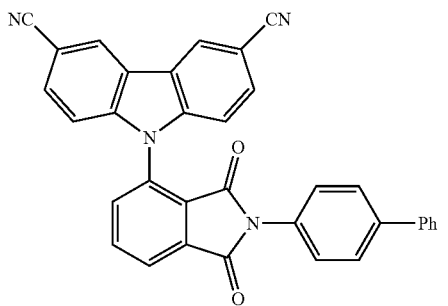
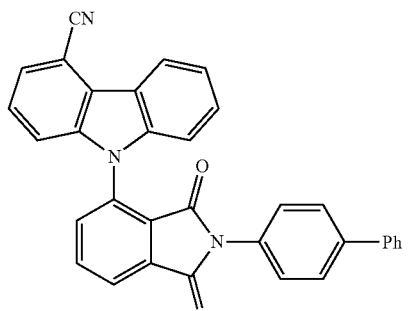
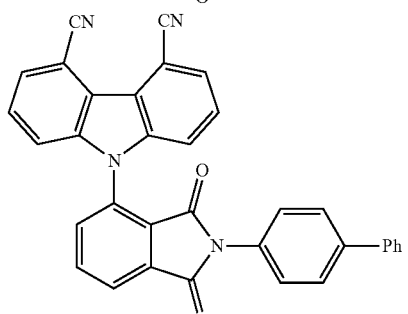

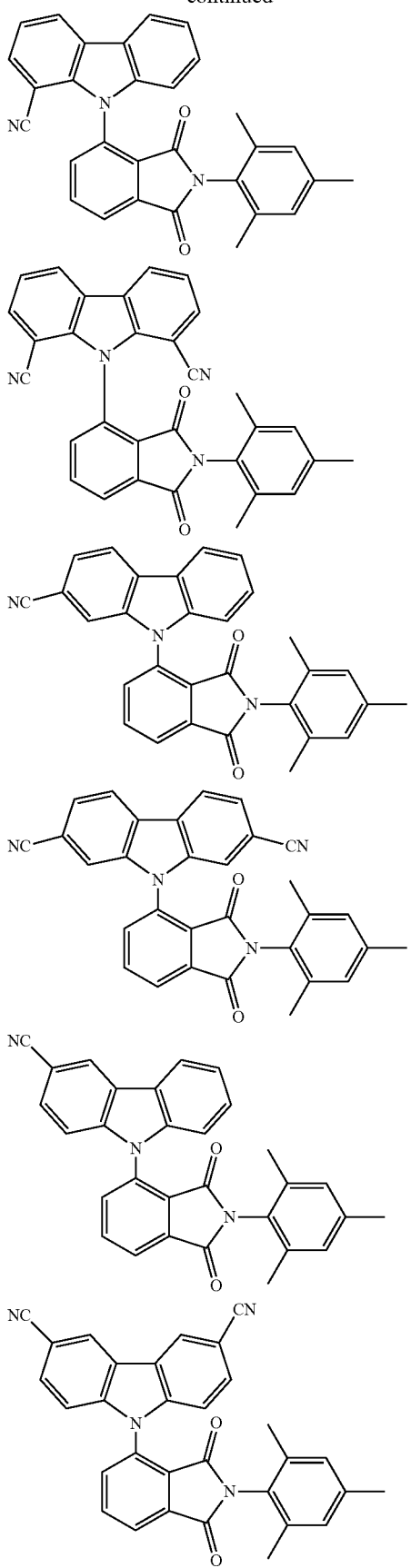
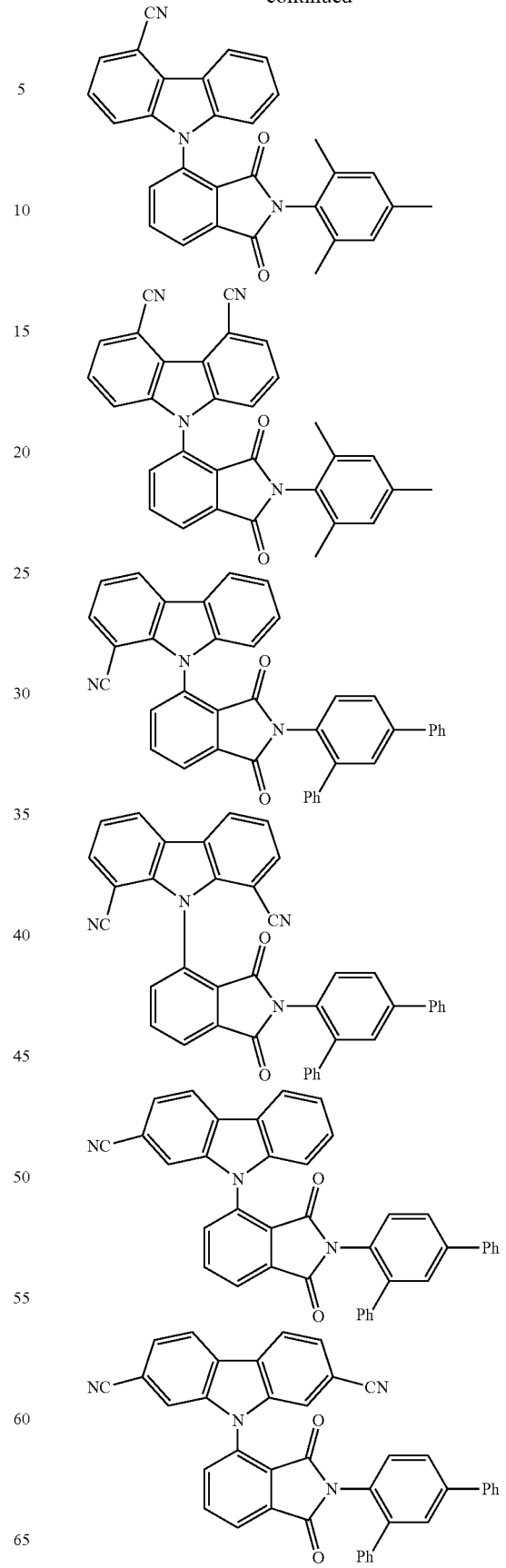

103
-continued
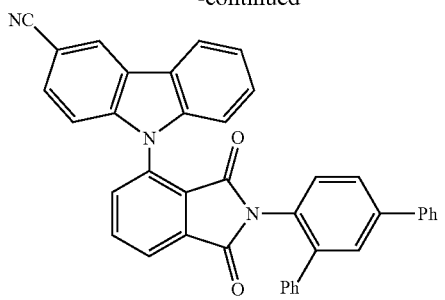
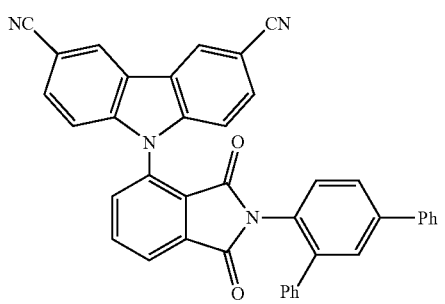
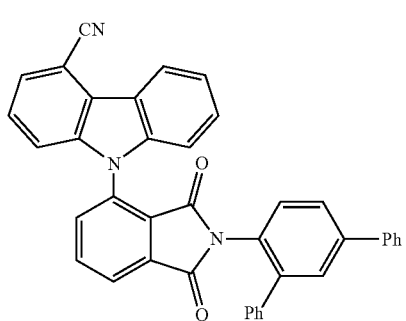
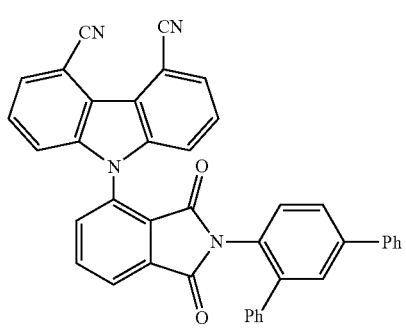
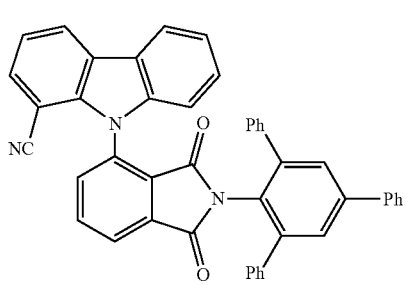
104
-continued
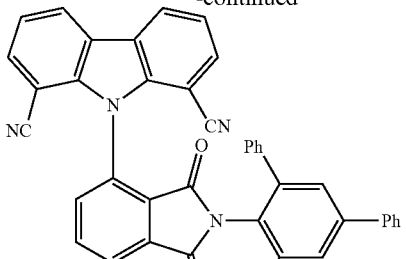
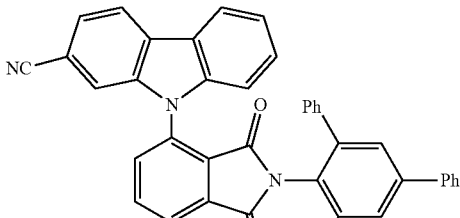
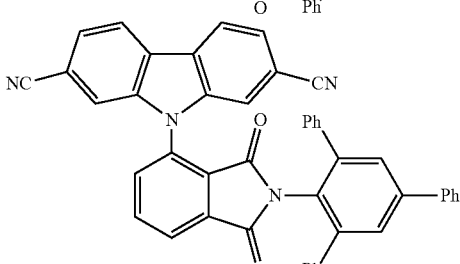
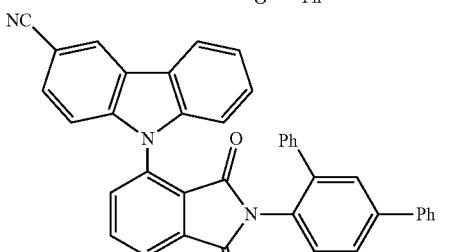
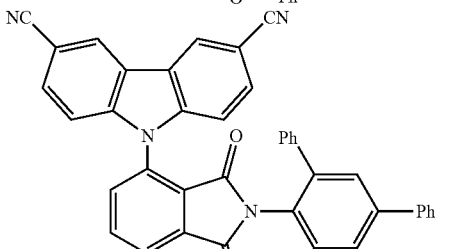
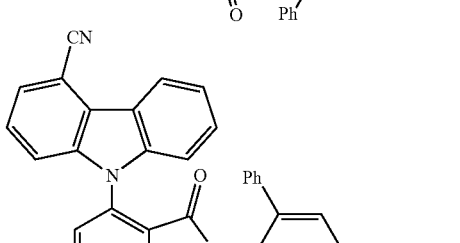
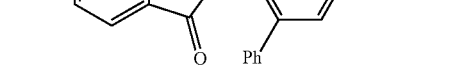

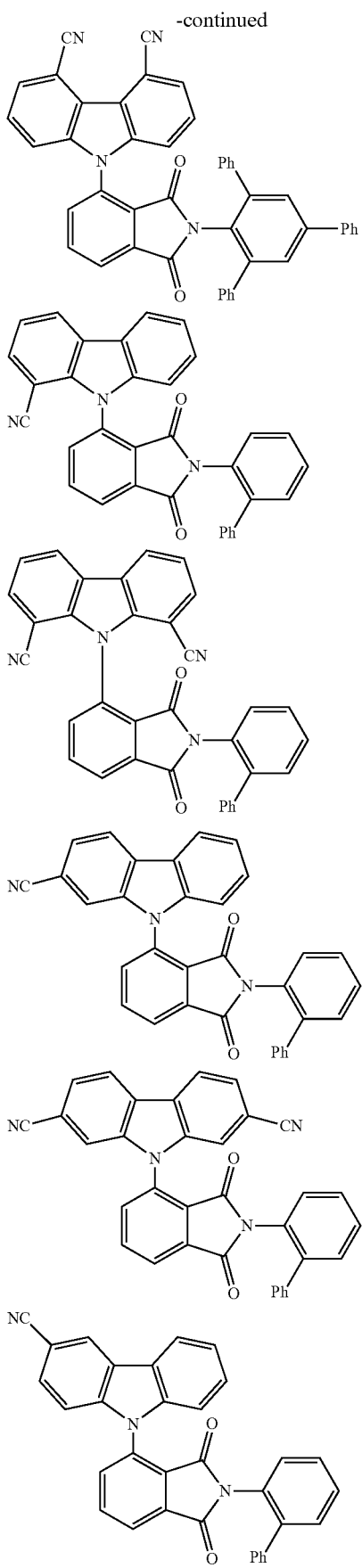
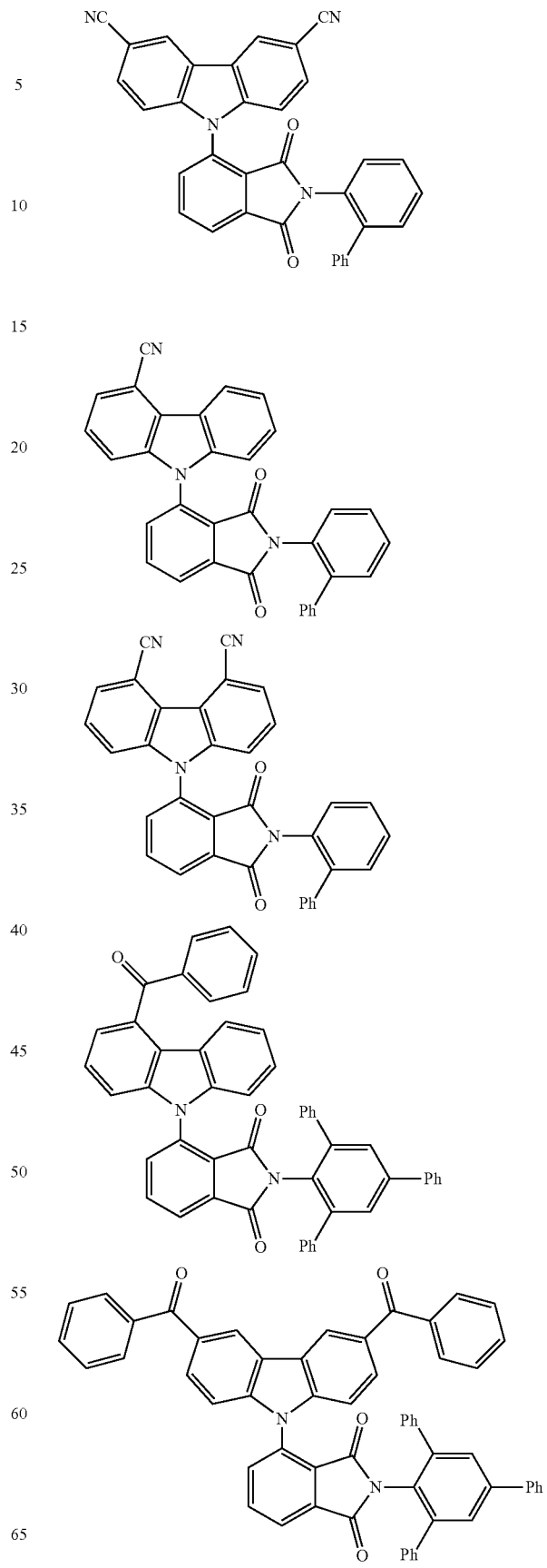

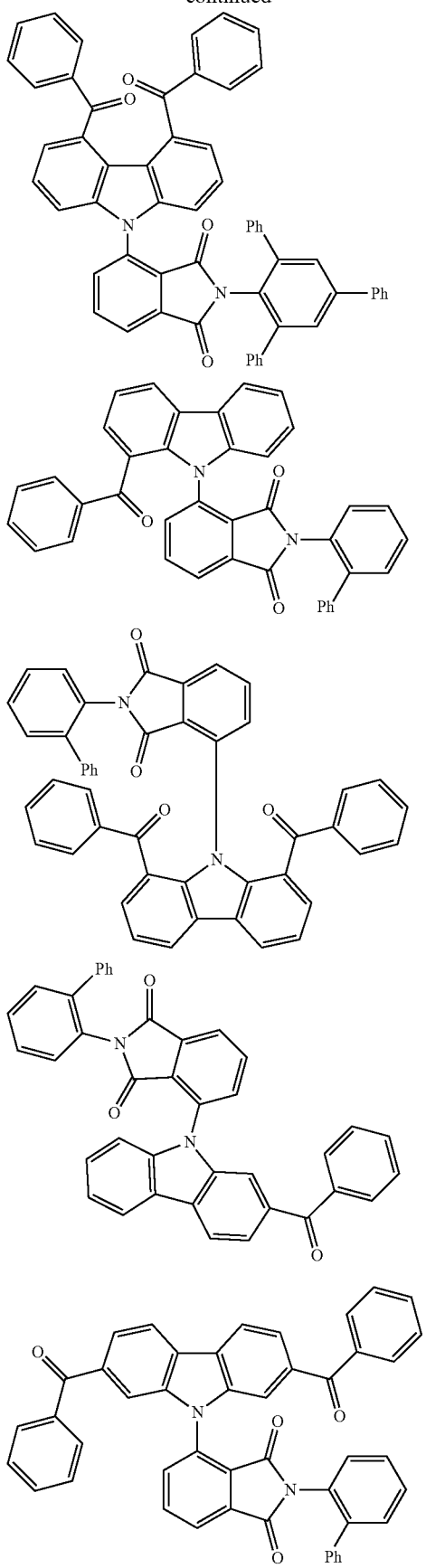
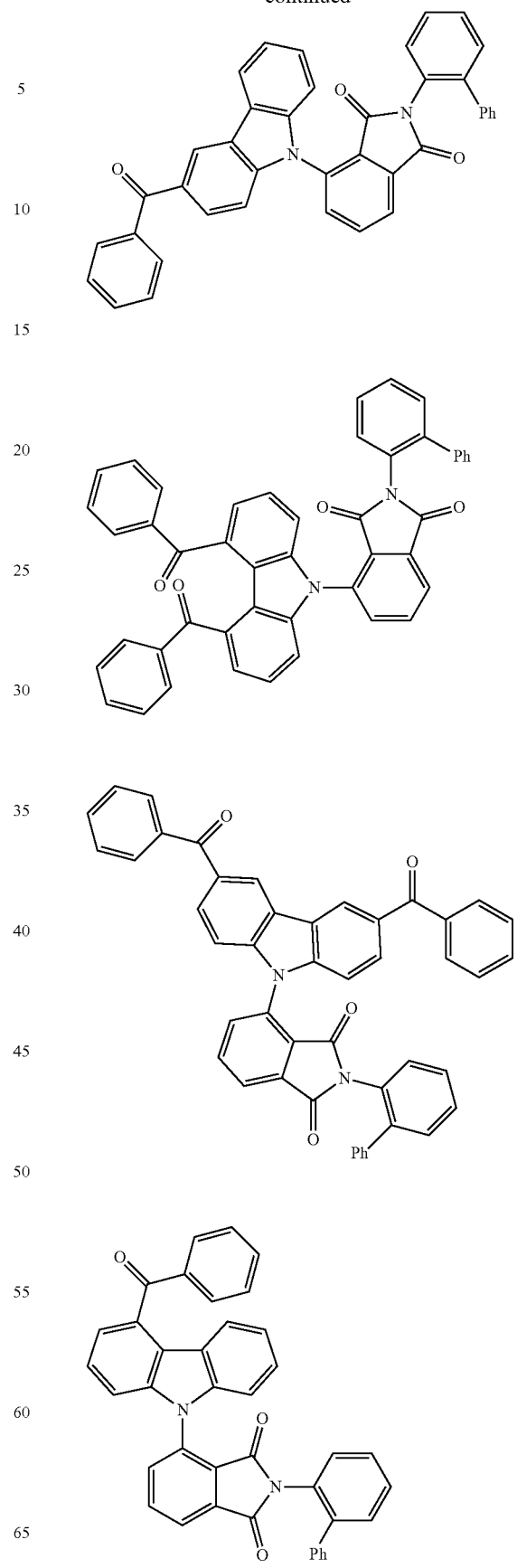

109
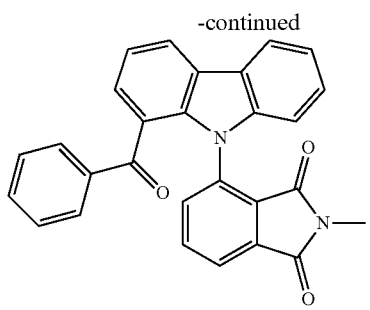
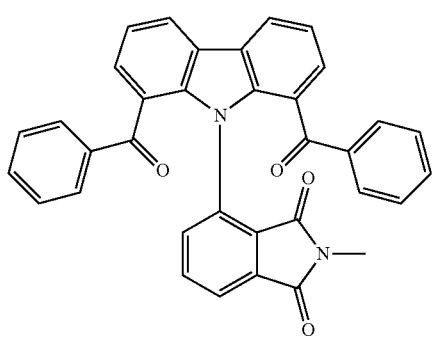
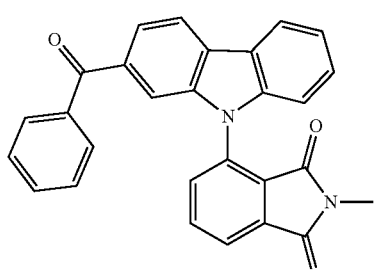
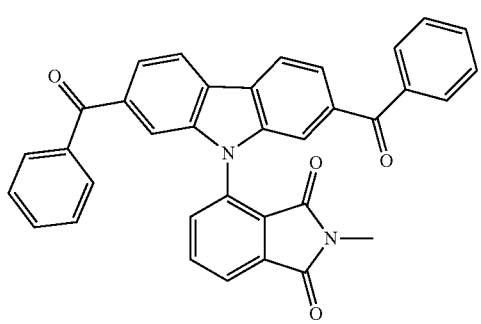
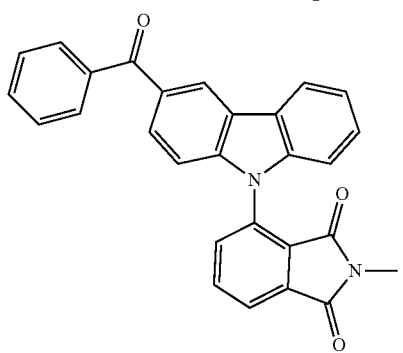
110
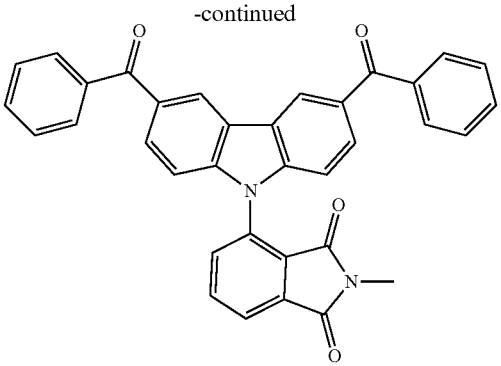
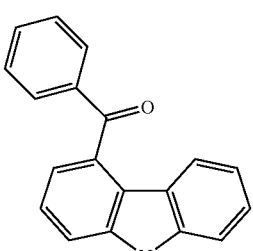
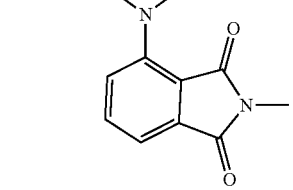
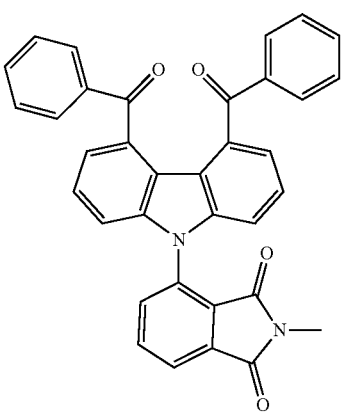
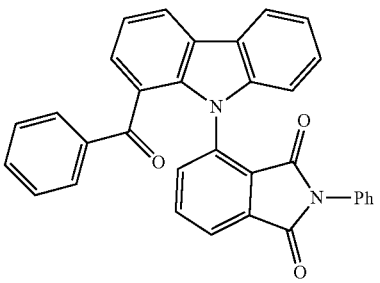

111
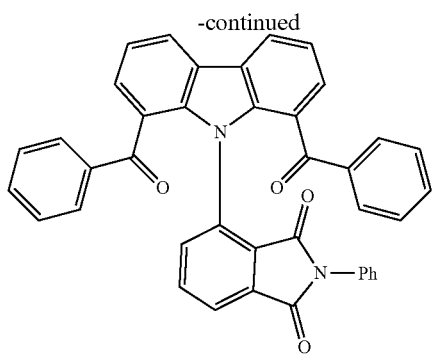
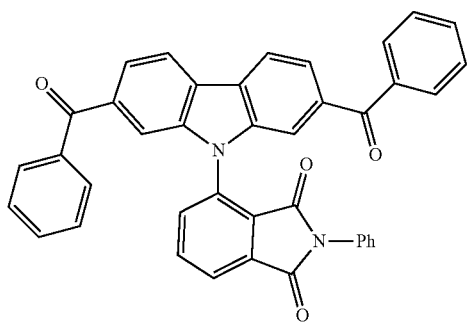
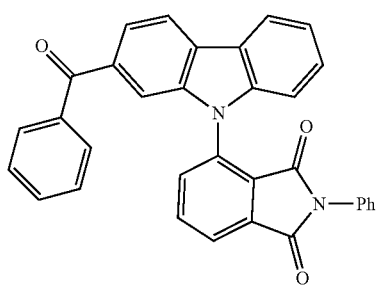
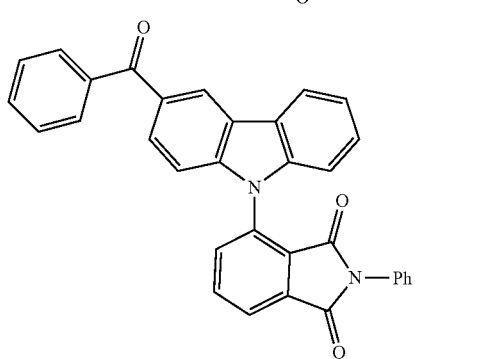
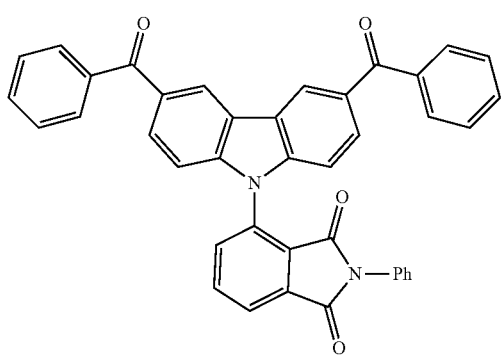
112
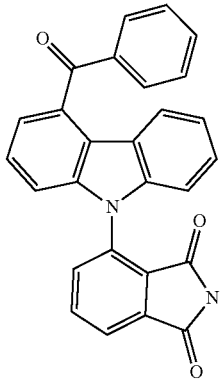
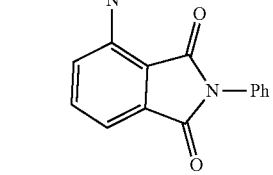
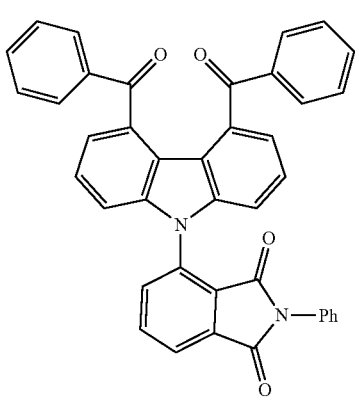
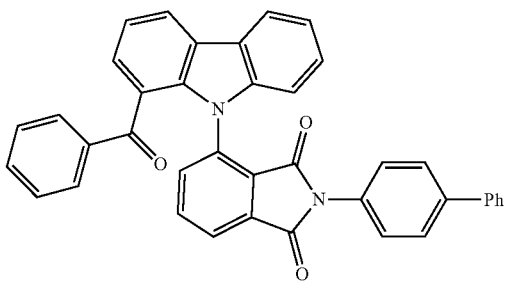
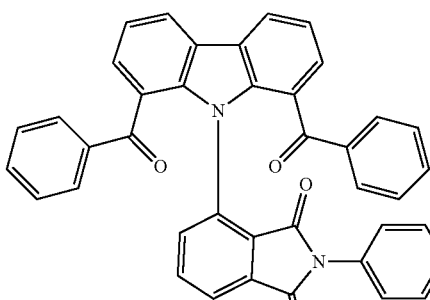
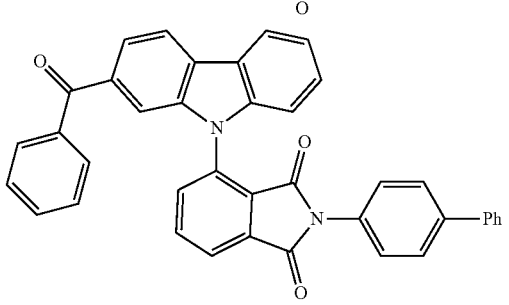

113
-continued
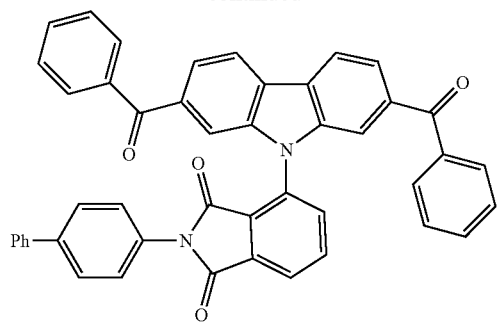
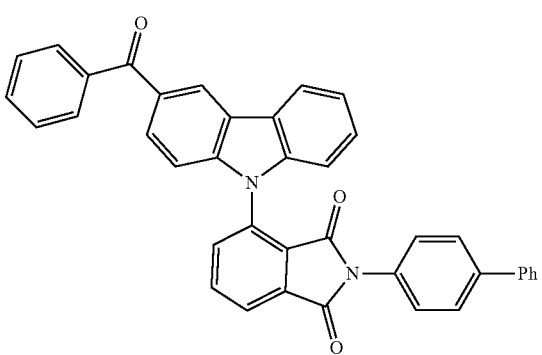
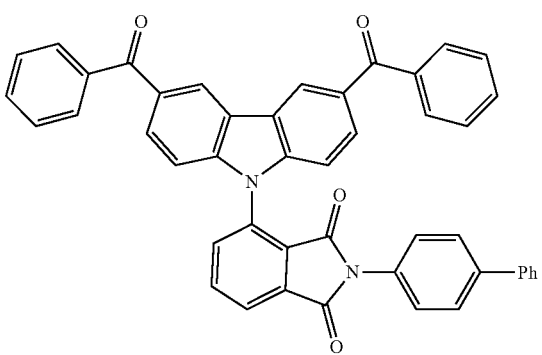
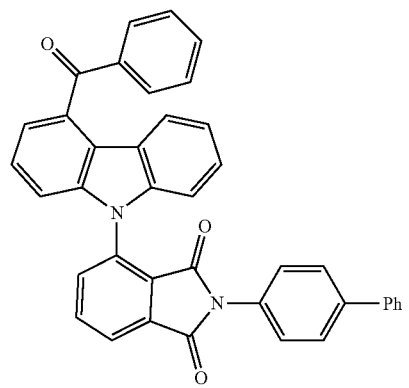
114
-continued
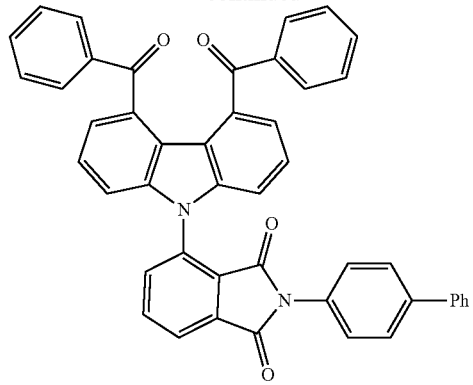
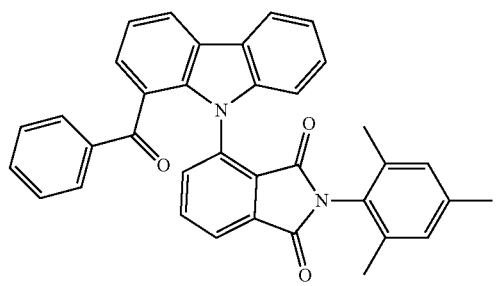
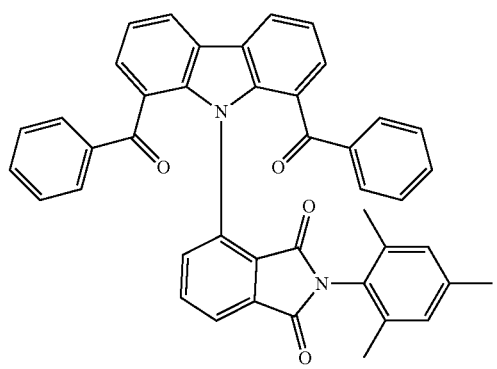
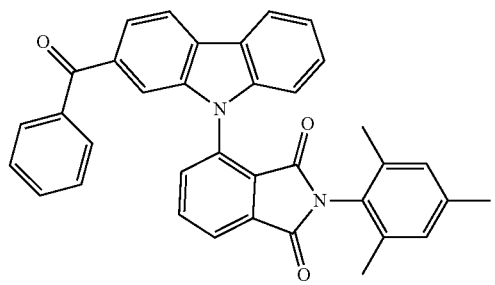
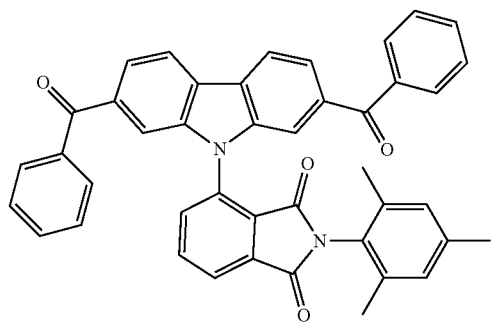

115
-continued
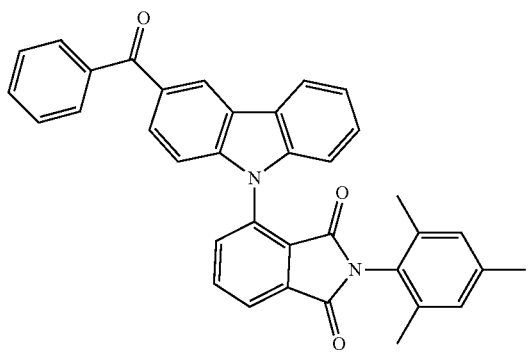
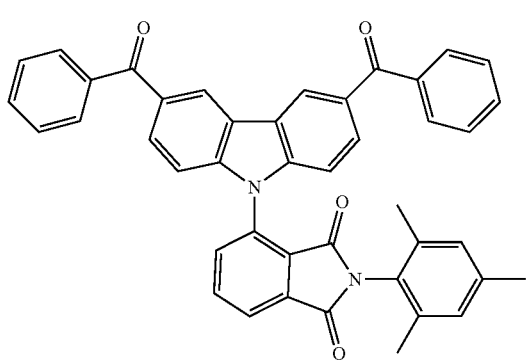
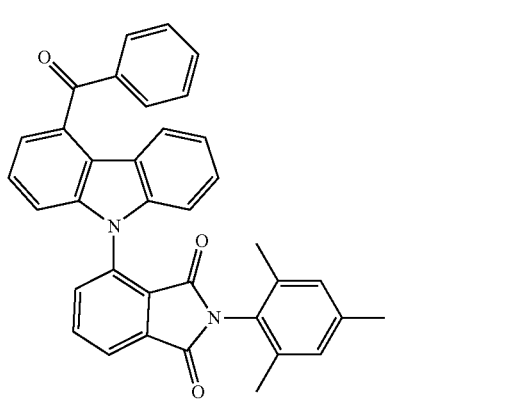
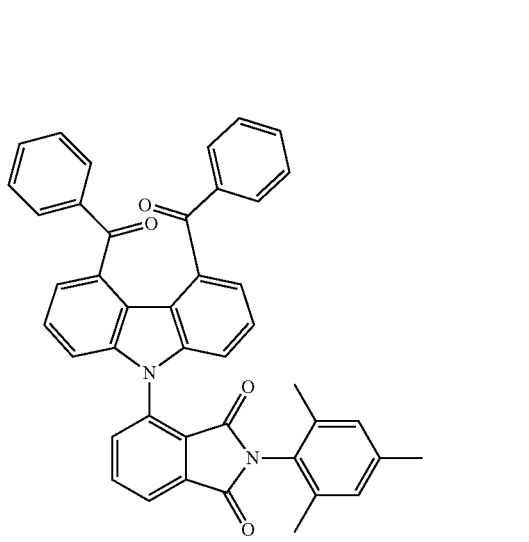
116
-continued
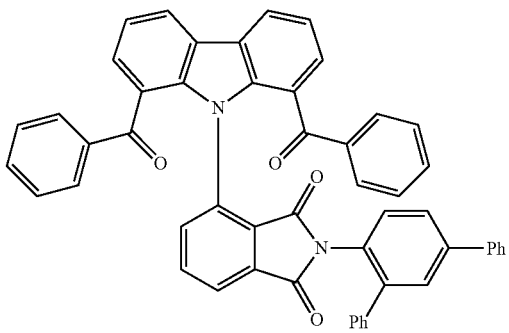
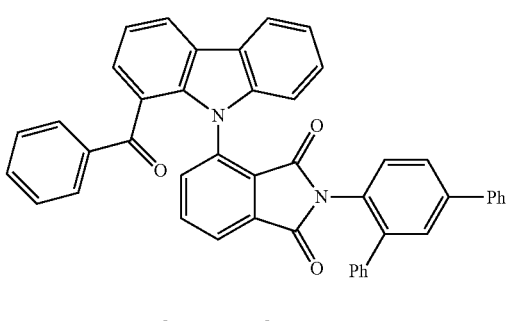
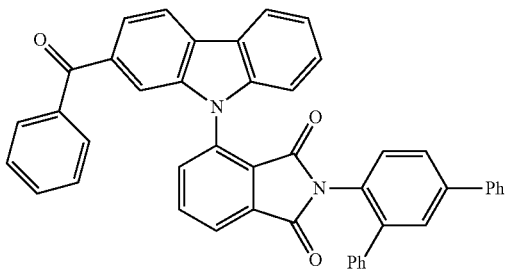
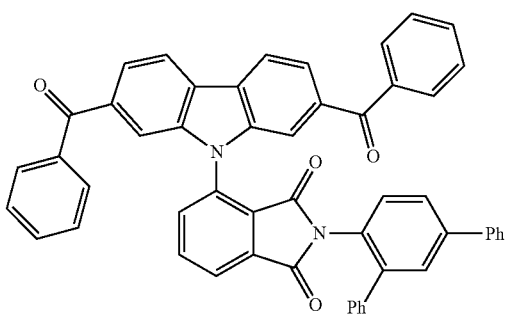
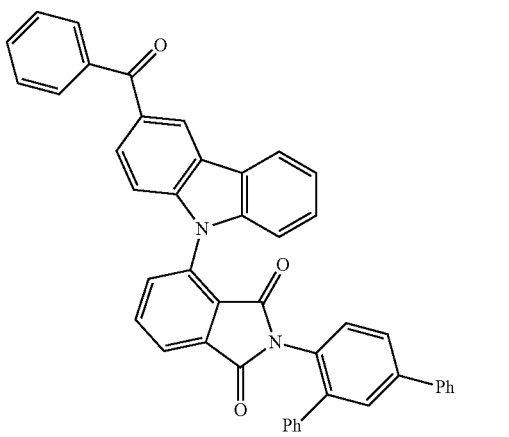

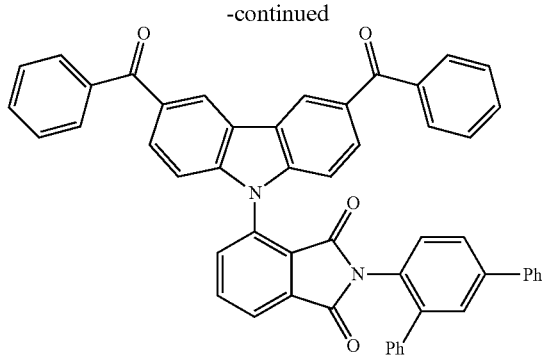
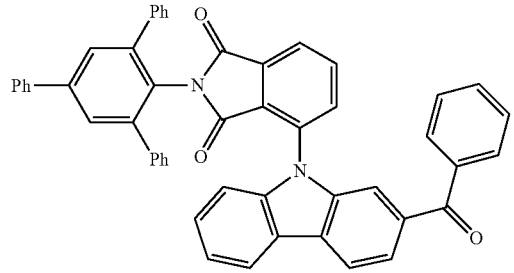
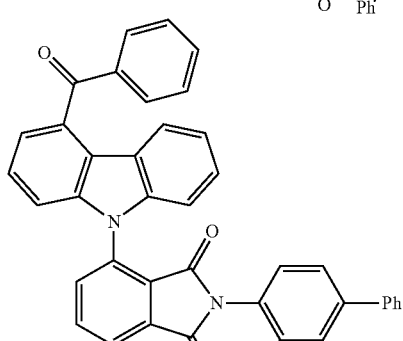
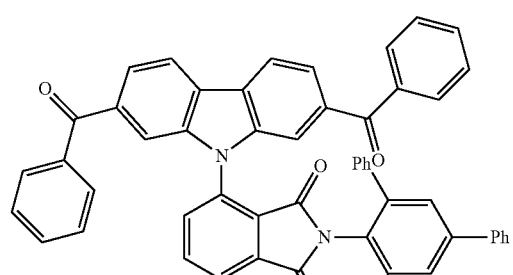
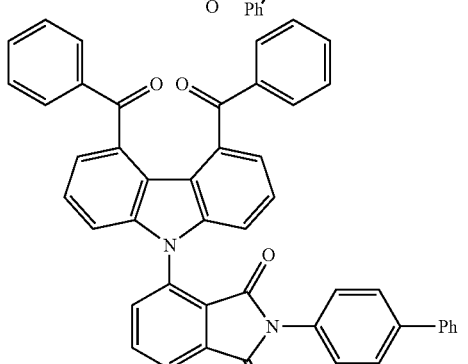
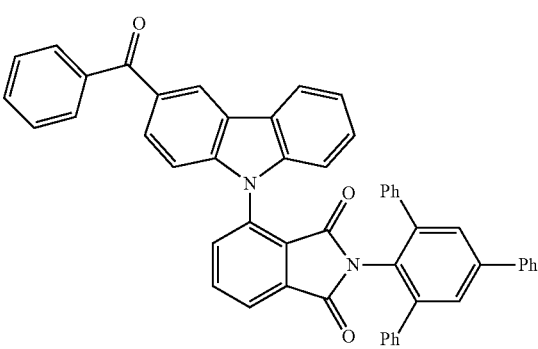
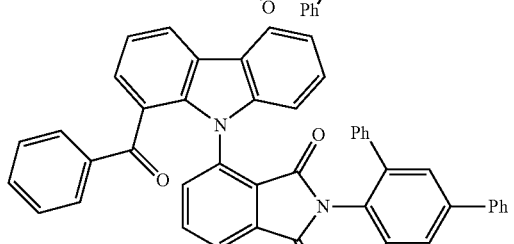
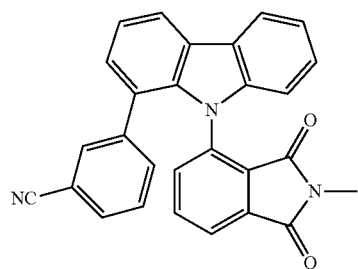
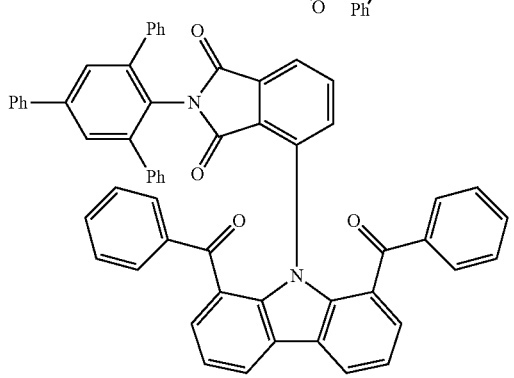
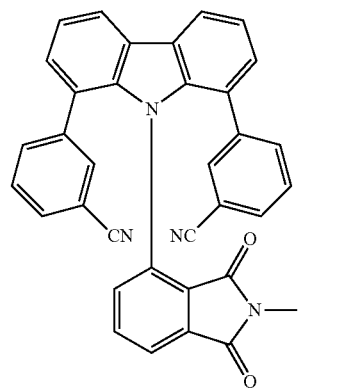

119
-continued
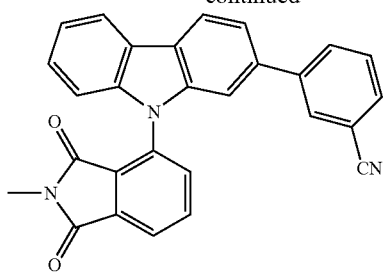
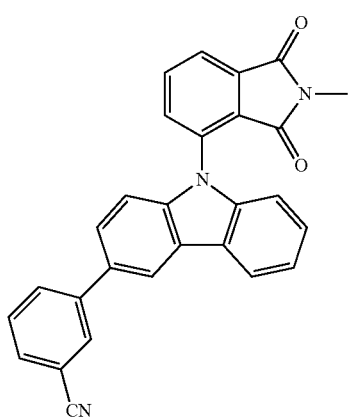
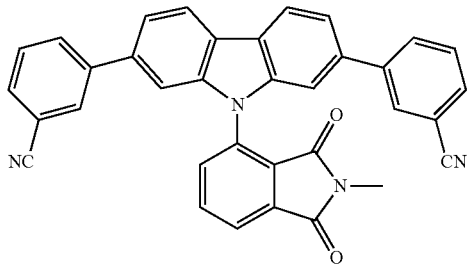
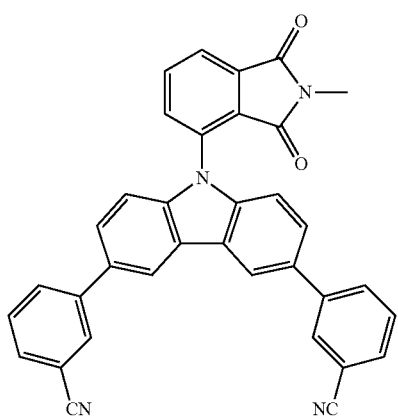
120
-continued
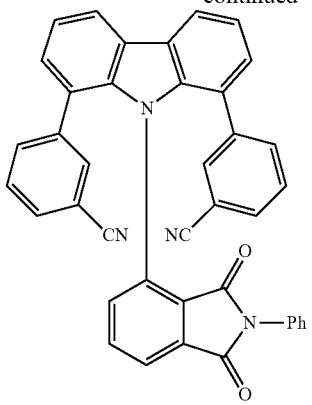
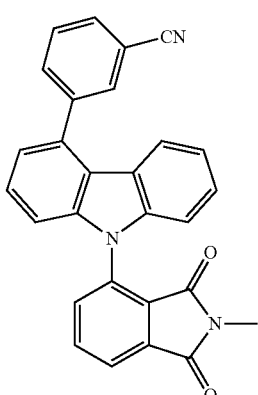
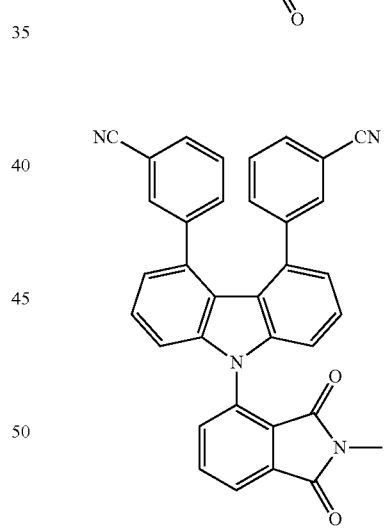
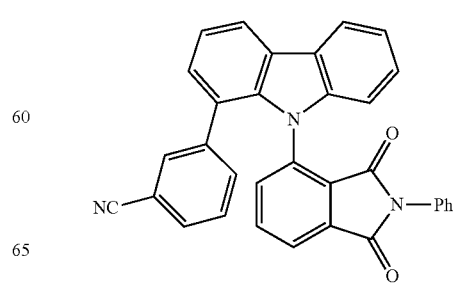

121
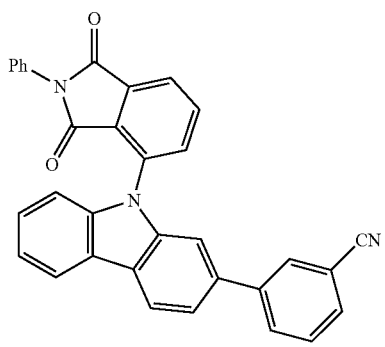
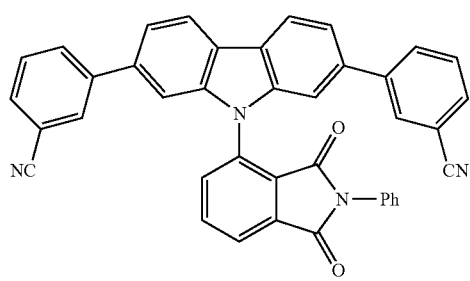
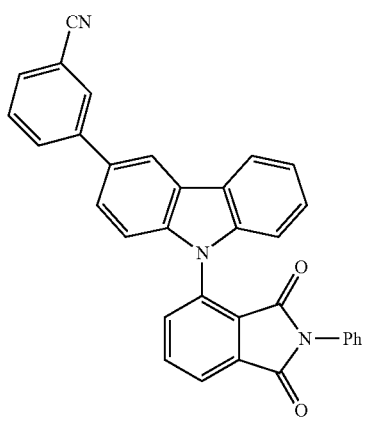
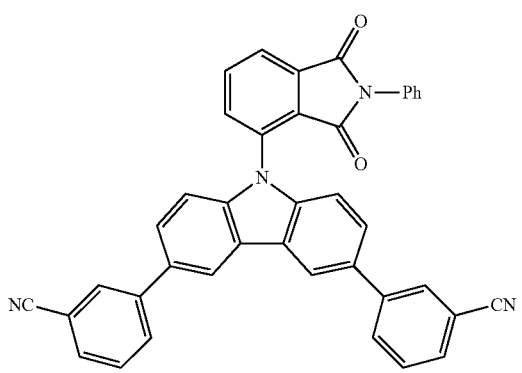
122
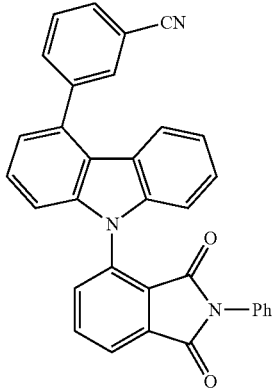
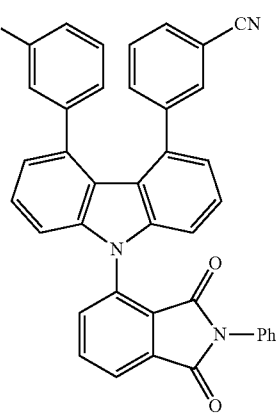
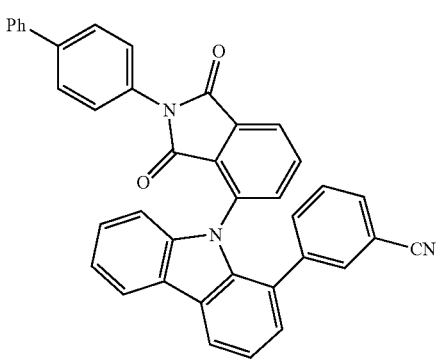
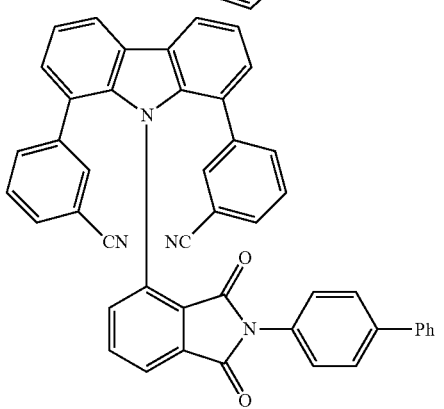

123
-continued
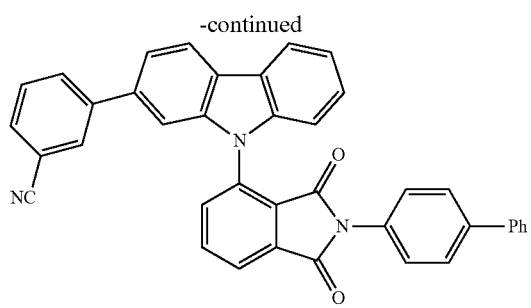
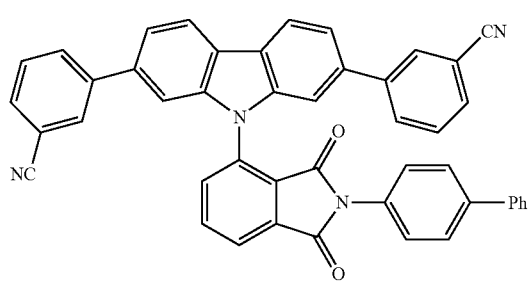
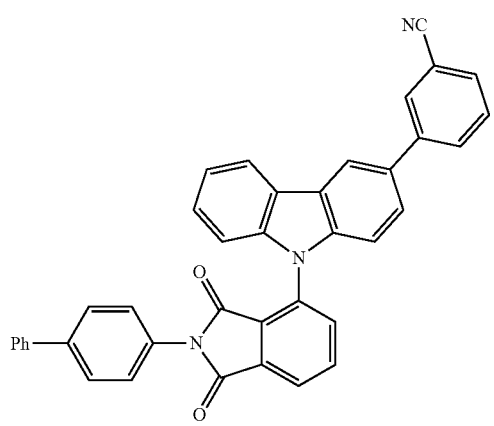
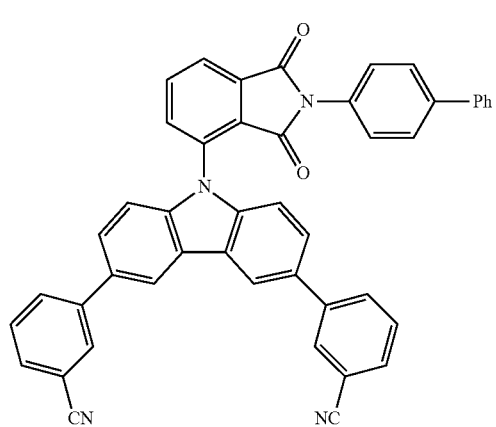
124
-continued
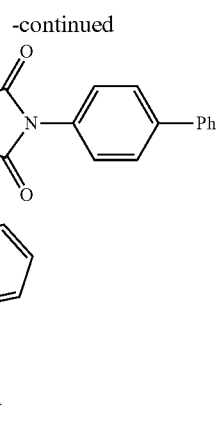
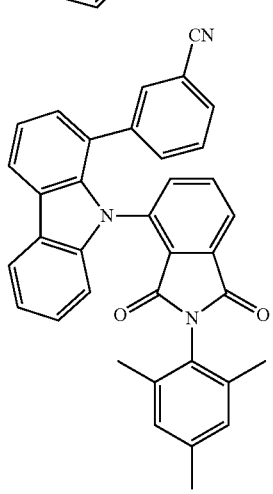
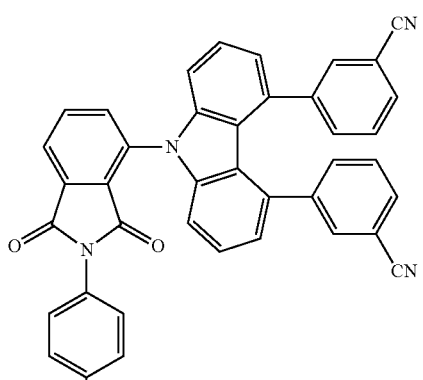
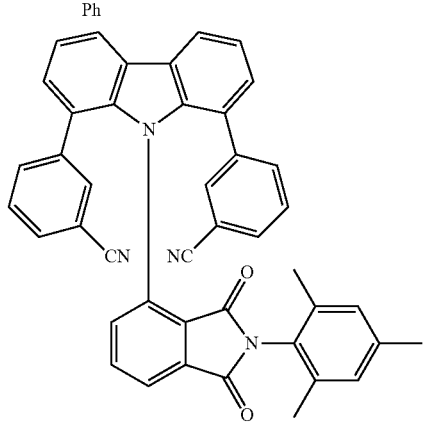

125
-continued
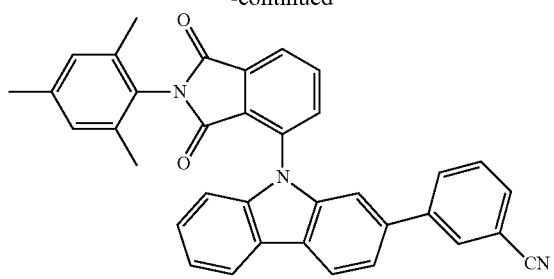
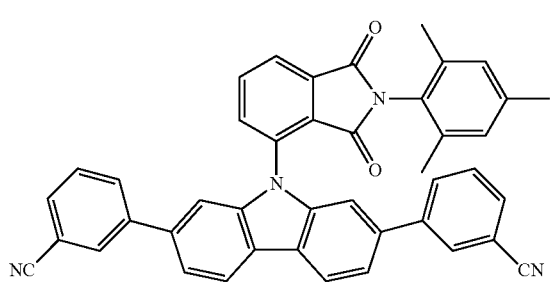
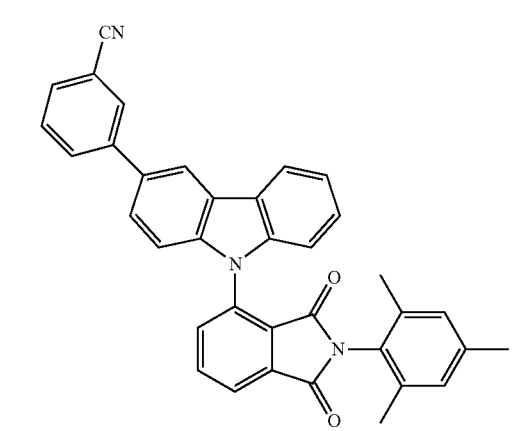
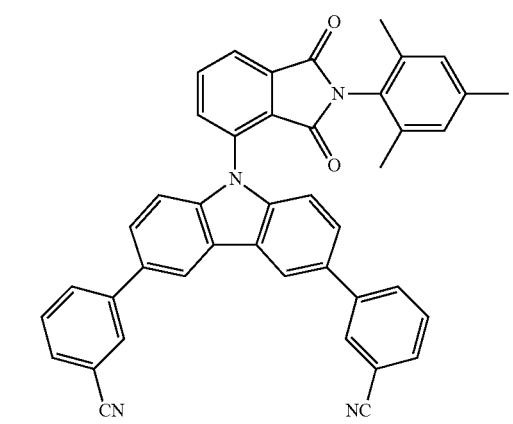
126
-continued
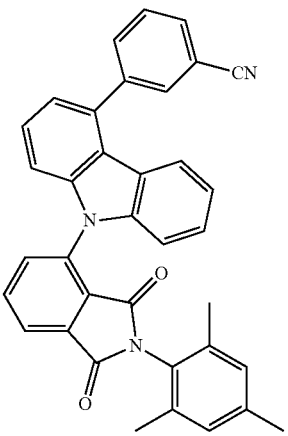
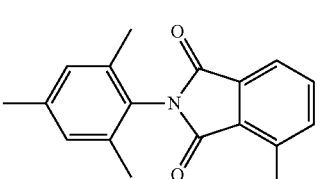
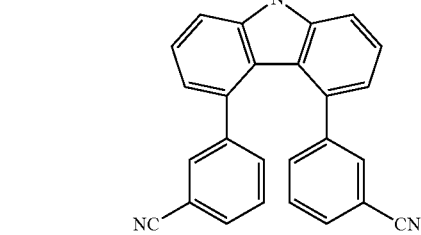
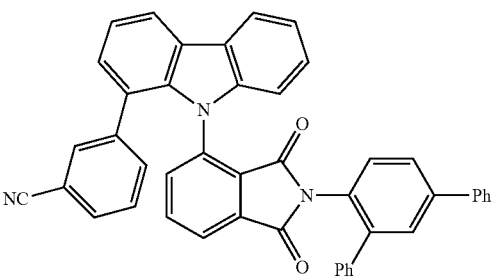
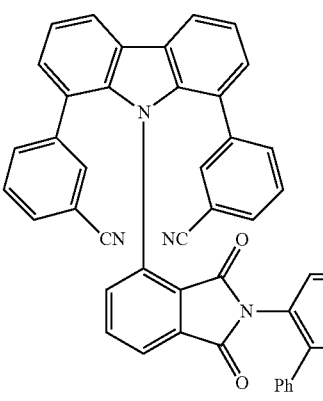

127
-continued
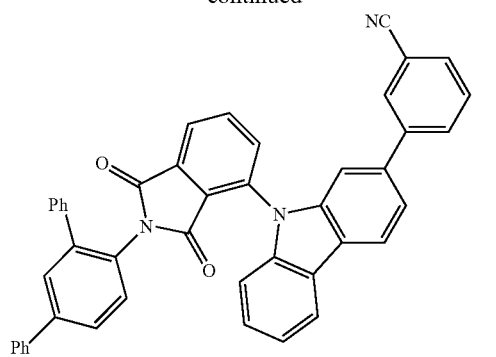
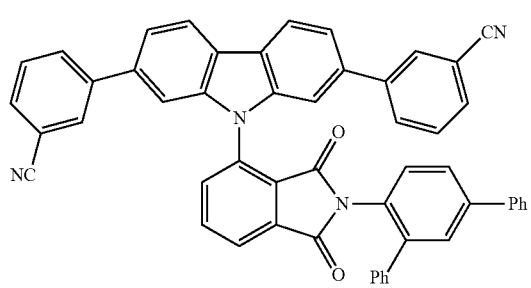
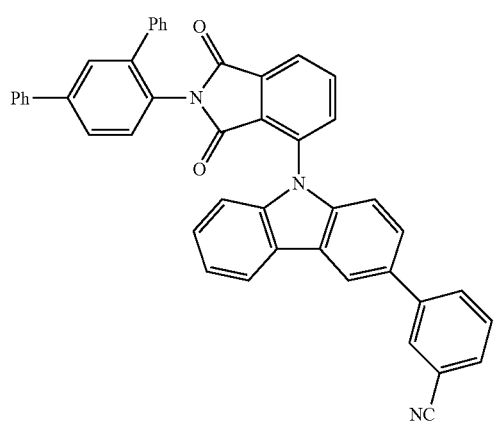
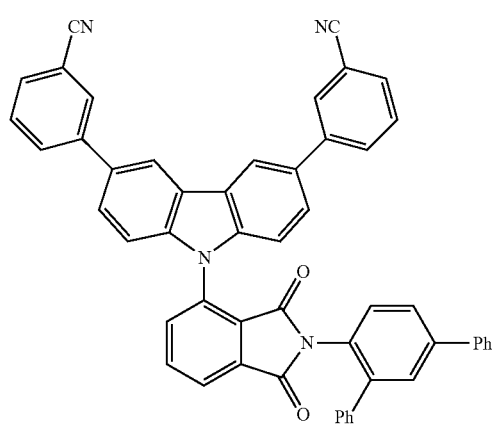
128
-continued
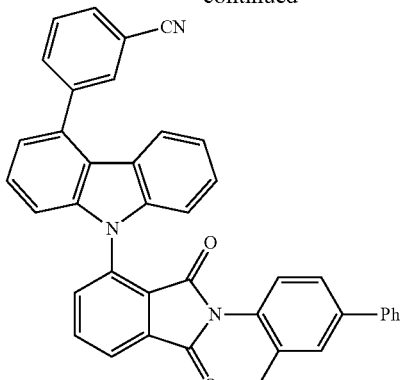
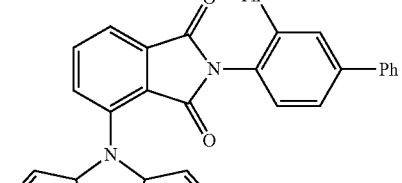
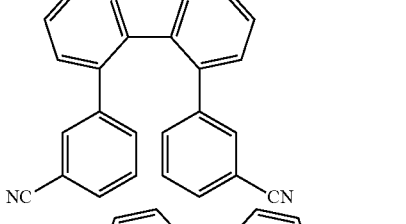
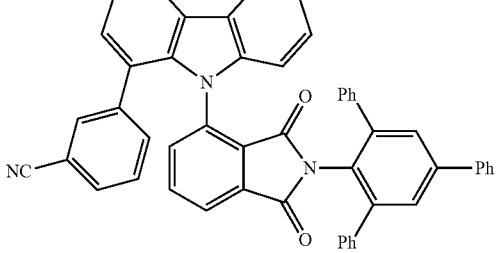
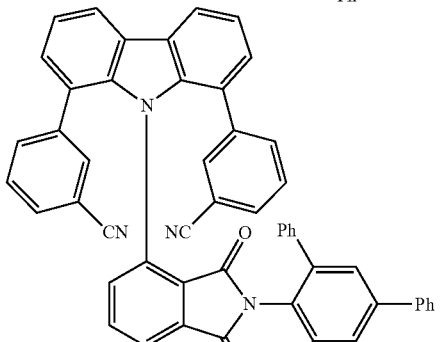
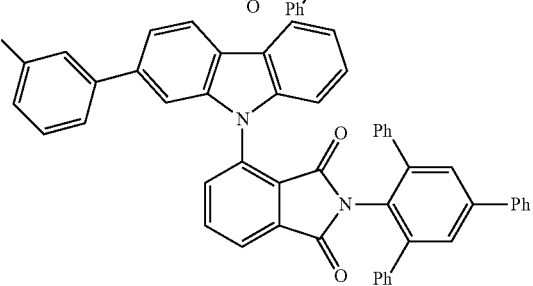

129
-continued
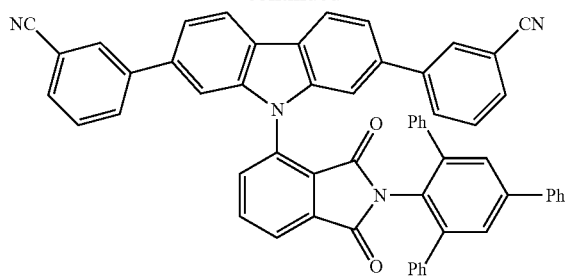
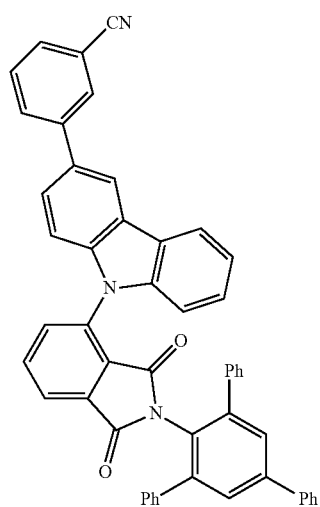
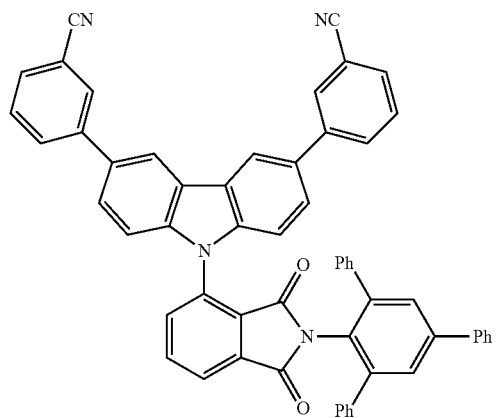
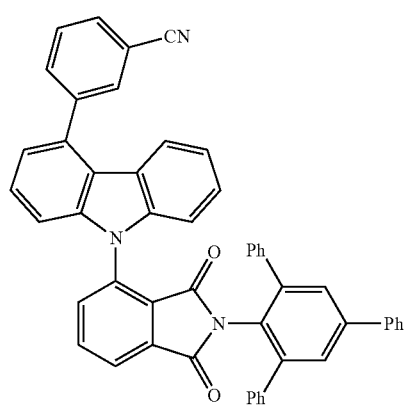
130
-continued
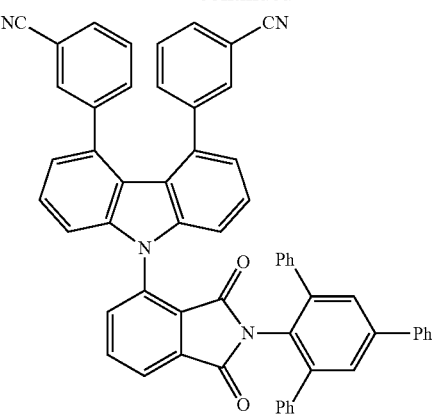
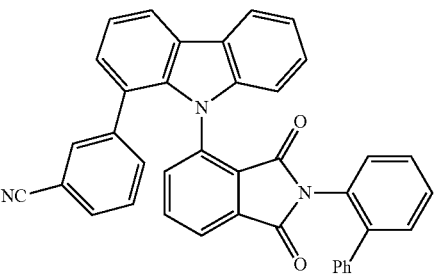
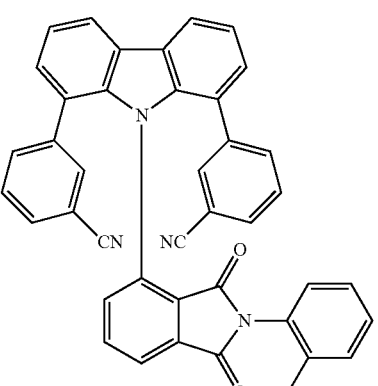
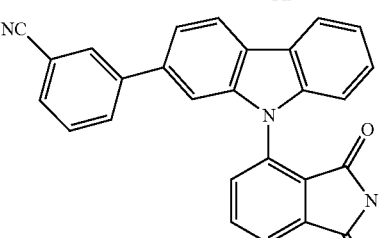
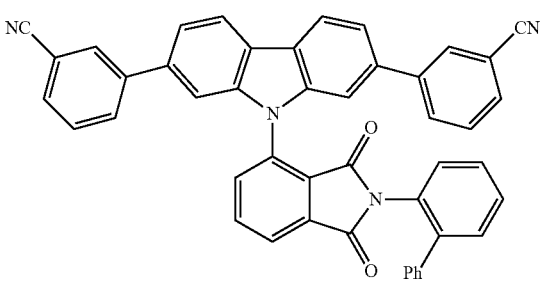

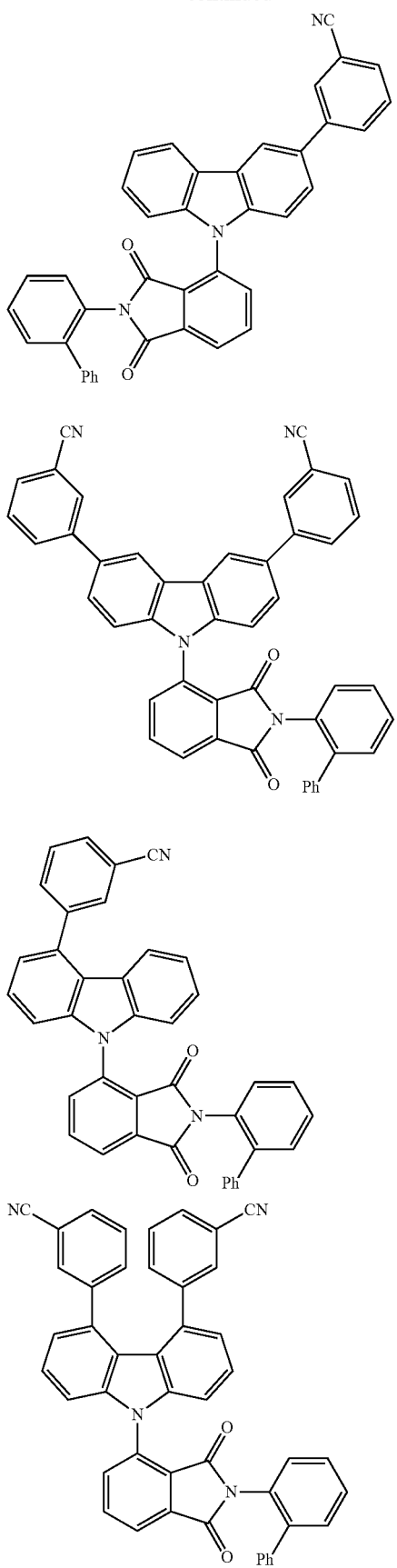
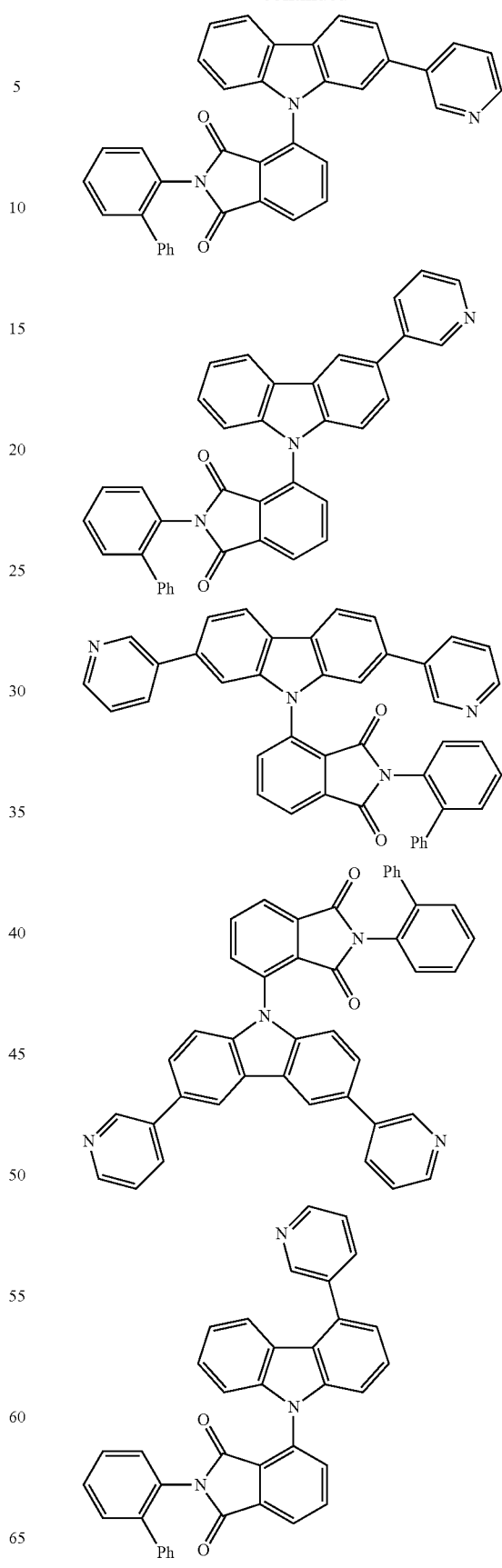

133
-continued
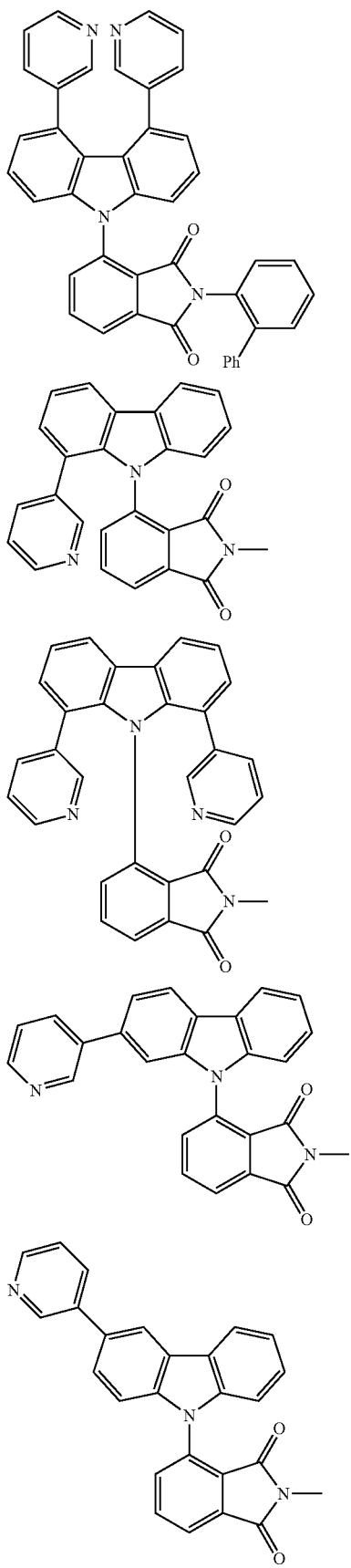
134
-continued
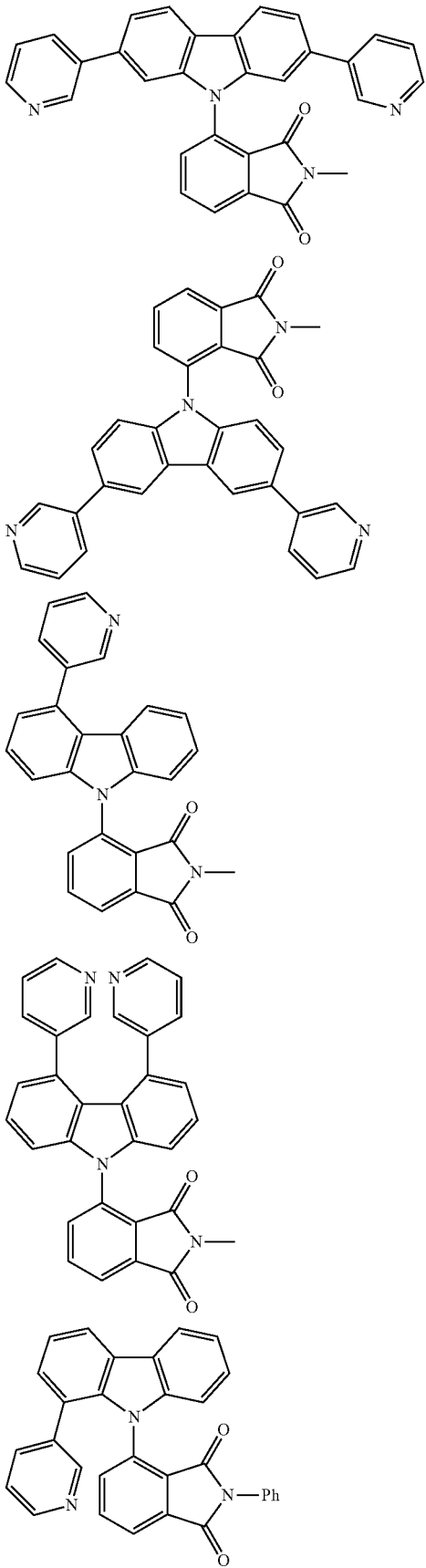

135
-continued
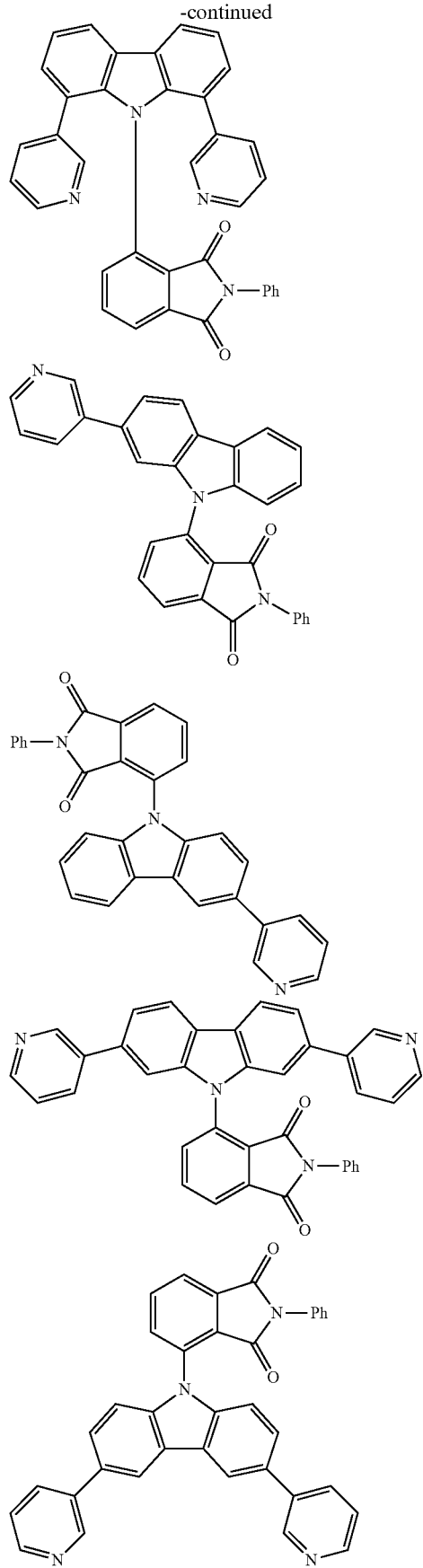
136
-continued
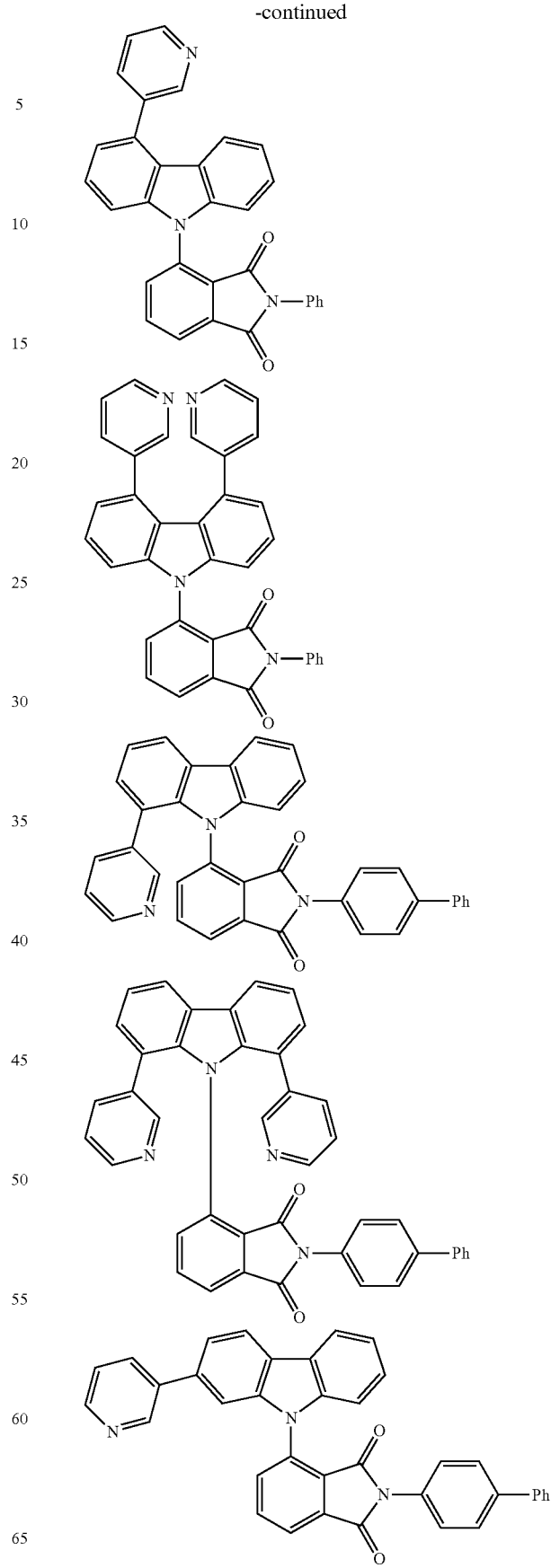

137
-continued
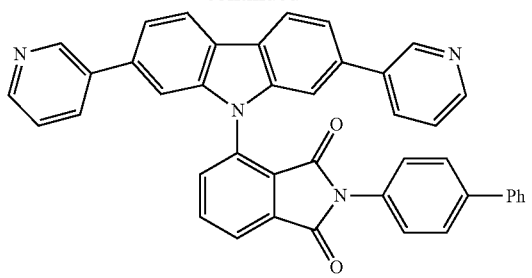
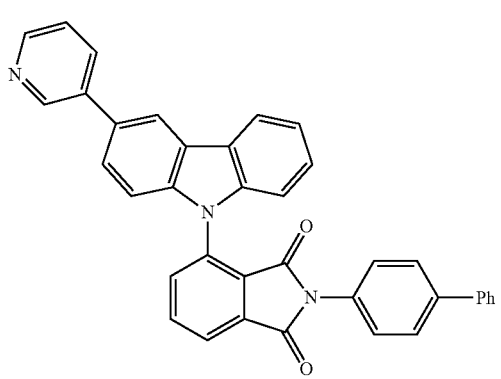
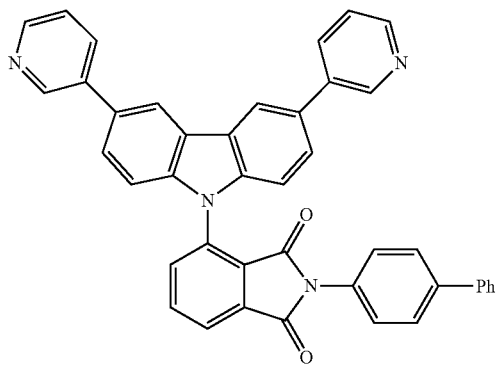
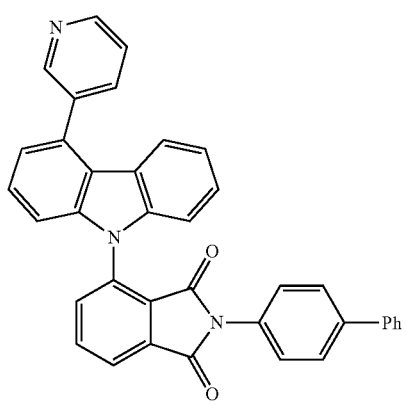
138
-continued
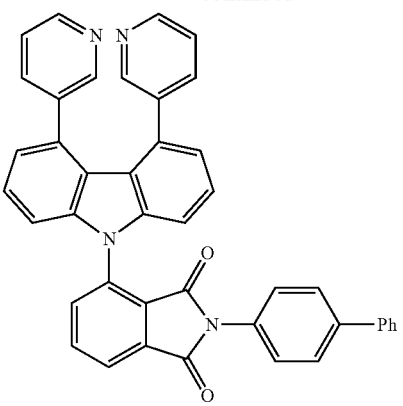
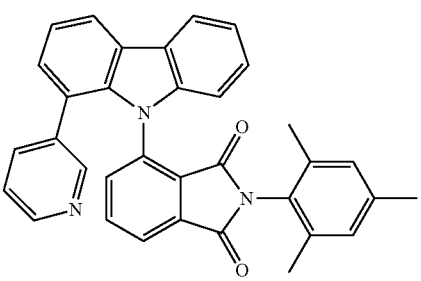
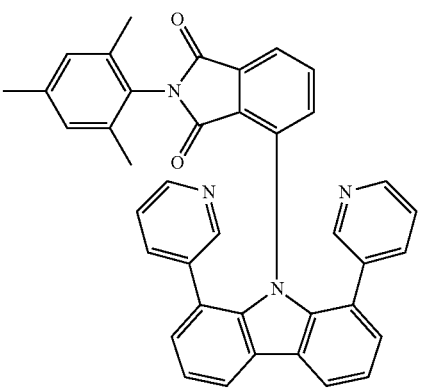
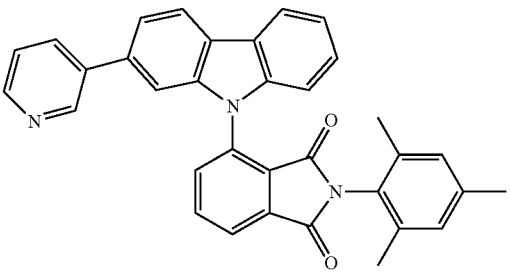
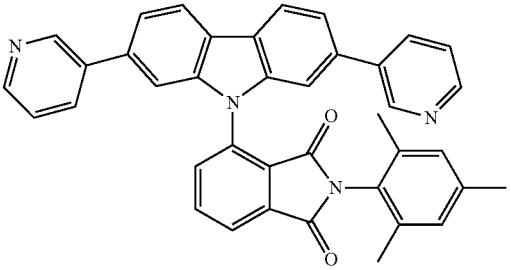

139
-continued
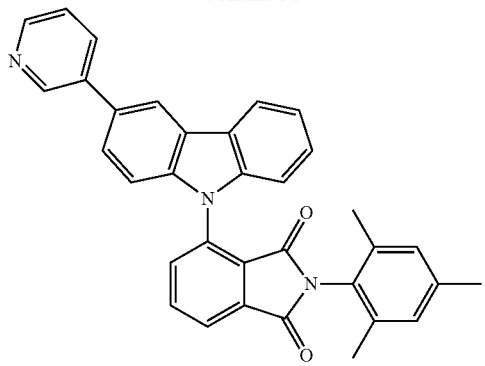
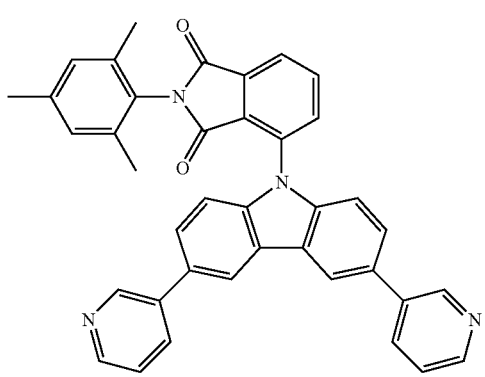
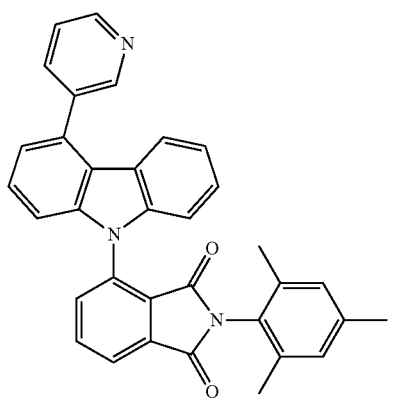
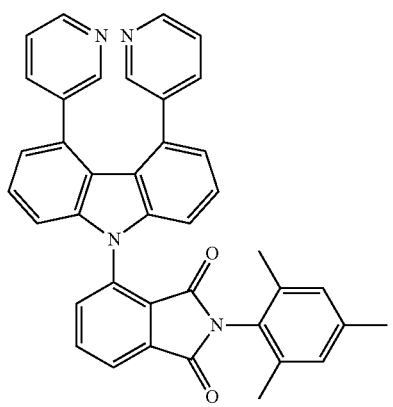
140
-continued
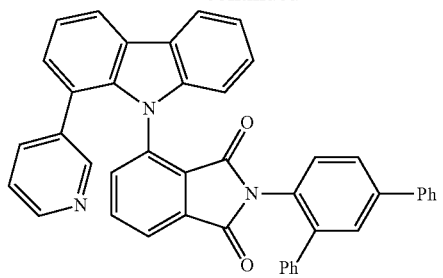
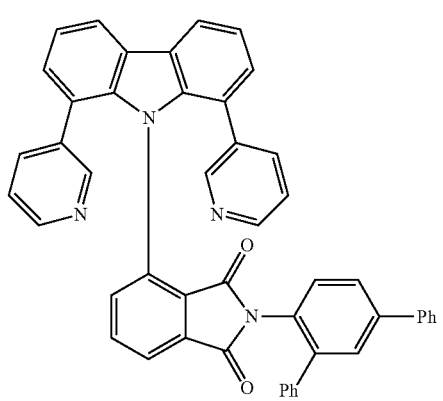
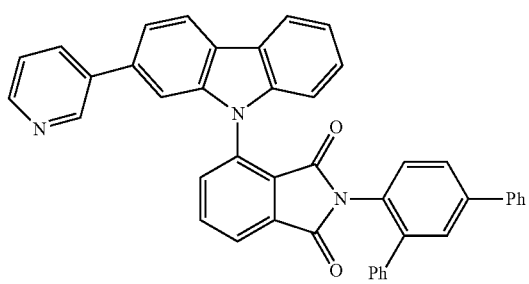
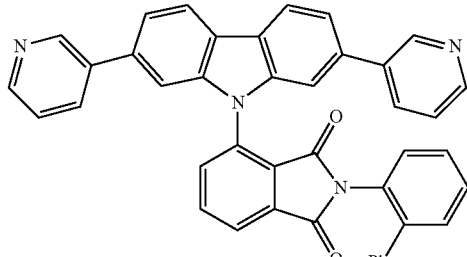
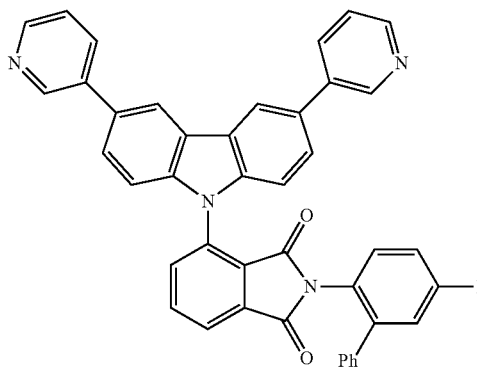

141
-continued
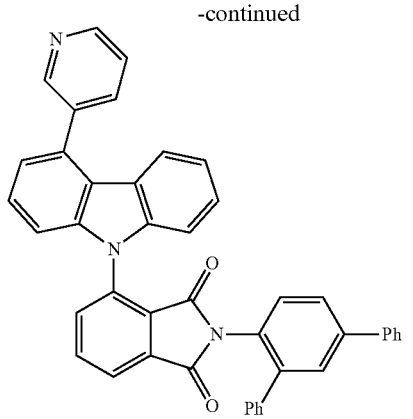
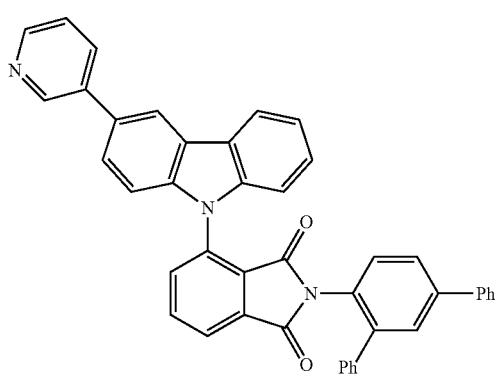
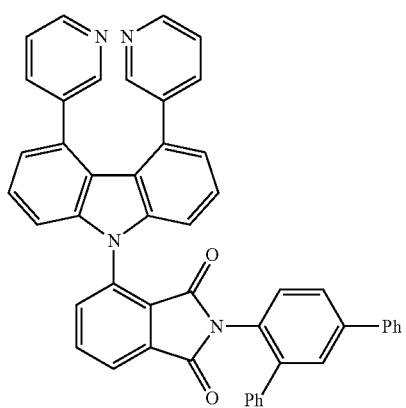
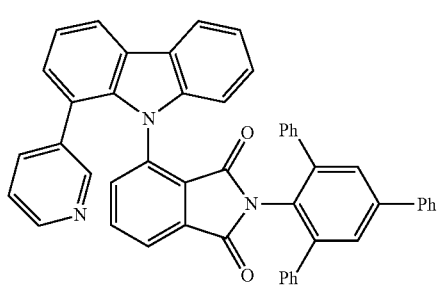
142
-continued
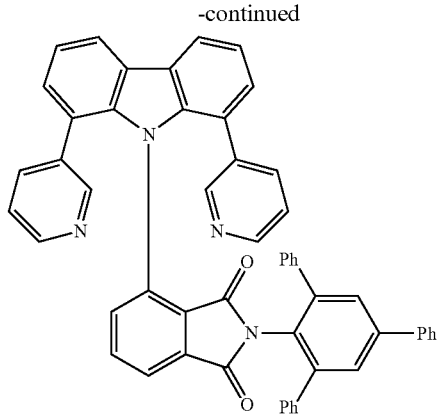
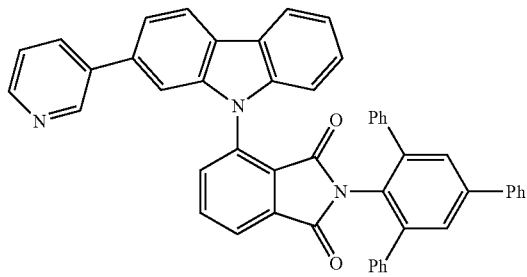
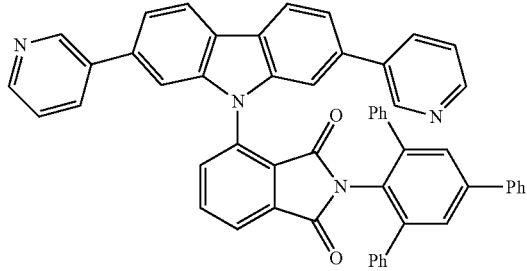
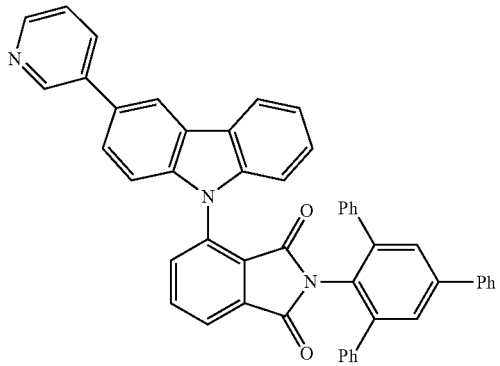
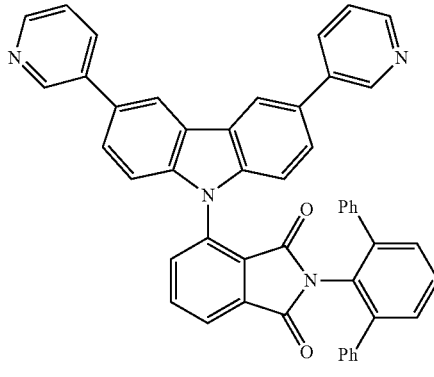

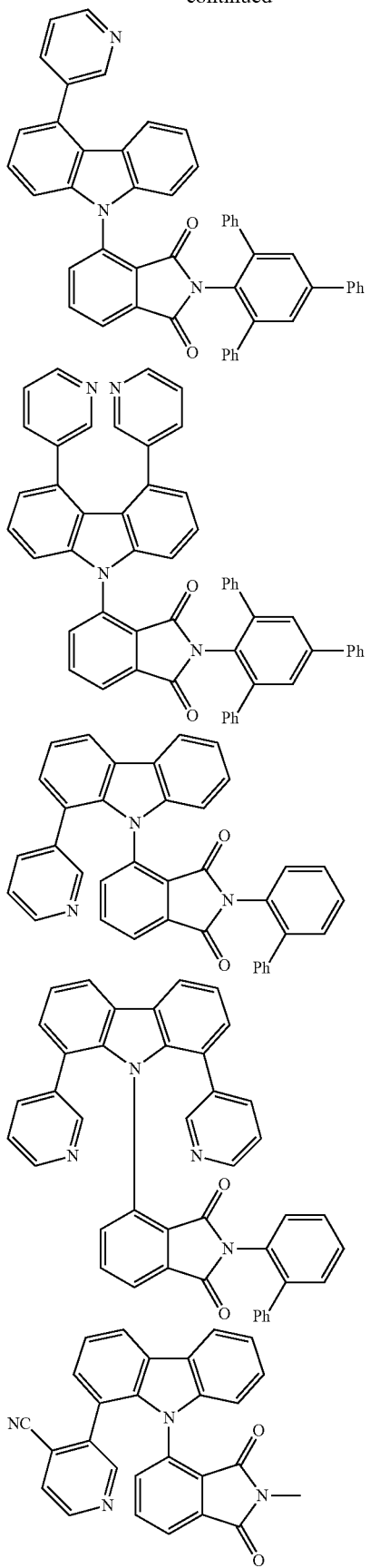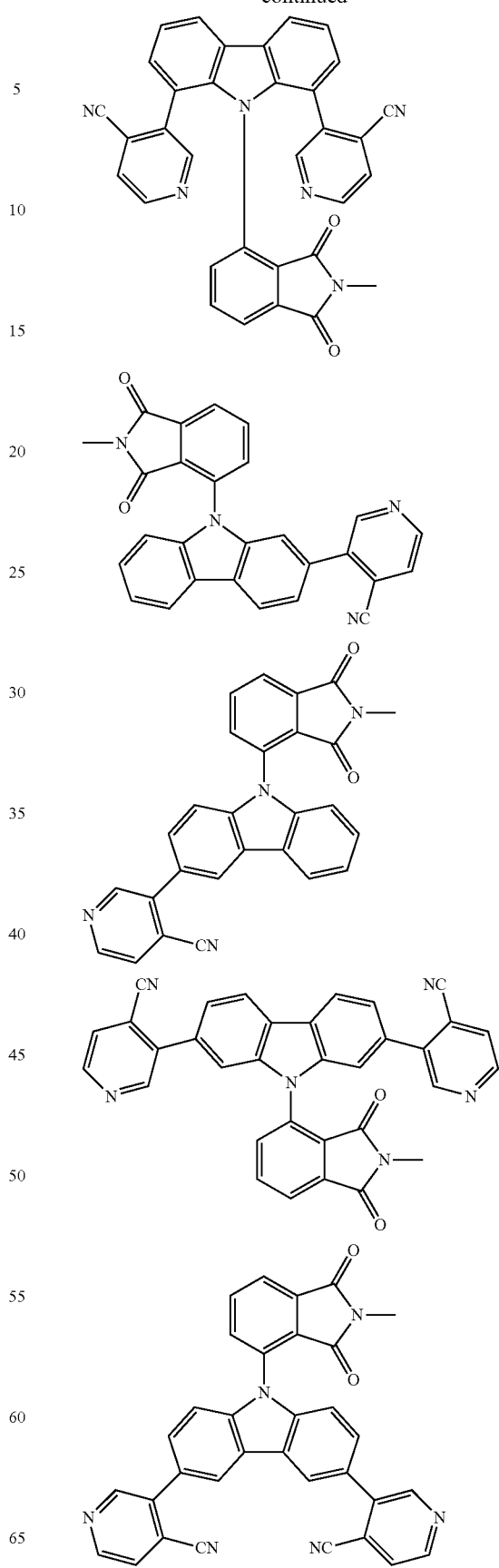

145
-continued
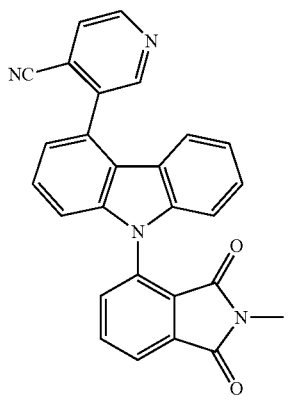
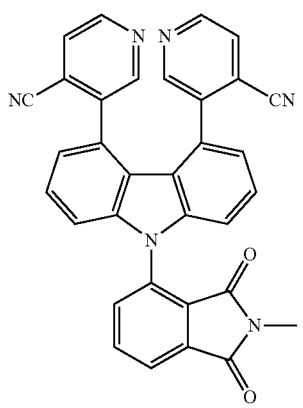
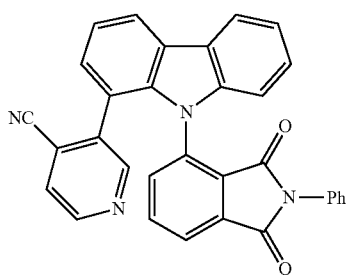
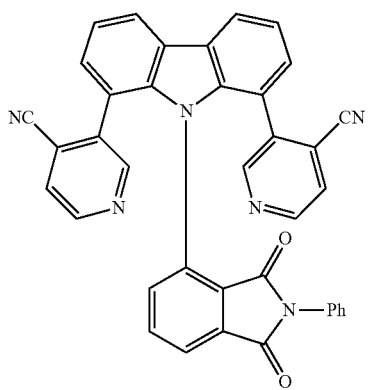
146
-continued
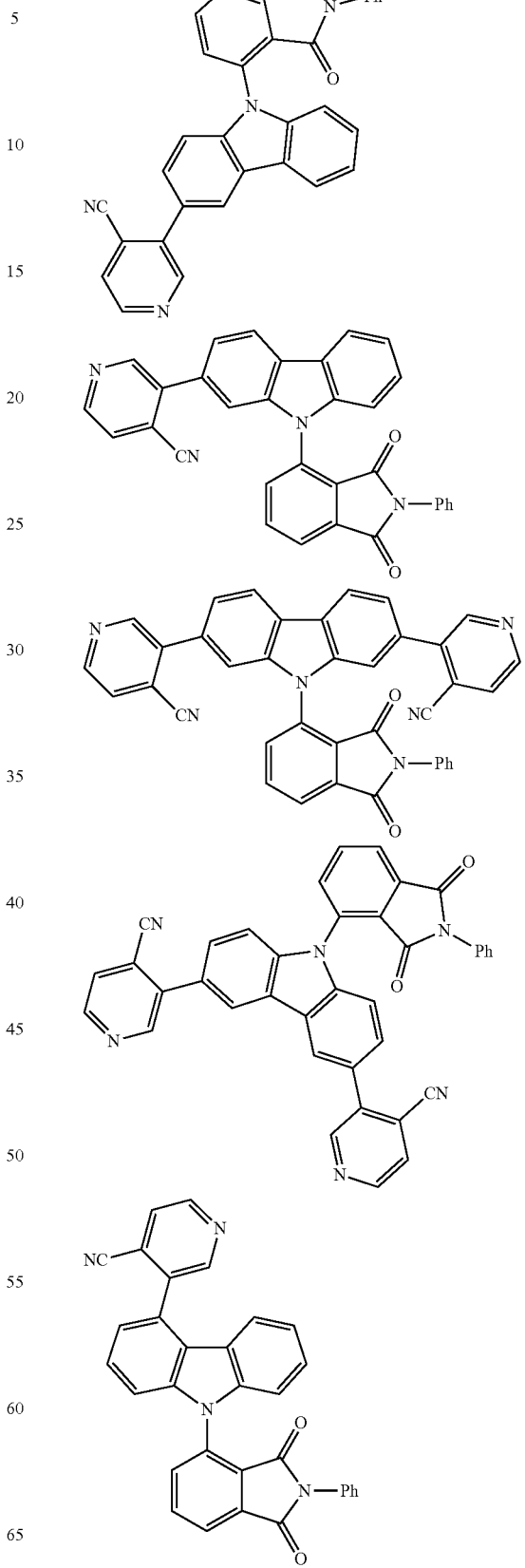

147
-continued
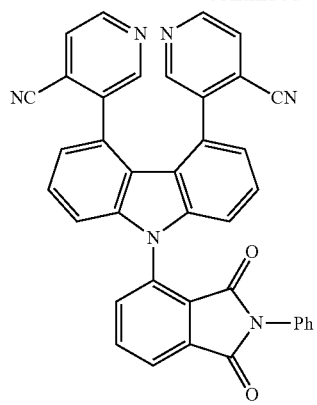
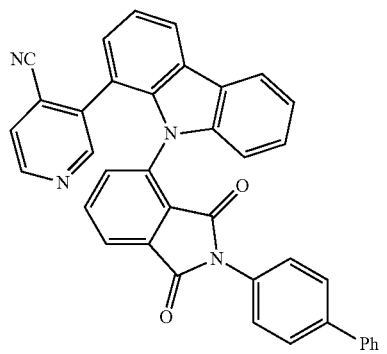
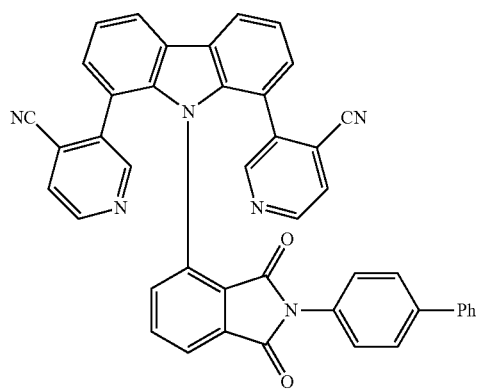
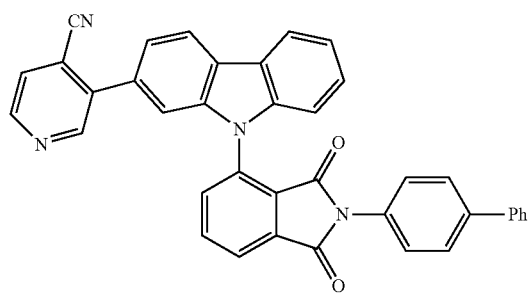
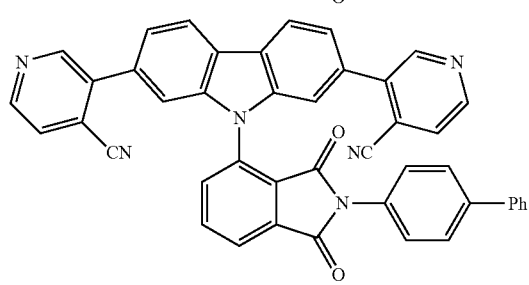
148
-continued
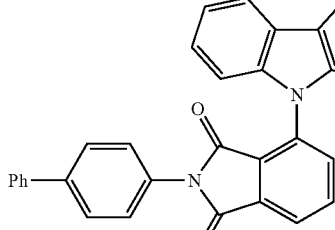
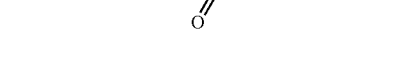

149
-continued
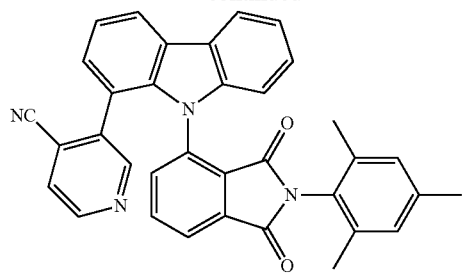
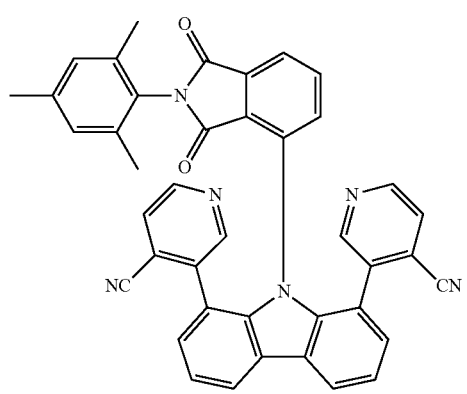
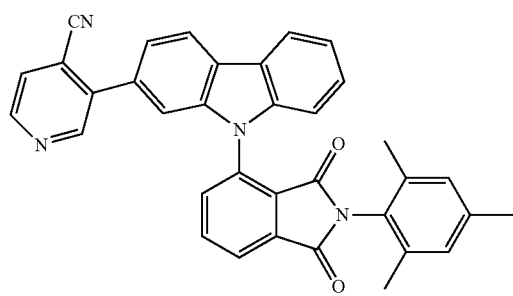
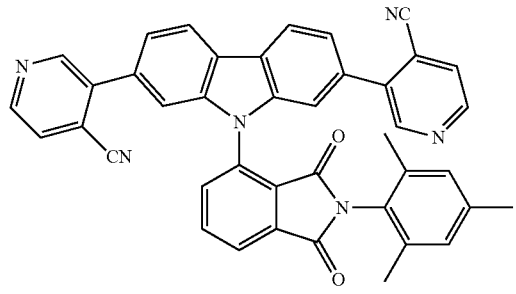
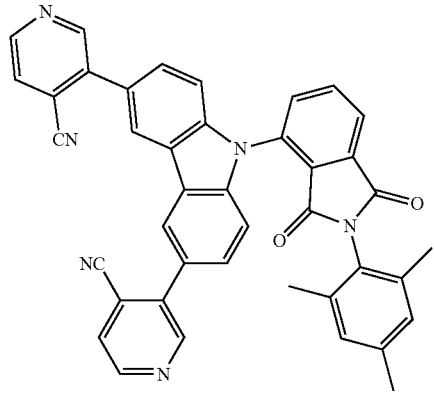
150
-continued
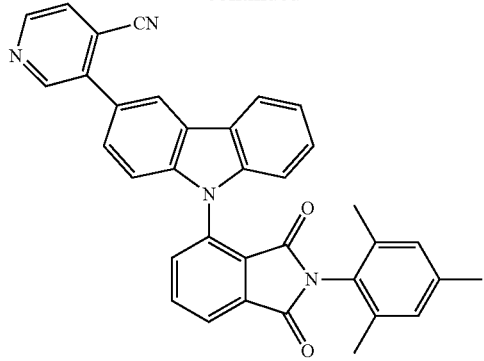
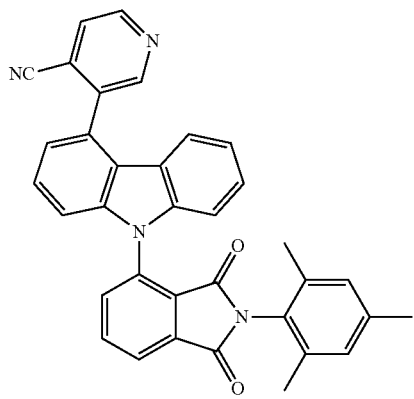
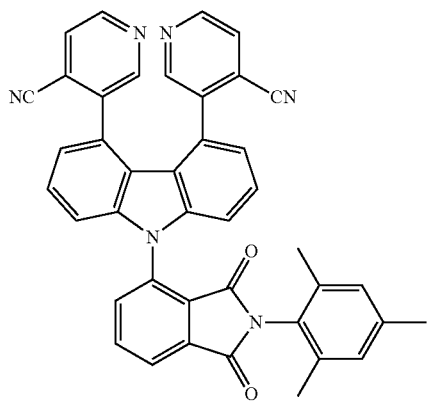
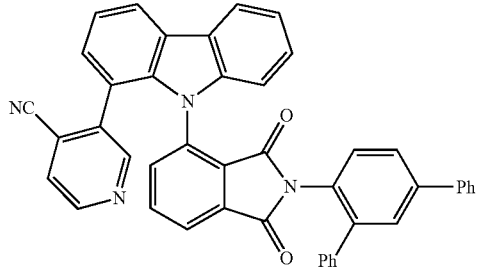

151
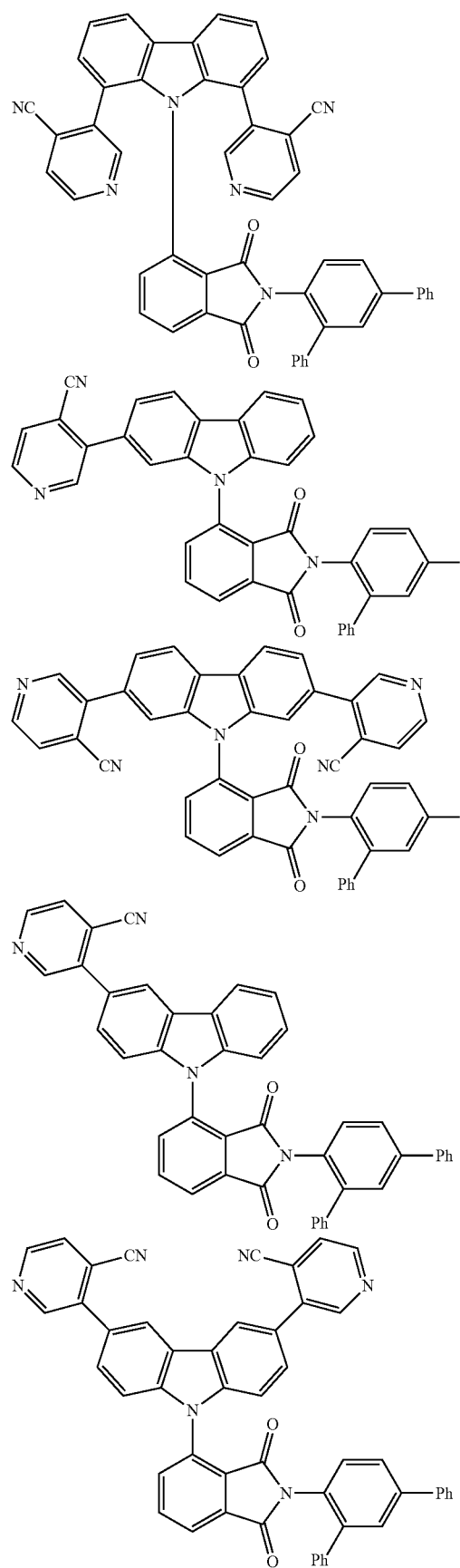
152
-continued
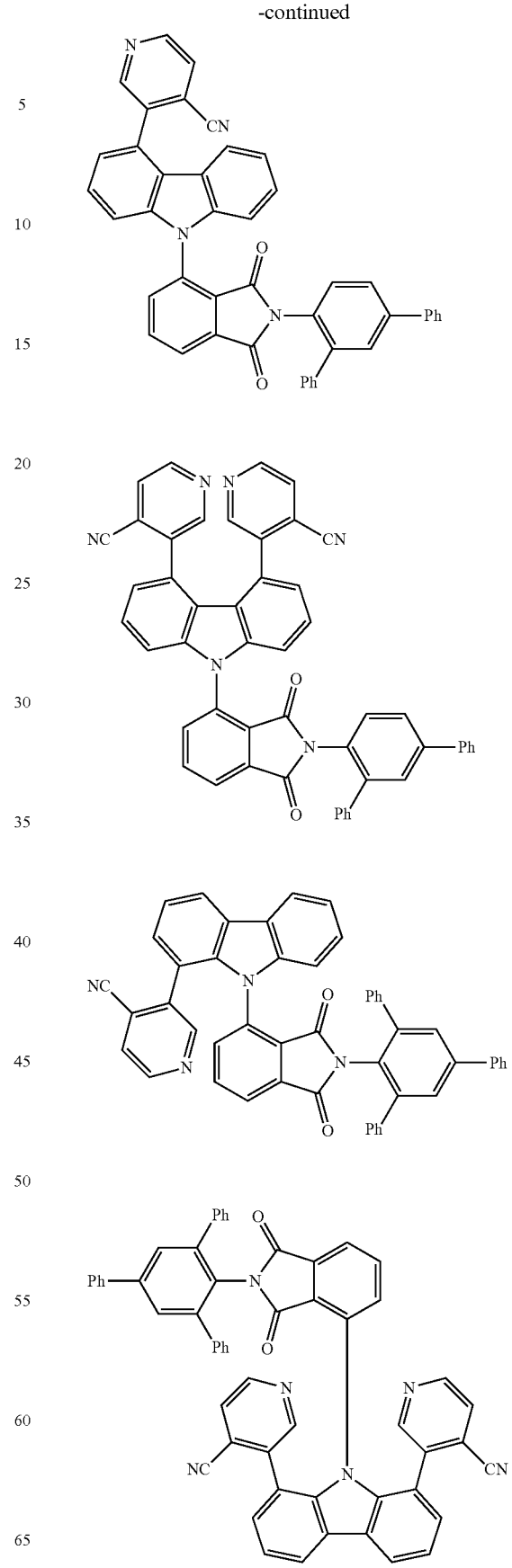

153
-continued
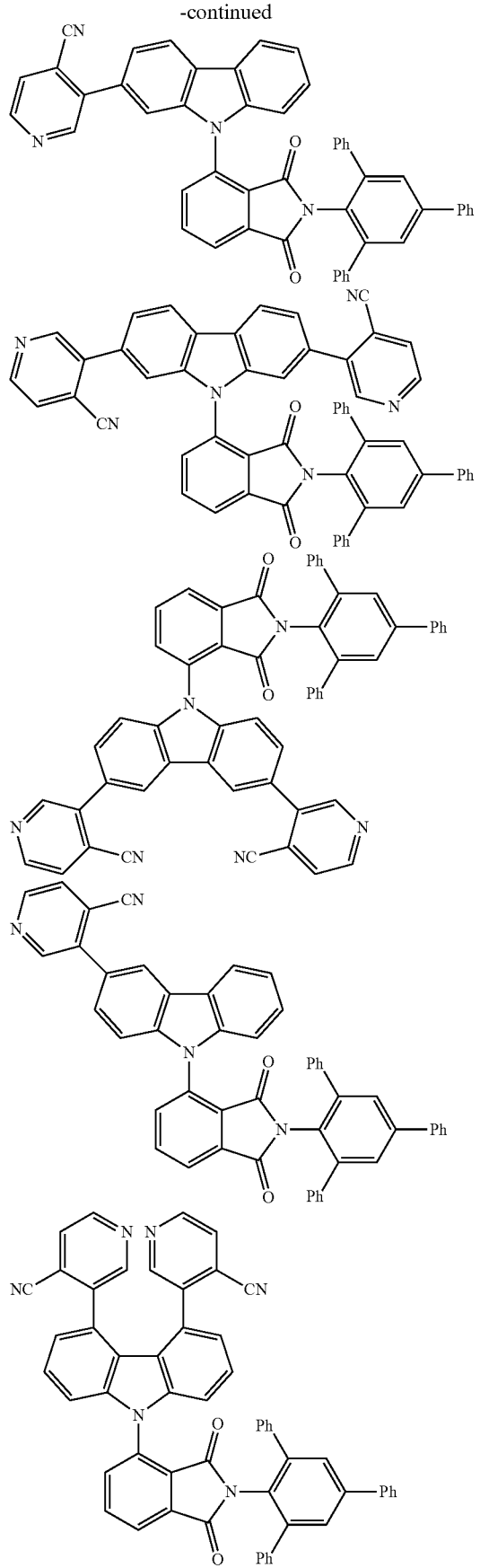
154
-continued
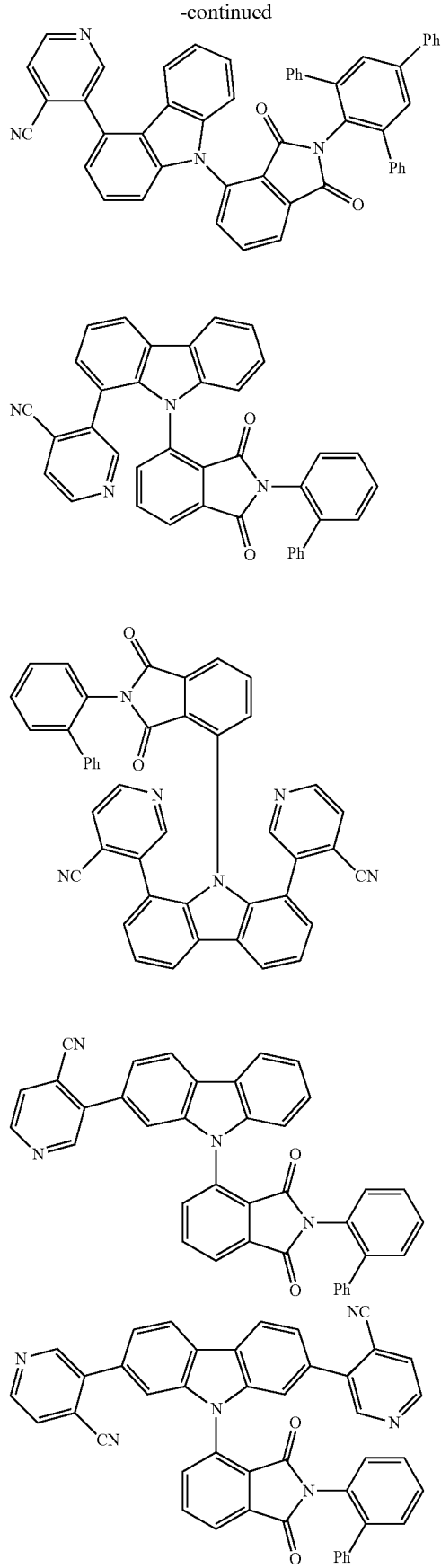

-continued
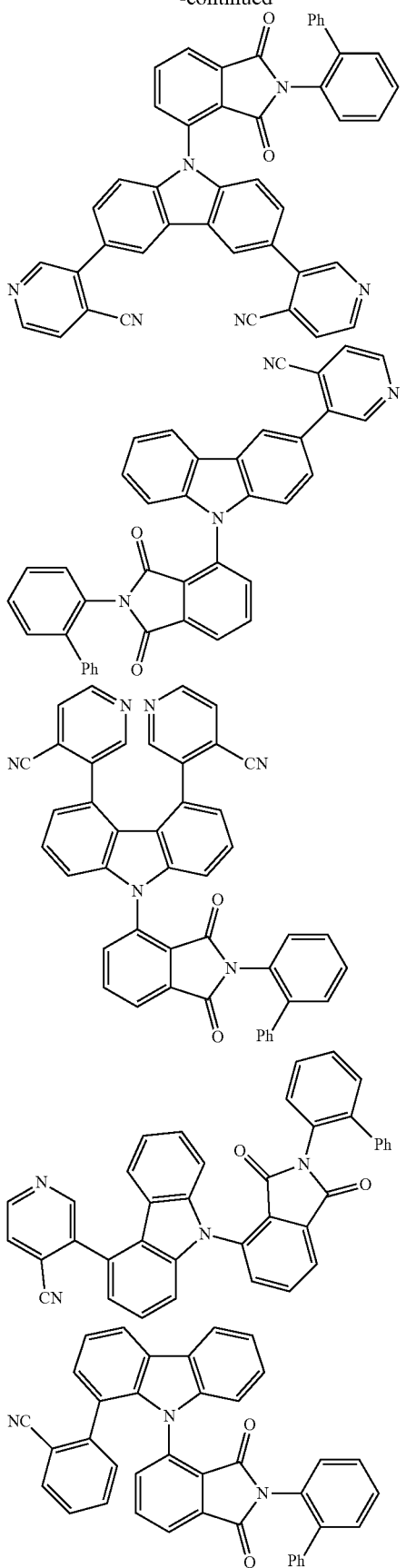
-continued
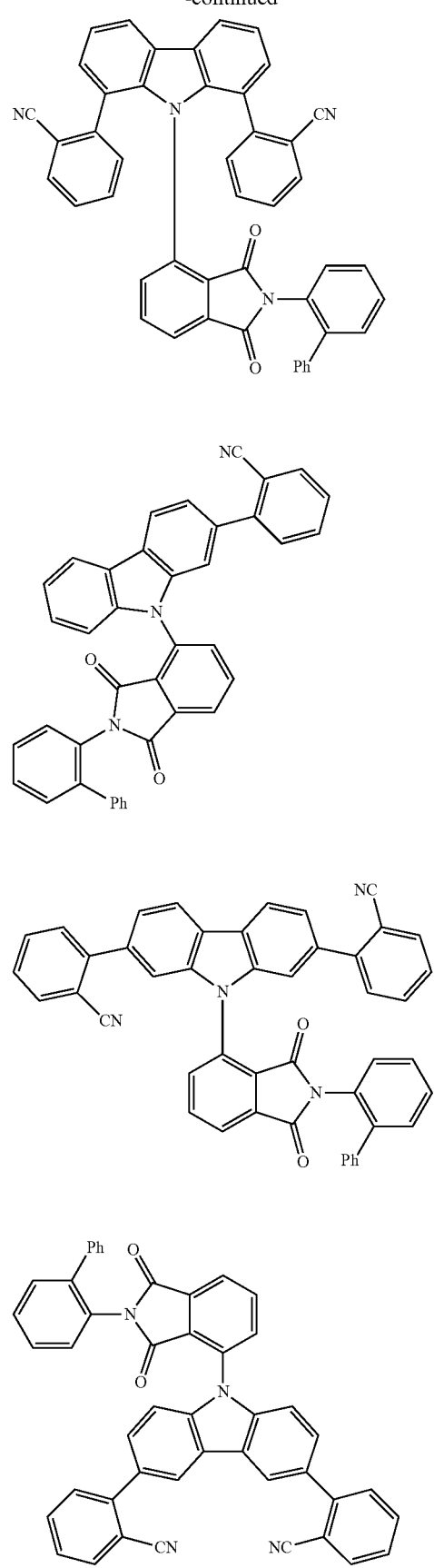

157
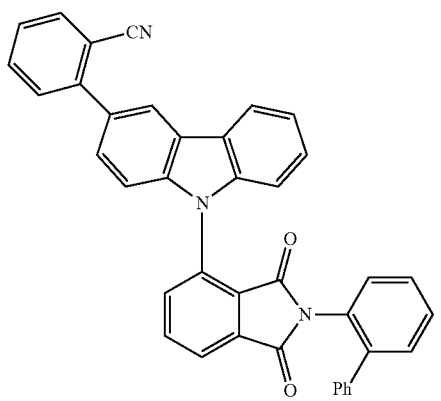
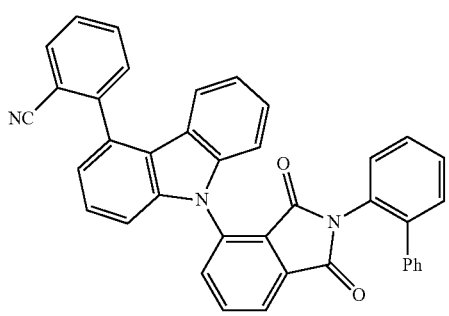
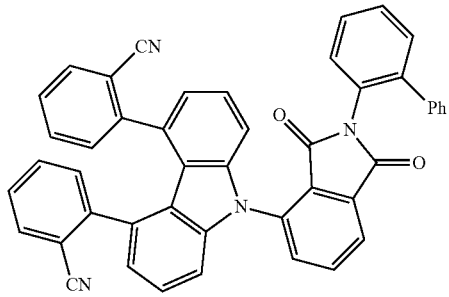
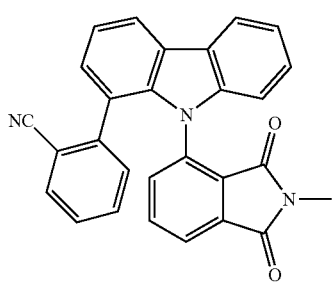
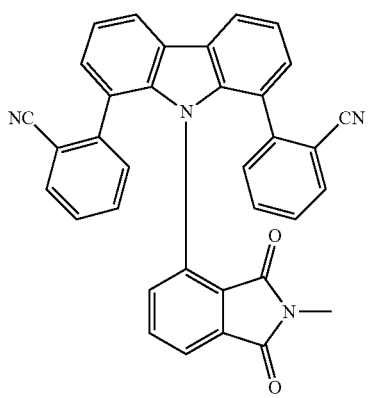
158
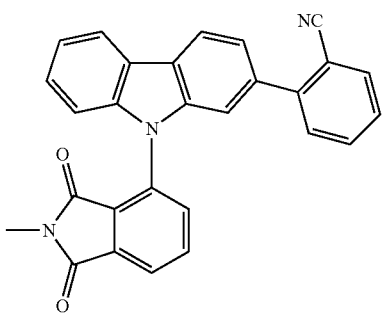
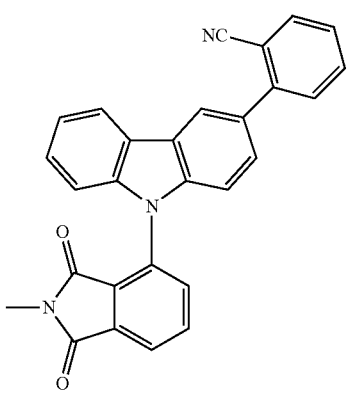
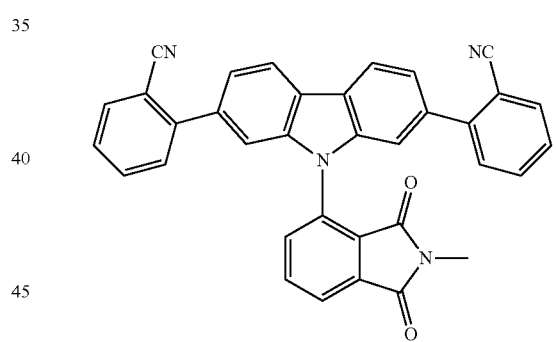
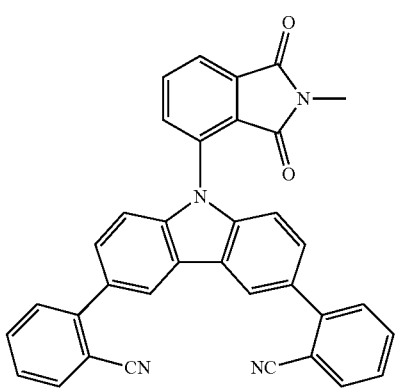

159
-continued
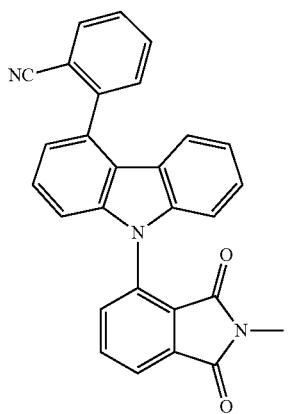
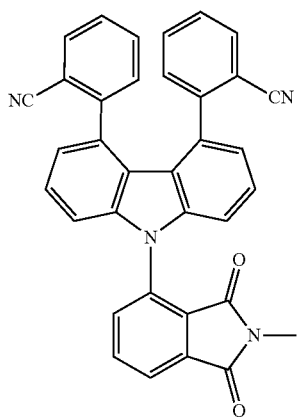
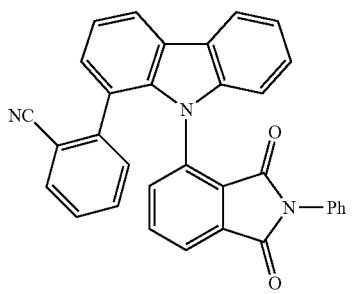
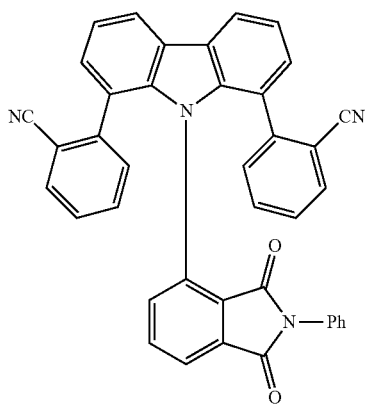
160
-continued
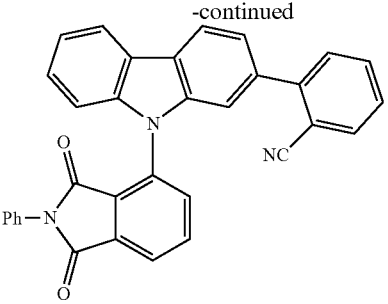
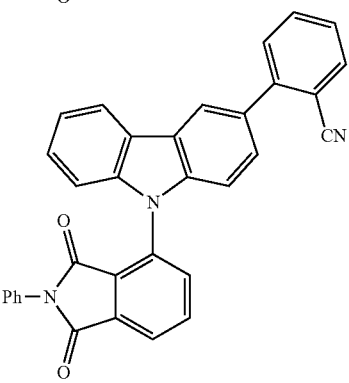
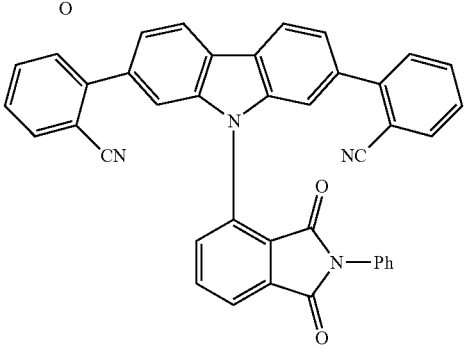
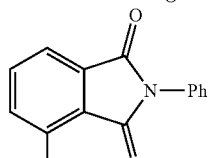
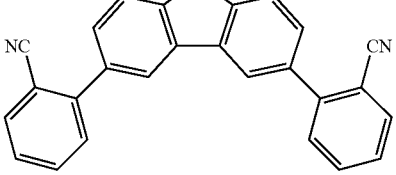
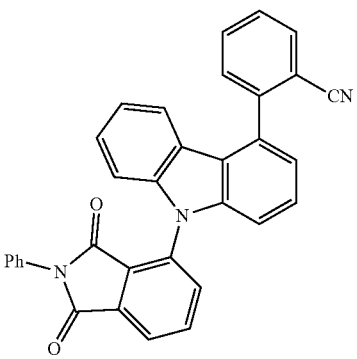
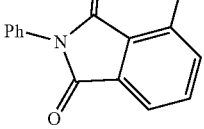

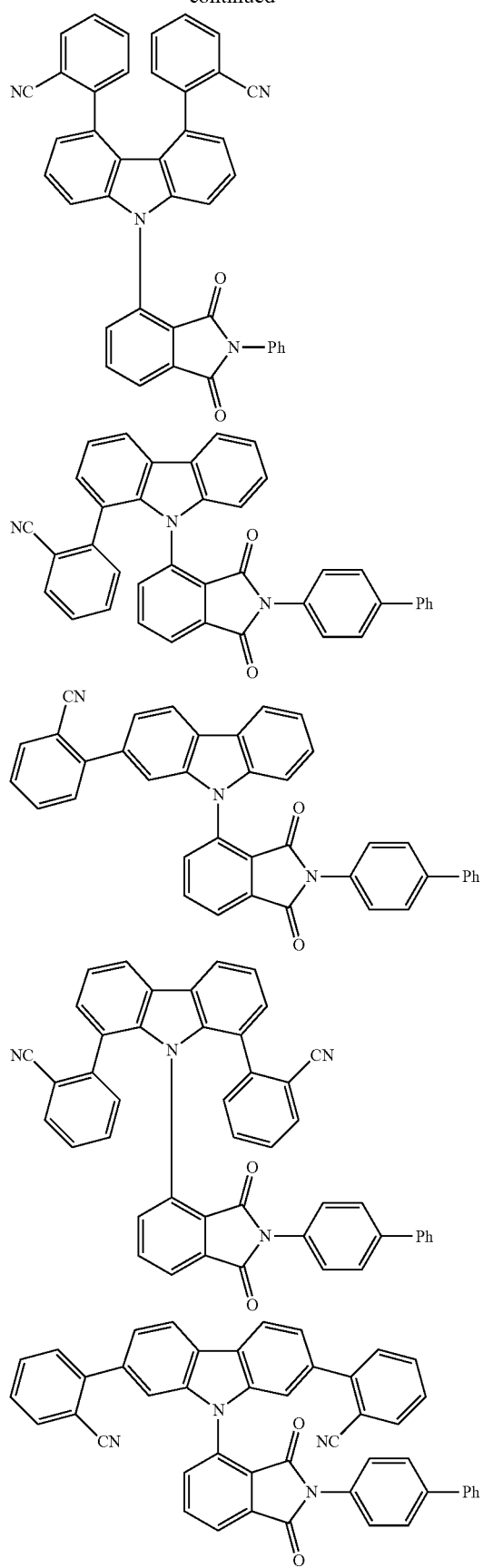

163
-continued
164
-continued
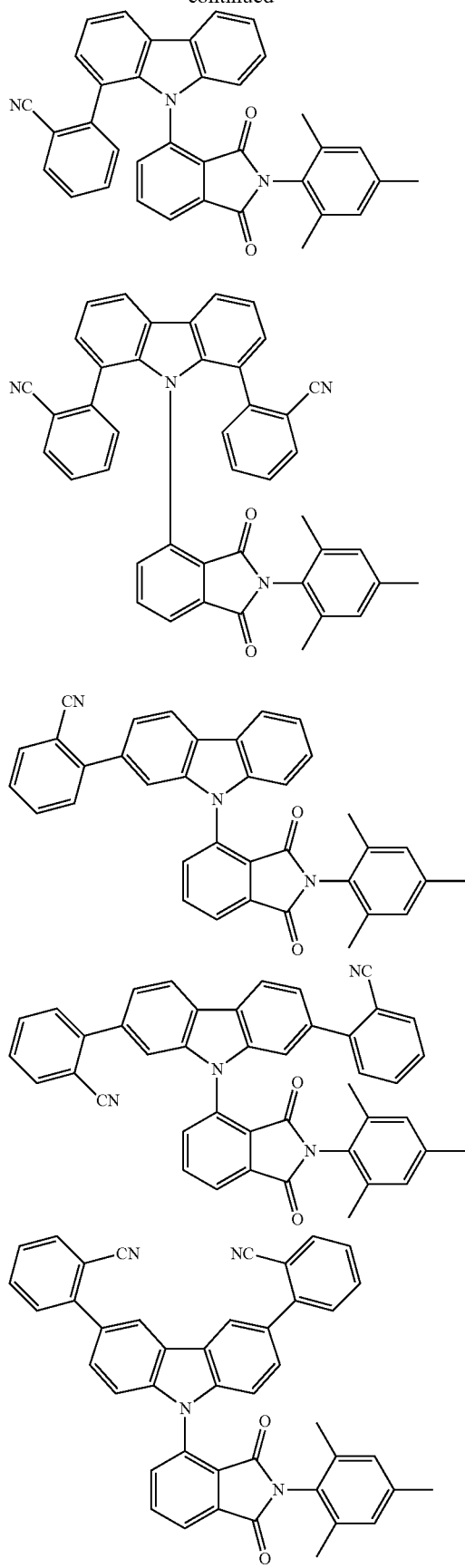
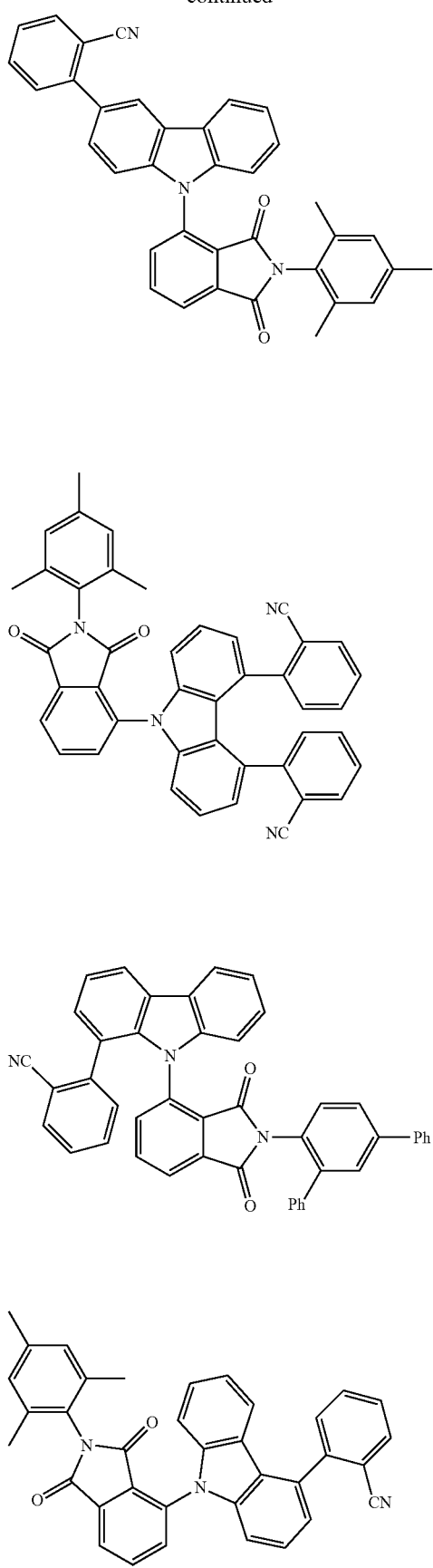

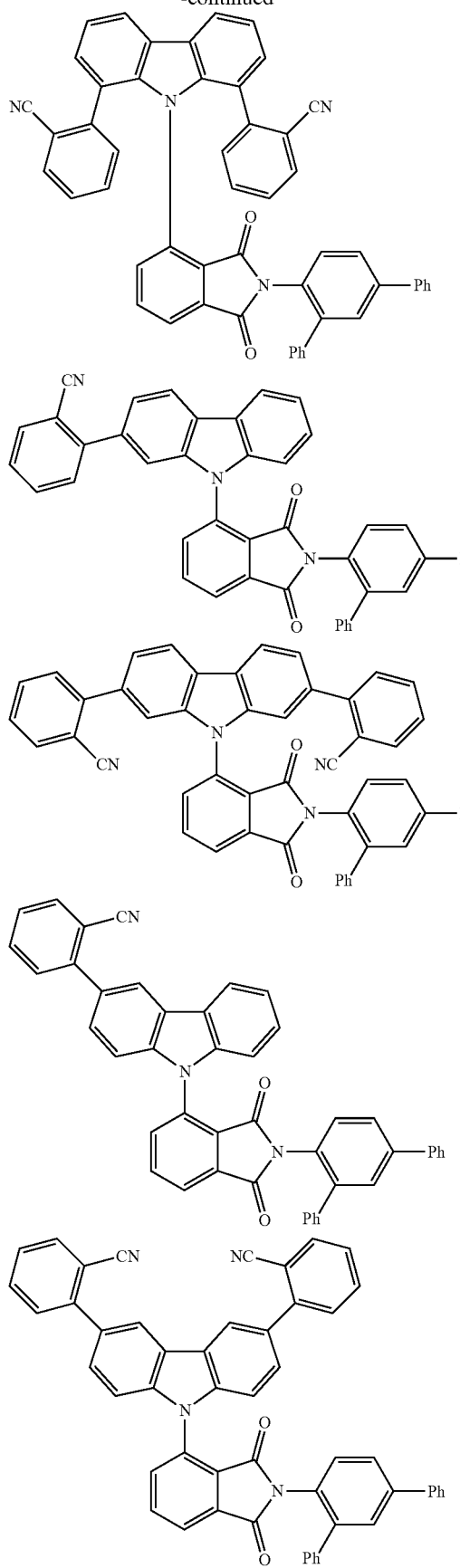
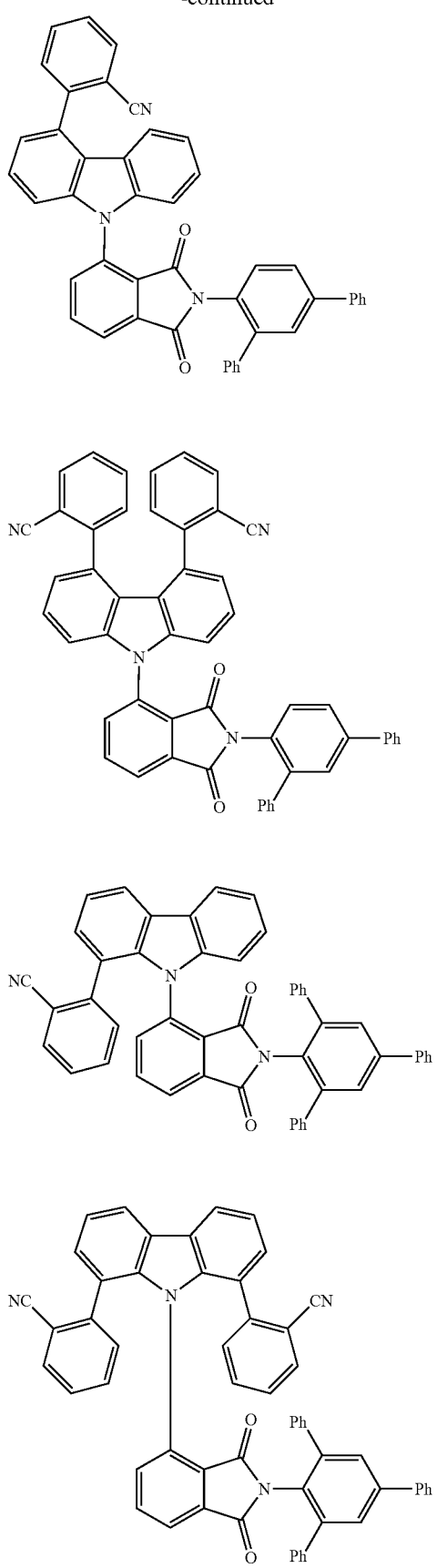

-continued
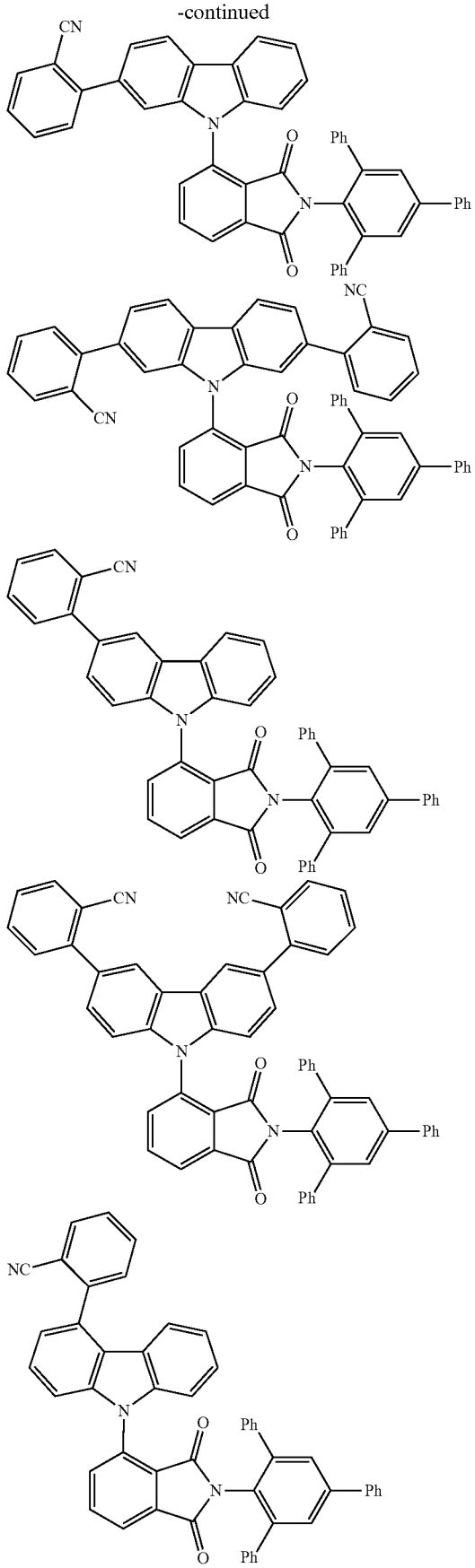
-continued
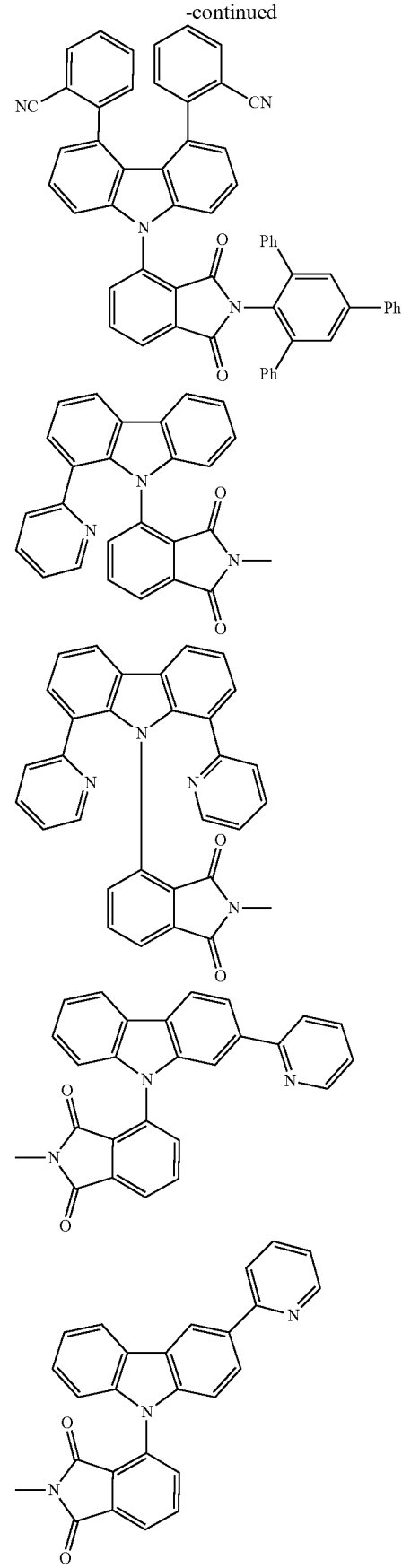

169
-continued
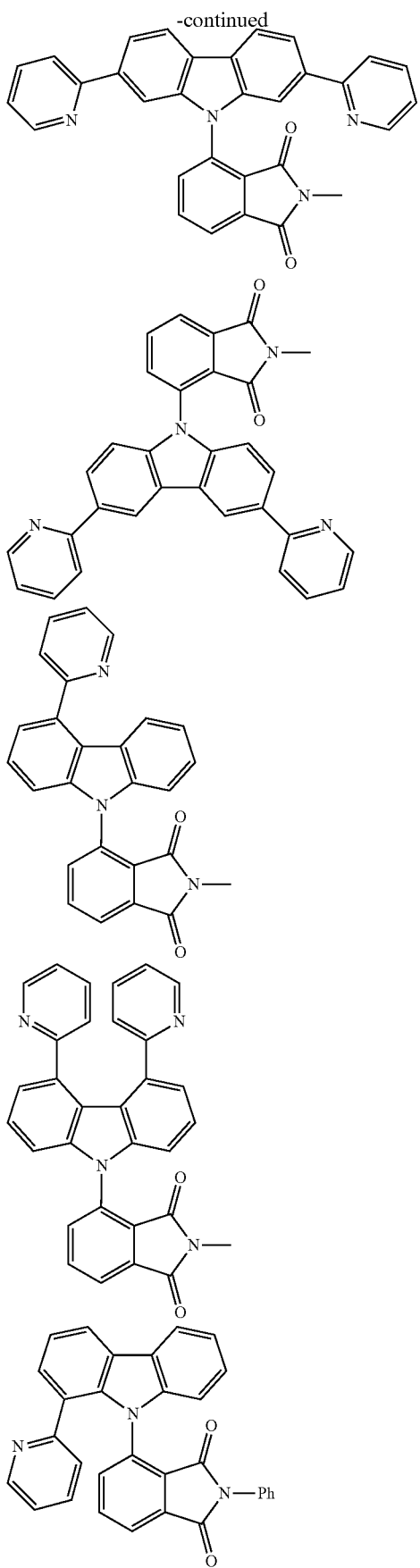
170
-continued
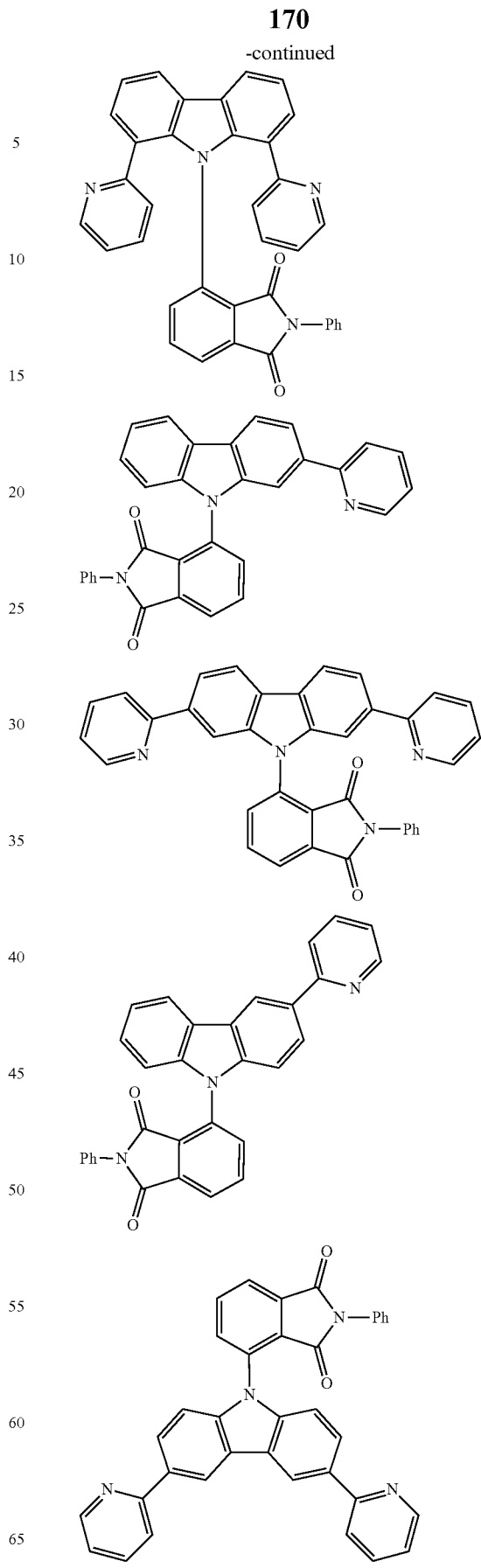

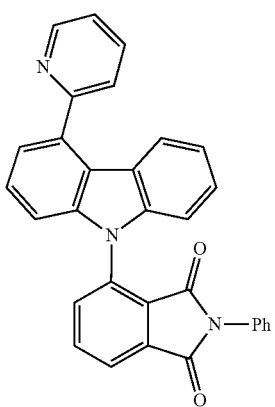
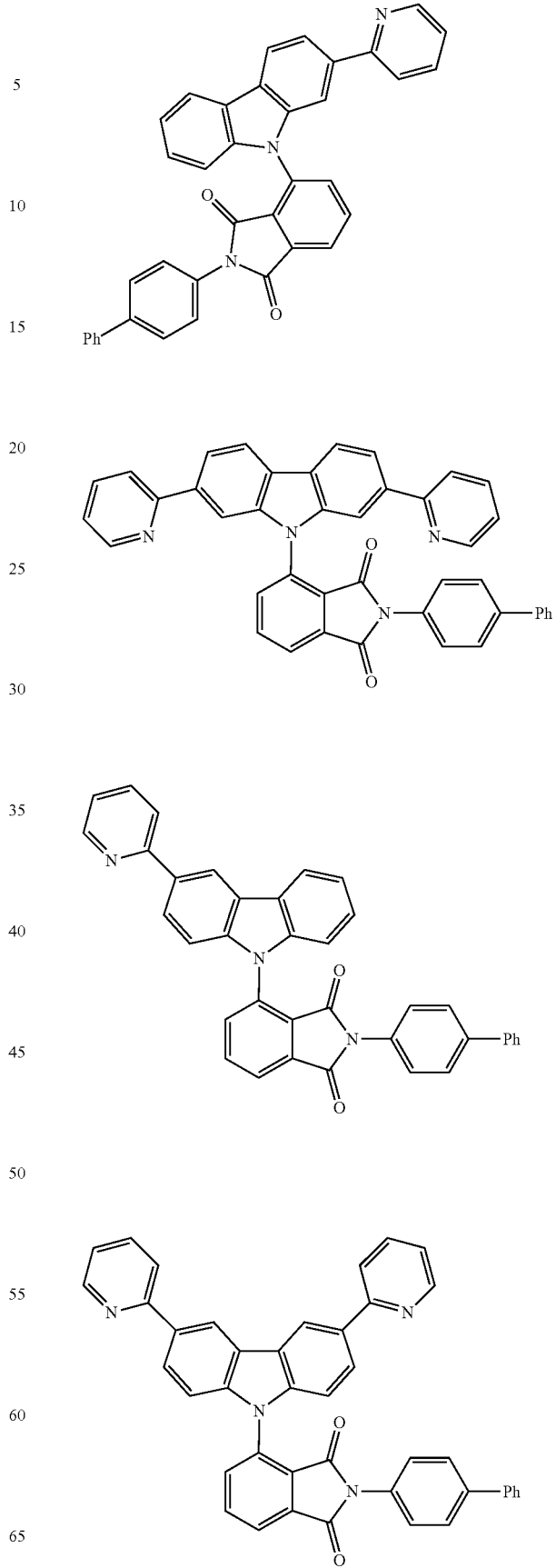

173
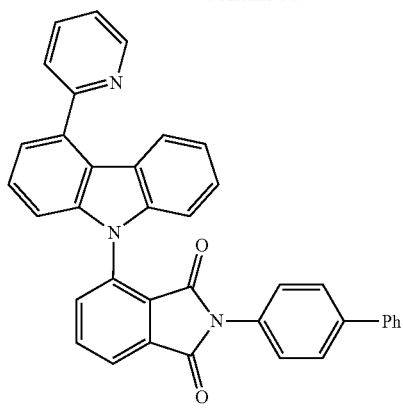
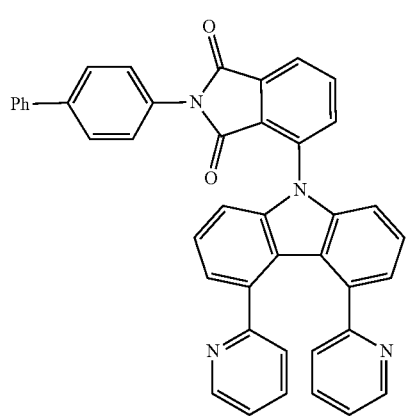
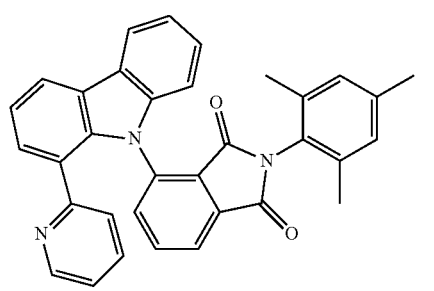
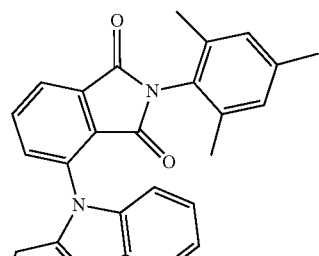
174
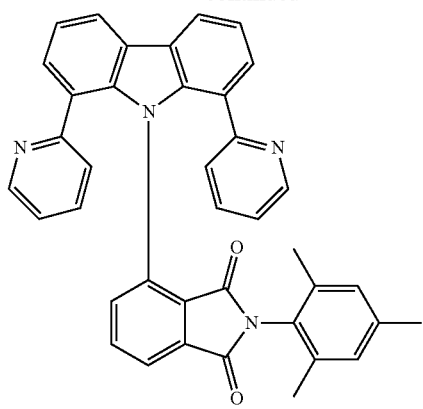
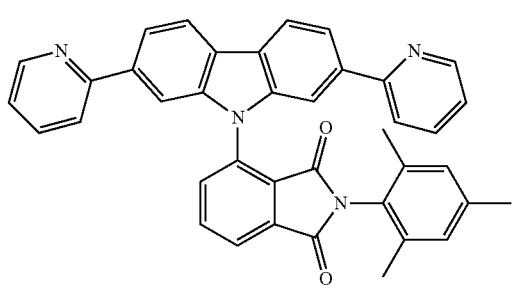
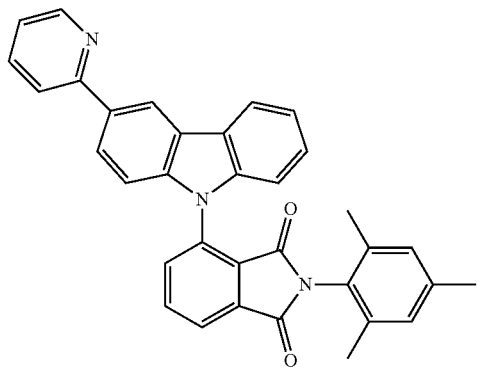
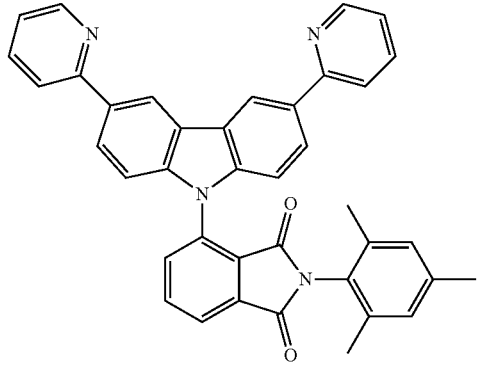

-continued
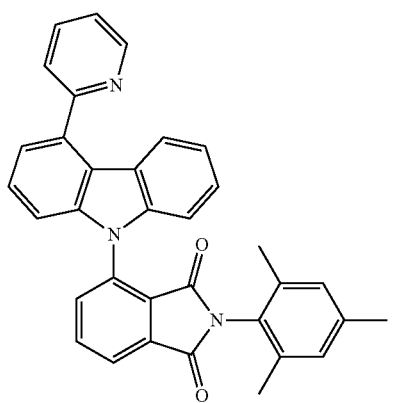
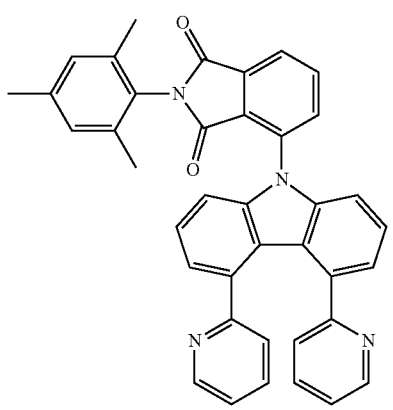
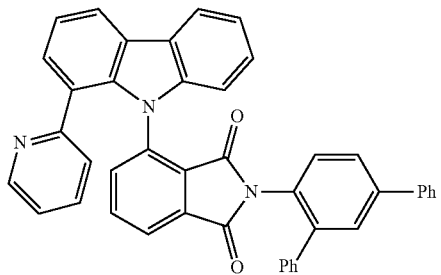
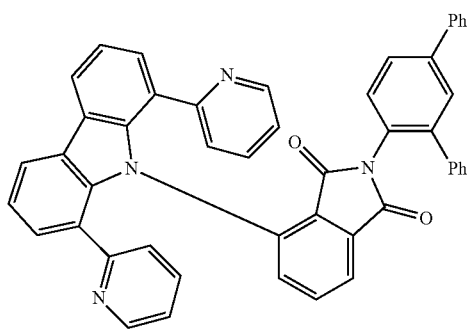
-continued
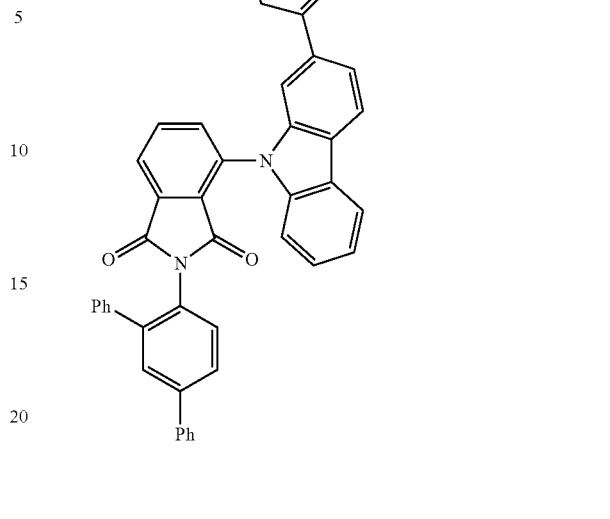
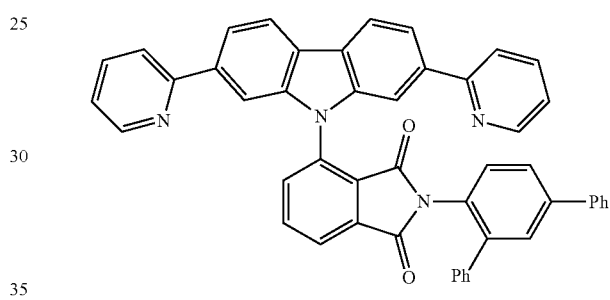
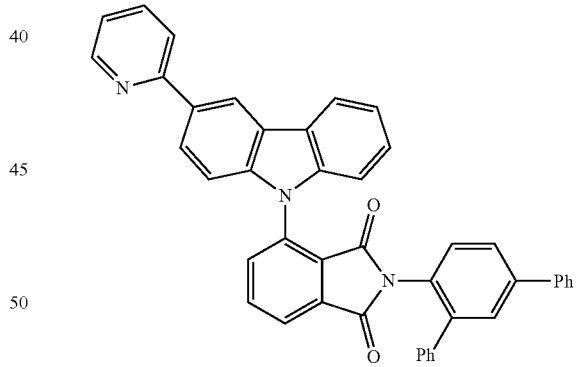
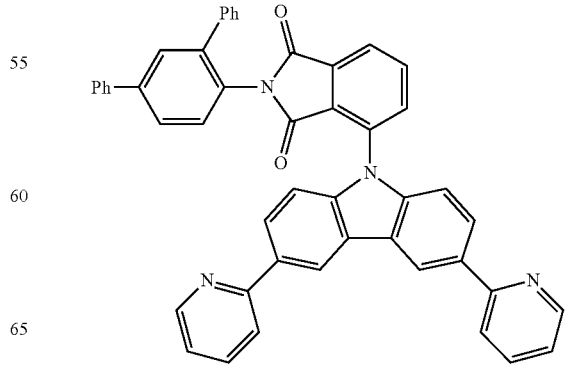

177
-continued
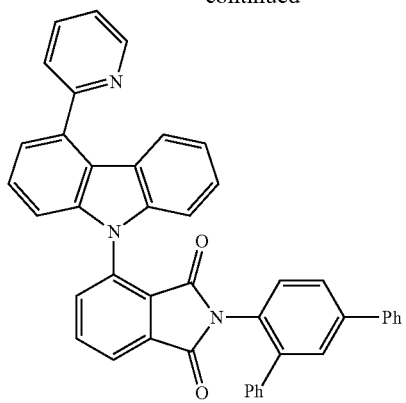
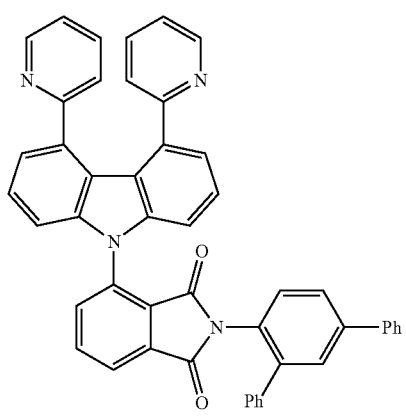
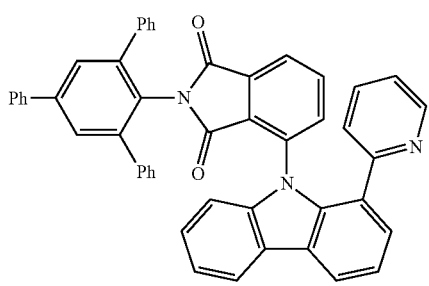
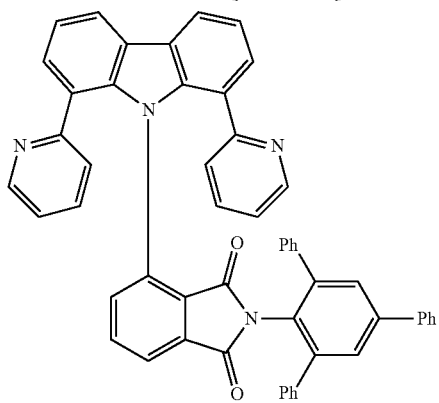
178
-continued
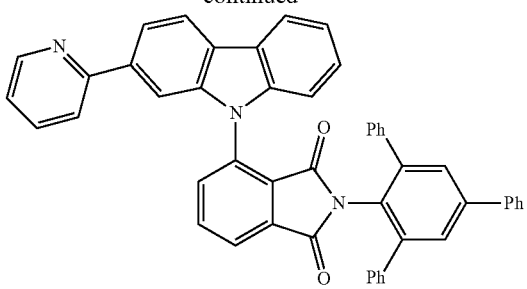
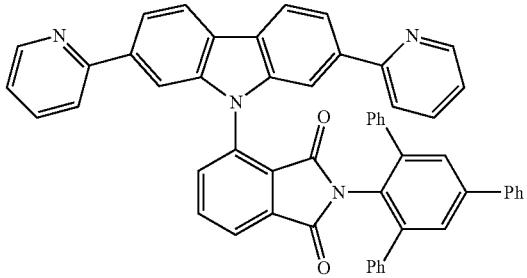
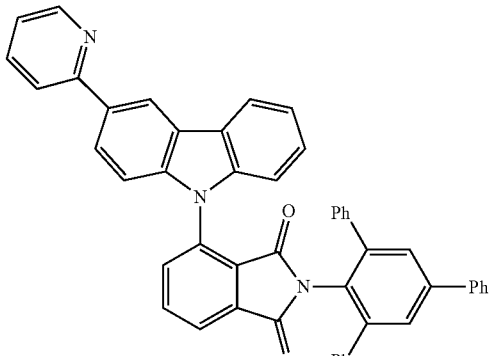
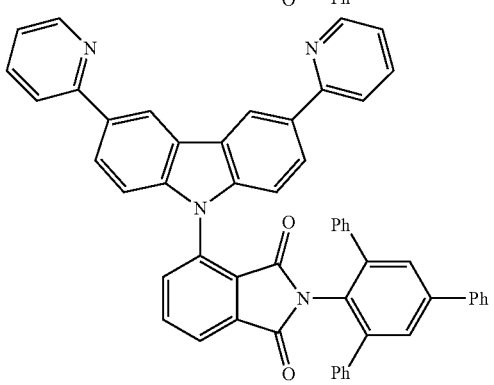
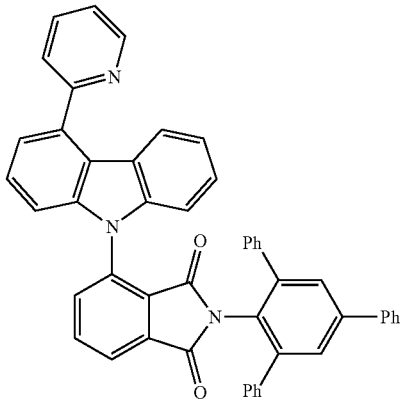

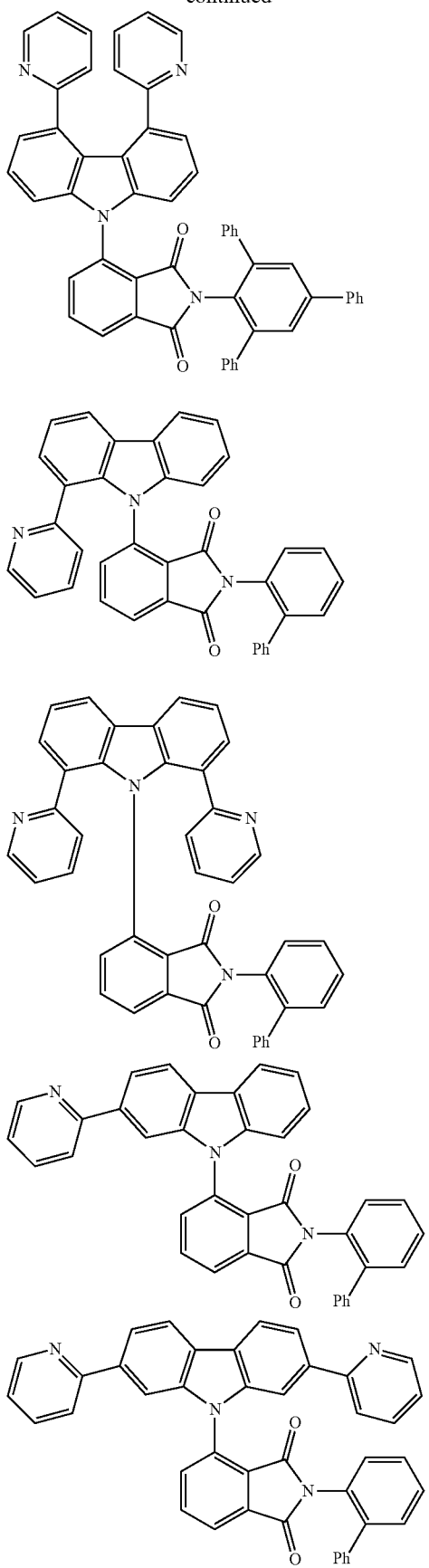
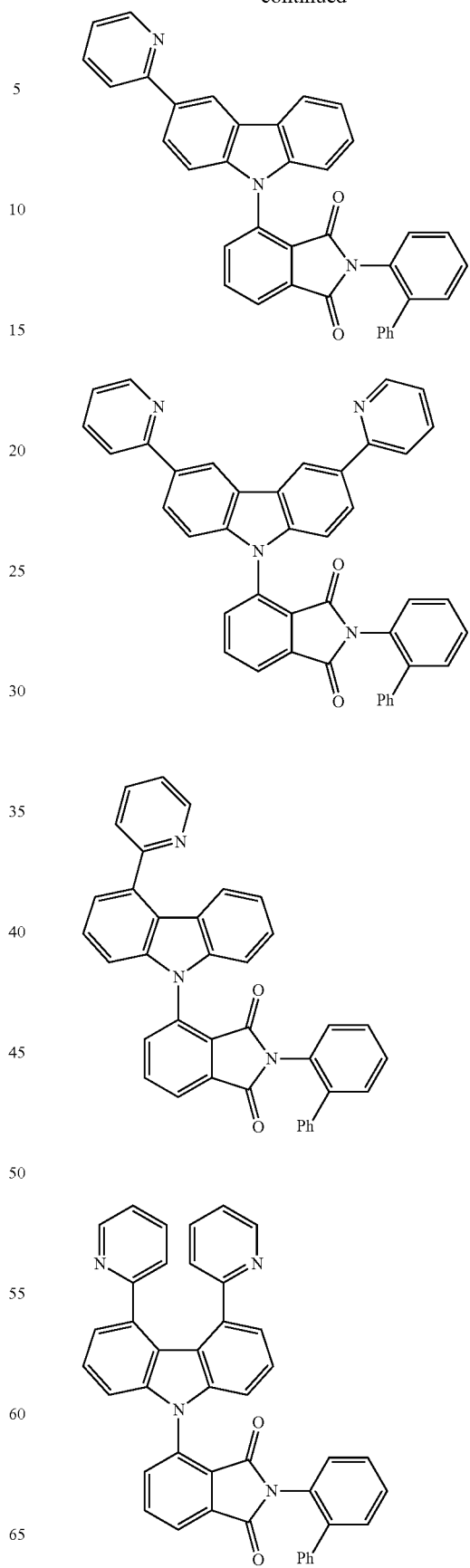

181
-continued
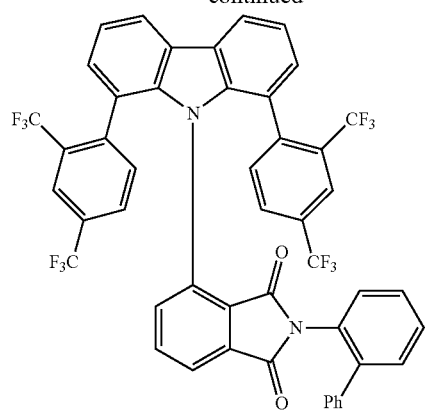
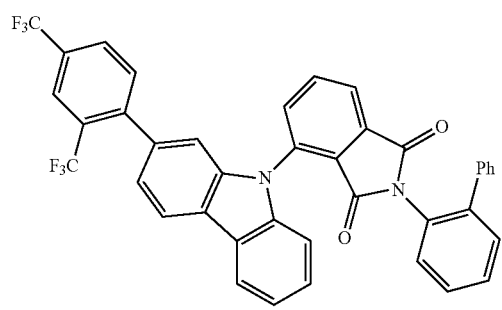
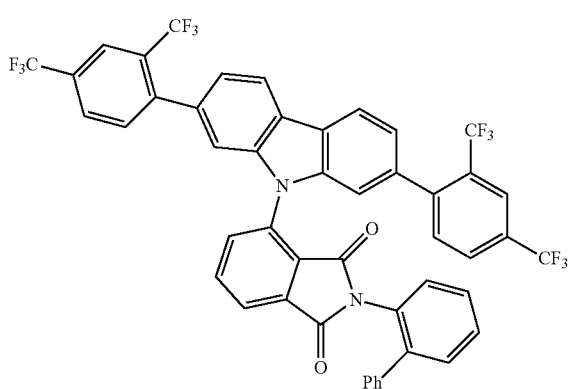
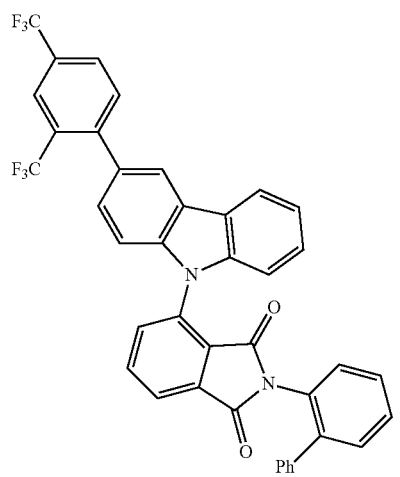
182
-continued
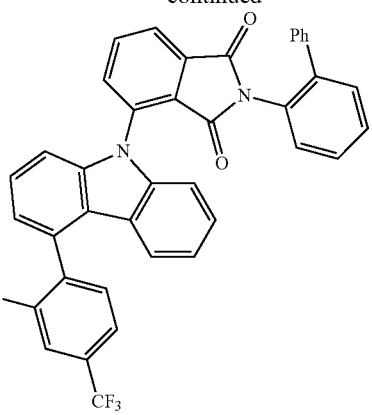
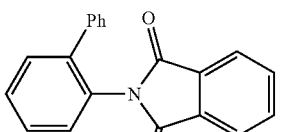
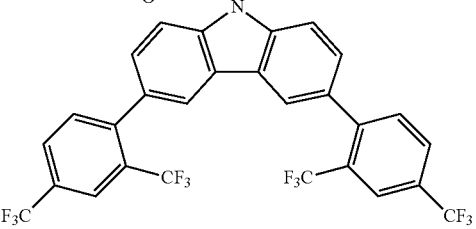
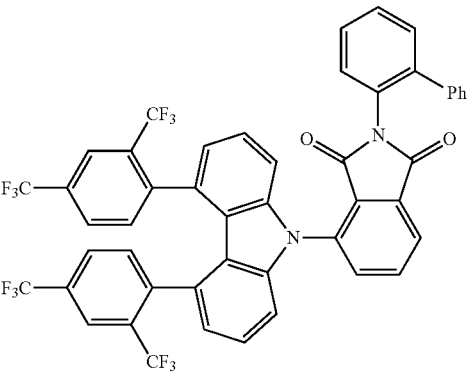
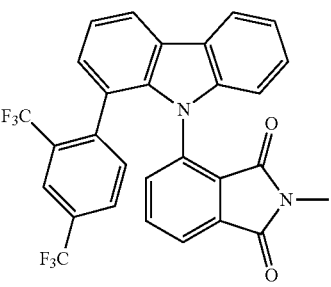

-continued
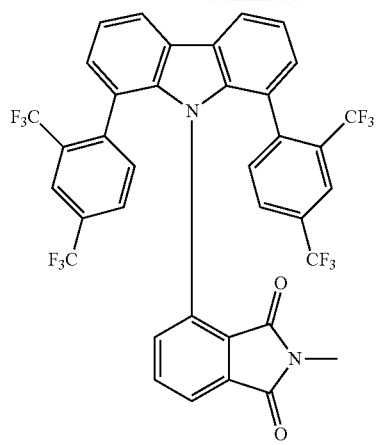
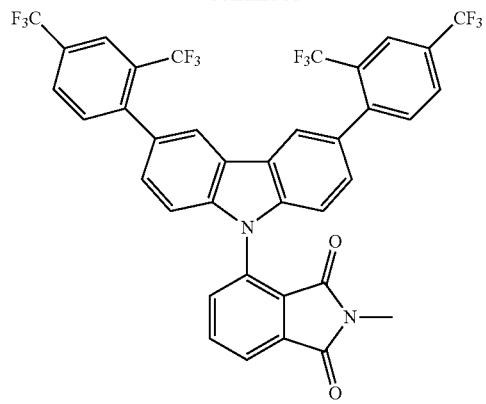
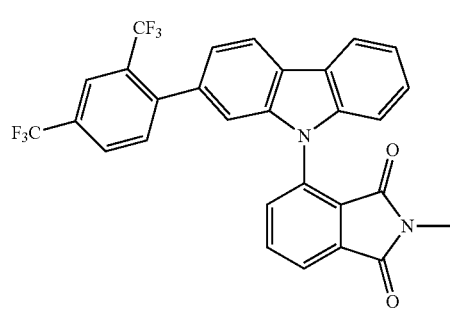
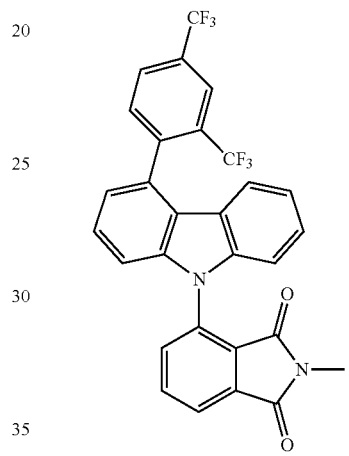
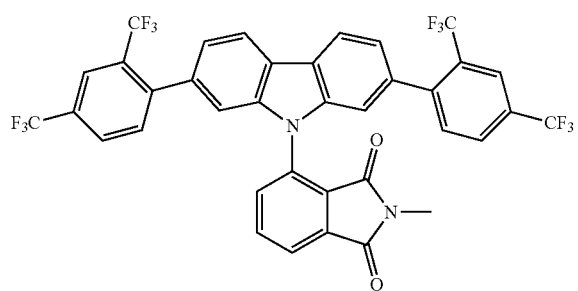
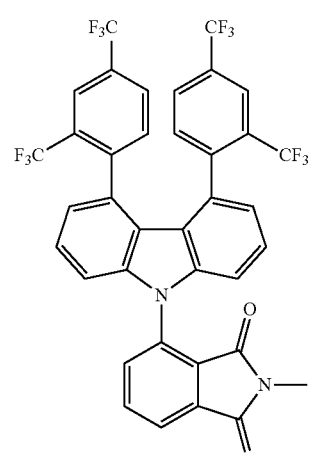
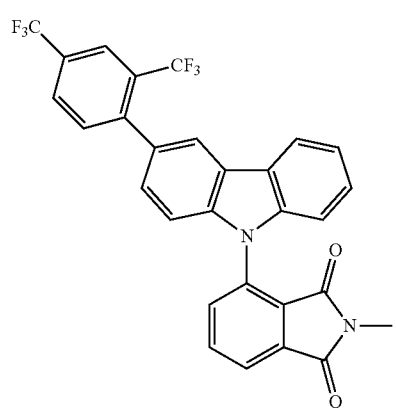
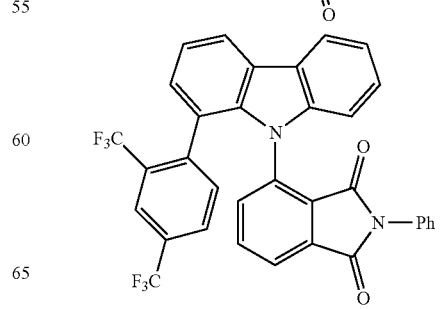

185
-continued
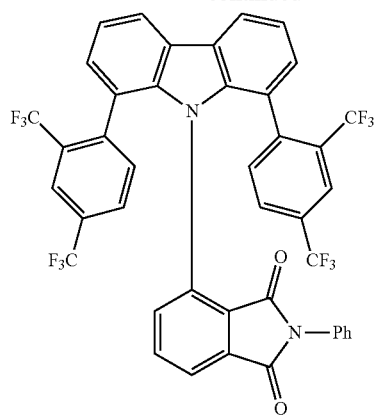
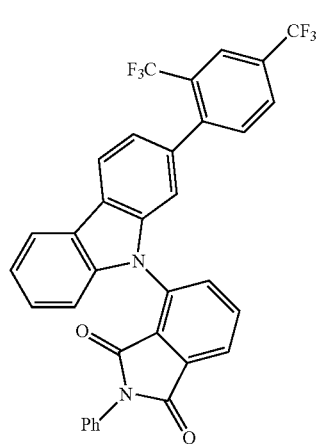
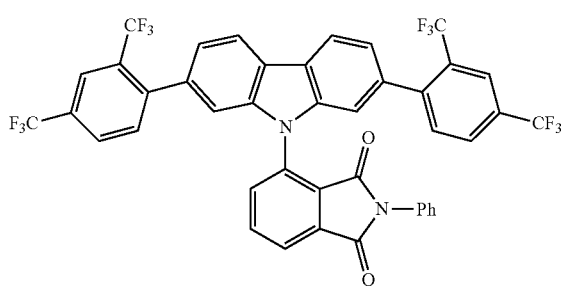
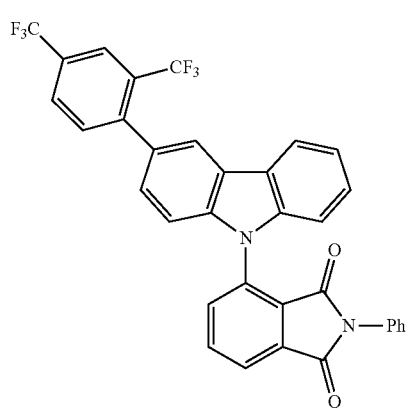
186
-continued
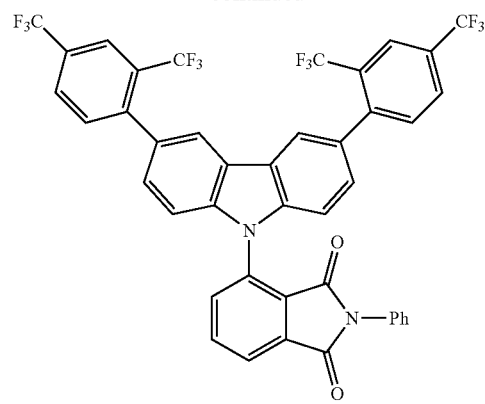
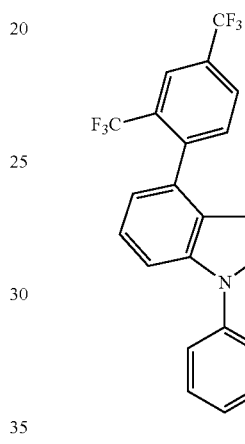
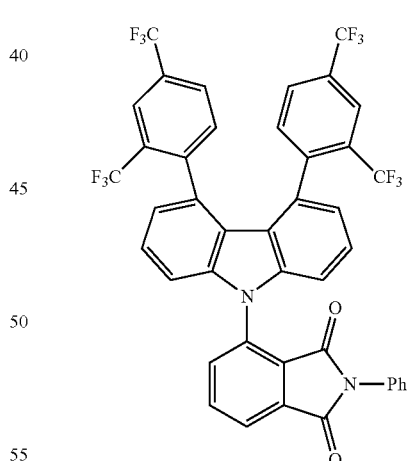
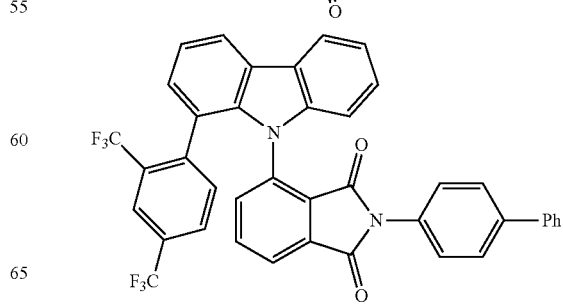

187
-continued
188
-continued
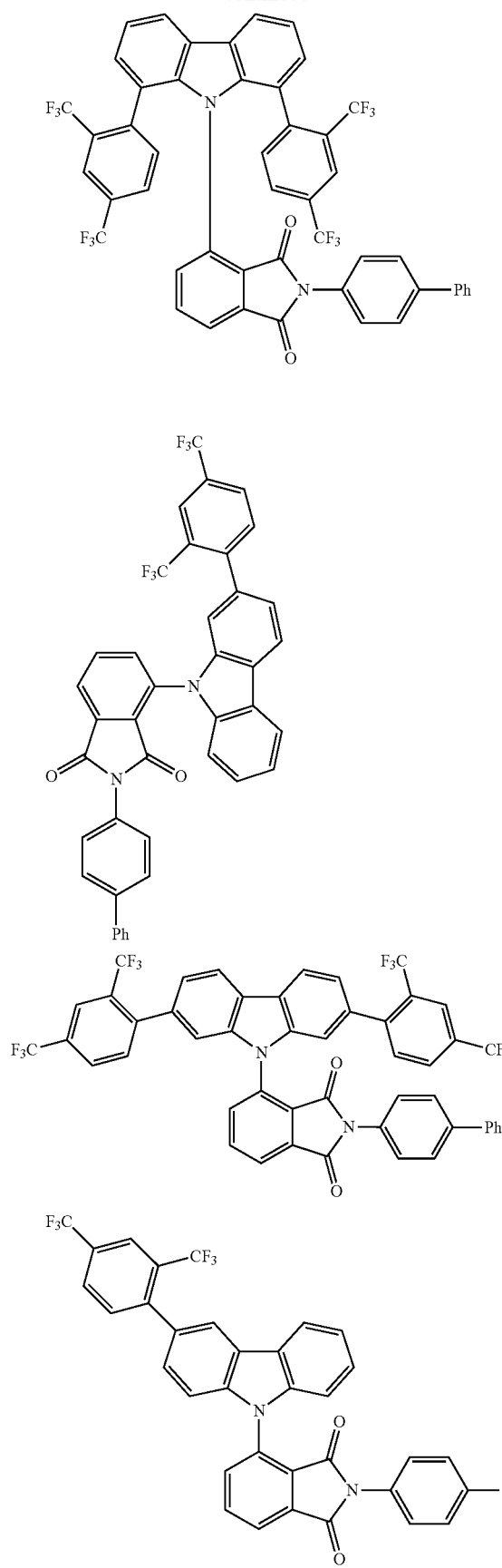
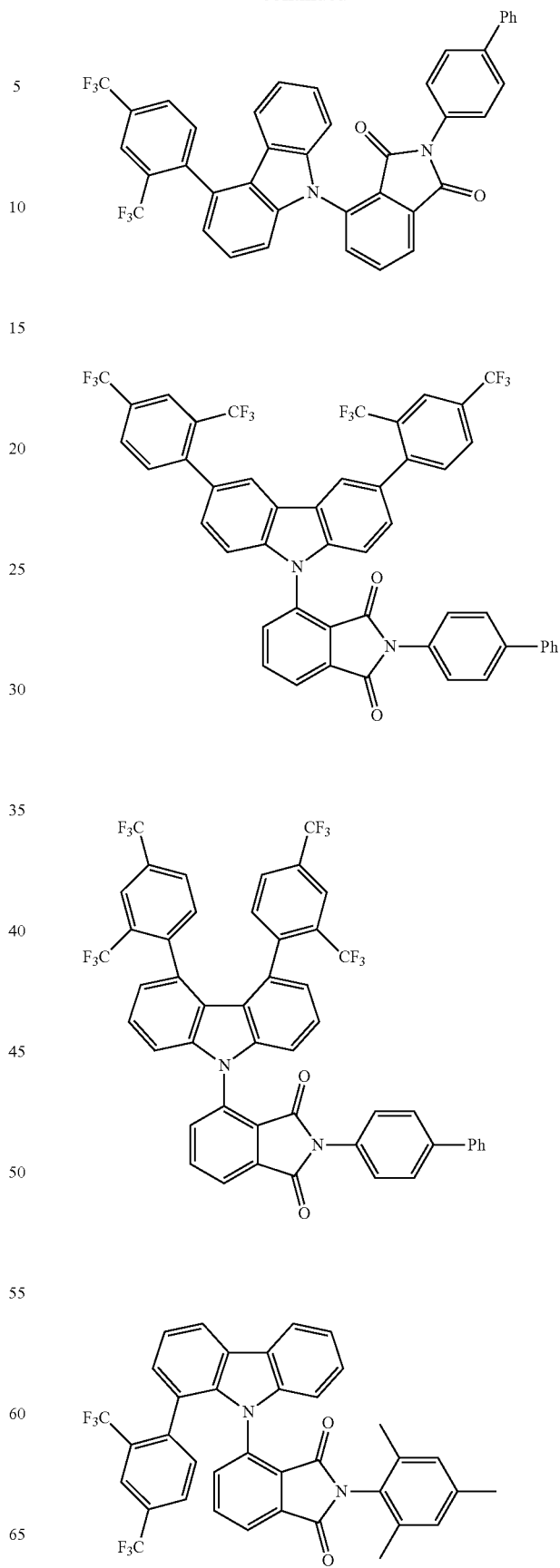

189
-continued
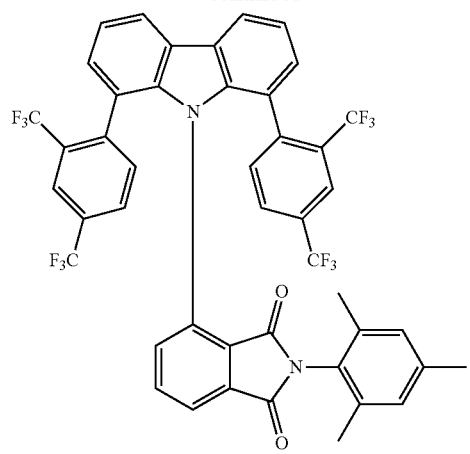
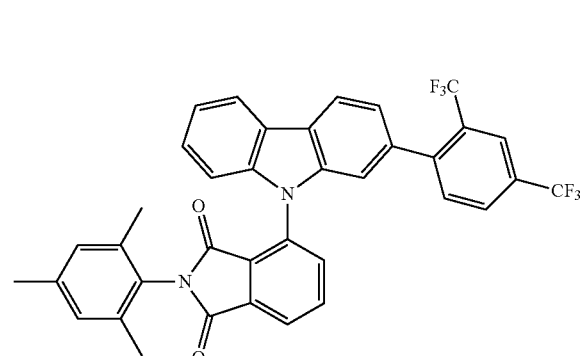
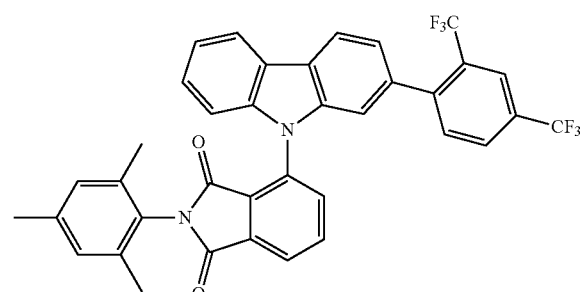
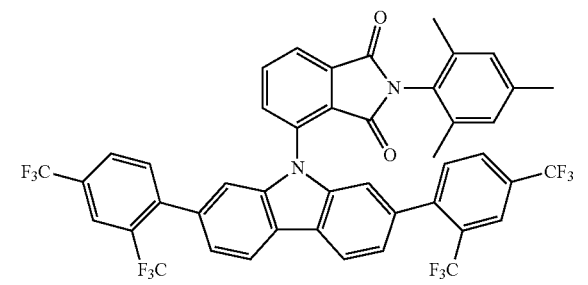
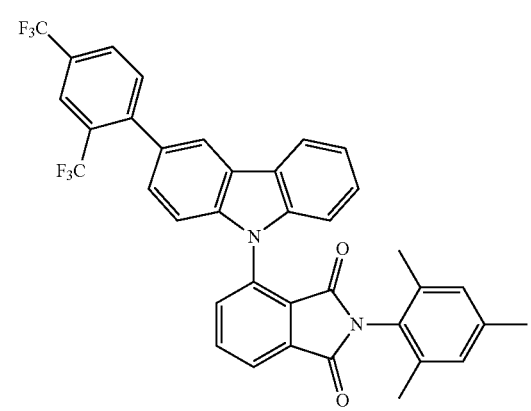
190
-continued
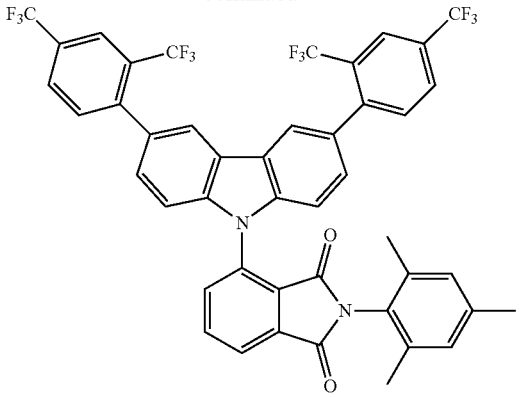
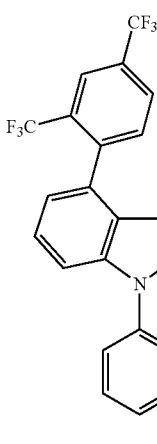
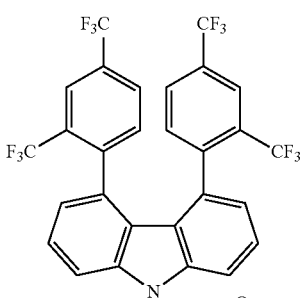
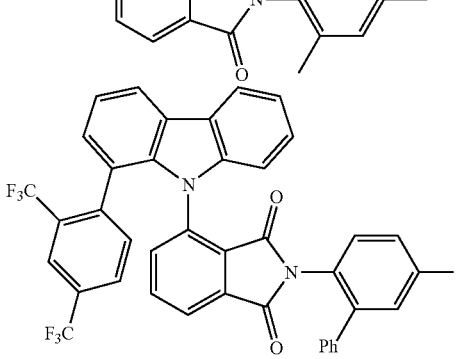

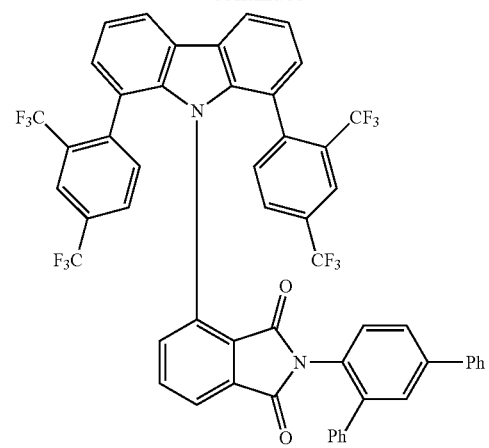
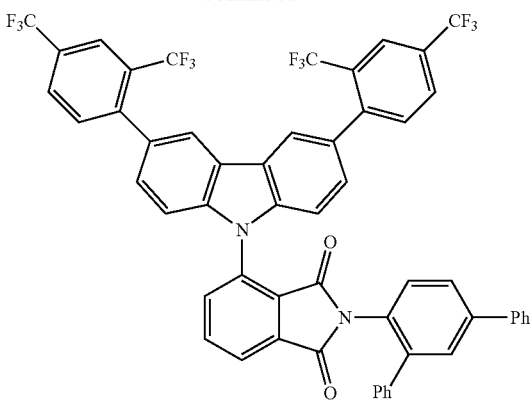
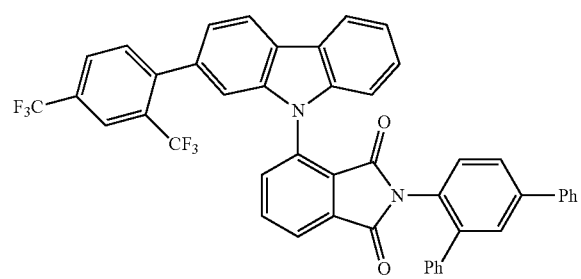
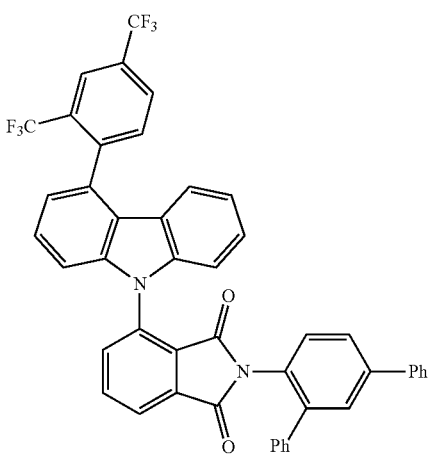
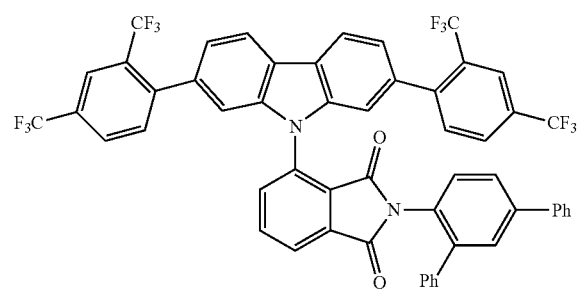
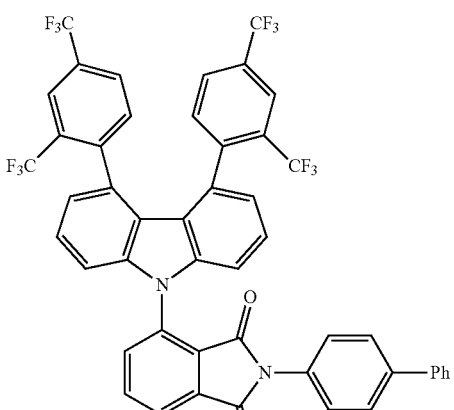
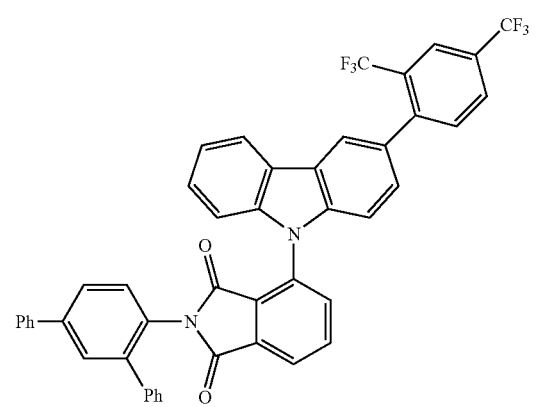
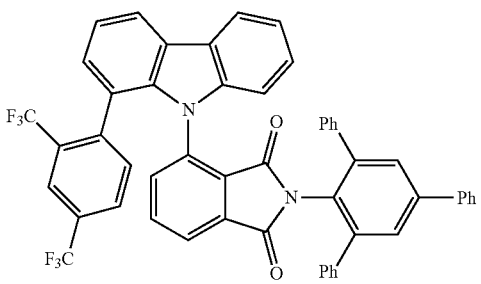

193
-continued
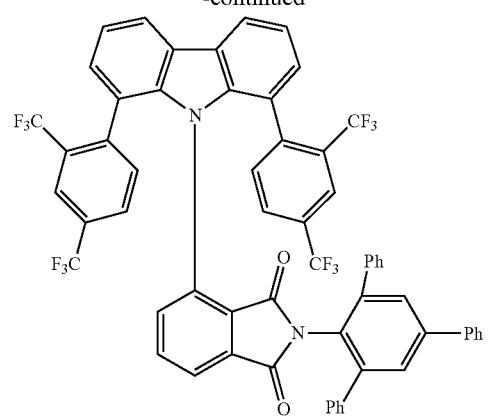
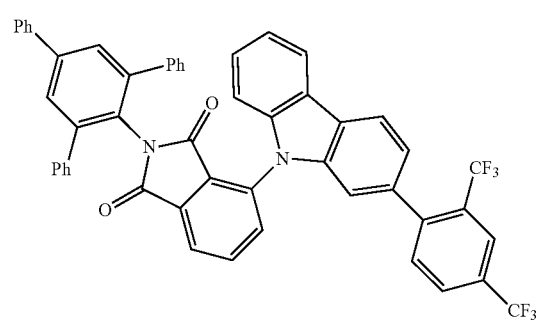
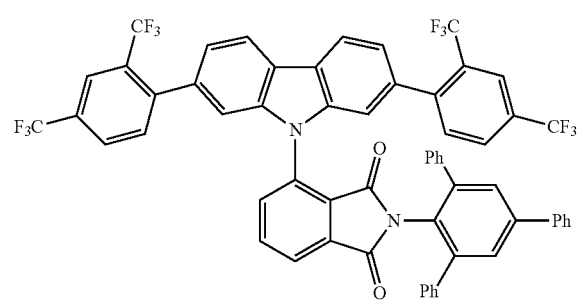
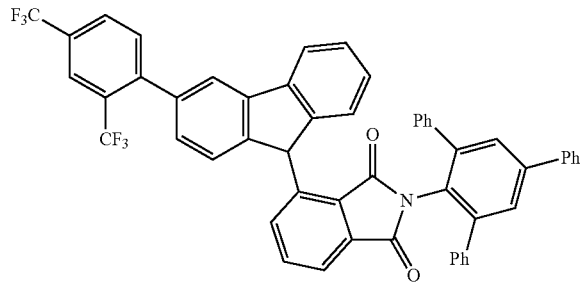
194
-continued
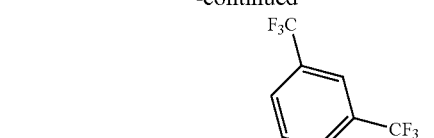
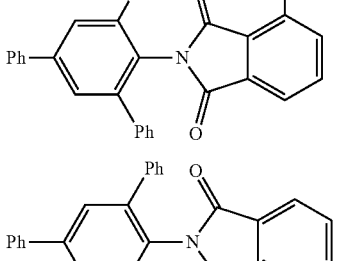
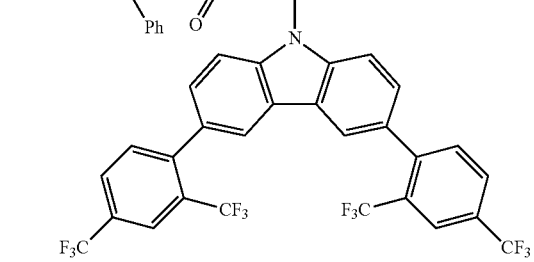
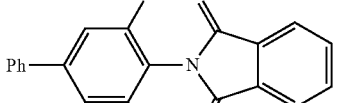
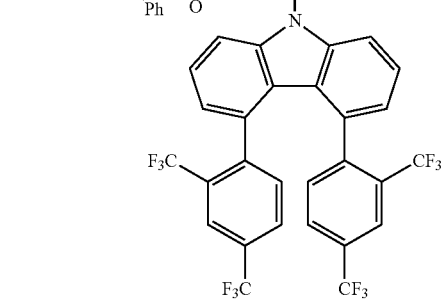
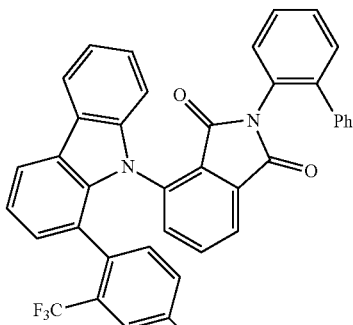

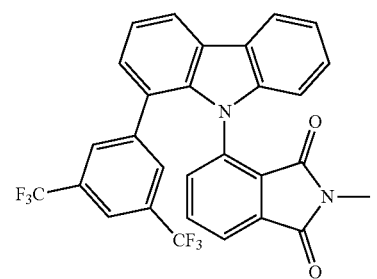
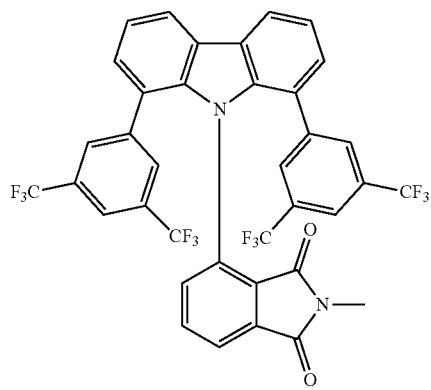
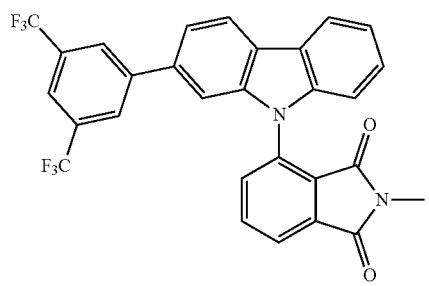
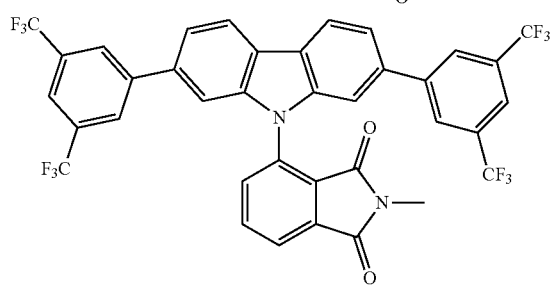
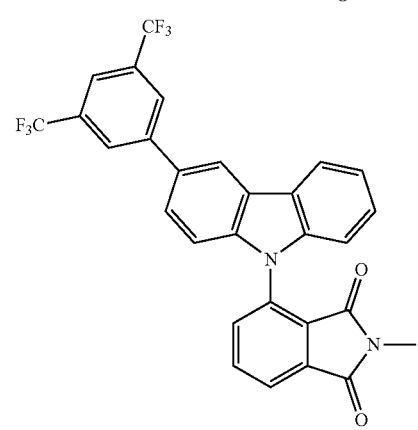
-continued
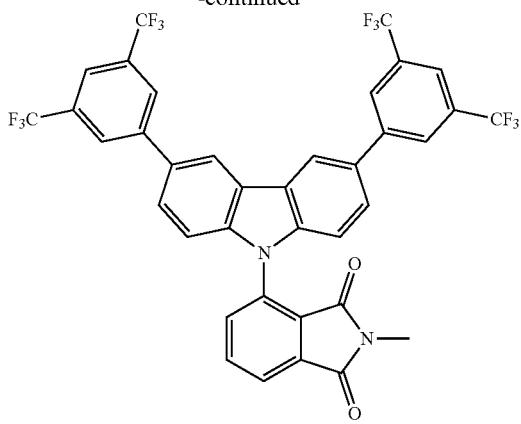
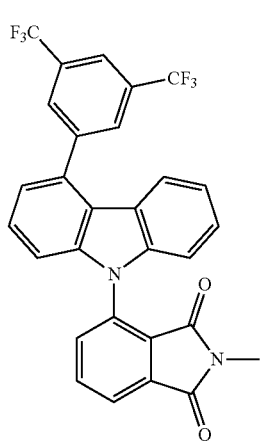
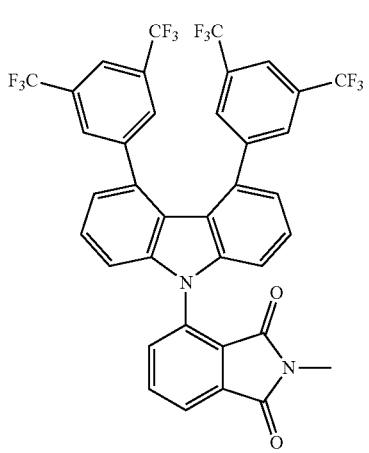
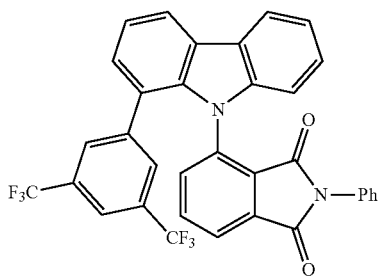

197
-continued
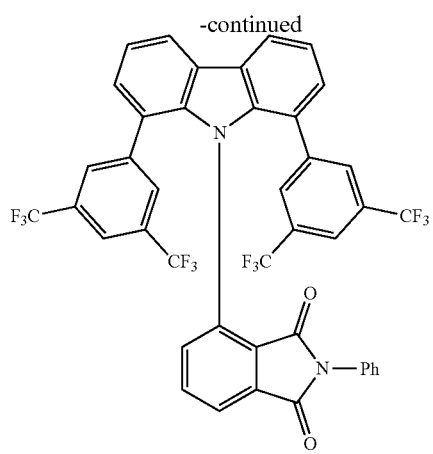
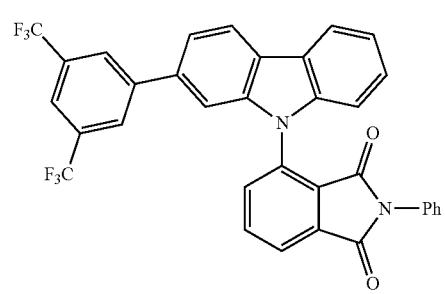
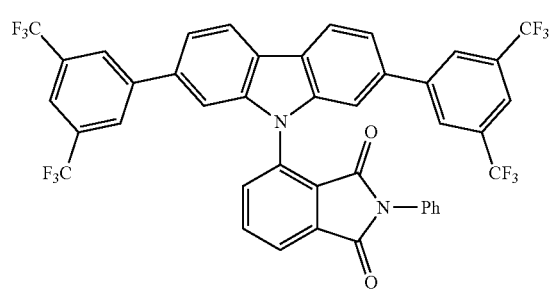
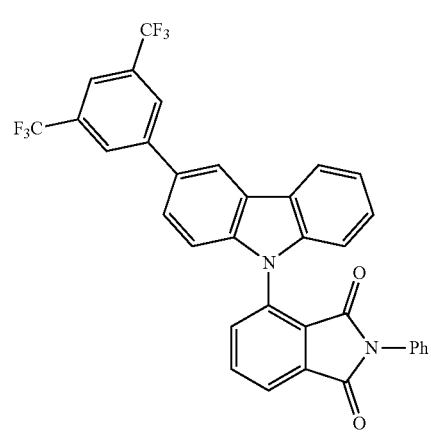
198
-continued
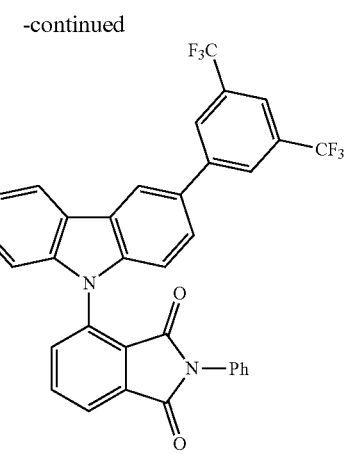
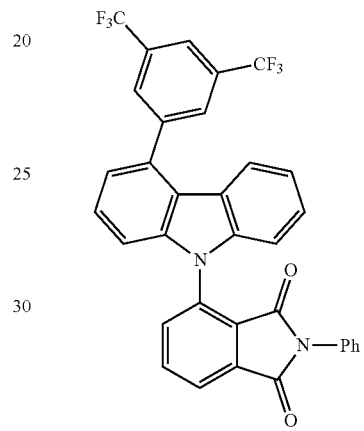
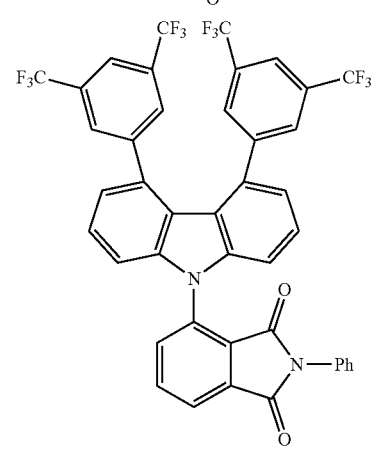
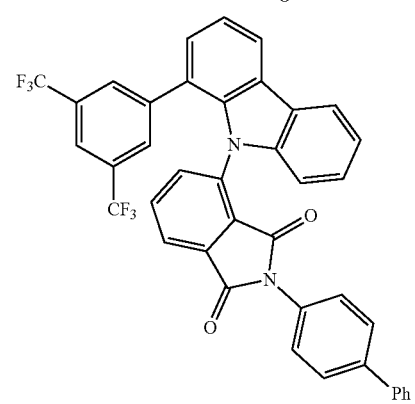

199
-continued
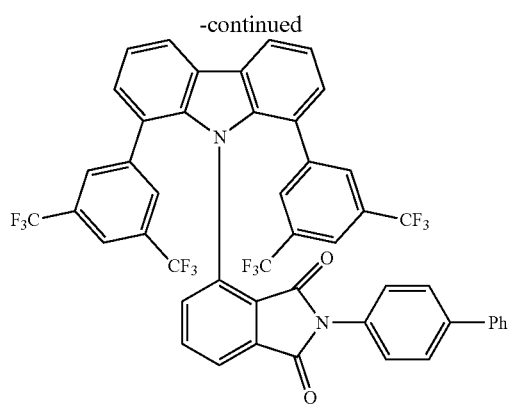
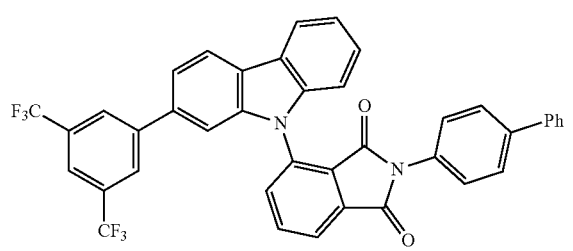
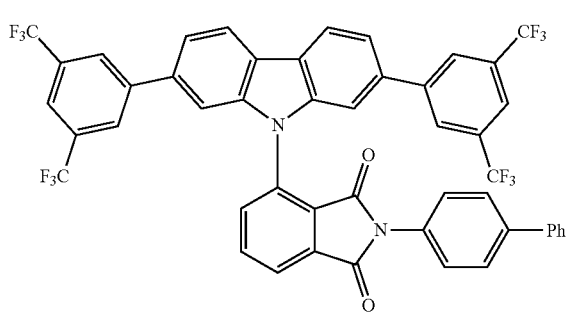
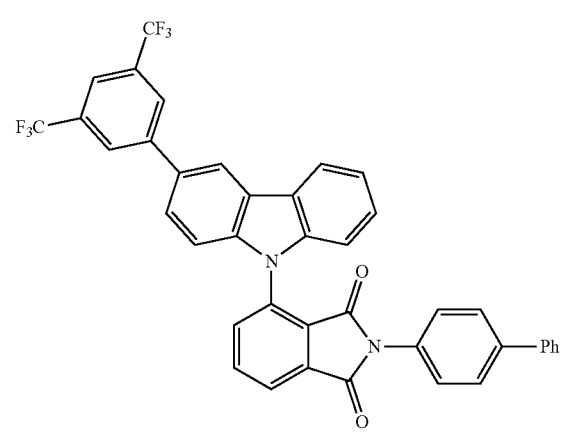
200
-continued
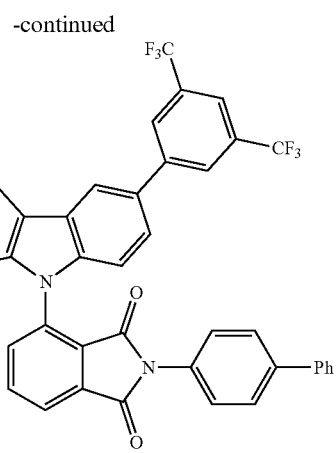
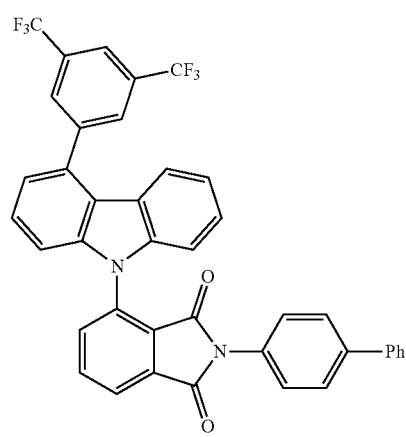
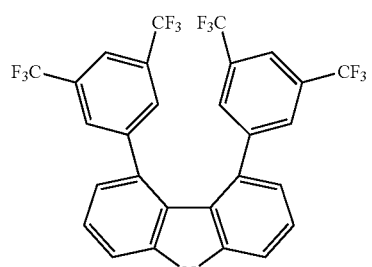
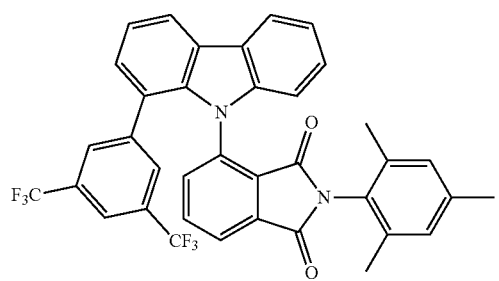

201
-continued
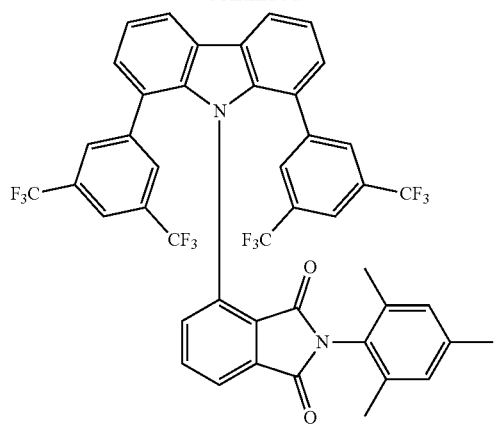
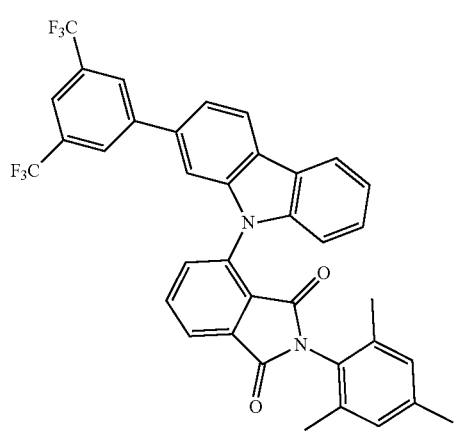
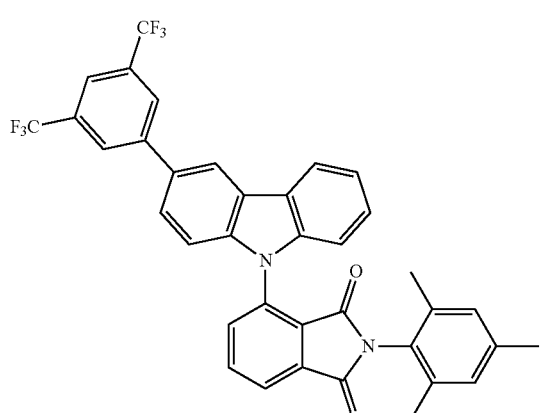
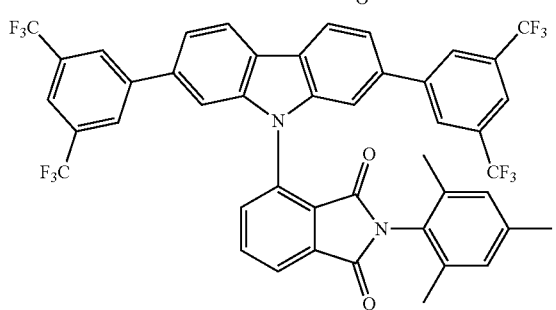
202
-continued
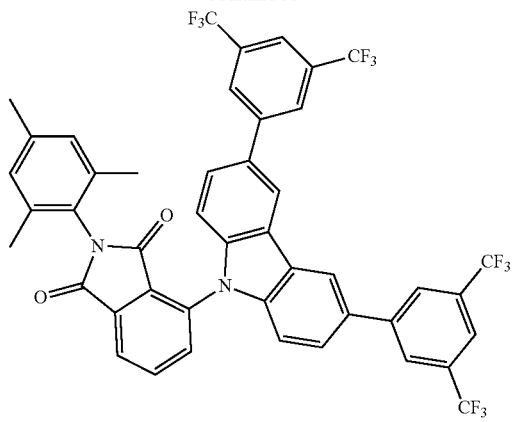
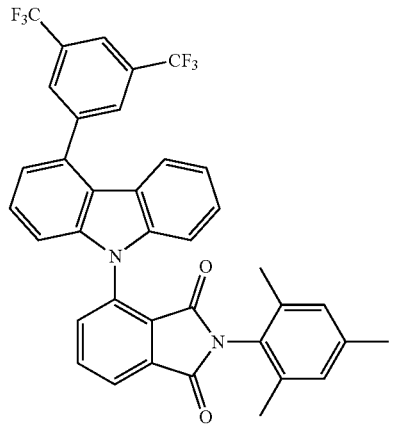
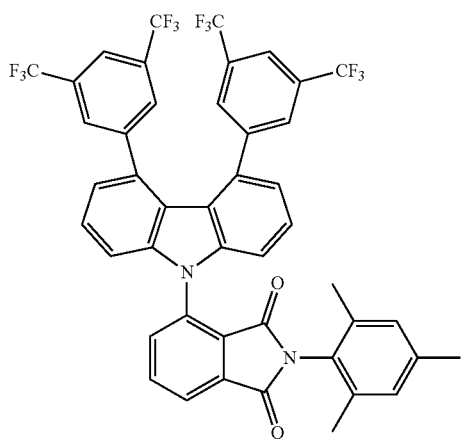
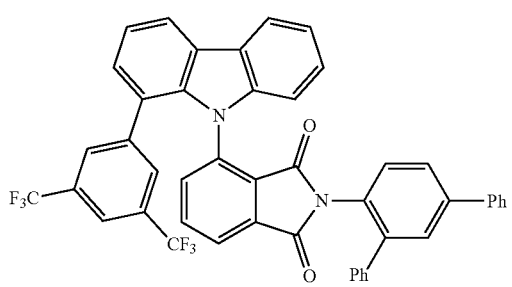

| 203 -continued | 204 -continued |
|---|---|
| 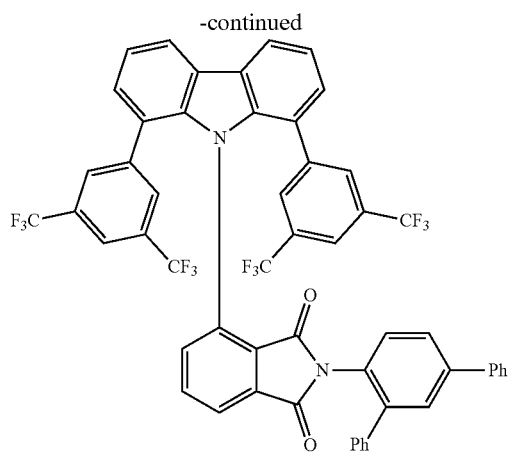 | 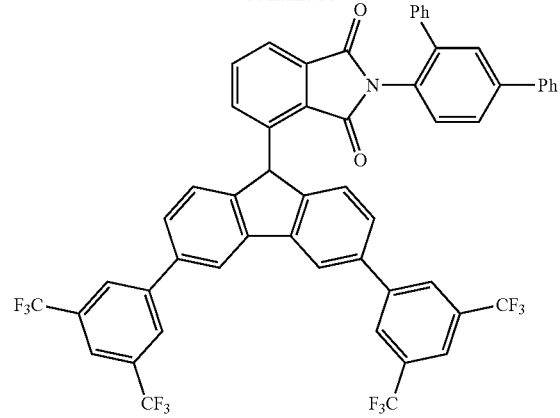 |
| 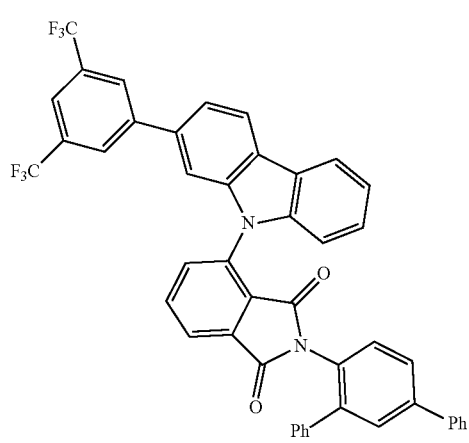 | 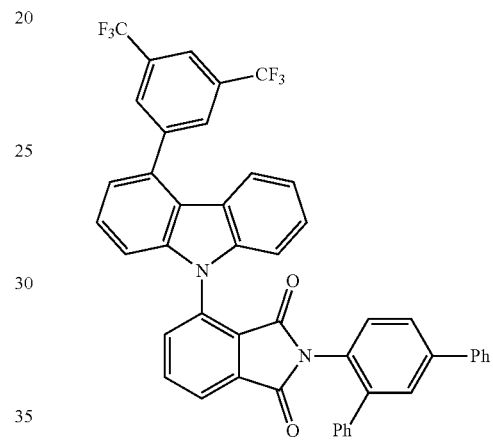 |
| 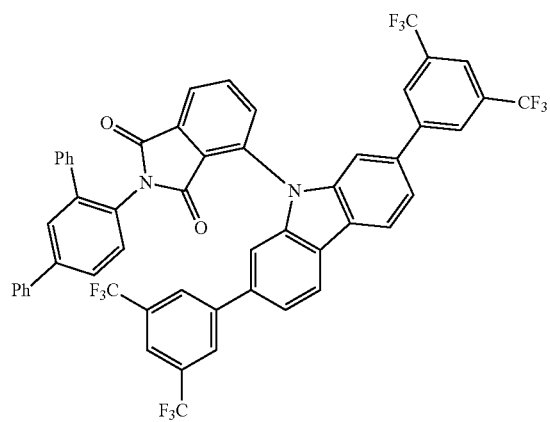 | 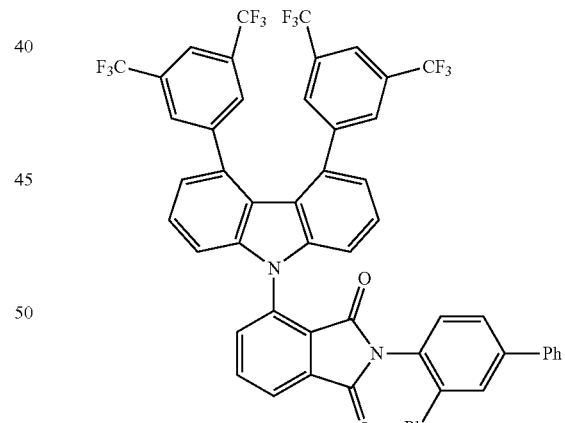 |
| 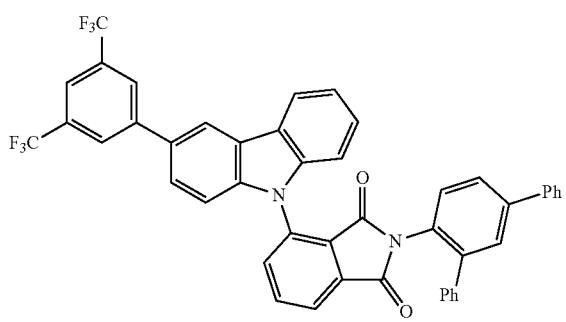 | 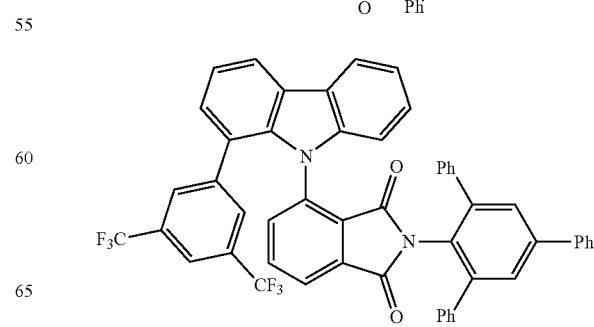 |

-continued
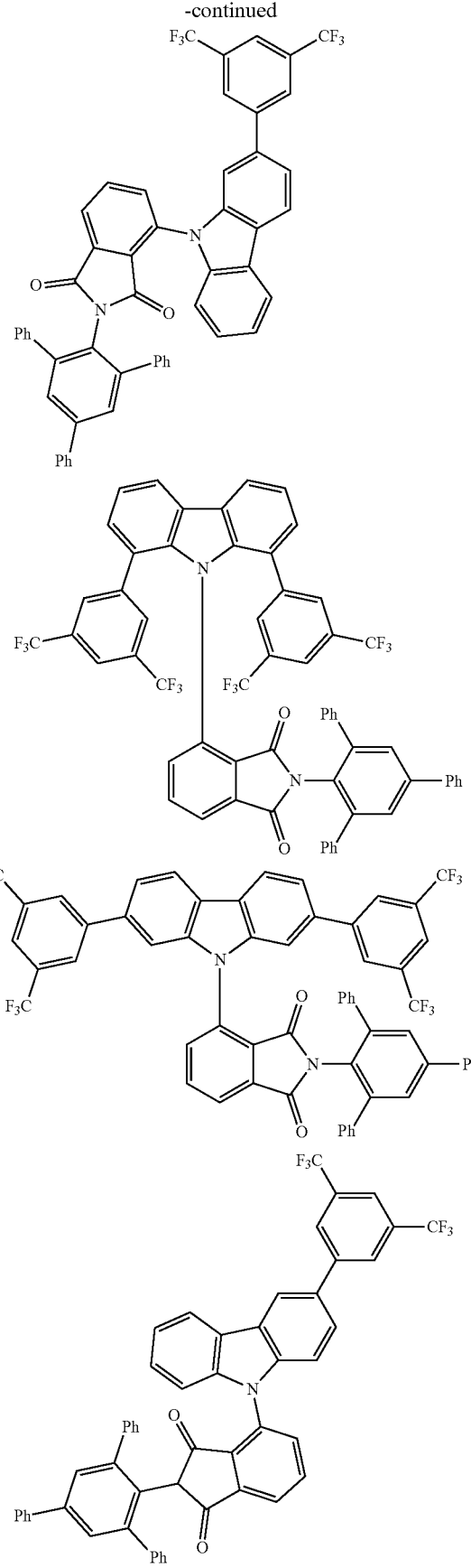
-continued
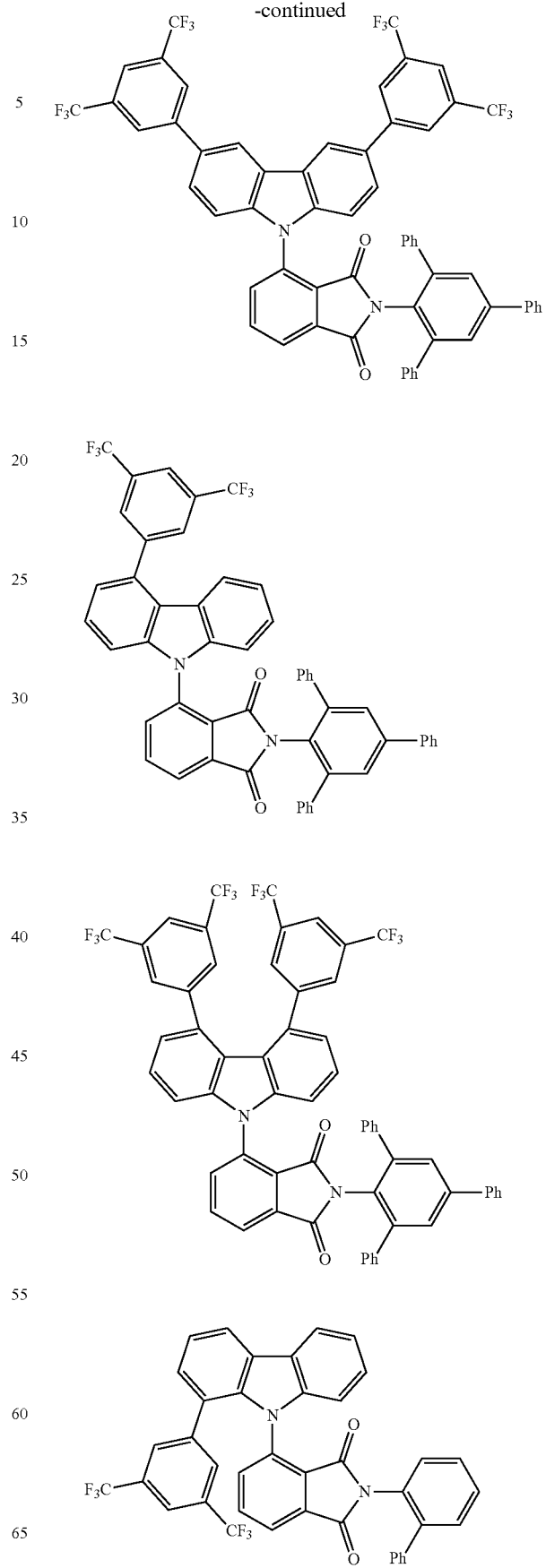

207
-continued
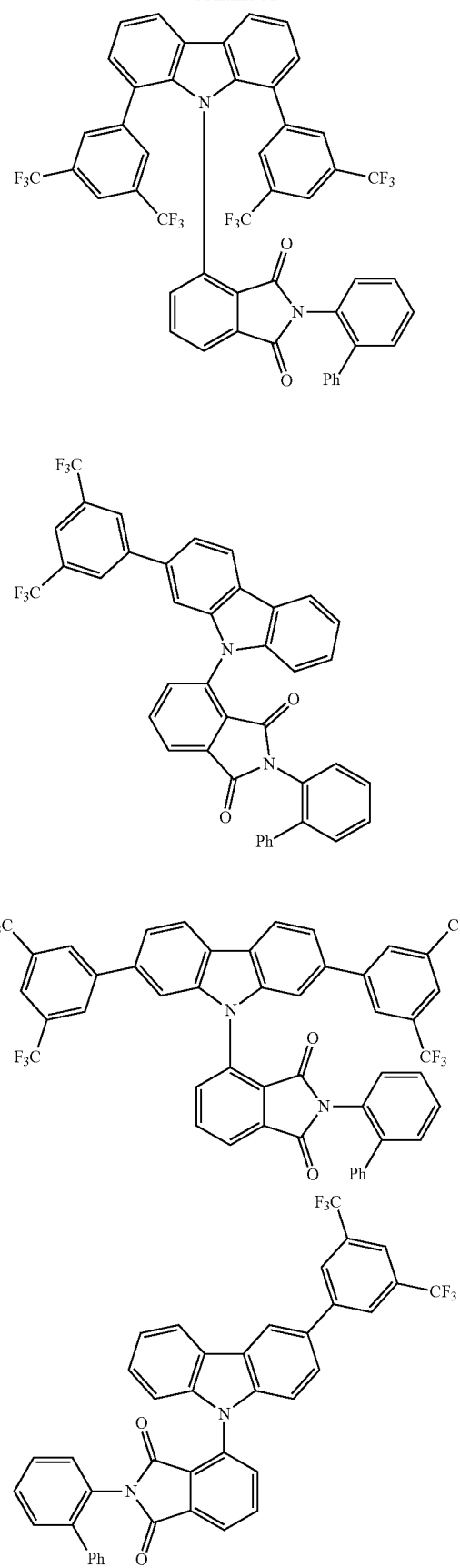
208
-continued
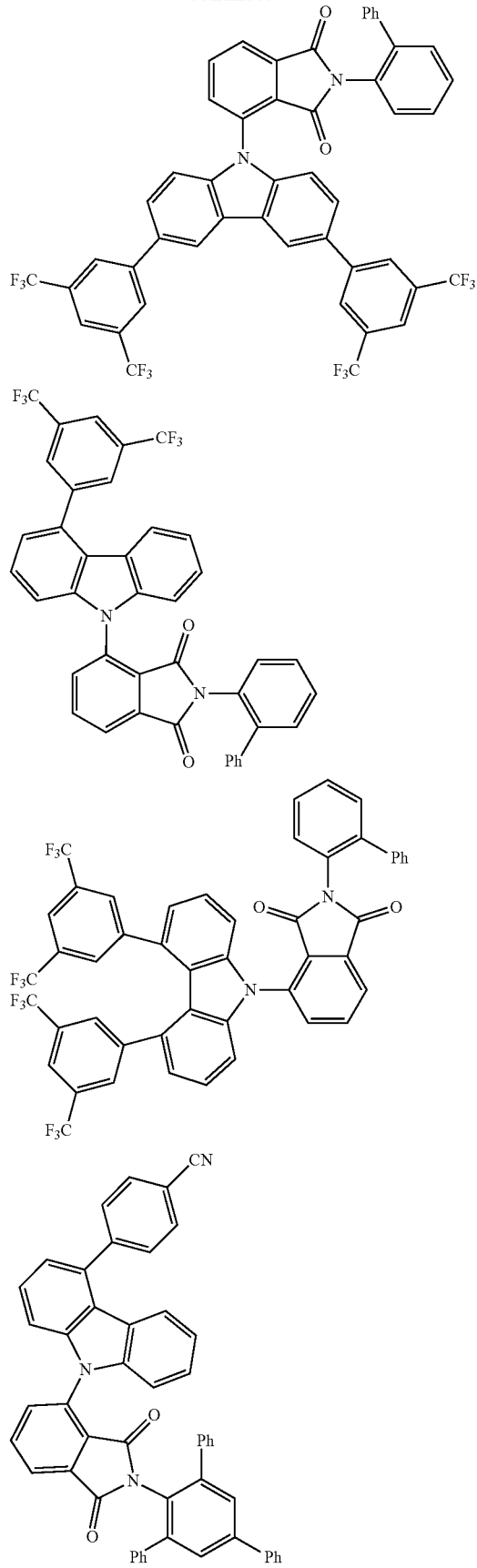

-continued
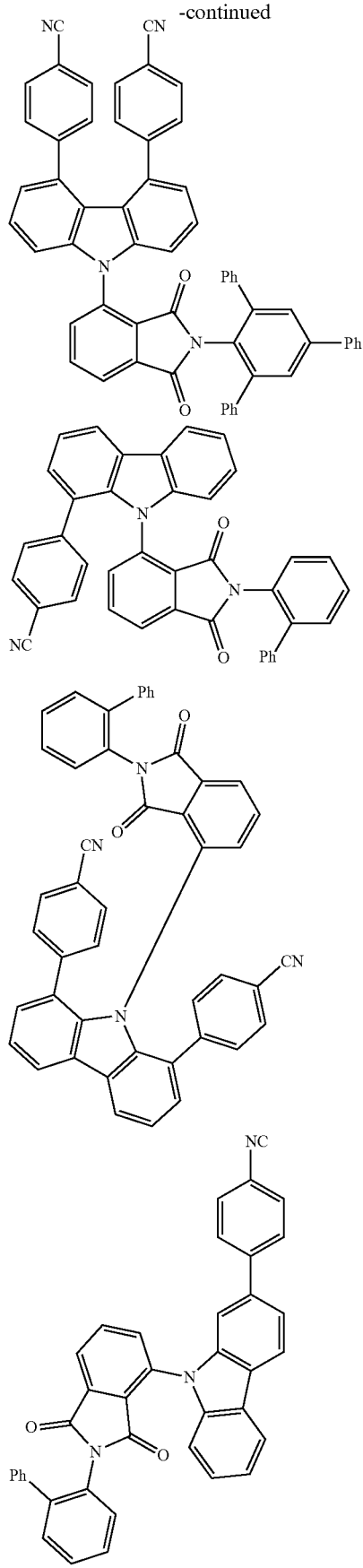
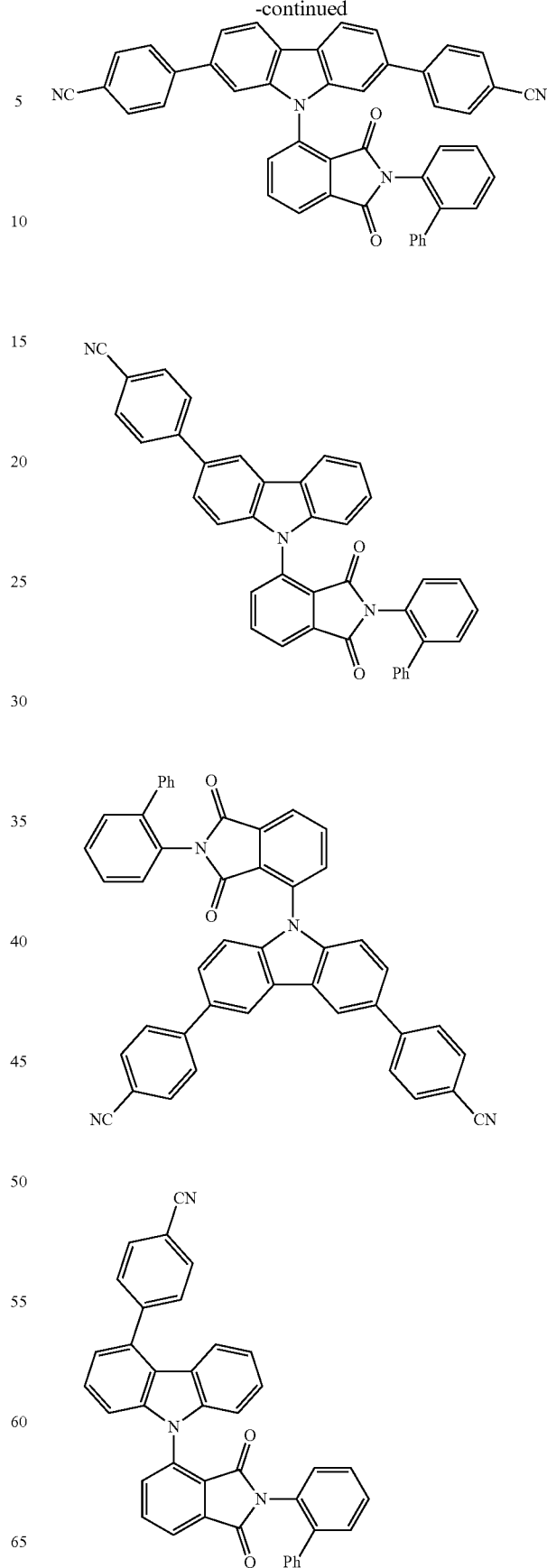

211
-continued
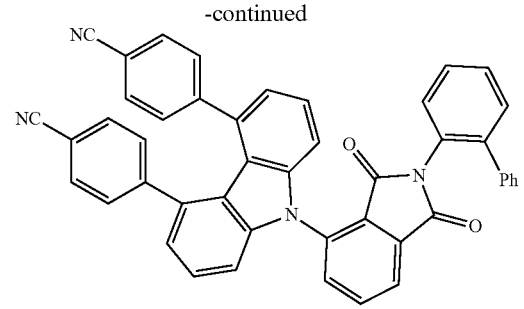
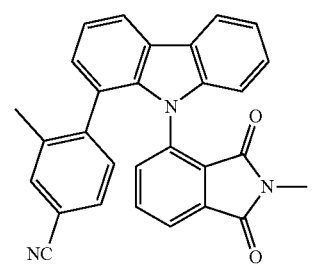
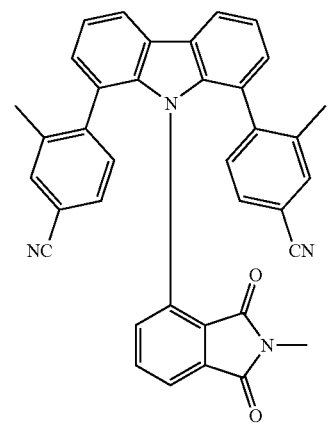
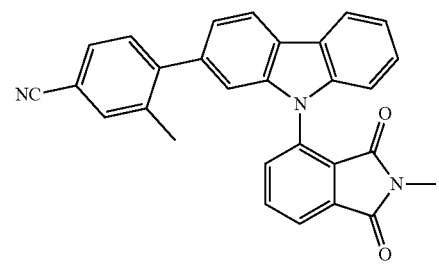
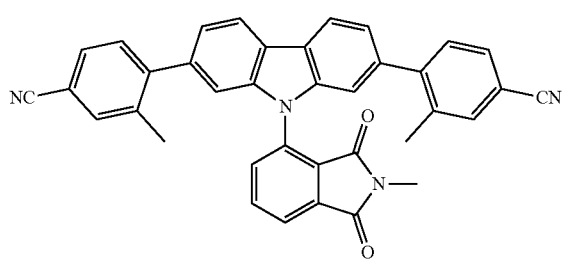
212
-continued
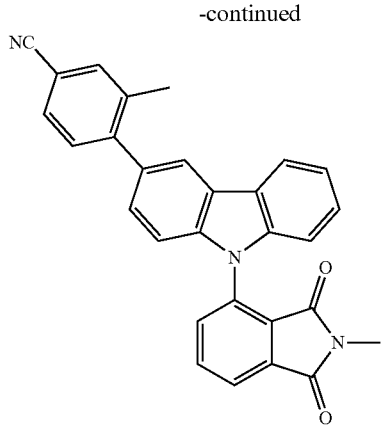
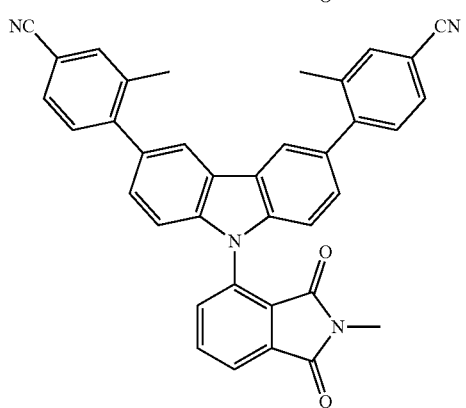
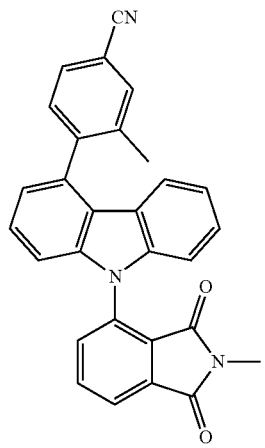
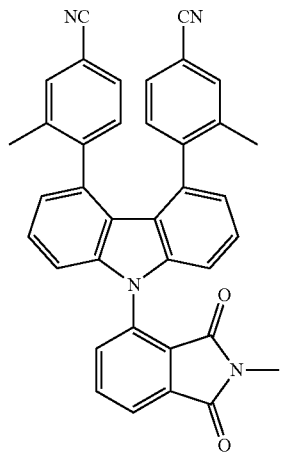

213
-continued
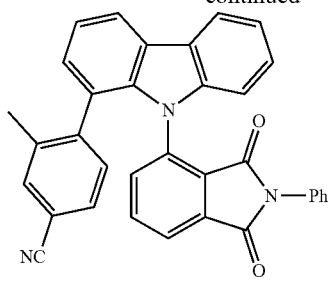
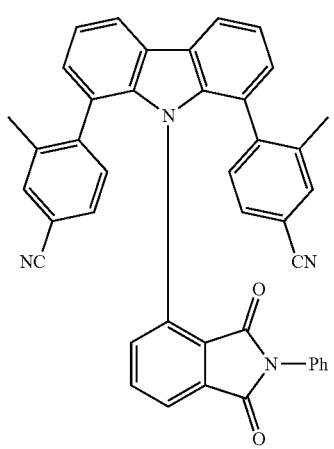
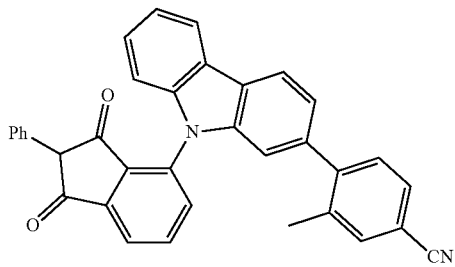
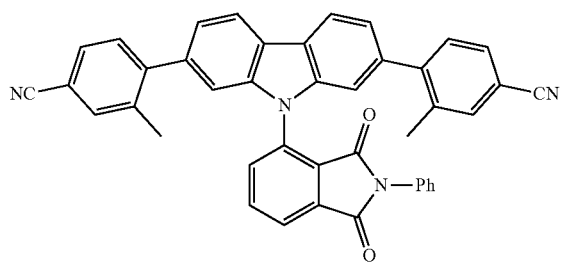
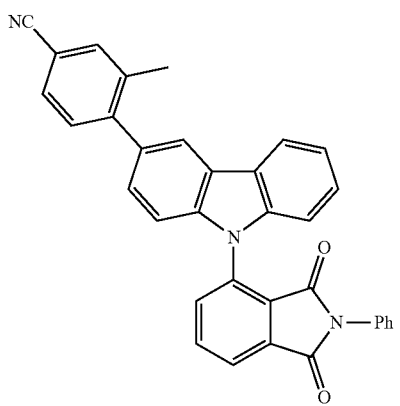
214
-continued
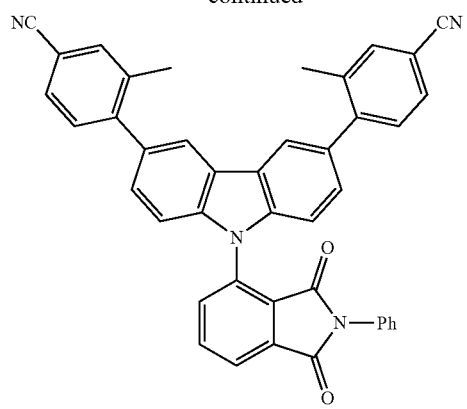
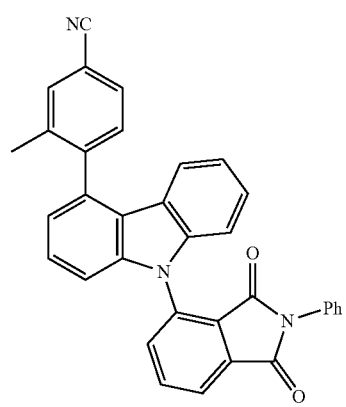
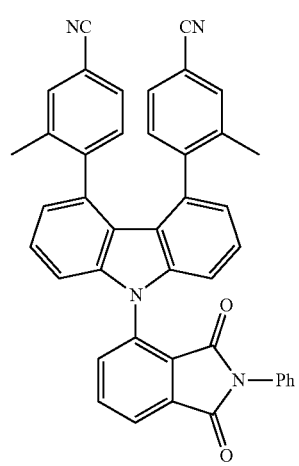
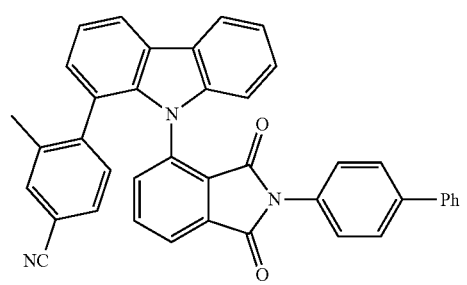

215
-continued
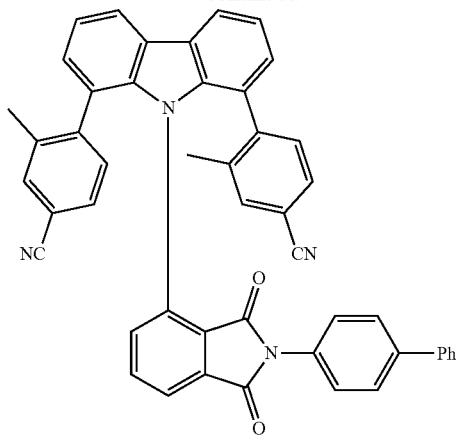
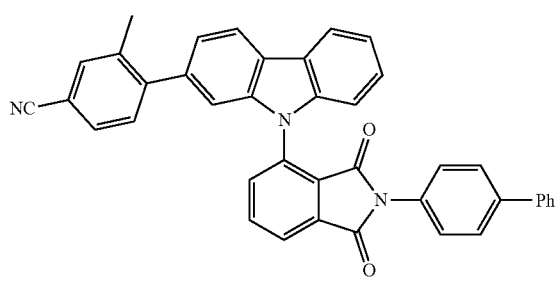
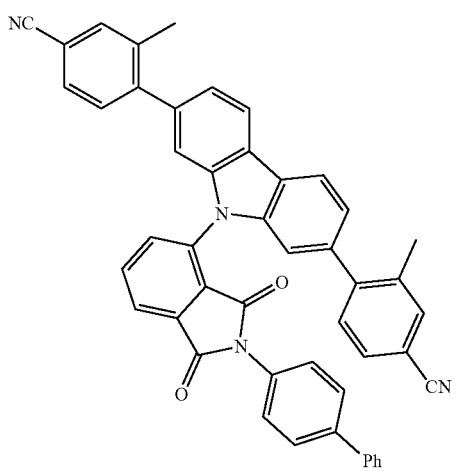
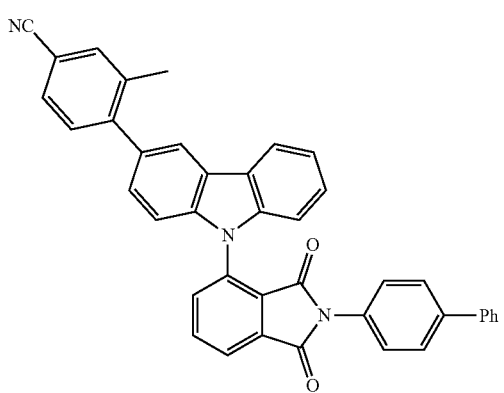
216
-continued
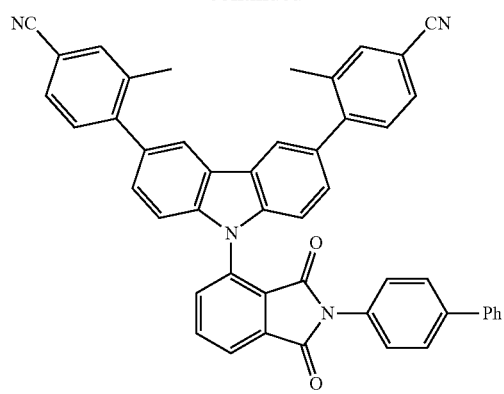
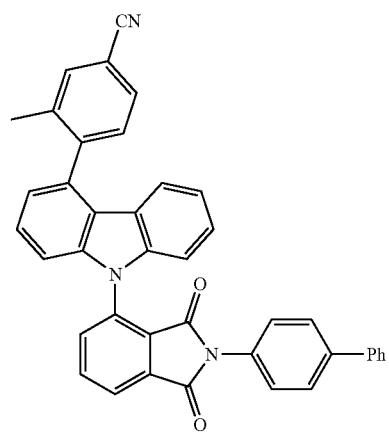
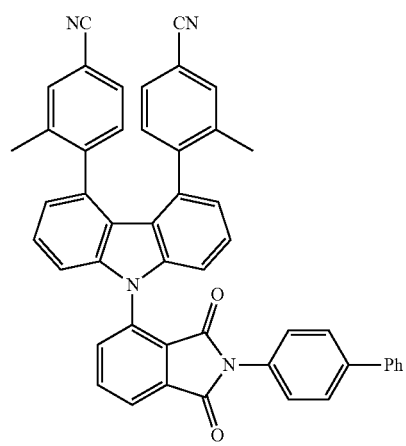
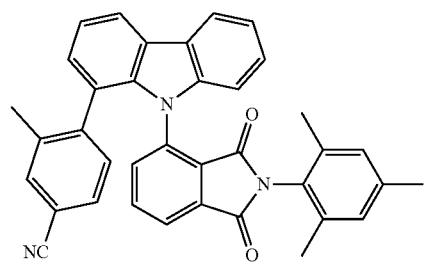

217
-continued
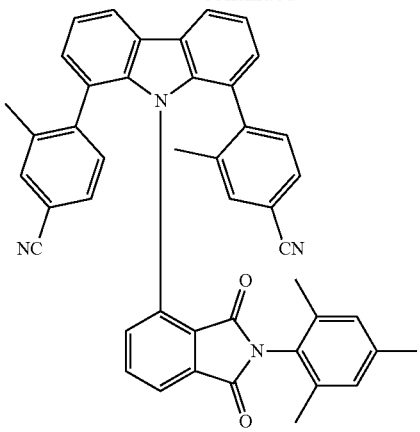
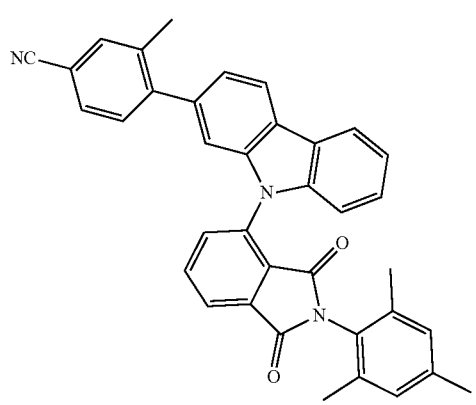
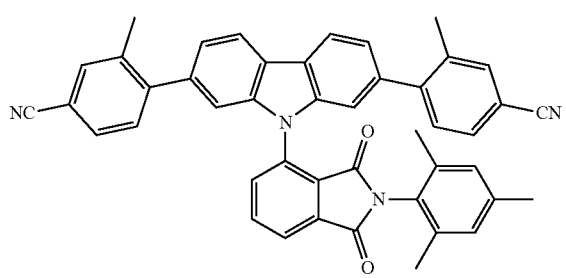
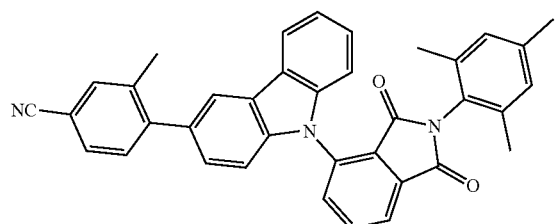
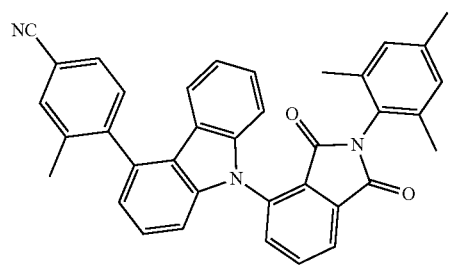
218
-continued
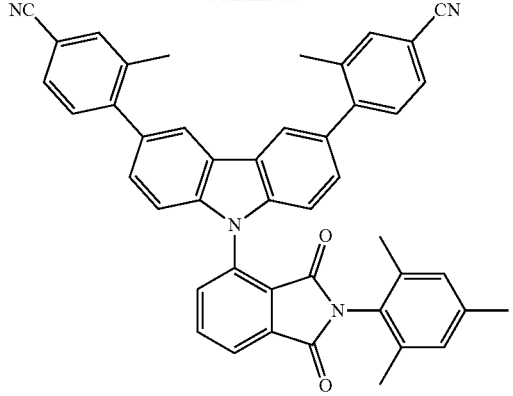
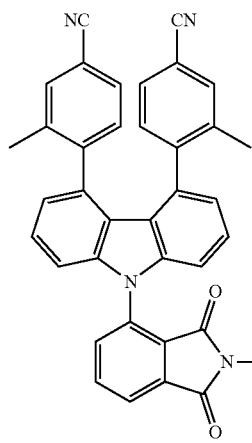
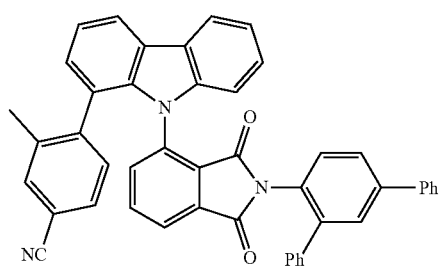
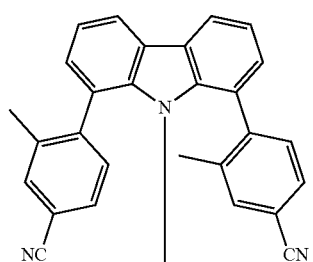
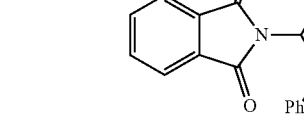

219
-continued
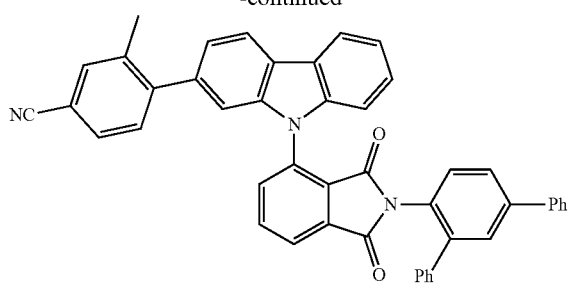
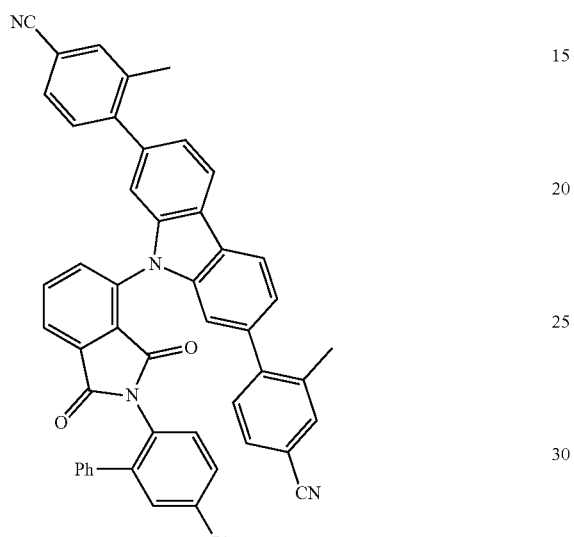
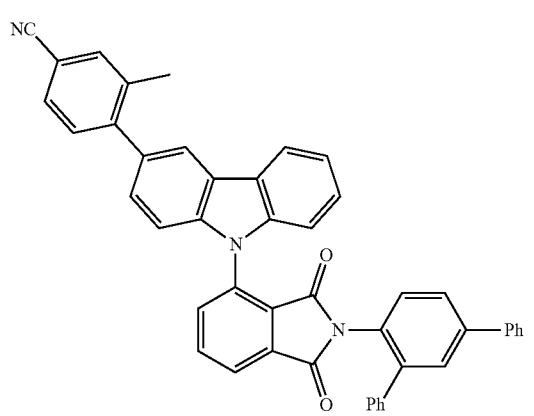
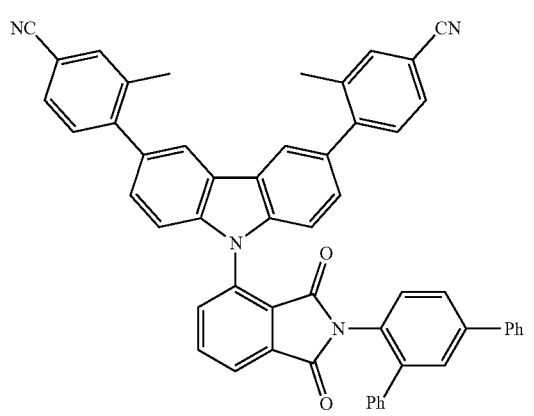
220
-continued
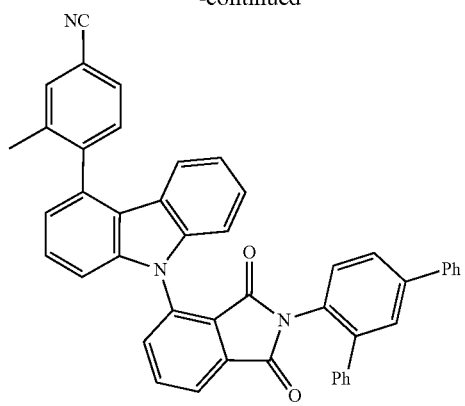
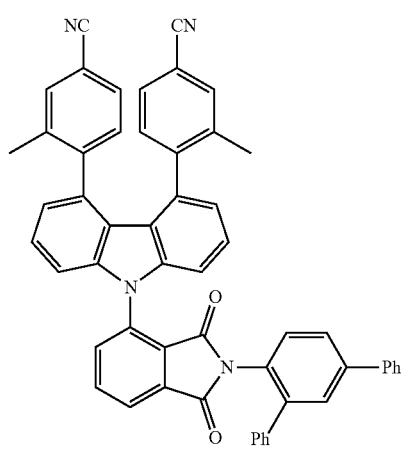
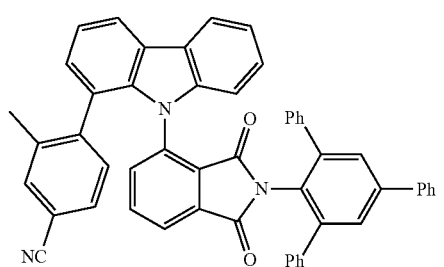
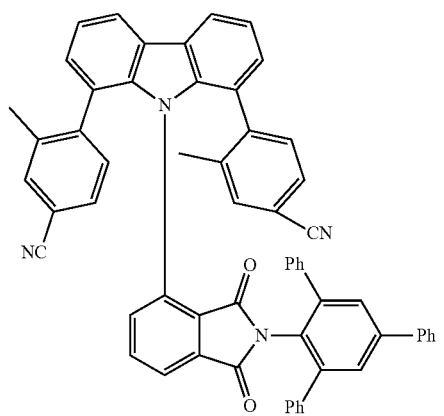

221
-continued
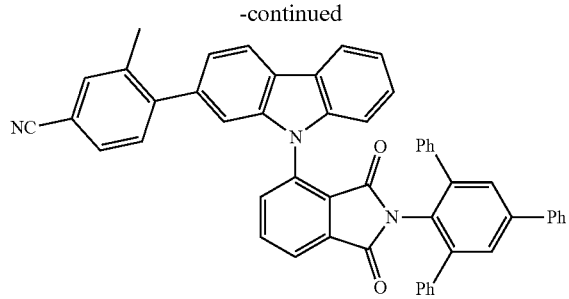
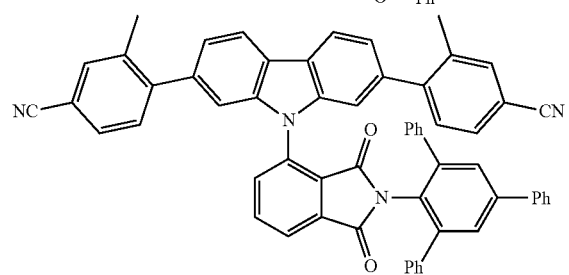
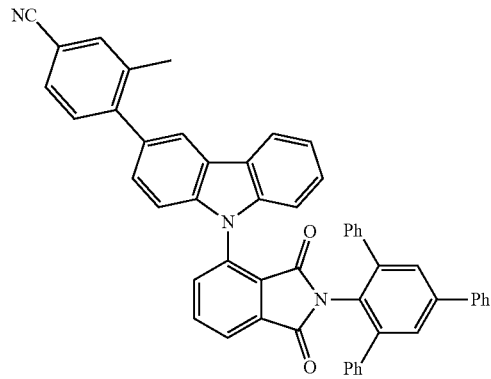
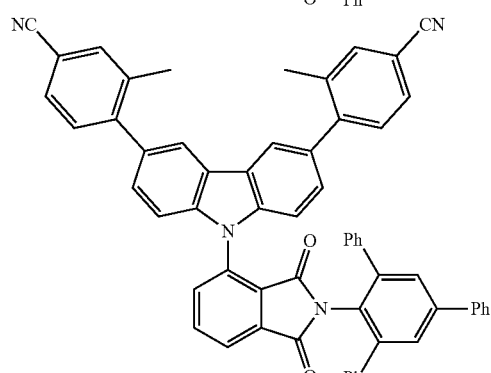
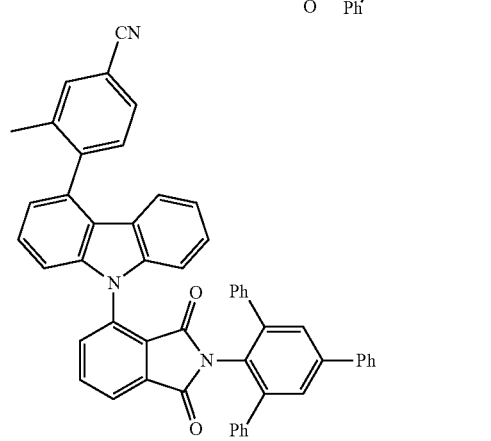
222
-continued
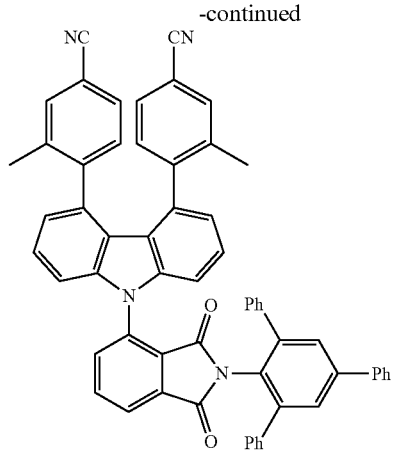
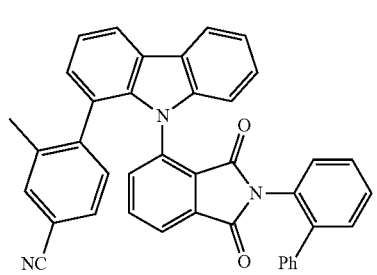
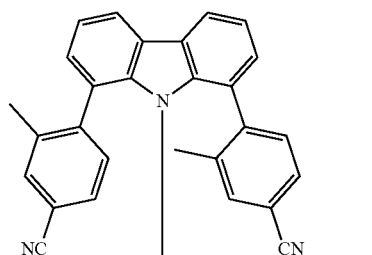
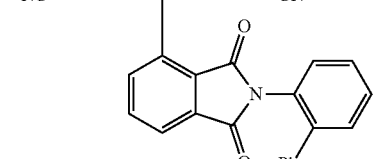
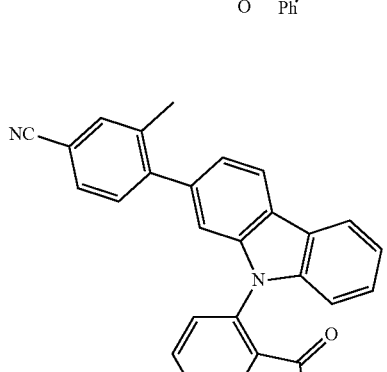
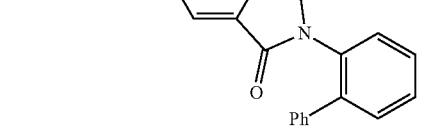

223
-continued
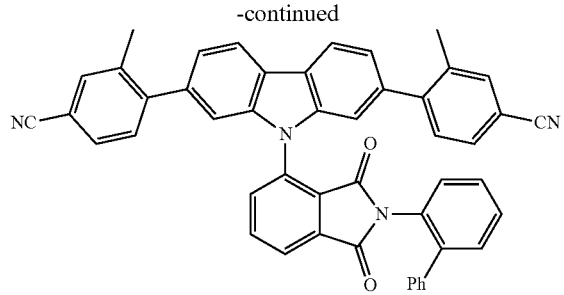
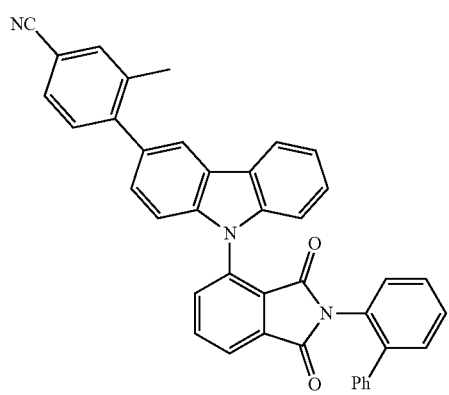
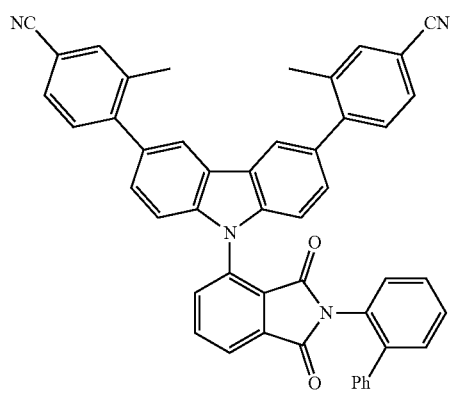
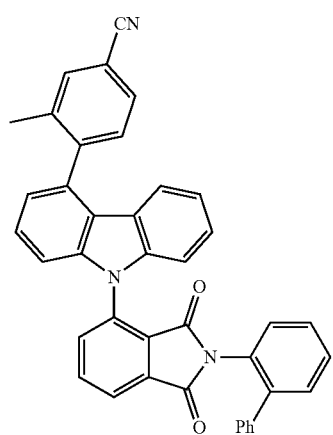
224
-continued
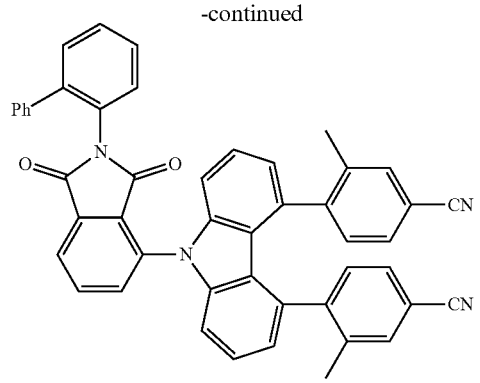
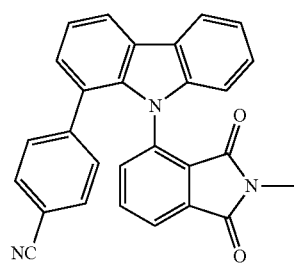
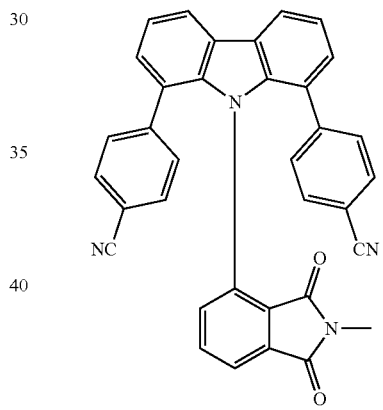
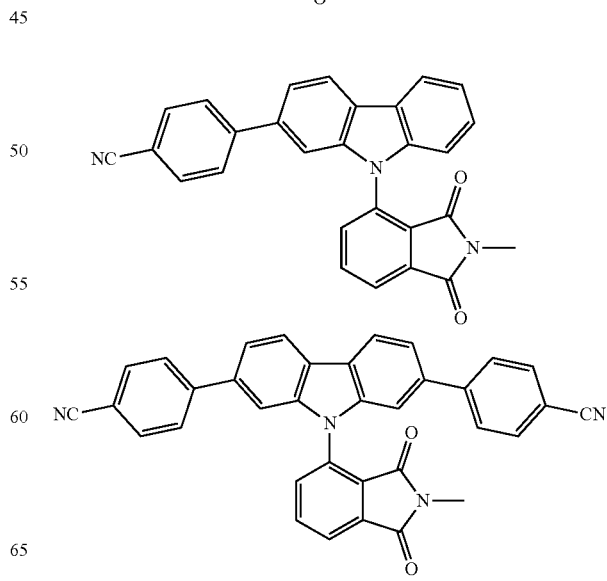

225
-continued
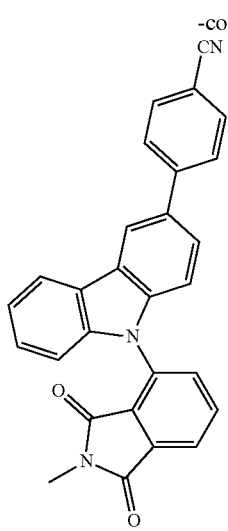
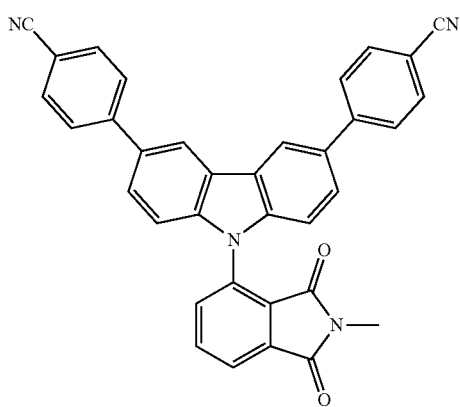
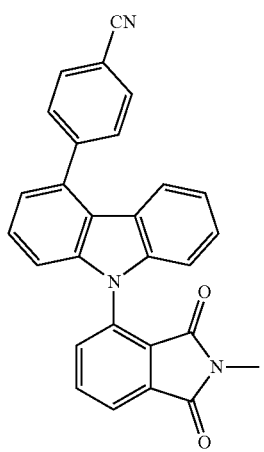
226
-continued
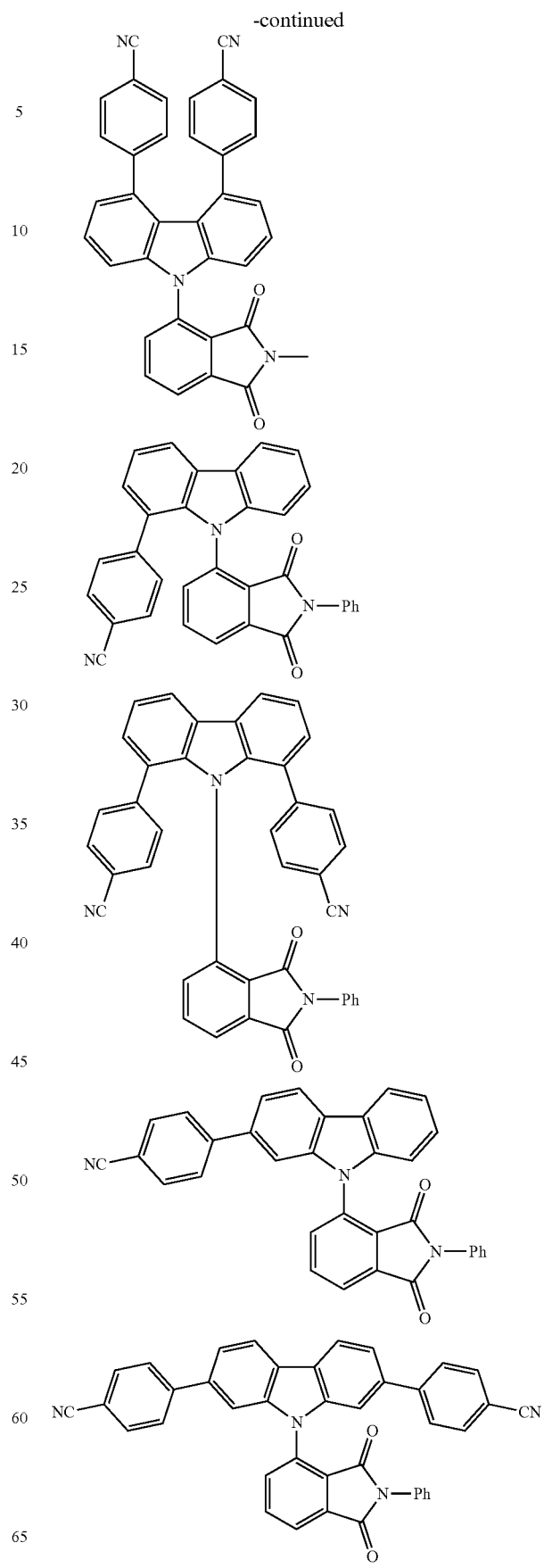

227
-continued
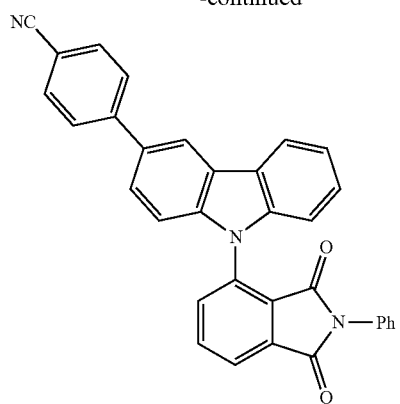
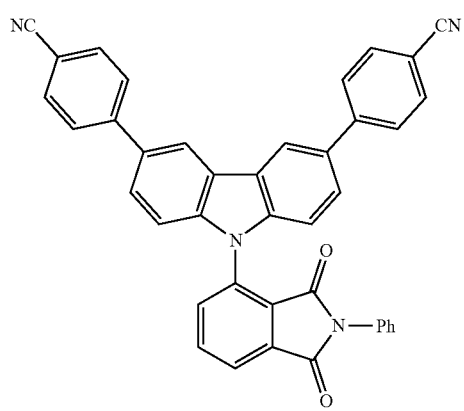
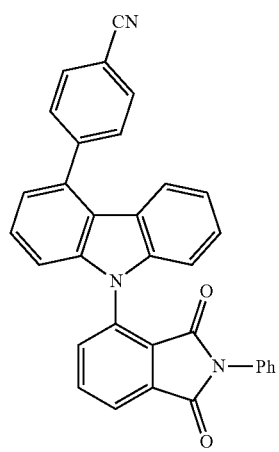
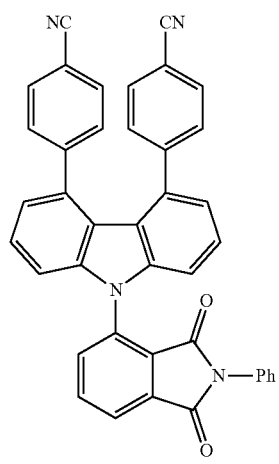
228
-continued
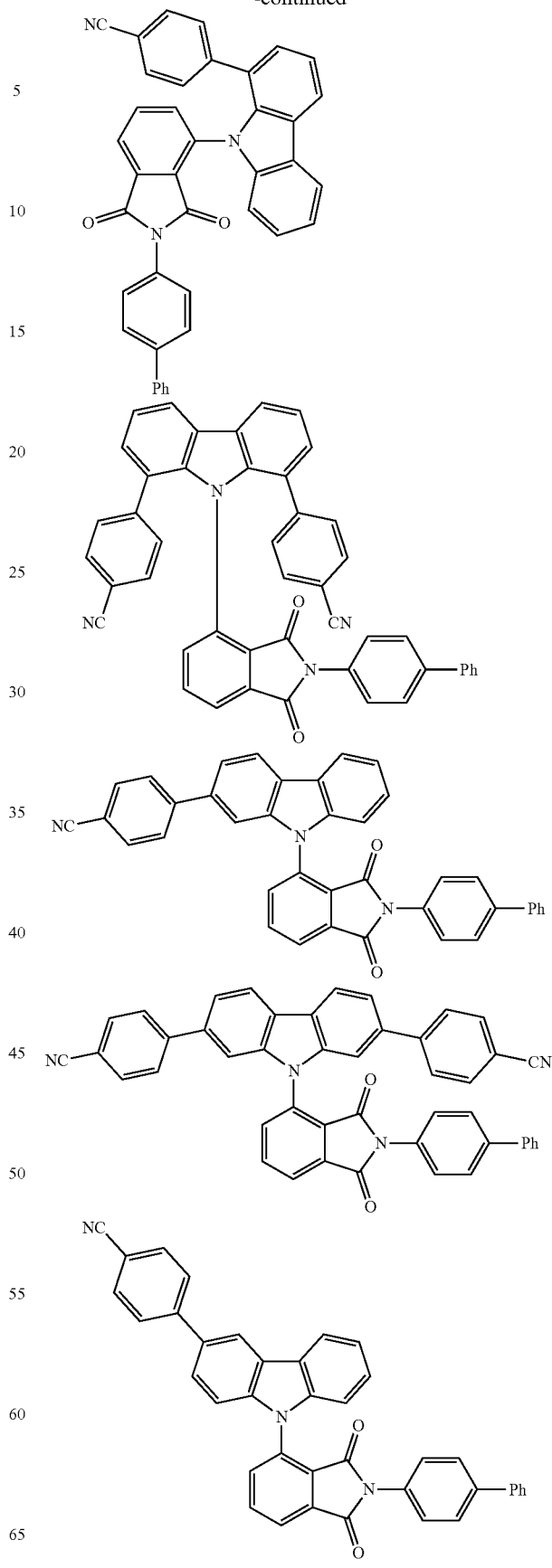

229
-continued
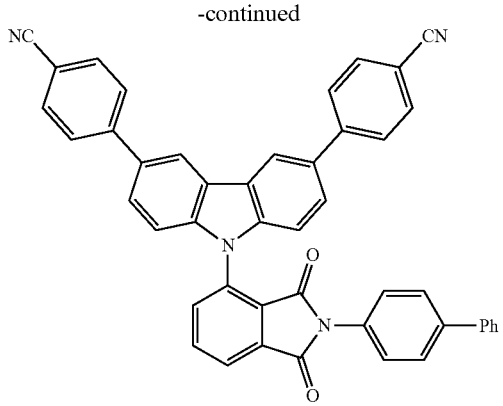
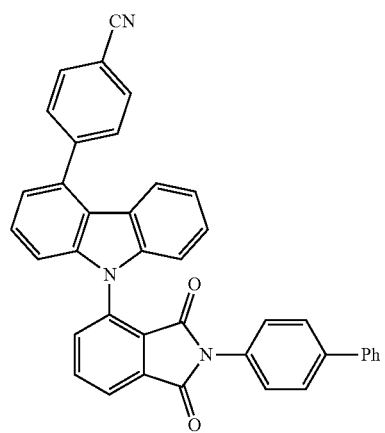
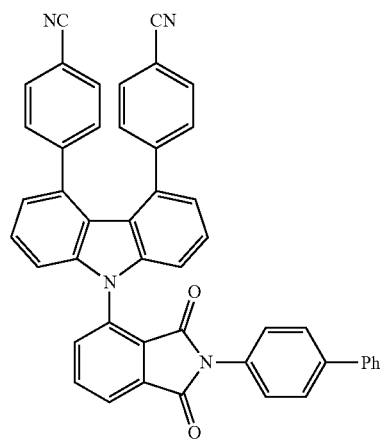
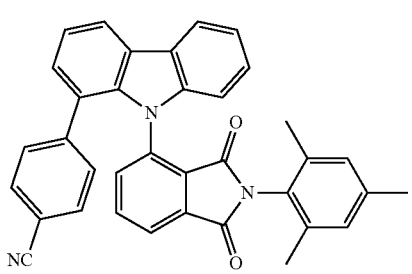
230
-continued
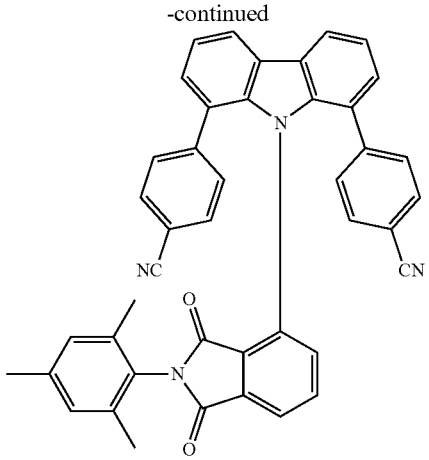
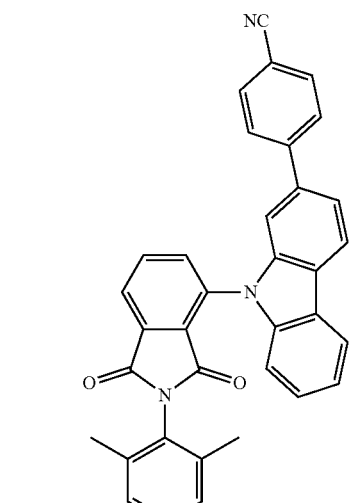
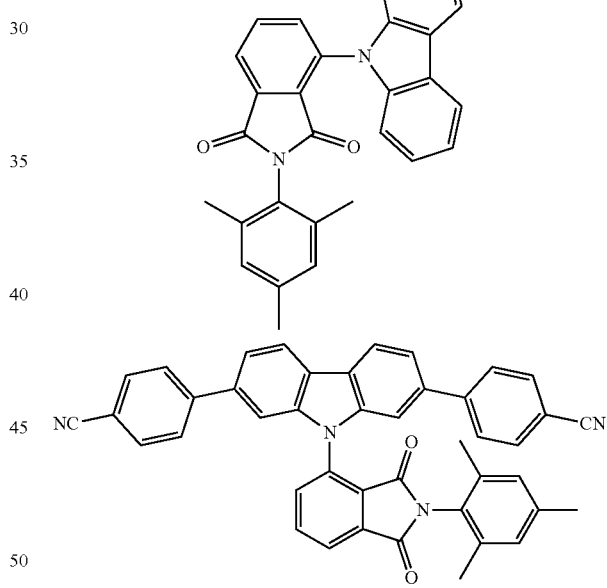
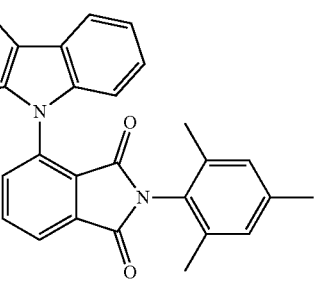

231
-continued
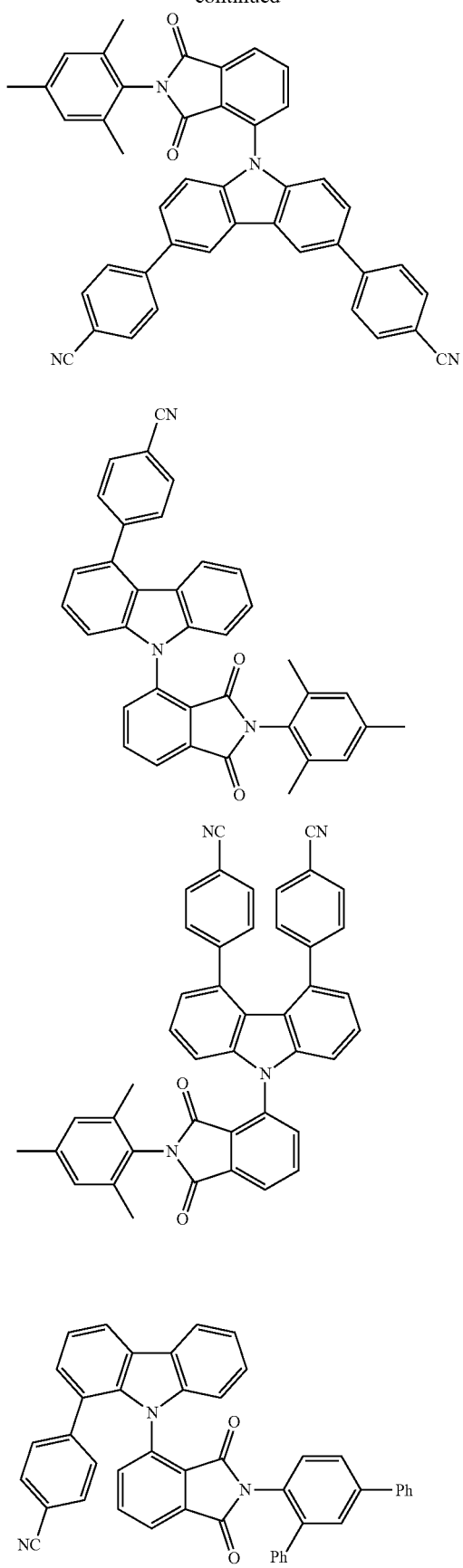
232
-continued
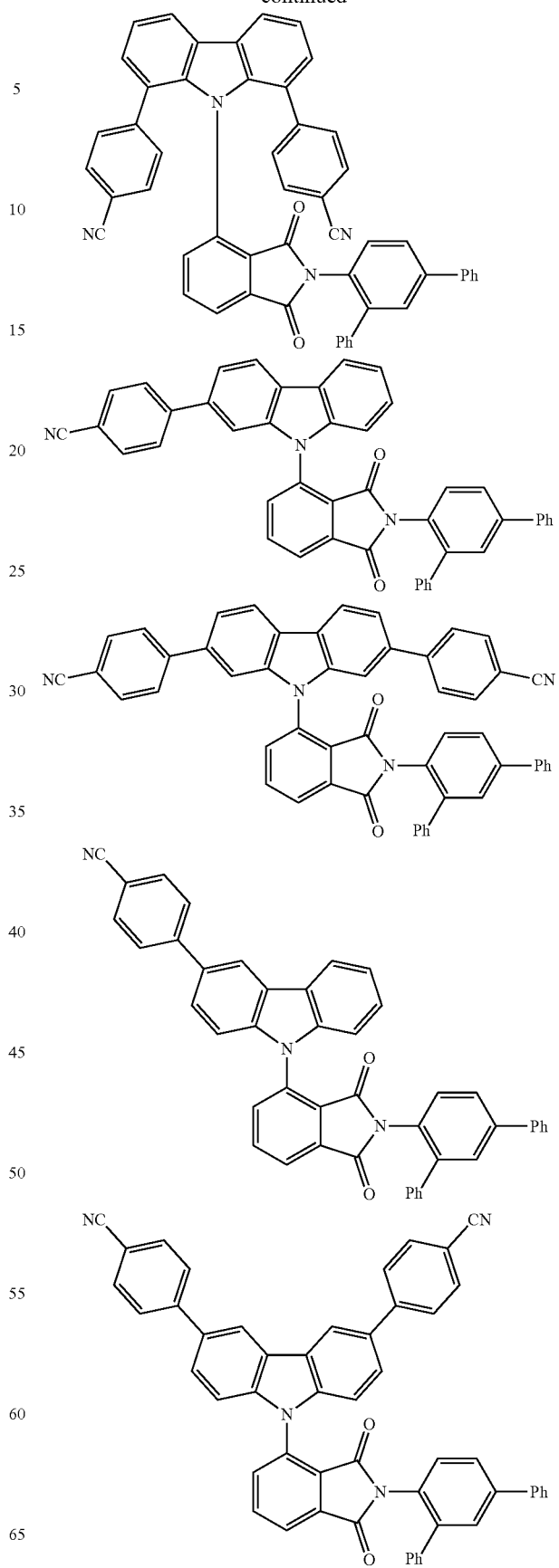

233
-continued
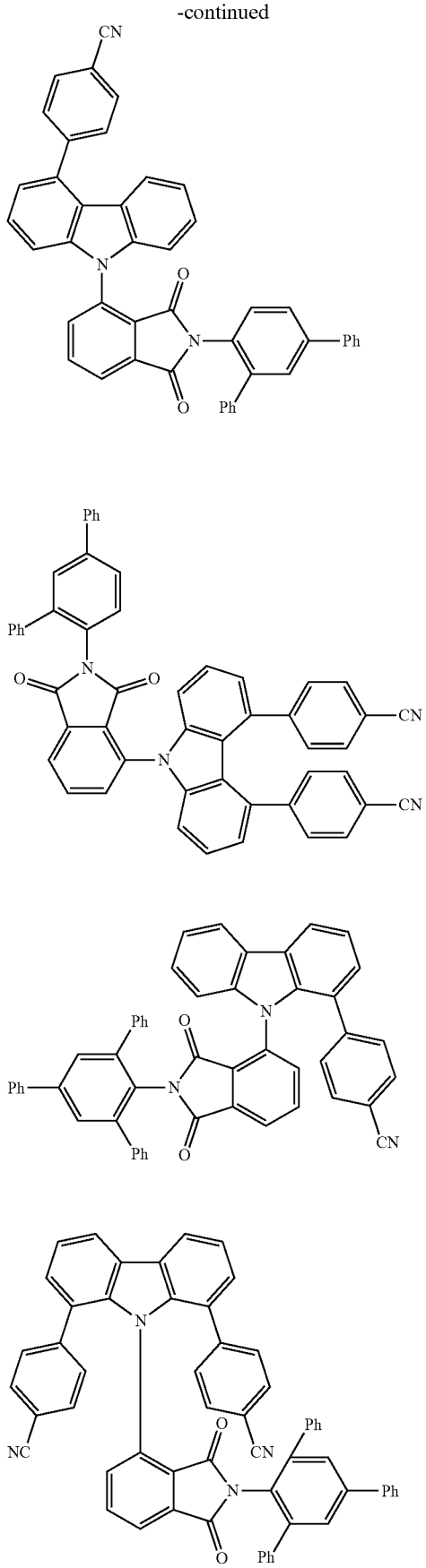
234
-continued
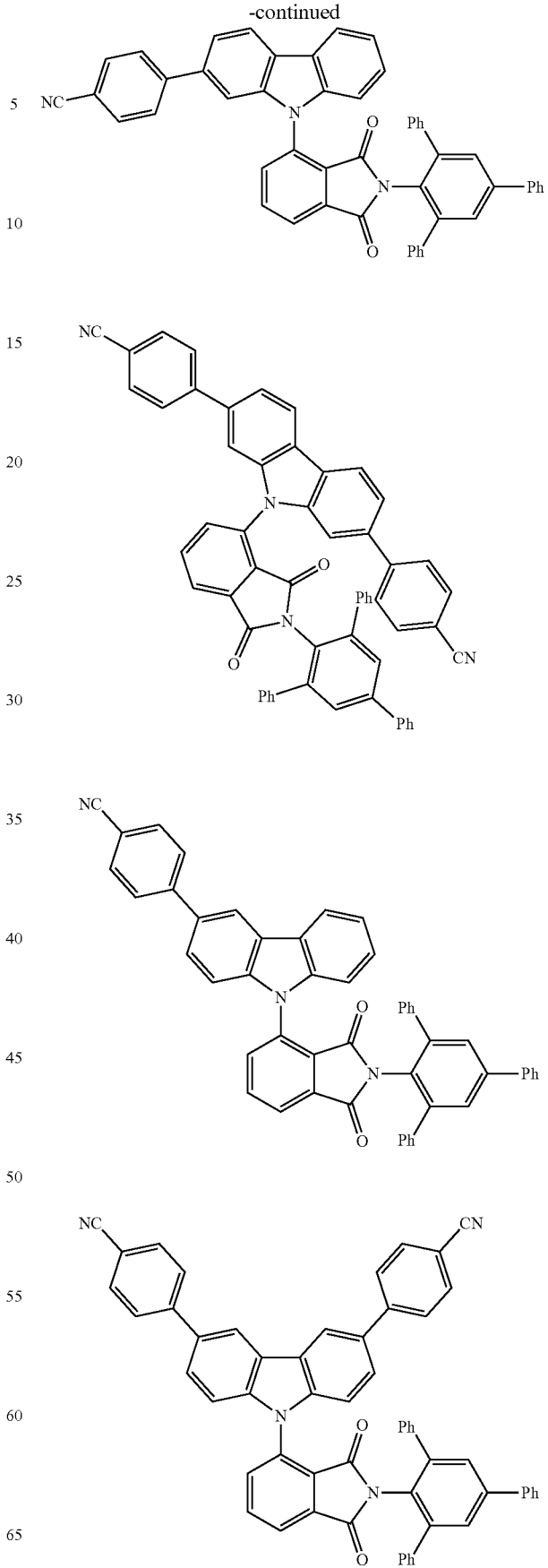

235
-continued
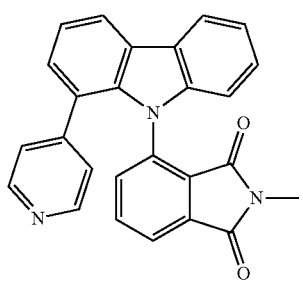
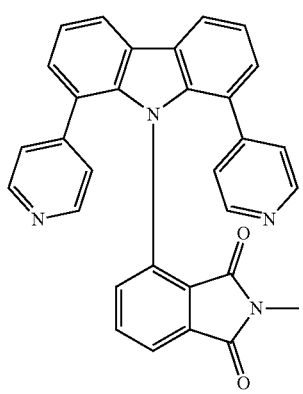
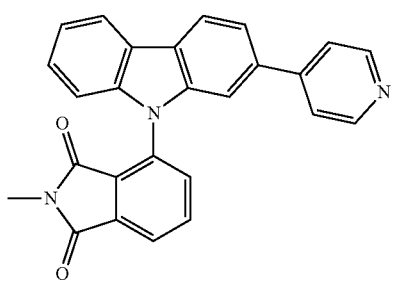
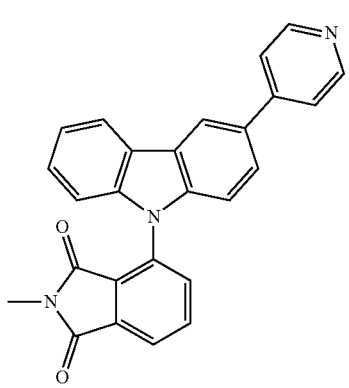
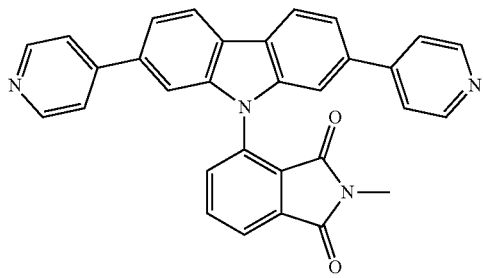
236
-continued
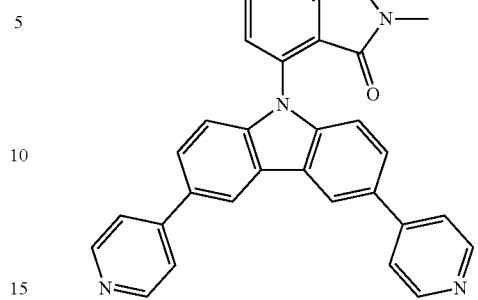
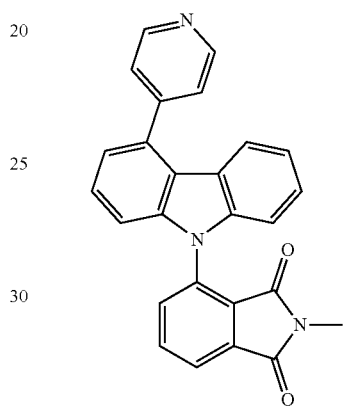
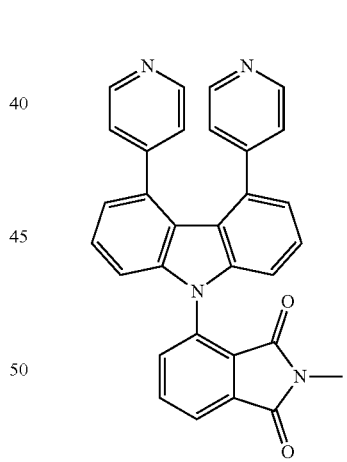
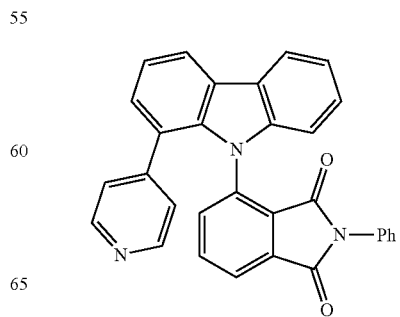

237
-continued
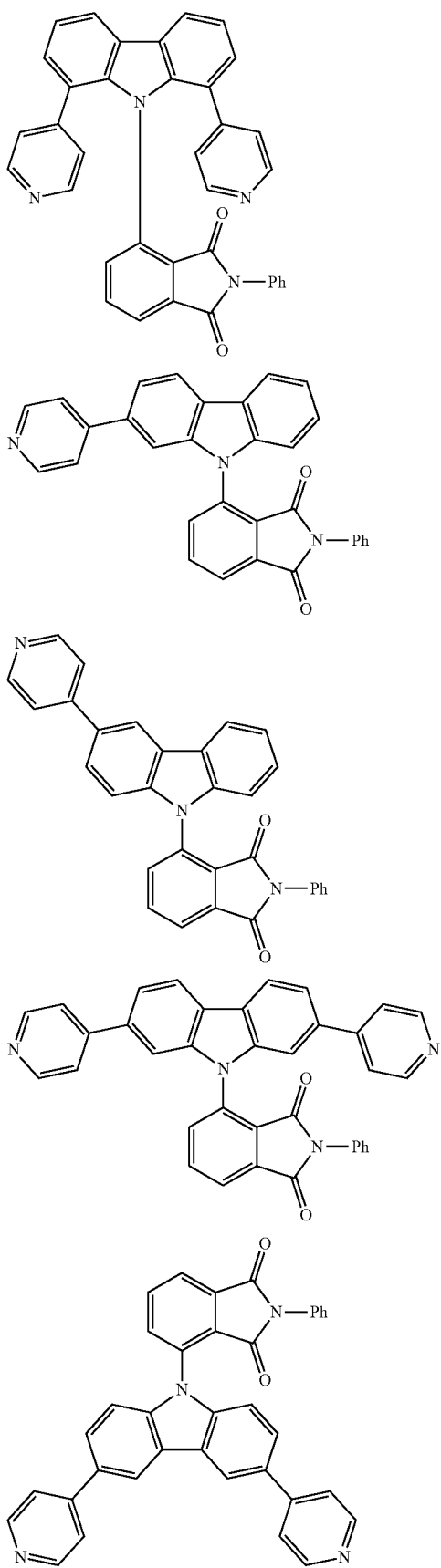
238
-continued
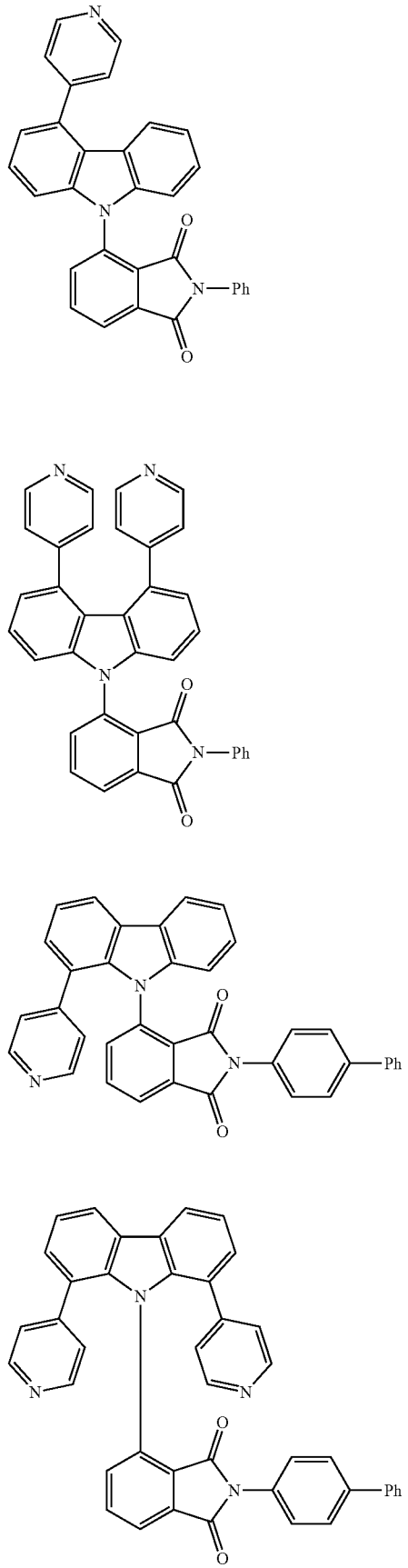

-continued
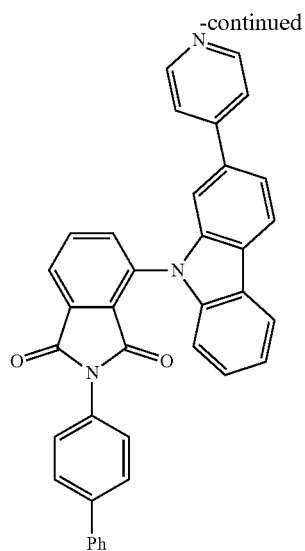
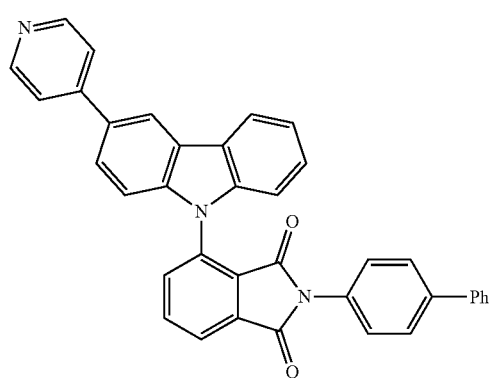
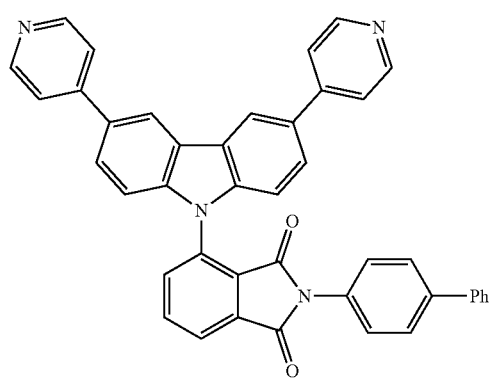
-continued
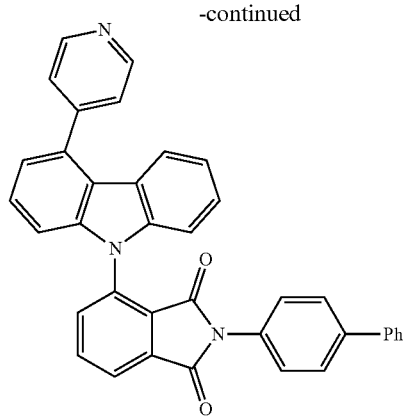
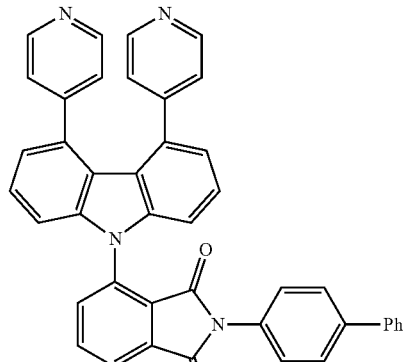
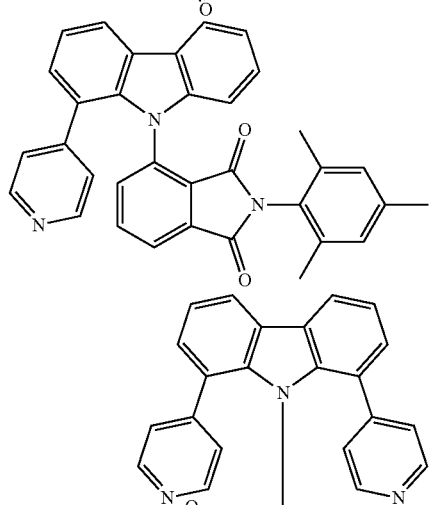
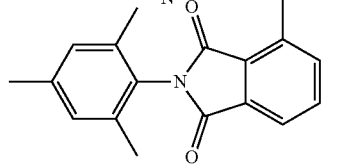
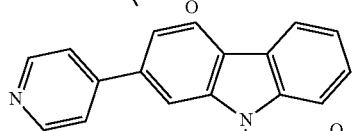

241
-continued
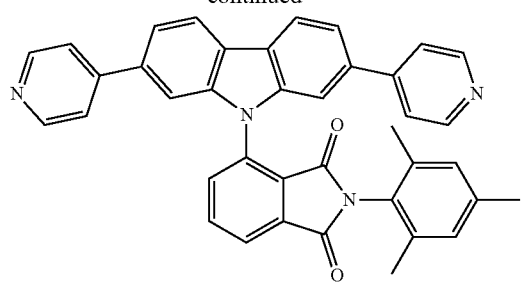
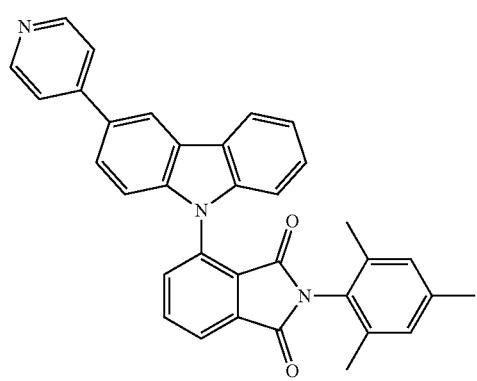
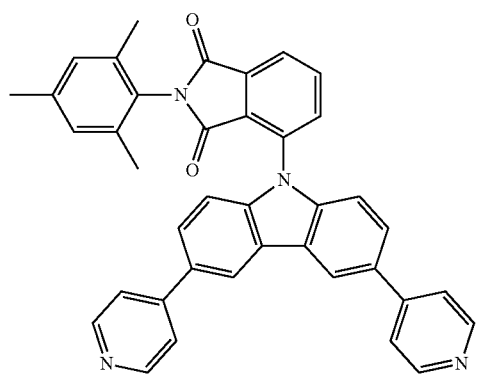
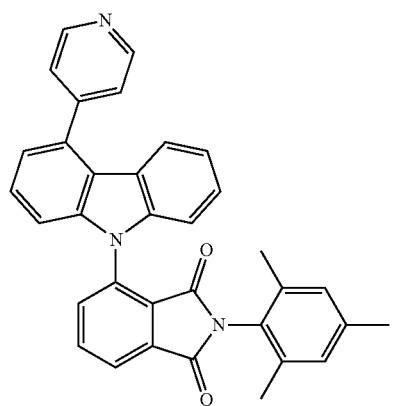
242
-continued
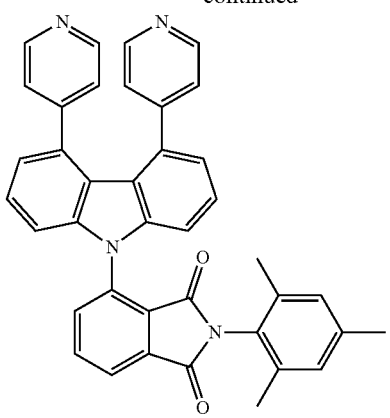
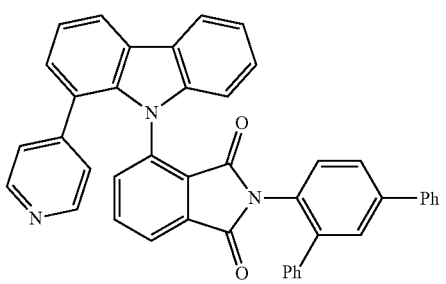
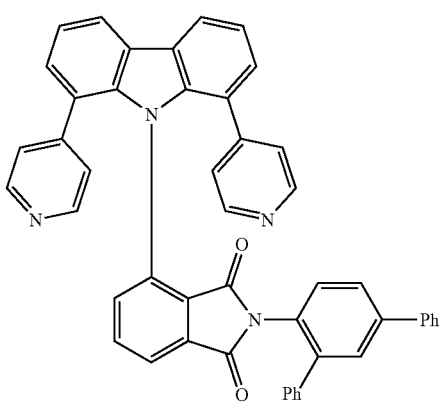
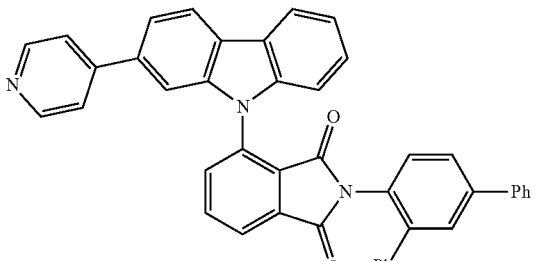
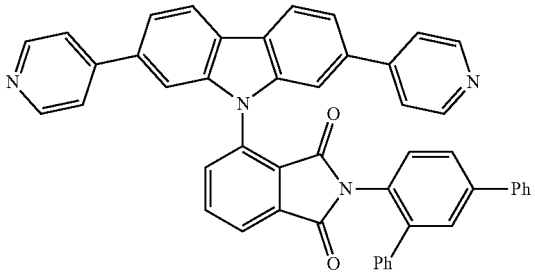

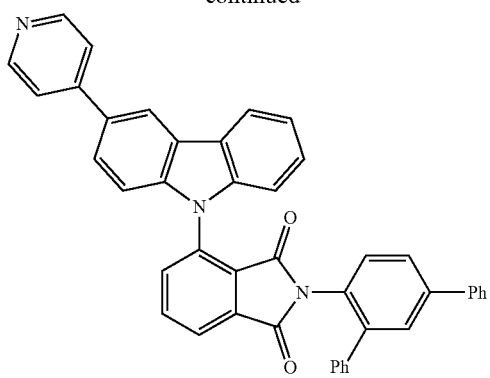
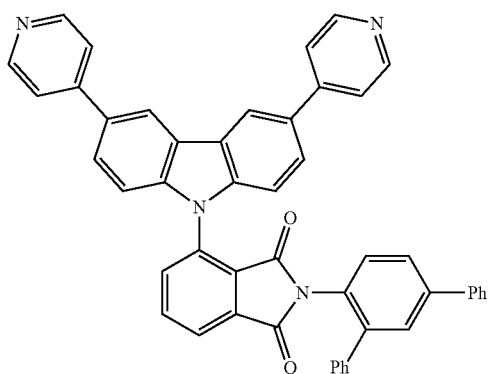
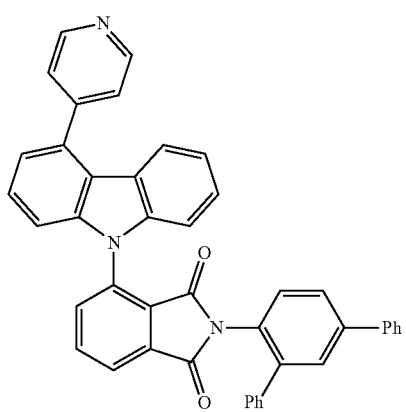
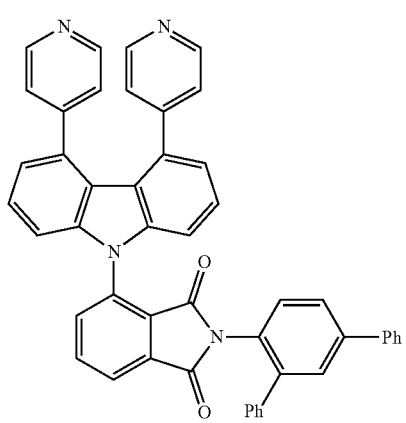
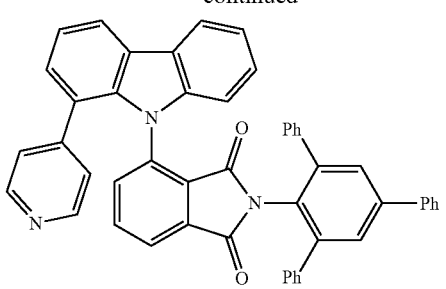
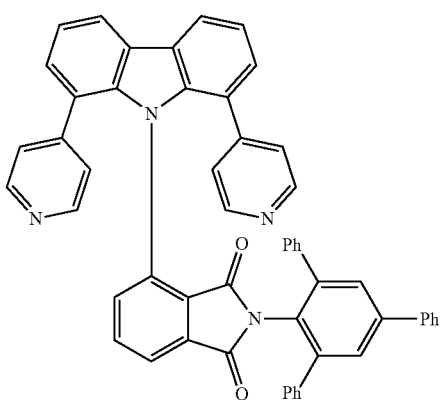
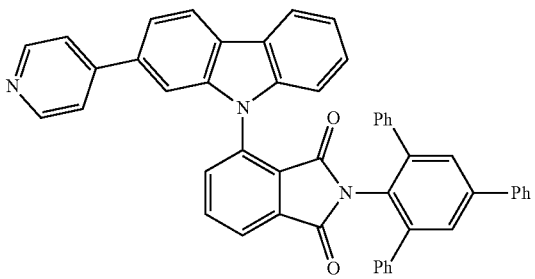
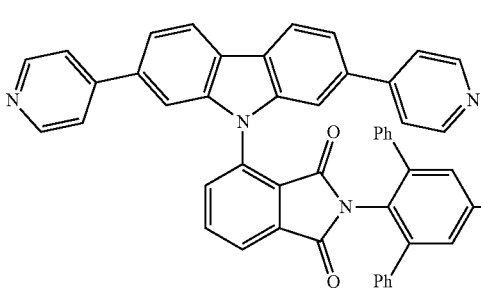

-continued
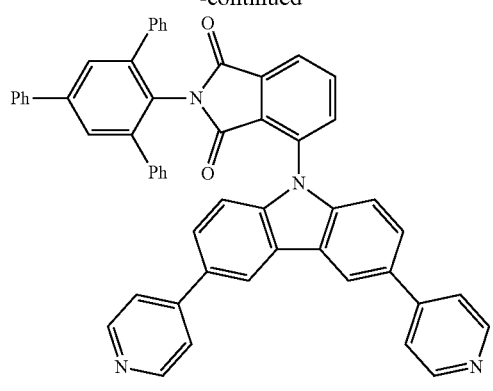
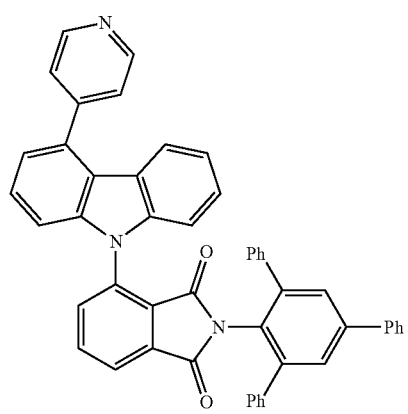
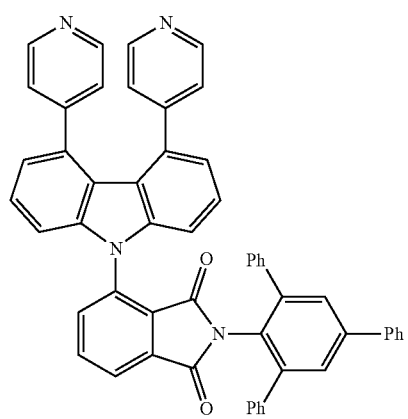
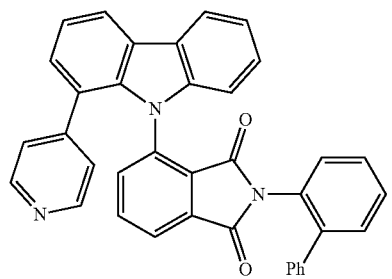
-continued
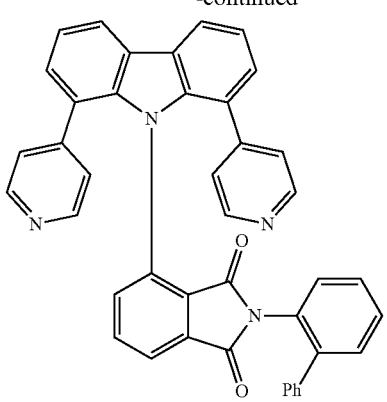
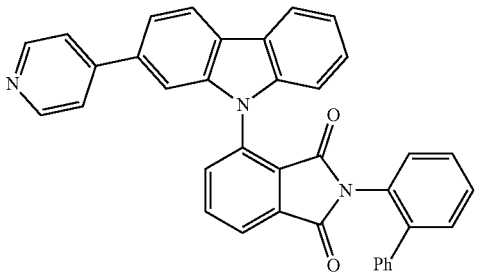
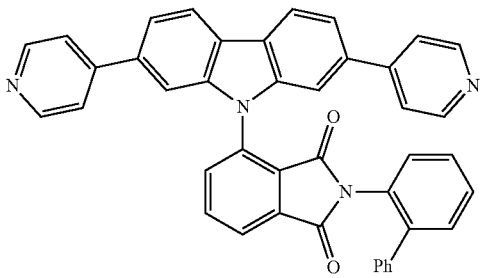
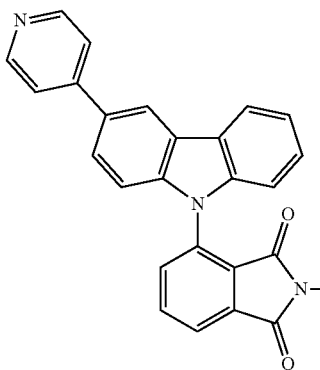
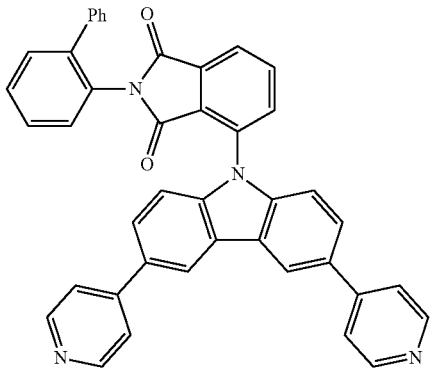

247
-continued
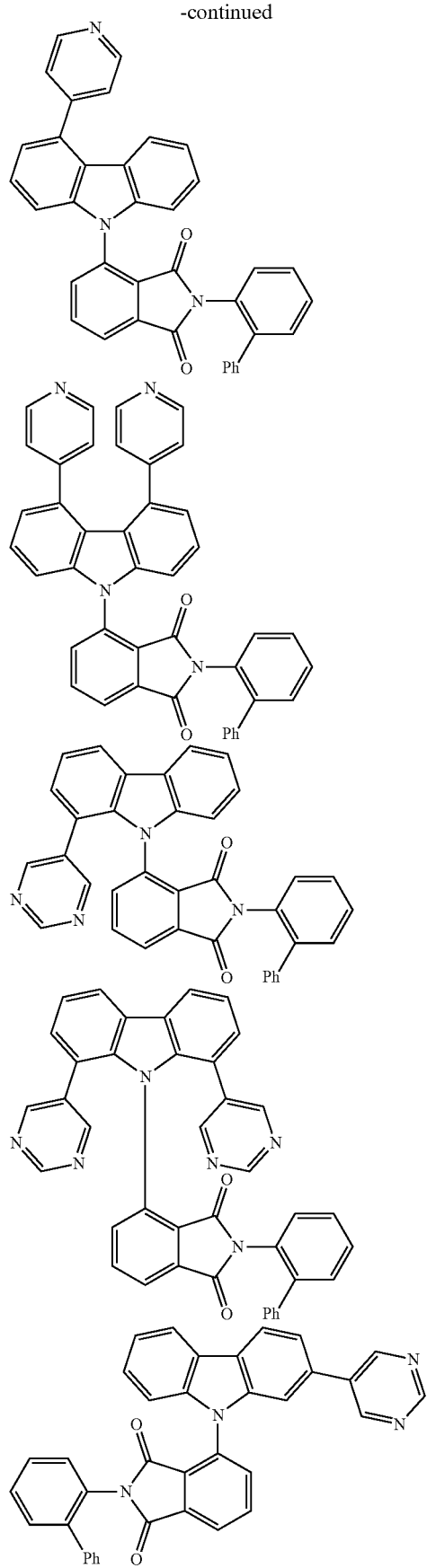
248
-continued
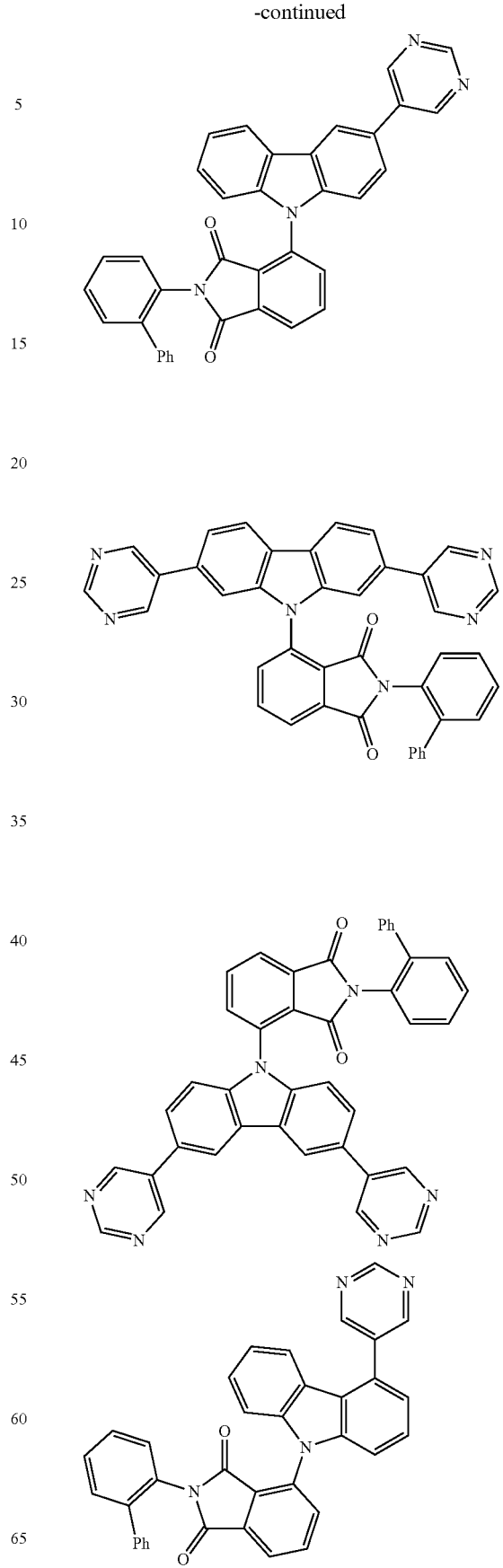

249
-continued
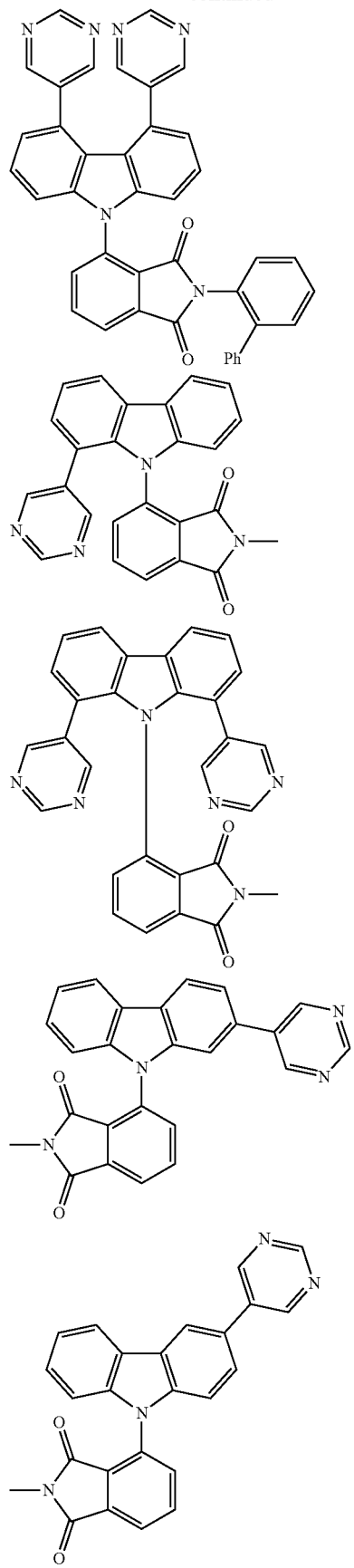
250
-continued
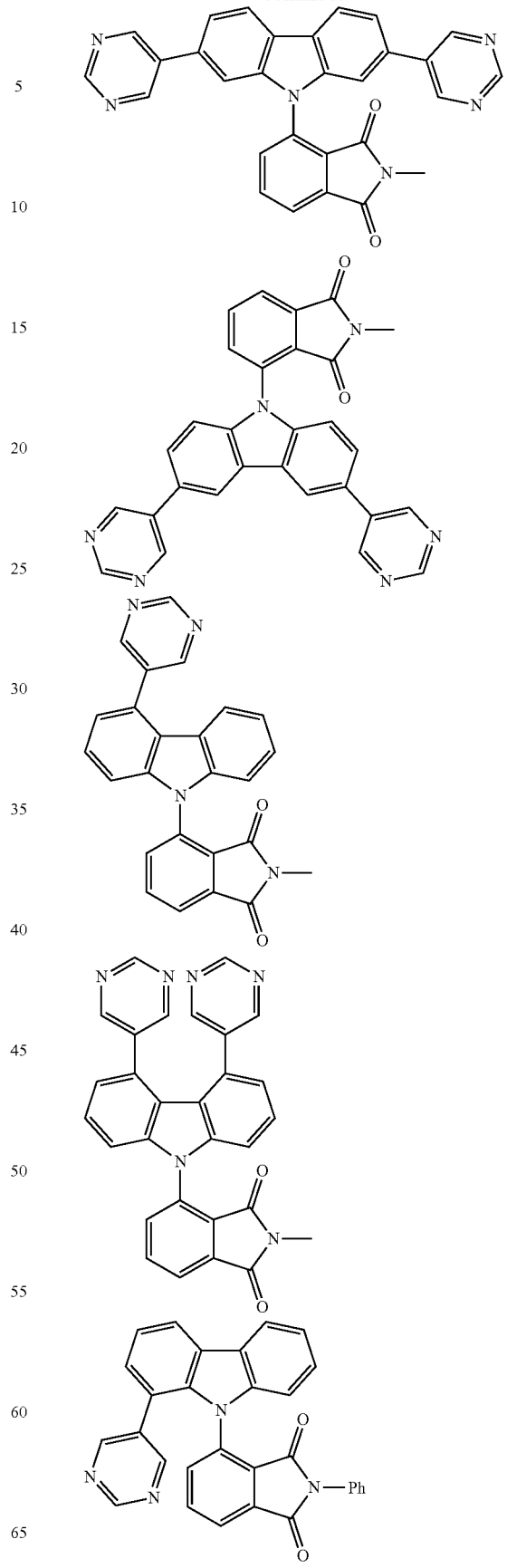

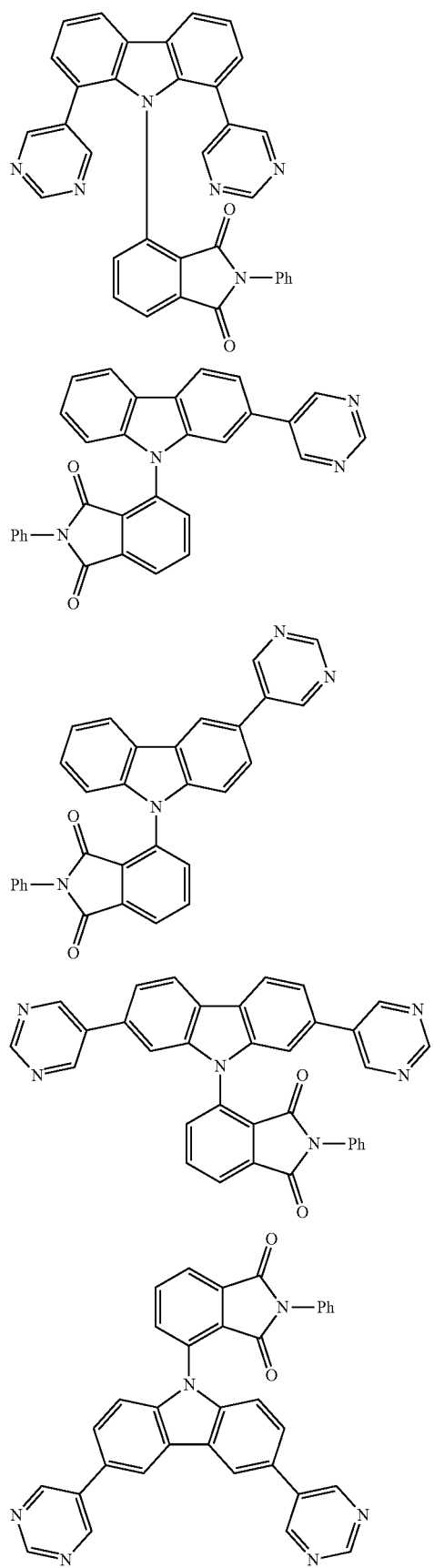
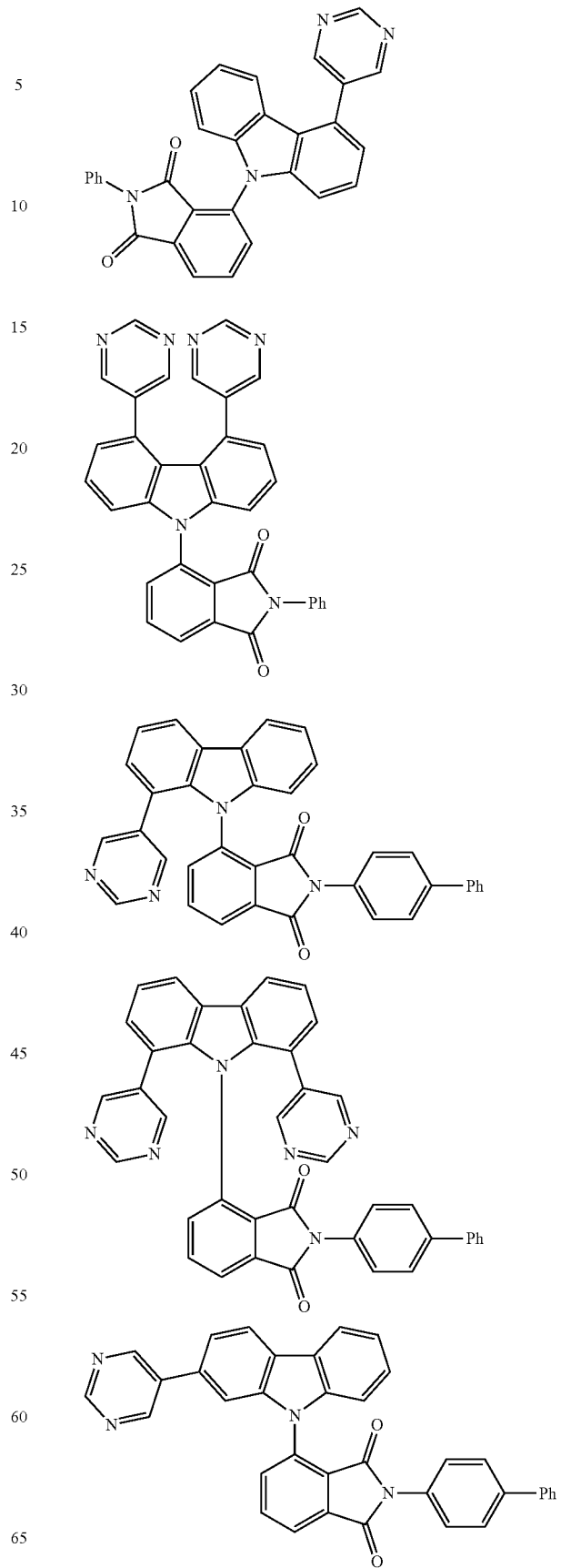

253
-continued
254
-continued
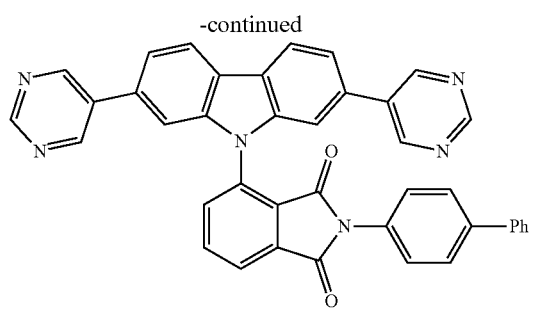
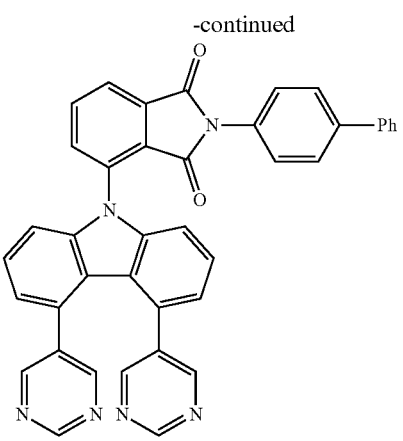
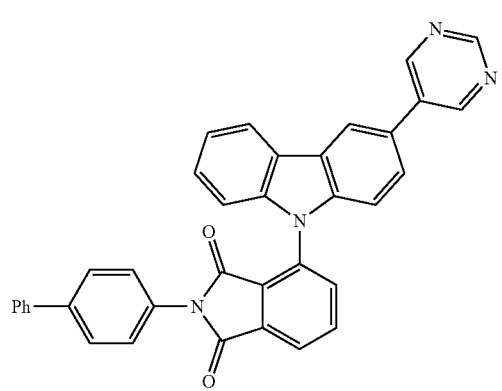
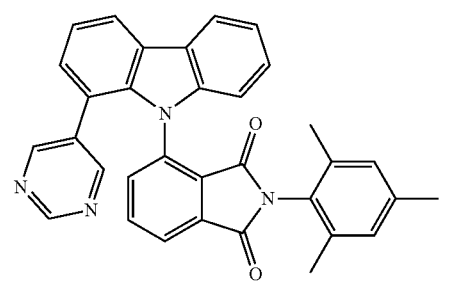
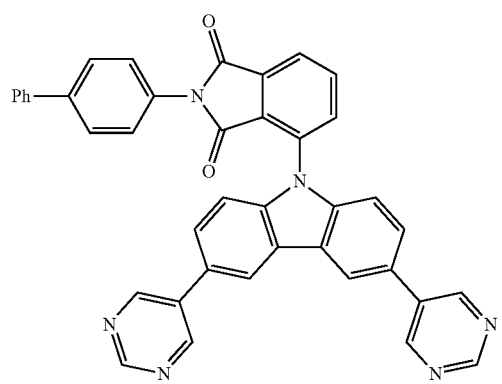
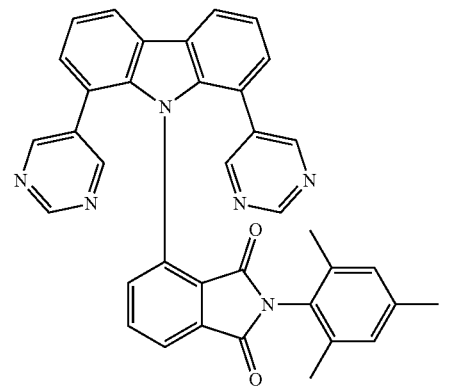
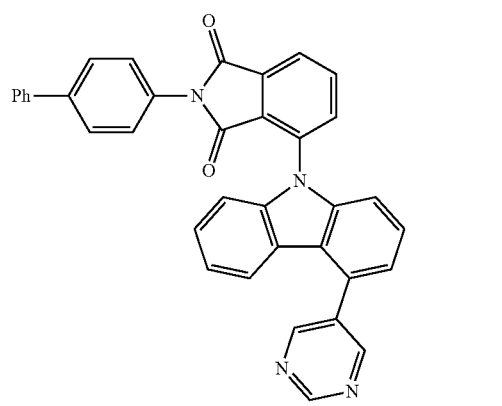
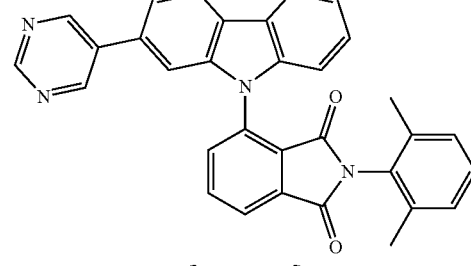
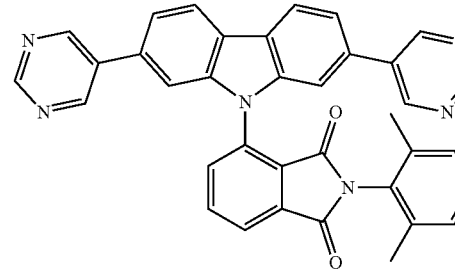

255
-continued
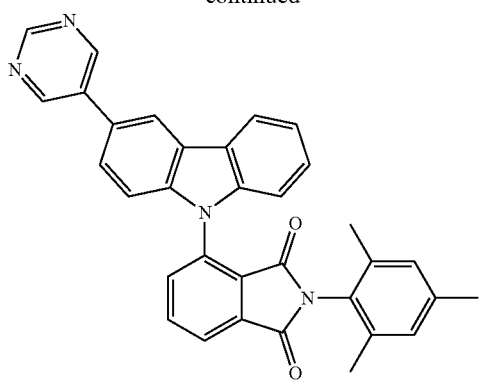
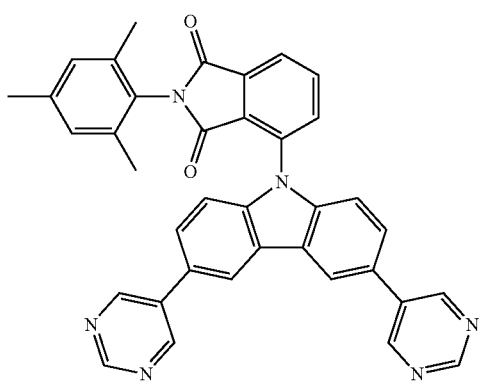
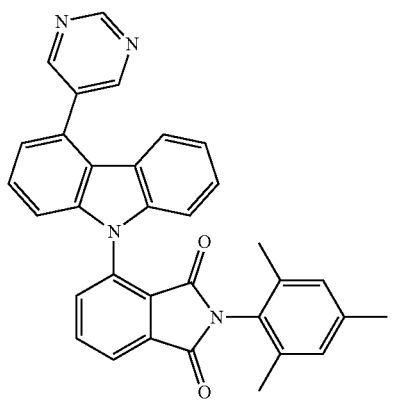
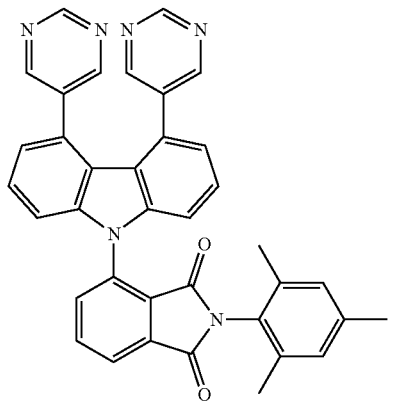
256
-continued
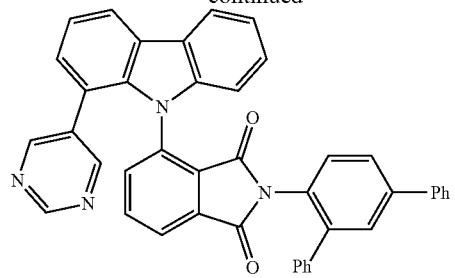
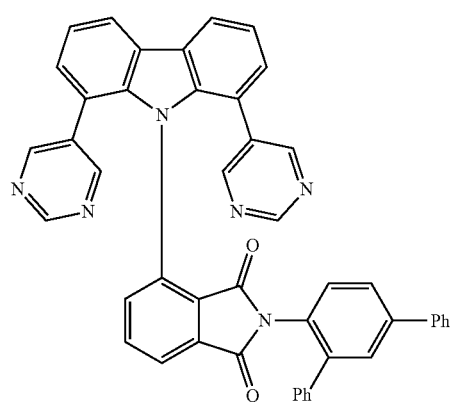
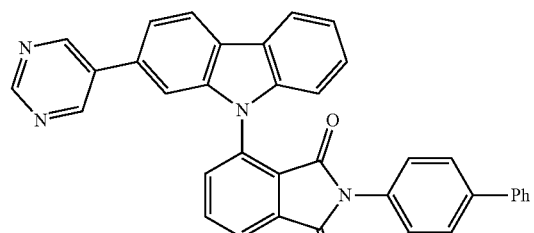
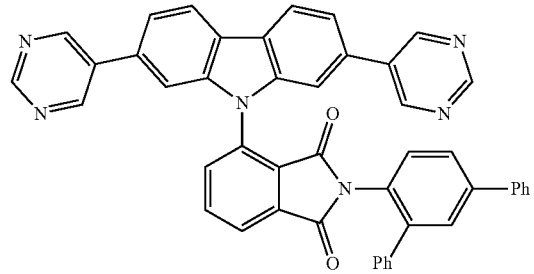
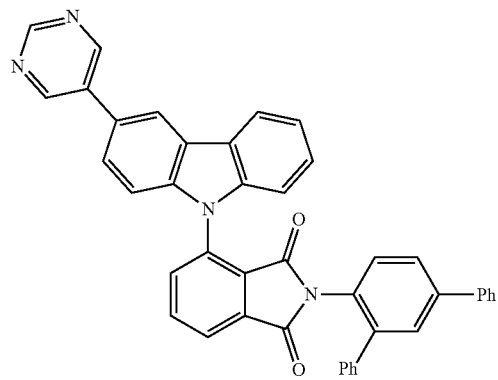

257
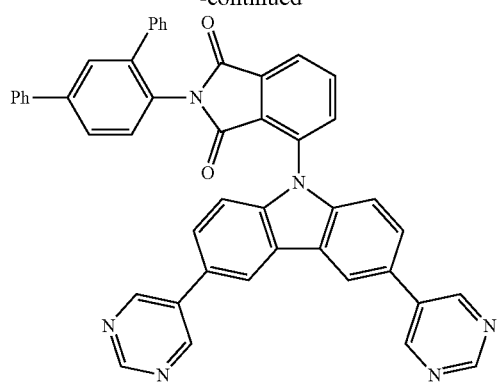
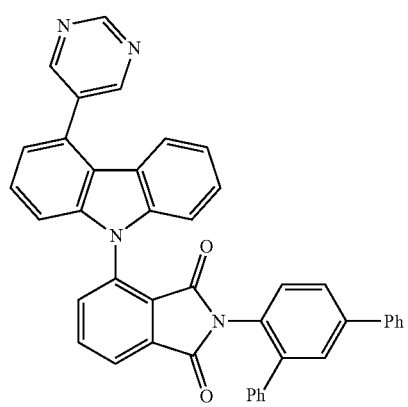
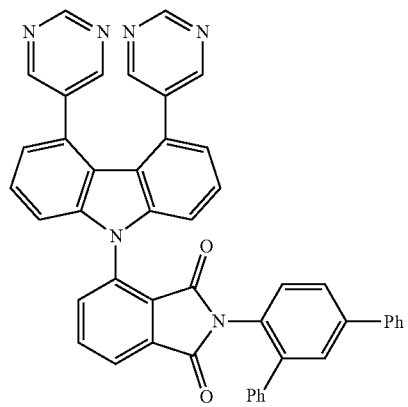
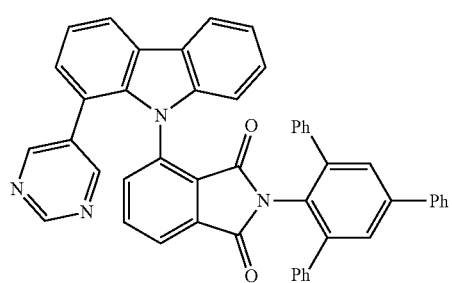
258
-continued
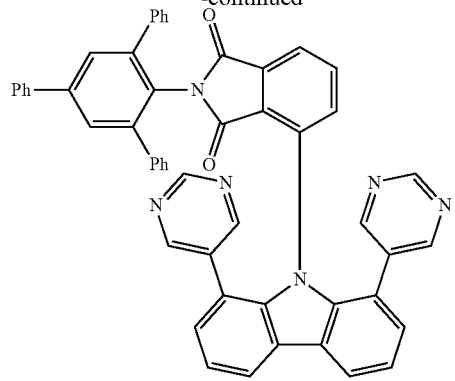
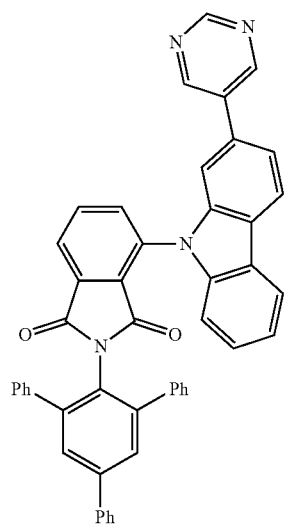
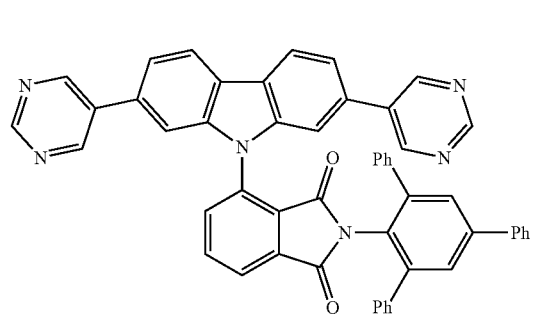
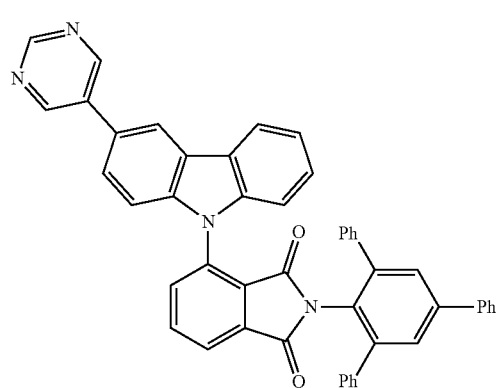

259
-continued
260
-continued
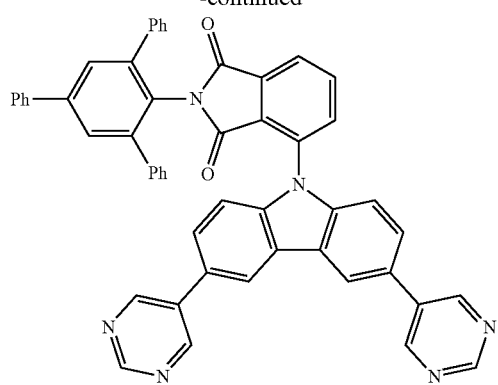
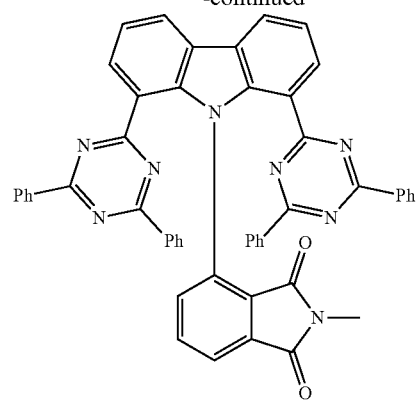
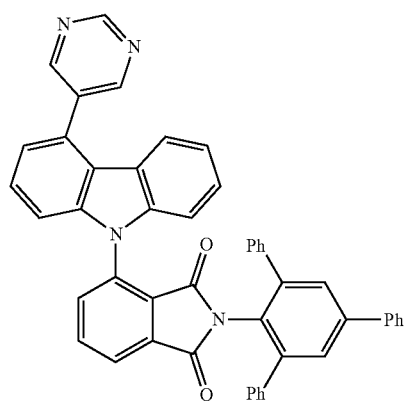
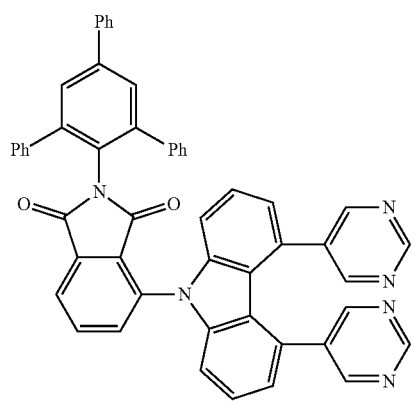
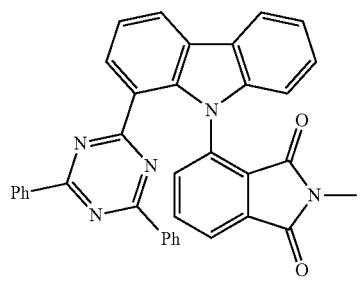
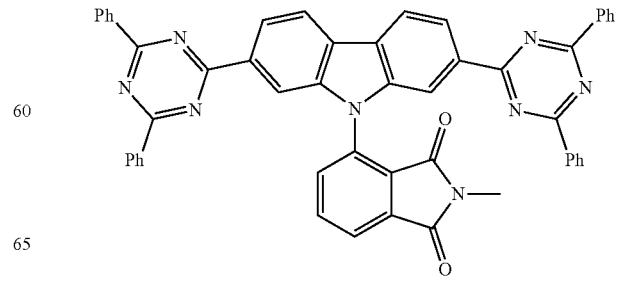

261
-continued
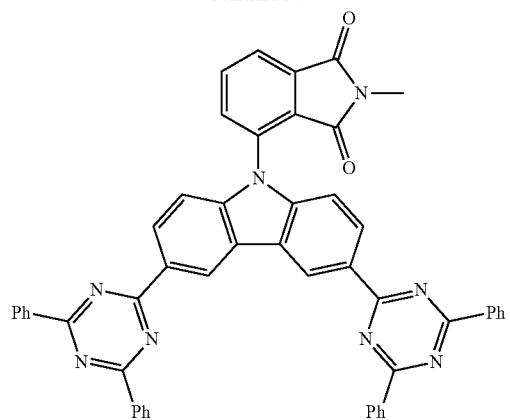
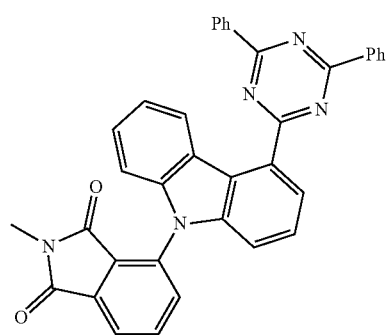
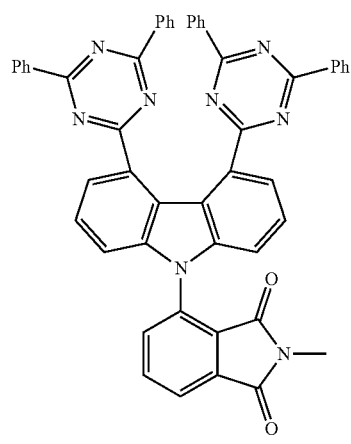
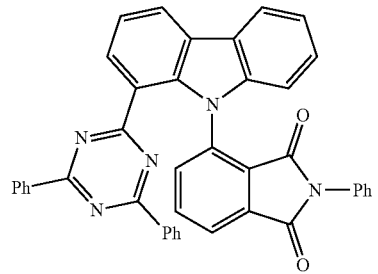
262
-continued
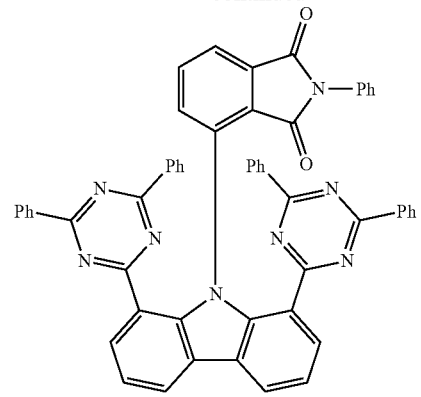
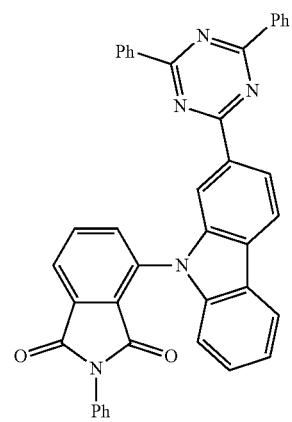
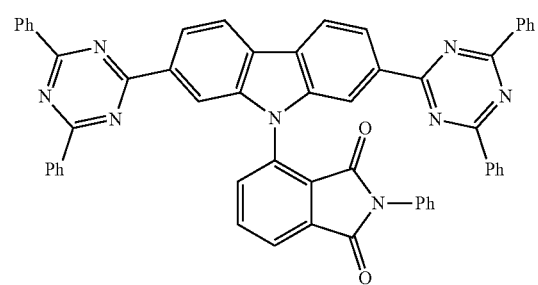
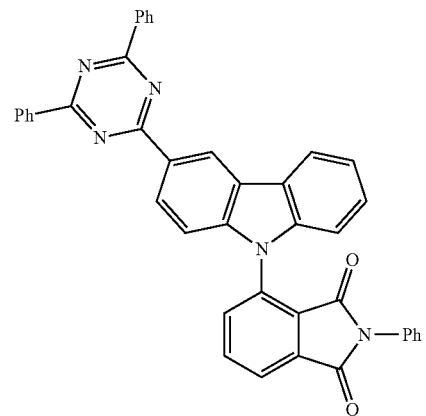

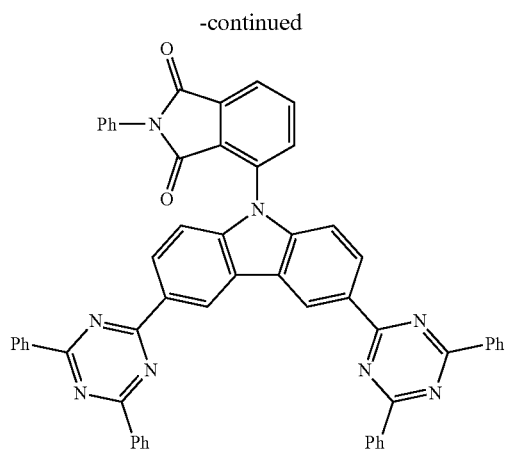
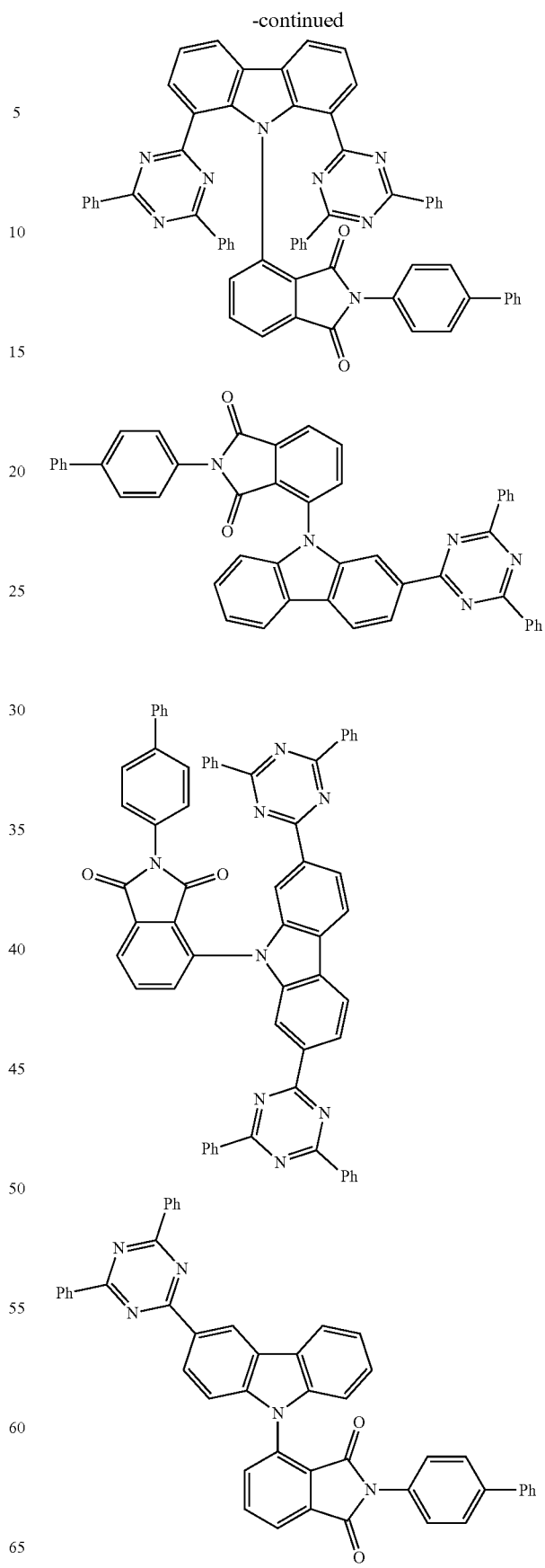

265
-continued
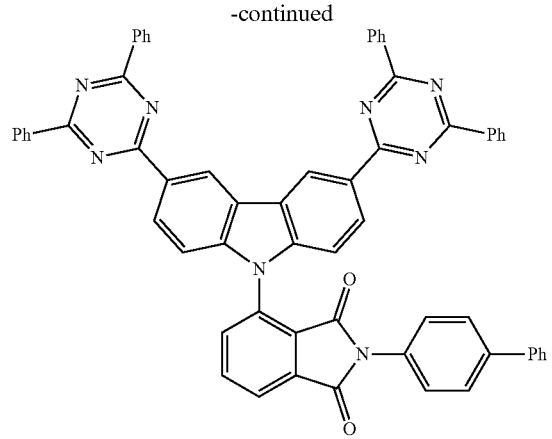
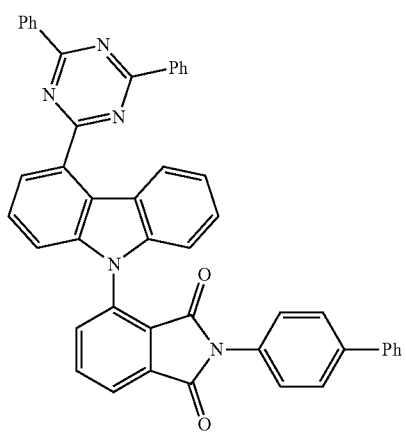
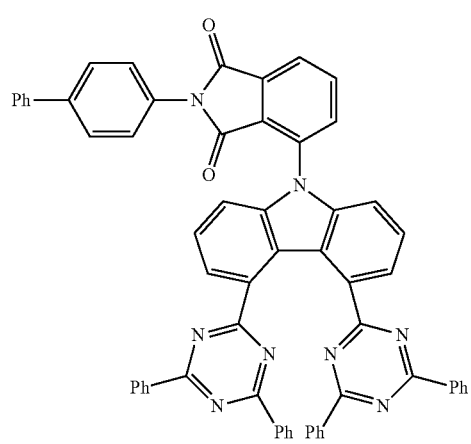
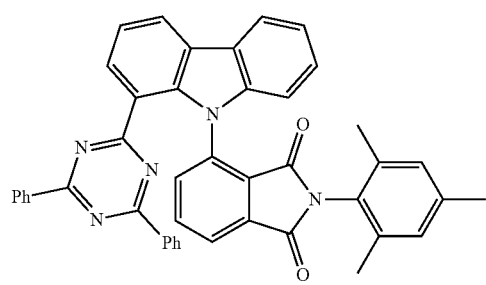
266
-continued
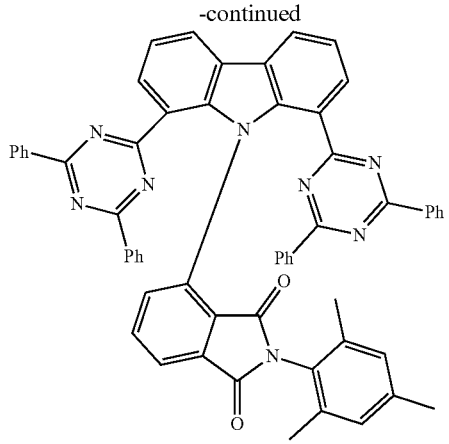
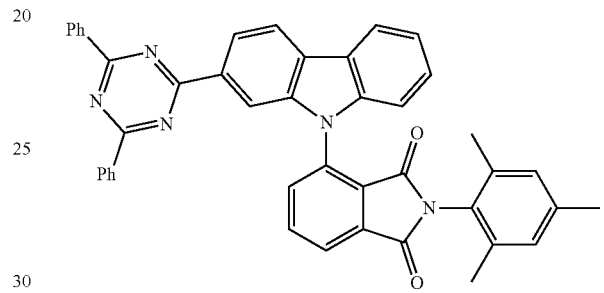
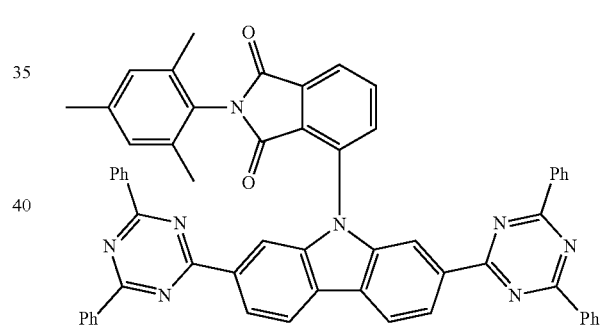
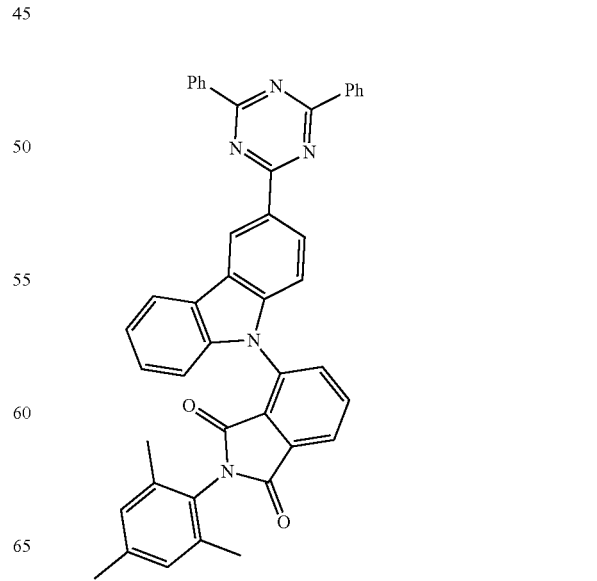

267
-continued
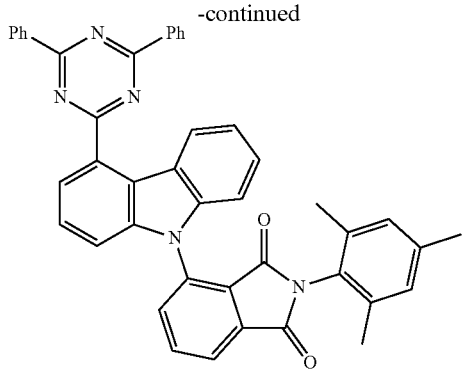
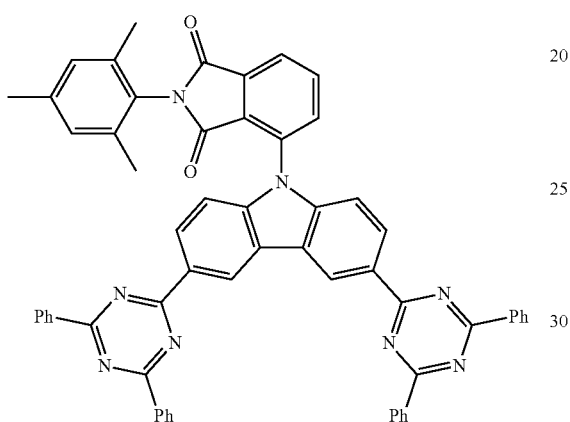
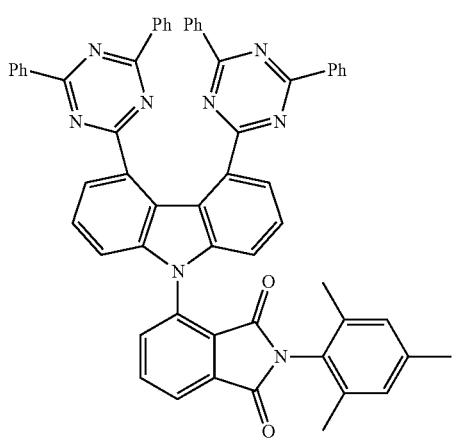
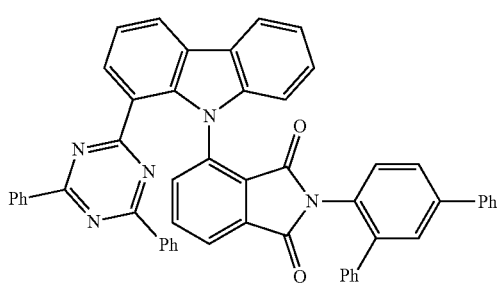
268
-continued
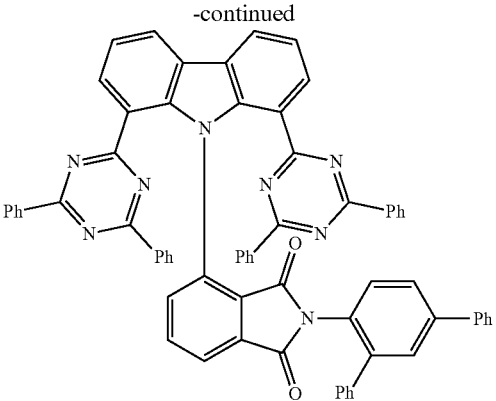
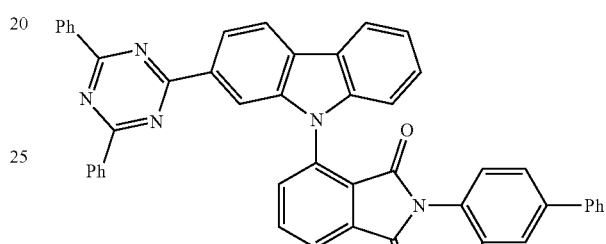
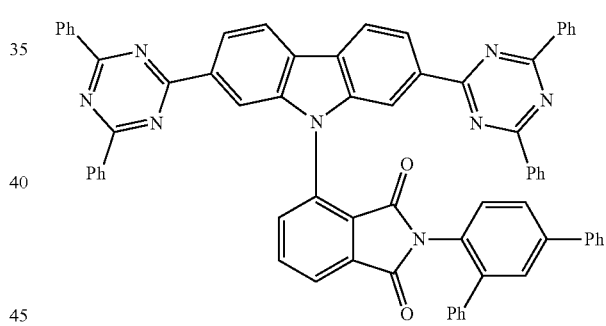
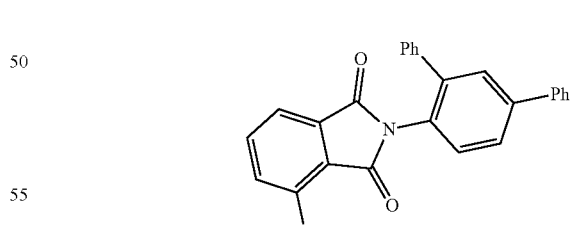

269
-continued
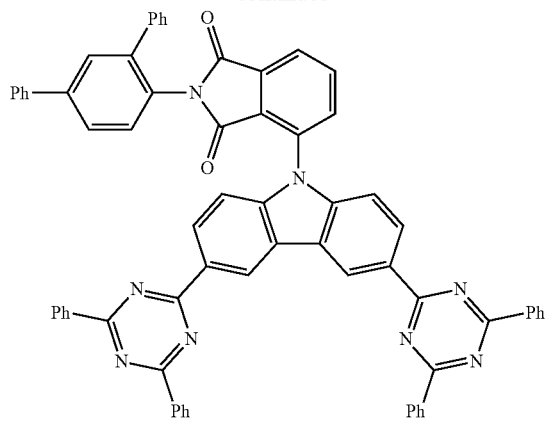
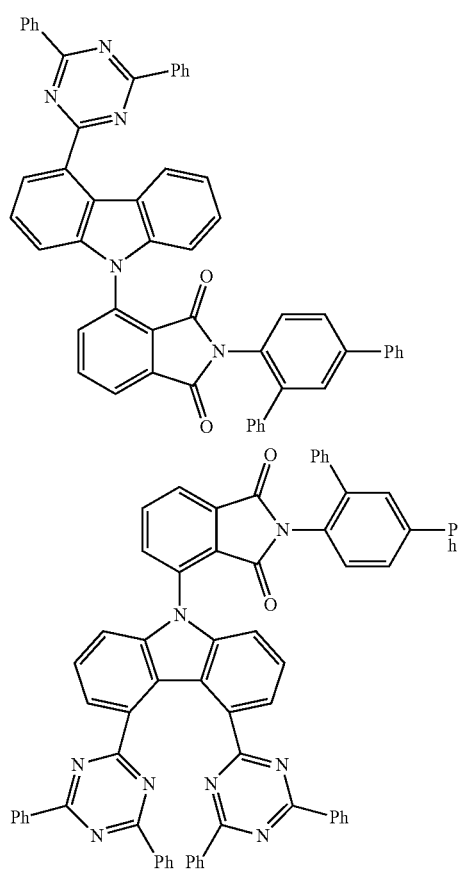
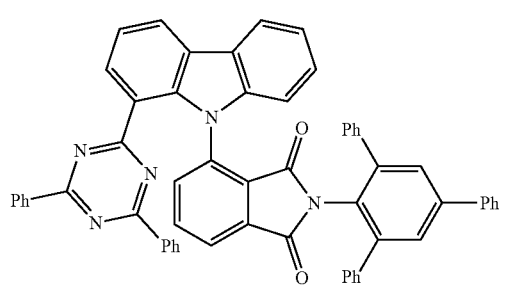
270
-continued
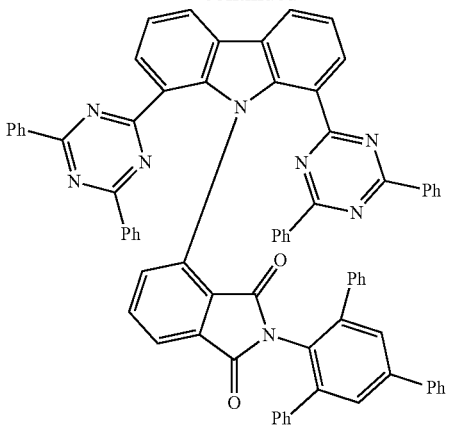
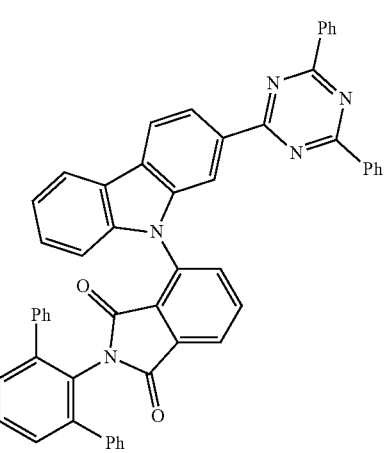
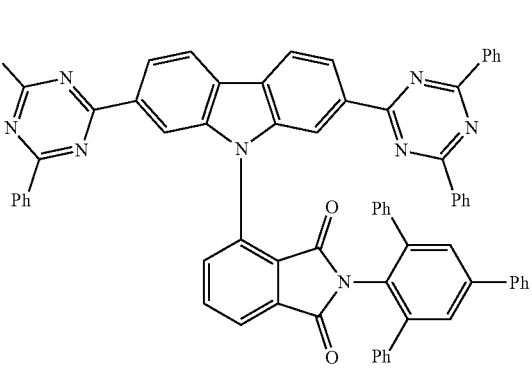
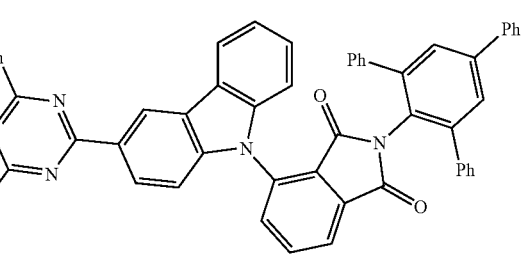

271
-continued
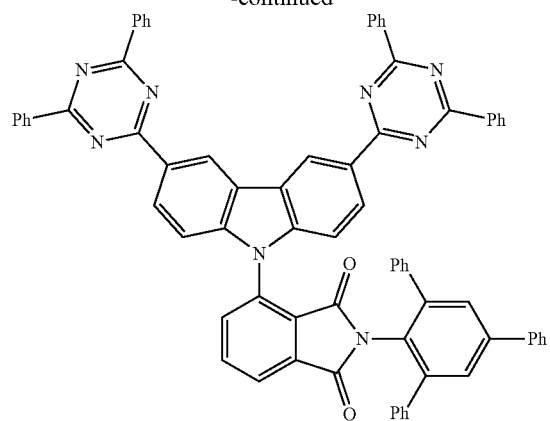
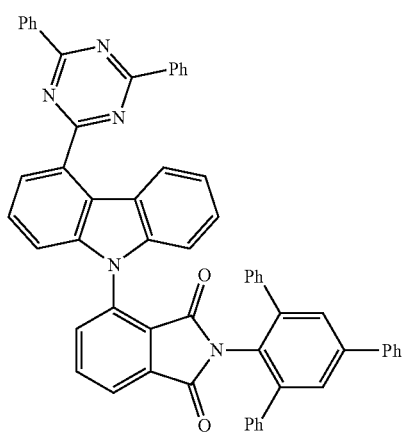
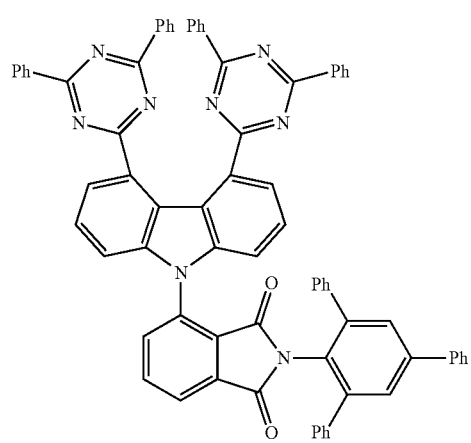
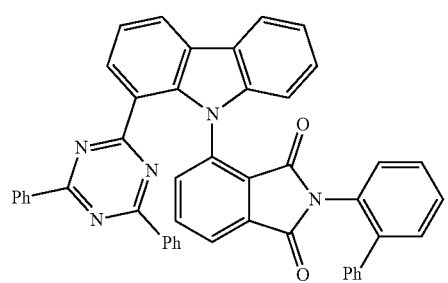
272
-continued
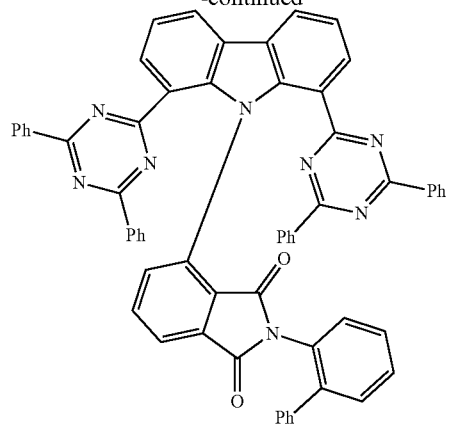
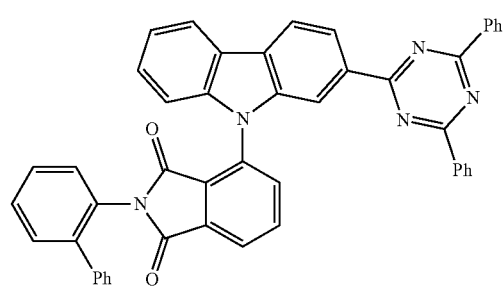
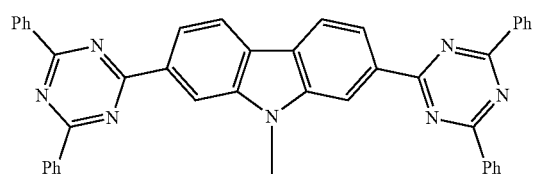
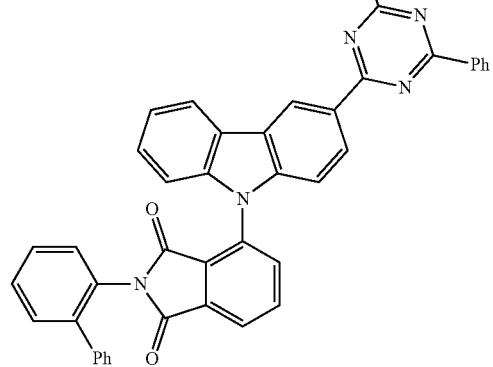

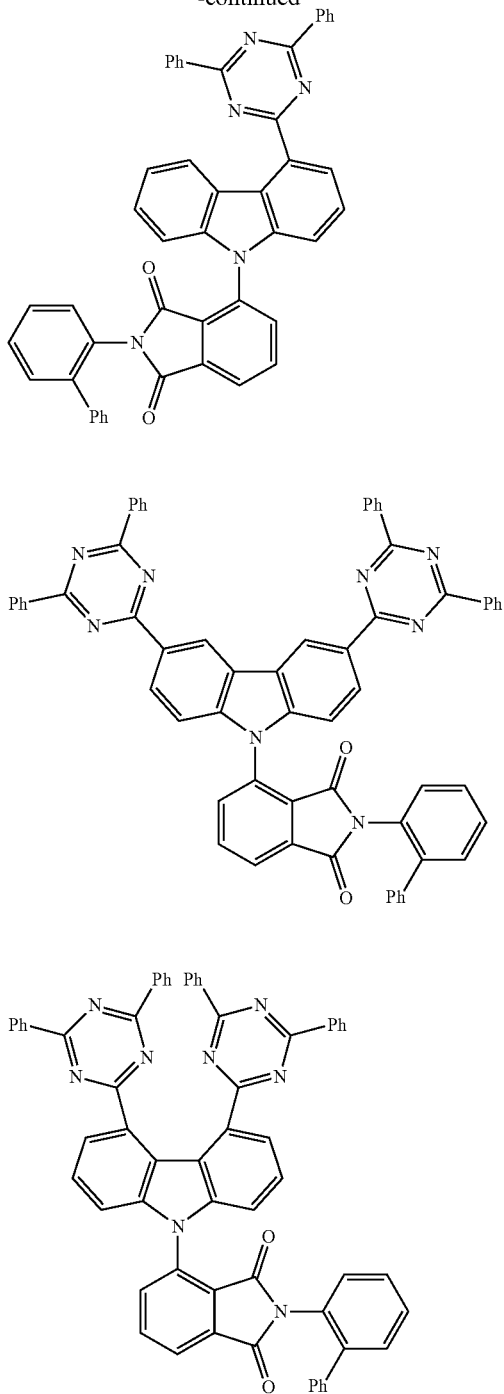

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An organic molecule comprising a structure of Formula A1:

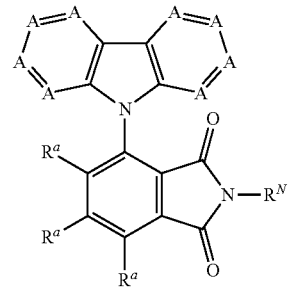

Formula A1 where
A at each instance is independently $CR^b$ or N;
$R^N$ is methyl, phenyl, xylyl, mesityl, naphthyl, biphenyl, naphthylphenyl, terphenyl or 2,4,6-triphenylphenyl;
$R^a$ at each instance is independently H, deuterium, an alkyl group or an aryl group;
$R^b$ at each instance is independently selected from the group consisting of:
H,
deuterium,
$CF_3$,
$C(=O)R^1$,
CN,
an alkyl group which is unsubstituted or substituted by one or more $R^2$,
an aryl group which is unsubstituted or substituted by one or more $R^2$ and is optionally additionally substituted by one or more unsubstituted alkyl groups and/or by one or more unsubstituted or alkyl-substituted aryl groups,
a heteroaryl group which is unsubstituted or substituted by $R^2$ and/or by one or more unsubstituted alkyl groups and/or by one or more unsubstituted or alkyl-substituted aryl groups and
a group of the sub-formula T1 or a group of the sub-formula T2:

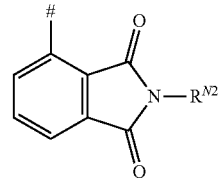

Sub-formula T1

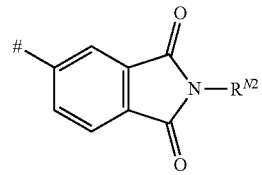

Sub-formula T2 where:
$R^{N2}$ is an alkyl group, an aryl group which is unsubstituted or substituted by one or more $R^{N3}$ or a heteroaryl group which is unsubstituted or substituted by one or more $R^{N3}$;
$R^{N3}$ is an alkyl group, an aryl group or a heteroaryl group;

R[1] at each instance is an aryl group which is unsubstituted or substituted by one or more R[2];

R[2] at each instance is independently F, CF$_3$ or CN;

where one to four A are N or at least one R[b] is selected from the group consisting of:
CF$_3$,
C(=O)R[1],
CN,
an alkyl group substituted by one or more R[2],
an aryl group substituted by one or more R[2], and optionally additionally substituted by one or more unsubstituted alkyl groups and/or by one or more unsubstituted or alkyl-substituted aryl groups,
a heteroaryl group which is unsubstituted or substituted by one or more R[2] and/or by one or more unsubstituted alkyl groups and/or by one or more unsubstituted or alkyl-substituted aryl groups and
a group of the sub-formula T1 or a group of the sub-formula T2:

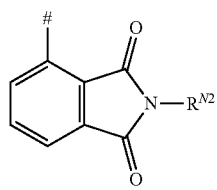

Sub-formula T1

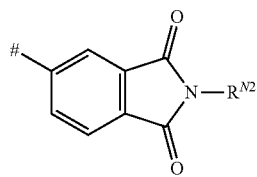

Sub-formula T2 and where # indicates the point via which the group of the sub-formula T1 or T2 is attached via a single bond.

2. The organic molecule according to claim 1, comprising a structure of Formula A2:

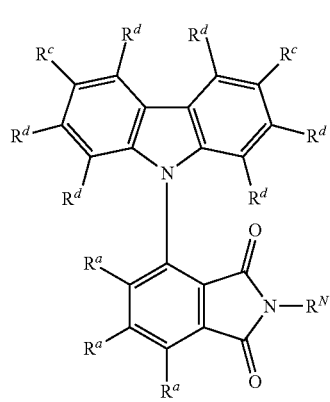

Formula A2 where
R[c] at each instance is independently selected from the group consisting of:
CF$_3$,
C(=O)R[1],
CN,
an alkyl group substituted by one or more R[2],
an aryl group substituted by one or more R[2], and optionally additionally substituted by one or more unsubstituted alkyl groups and/or by one or more unsubstituted or alkyl-substituted aryl groups,
a heteroaryl group which is unsubstituted or substituted by one or more R[2] and/or by one or more unsubstituted alkyl groups and/or by one or more unsubstituted or alkyl-substituted aryl groups and
a group of the sub-formula T1 or a group of the sub-formula T2:

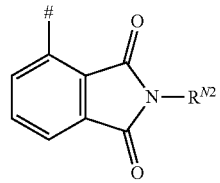

Sub-formula T1

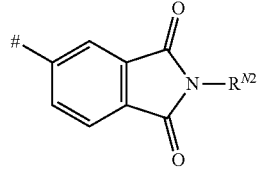

Sub-formula T2 where R[N2] is an alkyl group, an aryl group which is unsubstituted or substituted by one or more R[N3] or a heteroaryl group which is unsubstituted or substituted by one or more R[N3];

R[d] at each instance is independently selected from the group consisting of:
H,
deuterium,
CF$_3$,
C(=O)R[1],
CN,
an alkyl group which is unsubstituted or substituted by one or more R[2],
an aryl group which is unsubstituted or substituted by one or more R[2] and/or by one or more unsubstituted alkyl groups and/or by one or more unsubstituted or alkyl-substituted aryl groups,
a heteroaryl group which is unsubstituted or substituted by one or more R[2] and/or by one or more unsubstituted alkyl groups and/or by one or more unsubstituted or alkyl-substituted aryl groups, and
a group of the sub-formula T1 or a group of the sub-formula T2:

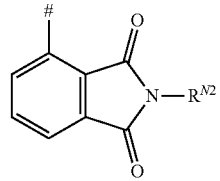

Sub-formula T1

-continued

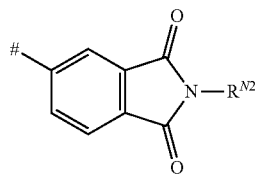
Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$;

and #, $R^a$, $R^1$, $R^2$ and $R^{N3}$ have the aforestated meanings.

3. The organic molecule according to claim 1, comprising a structure of Formula A3:

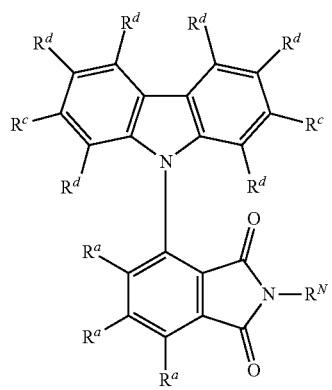
Formula A3 where $R^c$ at each instance is independently selected from the group consisting of:

CF$_3$,

C(=O)R$^1$,

CN, an alkyl group substituted by one or more R$^2$, an aryl group substituted by one or more R$^2$, and optionally additionally substituted by one or more unsubstituted alkyl groups and/or by one or more unsubstituted or alkyl-substituted aryl groups, a heteroaryl group which is unsubstituted or substituted by one or more R$^2$ and/or by one or more unsubstituted alkyl groups and/or by one or more unsubstituted or alkyl-substituted aryl groups and a group of the sub-formula T1 or a group of the sub-formula T2:

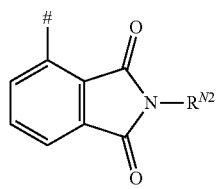
Sub-formula T1

-continued

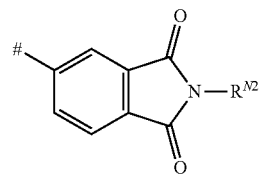
Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$;

$R^d$ is the same or different at each instance and is independently selected from the group consisting of:

H, deuterium,

CF$_3$,

C(=O)R$^1$,

CN, an alkyl group which is unsubstituted or substituted by one or more R$^2$, an aryl group which is unsubstituted or substituted by one or more R$^2$ and/or by one or more unsubstituted alkyl groups and/or by one or more unsubstituted or alkyl-substituted aryl groups, a heteroaryl group which is unsubstituted or substituted by R$^2$ and/or by one or more unsubstituted alkyl groups and/or by one or more unsubstituted or alkyl-substituted aryl groups and a group of the sub-formula T1 or a group of the sub-formula T2:

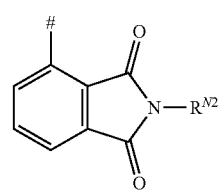
Sub-formula T1

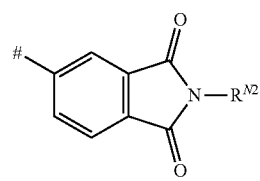
Sub-formula T2 where $R^{N2}$ is an alkyl group, an aryl group which is unsubstituted or substituted by one or more $R^{N3}$ or a heteroaryl group which is unsubstituted or substituted by one or more $R^{N3}$;

and #, $R^a$, $R^1$, $R^2$ and $R^{N3}$ have the aforestated meanings.

4. The organic molecule according to claim 1, comprising a structure of Formula A4:

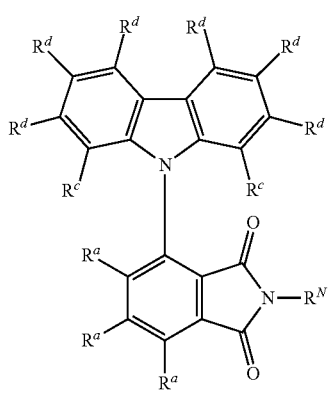

Formula A4 where
R$^c$ at each instance is independently selected from the group consisting of:
CF$_3$,
C(=O)R$^1$,
CN,
an alkyl group substituted by one or more R$^2$,
an aryl group substituted by one or more R$^2$, and optionally additionally substituted by one or more unsubstituted alkyl groups and/or by one or more unsubstituted or alkyl-substituted aryl groups,
a heteroaryl group which is unsubstituted or substituted by one or more R$^2$ and/or by one or more unsubstituted alkyl groups and/or by one or more unsubstituted or alkyl-substituted aryl groups and
a group of the sub-formula T1 or a group of the sub-formula T2:

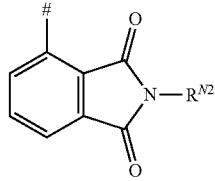

Sub-formula T1

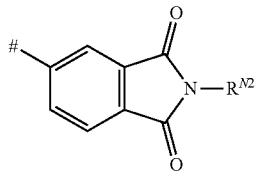

Sub-formula T2 where R$^{N2}$ is an alkyl group, an aryl group which is unsubstituted or substituted by one or more R$^{N3}$ or a heteroaryl group which is unsubstituted or substituted by one or more R$^{N3}$;
R$^d$ is the same or different at each instance and is independently selected from the group consisting of:
H,
deuterium,
CF$_3$,
C(=O)R$^1$,
CN,
an alkyl group which is unsubstituted or substituted by one or more R$^2$,
an aryl group which is unsubstituted or substituted by one or more R$^2$ and/or by one or more unsubstituted alkyl groups and/or by one or more unsubstituted or alkyl-substituted aryl groups,
a heteroaryl group which is unsubstituted or substituted by R$^2$ and/or by one or more unsubstituted alkyl groups and/or by one or more unsubstituted or alkyl-substituted aryl groups and
a group of the sub-formula T1 or a group of the sub-formula T2:

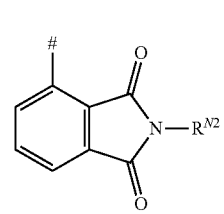

Sub-formula T1

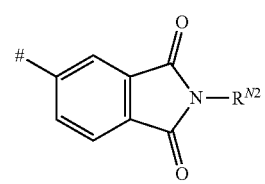

Sub-formula T2 where R$^{N2}$ is an alkyl group, an aryl group which is unsubstituted or substituted by one or more R$^{N3}$ or a heteroaryl group which is unsubstituted or substituted by one or more R$^{N3}$;
and #, R$^a$, R$^1$, R$^2$ and R$^{N3}$ have the aforestated meanings.

5. The organic molecule according to claim 1, where the organic molecule has at least one CN group.

6. The organic molecule according to claim 2, where the organic molecule has at least one CN group.

7. The organic molecule according to claim 3, where the organic molecule has at least one CN group.

8. The organic molecule according to claim 4, where the organic molecule has at least one CN group.

9. A composition comprising:
(a) at least one organic molecule according to claim 1 as an emitter and/or host;
(b) one or more emitter and/or host materials different from the at least one organic molecule according to claim 1; and
(c) optionally one or more dyes and/or one or more solvents.

10. An optoelectronic device comprising the organic molecule according to claim 1.

11. The optoelectronic device according to claim 10, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

12. The optoelectronic device according to claim 10, wherein the organic molecule is one of an emitter and an absorber in the optoelectronic device.

13. The optoelectronic device according to claim 12, wherein a proportion of the organic molecule in the emitter or the absorber is in the range of 1% to 80%.

14. The optoelectronic device according to claim 10, comprising:
- a substrate;
- an anode;
- a cathode, wherein the anode or the cathode is applied to the substrate; and
- at least one light-emitting layer is disposed between the anode and the cathode and which comprises the organic molecule.

15. An optoelectronic device comprising the organic molecule according to claim 2.

16. The optoelectronic device according to claim 15, wherein the organic molecule is one of an emitter and an absorber in the optoelectronic device.

17. An optoelectronic device comprising the composition according to claim 9.

18. The optoelectronic device according to claim 17, comprising:
- a substrate;
- an anode;
- a cathode, wherein the anode or the cathode is disposed on the substrate; and
- at least one light-emitting layer disposed between the anode and the cathode and which comprises the composition.

19. The optoelectronic device according to claim 17, wherein the composition is one of an emitter and an absorber in the optoelectronic device.

20. A process for producing an optoelectronic component, comprising processing of the organic molecule according to claim 1 by an evaporation process or from a solution.

* * * * *